US008143005B2

(12) United States Patent
Rouleau et al.

(10) Patent No.: US 8,143,005 B2
(45) Date of Patent: *Mar. 27, 2012

(54) NUCLEIC ACIDS ENCODING SODIUM CHANNEL SCN1A ALPHA SUBUNIT PROTEINS AND MUTATIONS ASSOCIATED WITH EPILEPSY

(75) Inventors: Guy A. Rouleau, Montreal (CA); Ronald G. Lafrenière, Verdun (CA); Daniel Rochefort, Laval (CA)

(73) Assignee: McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/637,219

(22) Filed: Dec. 14, 2009

(65) Prior Publication Data

US 2010/0092990 A1  Apr. 15, 2010

Related U.S. Application Data

(60) Continuation of application No. 10/664,423, filed on Sep. 17, 2003, now Pat. No. 7,655,460, which is a division of application No. 09/718,355, filed on Nov. 24, 2000, now abandoned.

(60) Provisional application No. 60/167,623, filed on Nov. 26, 1999.

(51) Int. Cl.
| C12Q 1/68 | (2006.01) |
| C12N 1/21 | (2006.01) |
| C12N 15/00 | (2006.01) |
| C12N 15/11 | (2006.01) |
| C12N 15/12 | (2006.01) |

(52) U.S. Cl. ............ 435/6.11; 435/6.12; 435/6.16; 435/6.17; 435/320.1; 435/252.3; 536/23.5

(58) Field of Classification Search .................. None
See application file for complete search history.

(56) References Cited

U.S. PATENT DOCUMENTS

| 5,223,409 | A |  | 6/1993 | Ladner et al. |
| 5,482,845 | A |  | 1/1996 | Soares et al. |
| 5,871,940 | A |  | 2/1999 | Hall et al. |
| 6,030,810 | A |  | 2/2000 | Delgato et al. |
| 6,110,672 | A |  | 8/2000 | Mandel et al. |
| 6,673,549 | B1 |  | 1/2004 | Furness et al. |
| 7,078,515 | B2 | * | 7/2006 | Wallace et al. ............ 536/23.5 |
| 7,485,449 | B2 |  | 2/2009 | Rouleau et al. |
| 7,528,093 | B2 |  | 5/2009 | Rouleau et al. |
| 7,655,460 | B2 | * | 2/2010 | Rouleau et al. ............ 435/325 |
| 2002/0076780 | A1 | * | 6/2002 | Turner et al. ............ 435/183 |

FOREIGN PATENT DOCUMENTS

| WO | WO 96/14077 |   | 5/1996 |
| WO | 97/01577    | * | 1/1997 |
| WO | WO 99/21875 |   | 5/1999 |

OTHER PUBLICATIONS

Noda 1987 (Journal of Receptor Research 7:467-497).*
Malo (1994. Cytogenet Cell Genet 67:178-186).*
Current Protocols in Molecular Biology (1989-1996, pp. 6.0.3-6.0.5, 6.1.1-6.1.4, 6.3.1-6.3.6, and 6.5.1-6.5.2).*
Noda 1984 (Nature 312:121-127).*
Sangameswaran 1996 (Journal of Biological Chemistry 271:5953-5956).*
Gonzalez et al., "Modification of tau to an Alzheimer's type protein interferes with its interaction with microtubules," Cell. Mol. Biol., 44:1117-1127, 1998.
Greenberg et al., "Juvenile myoclonic epilepsy (JME) may be linked to the BF and HLA loci on human chromosome 6," Am. J. Med. Genet., 31:185-192, 1988.
Guipponi et al., "Linkage mapping of benign familial infantile convulsions (BFIC) to chromosome 19q," Hum. Mol. Genet., 6:473-477, 1997.
Gyapay et al., "The 1993-94 Genethon human genetic linkage map," Nat Genet. 7:246-339, 1994.
Hamill et al., "Improved patch-clamp techniques for high-resolution current recording from cells and cell-free membrane patches," PflUgers Archiv., 391:85-100, 1981.
Hartshorne and Catterall, "The sodium channel from rat brain. Purification and subunit composition," J. Biol. Chem., 259:1667-1675, 1984.
Harvald, "Hereditary Factors Elucidated by Twin Studies". 1965.
Honig, "Protein Folding: From the Levinthal Paradox to Structure Prediction," J. Mol. Biol., 293:283-293, 1999.
Hu et al., "alpha1-Adrenergic receptor stimulation of mitogenesis in human vascular smooth muscle cells: role of tyrosine protein kinases and calcium in activation of mitogen-activated protein kinase," Journ. Pharmacology Experimental therapeutics, 290:28-37, 1999.
Kawai et al., "Death-associated protein kinase 2 is a new calcium/calmodulin-dependent protein kinase that signals apoptosis through its catalytic activity," Oncogene, 18:3471-3480, 1999. Kienle et al., "Electropolymerization of a phenol-modified peptide for use in receptor-ligand interactions studied by surface plasmon resonance," Biosensors and Bioelectronics, 12:779-786, 1997.
Kohlhardt, M, "Different temperature sensitivity of cardiac Na+ channels in cell-attached and cell-free conditions", Am J Physiol. Oct. 1990;259(4 Pt 1):C599-604.
Kohlhardt, M, "Gating Properties of Cardiac Na + Channels in Cell-Free Conditions", J. Membrane Biol. 122, 11-21 (1991).
Kohling, "Voltage-gated Sodium Channels in Epilepsy," Epilepsia, 43:1278-1295, 2002.
Komada et al., "Hrs, a FYVE finger protein localized to early endosomes, is implicated in vesicular traffic and required for ventral folding morphogenesis," Genes & Dev., 13:1475-1485, 1999.
Lam et al., "A new type of synthetic peptide library for identifying ligand-binding activity," Nature, 354:82-84, 1991.

(Continued)

*Primary Examiner* — Daniel E Kolker
(74) *Attorney, Agent, or Firm* — Goudreau Gage Dubuc; Charles Goyer

(57) ABSTRACT

The present invention relates to epilepsy. More particularly, the present invention relates to idiopathic generalized epilepsy (IGE) and to the identification of three genes mapping to chromosome 2, which show mutations in patients with epilepsy. The invention further relates to nucleic acid sequences, and protein sequences of these loci (SCNA) and to the use thereof to assess, diagnose, prognose or treat epilepsy, to predict an epileptic individual's response to medication and to identify agents which modulate the function of the SCNA. The invention also provides screening assays using SCN1A, SCN2A and/or SCN3A which can identify compounds which have therapeutic benefit for epilepsy and related neurological disorders.

19 Claims, 21 Drawing Sheets

OTHER PUBLICATIONS

Lam, K.S., "Application of combinatorial library methods in cancer research and drug discovery," Anti-Cancer Drug Design, 12:145-167, 1997.

Lanthrop et al., "Easy calculations of lod scores and genetic risks on small computers," Am. J. Genet., 36:460-465, 1984.

Lennox et al., Epilepsy and related disorders, Little Brown, pp. 532-574, 1960.

Leppert et al., "Benign familial neonatal convulsions linked to genetic markers on chromosome 20," Nature, 337:647-648, 1989.

Lewis et al., "Genetic heterogeneity in benign familial neonatal convulsions: identification of a new locus on chromosome 8q," Am. J. Hum. Genet., 53:670-675, 1993.

Liu, L., "Calcium-dependent self-association of annexin II: a possible implication in exocytosis," Cell. Signal., 11:317-324, 1999.

Lu and Brown, "Isolation of a human-brain sodium-channel gene encoding two isoforms of the subtype III .alpha.-subunit," J. Mol. Neuro., 10:67-70, 1998.

Malo et al., "Targeted gene walking by low stringency polymerase chain reaction: assignment of a putative human brain sodium channel gene (SCN3A) to chromosome 2q24-31," Proc. Natl. Acad. Sci., USA, 91:2975-2979, 1994.

McConnell et al., "The cytosensor microphysiometer: biological applications of silicon technology," Science, 257:1906-1912, 1992.

McPhee et al., "A critical role for the S4-S5 intracellular loop in domain IV of the sodium channel alpha-subunit in fast inactivation," J. Biol. Chem., 273:1121-1129, 1998.

Miyaji-Yamaguchi et al., "Coiled-coil structure-mediated dimerization of template activating factor-I is critical for its chromatin remodeling activity," Journal of Mol. Biol., 290:547-557, 1999.

Morvan et al., "alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)].," Nucleic Acids Research, 14:5019-5035, 1986.

Moulard et al., "Identification of a new locus for generalized epilepsy with febrile seizures plus (GEFS+) on chromosome 2q24-q33," Am. J. Hum. Genet., 65:1396-1400, 1999.

Muir et al., "Phase II clinical trial of sipatrigine (619C89) by continuous infusion in acute stroke," Cerebrovascular Diseases, 10:431-436, 2000.

Nakashima et al., "Signaling pathways for tumor necrosis factor-alpha and interleukin-6 expression in human macrophages exposed to titanium-alloy particulate debris in vitro," J. Bone Joint Surg. Am., 81:603-615, 1999.

NCBI accession No. NM_001 081676 printed Oct. 1, 2007.

NCBI accession No. NM_001 081677 printed Oct. 1, 2007.

Nielsen, P.E., "Applications of peptide nucleic acids," Curr. Opin. Biotechnol., 10:71-75, 1999.

Noda, "Existence of distinct sodium channel messenger RNAs in rat brain," 1986. Nature 320:188-192.

Okuwaki et al., "Template activating factor-I remodels the chromatin structure and stimulates transcription from the chromatin template," J. Biol. Chem., 273:34511-34518, 1998.

Ottaman et al., "Localization of a gene for partial epilepsy to chromosome 10q," Nat. Genet., 10:56-60, 1995.

Ottaman et al., "Segregation analysis of cryptogenic epilepsy and an empirical test of the validity of the results," Am. J. Hum. Genet., 60:667-675, 1997.

Ottman et al., "Seizure risk in offspring of parents with generalized versus partial epilepsy," Epilepsia, 30:157-161, 1989.

Plummer and Meisler, "Evolution and diversity of mammalian sodium channel genes," Genomics, 57:323-331, 1999.

Pugsley et al., "Effects of bisaramil, a novel class I antiarrhythmic agent, on heart, skeletal muscle and brain Na+ channels," Eur. J. Pharmacol., 342:93-104, 1998.

Ragsdale et al., "Sodium channels as 1-15 molecular targets for antiepileptic drugs." Brain Research. Brain Research Reviews, 1998, vol. 26, No. 1, pp. 16-28.

Raymond et al., "Expression of Alternatively Spliced Sodium Channel alpha-Subunit Genes—Unique Splicing Patterns Are Observed in Dorsal Root Ganglia", Journal of Biological Chemistry, 279(44):46234-46241, 2004.

Reckziegel et al., "Electrophysiological characterization of Na+ currents in acutely isolated human hippocampal dentate granule cells", J Physiol. 1998. 509( Pt 1):139-50.

Rudinger, in "Peptide Hormones" (ed., J.A. Parsons) University Park Press, Baltimore, pp. 1-7 (1976).

Rudy, "Introduction: Molecular Diversity of Ion Channels and Cell Function," Annals of the New York Academy of Sciences, 868:1-12, 1999.

Schroeder et al., "Moderate loss of function of cyclic-AMP-modulated KCNQ2/KCNQ3 K+ channels causes epilepsy," Nature, 396:687-690, 1998.

Scott et al., "Searching for peptide ligands with an epitope library," Science, 249:386-390, 1990.

Sequence alignment for NCBI Accession No. X03638.

Sequence alignment for US 6,110,672 sequence 14.

Sequence alignments for SEQ ID No. 65, Gen Bank accession Nos. AF035685 and AF035686.

Sillampaa et al., "Genetic factors in epileptic seizures: evidence from a large twin population," ActaNeurol. Scand., 84:523, 1991.

Singh et al., "A novel potassium channel gene, KCNQ2, is mutated in an inherited epilepsy of newborns," Nat. Genet., 18:25-29, 1998.

Sjolander et al., "Integrated fluid handling system for biomolecular interaction analysis," Anal. Chem., 63:2338-2345, 1991.

Steinlein et al., "A missense mutation in the neuronal nicotinic acetylcholine receptor alpha 4 subunit is associated with autosomal dominant nocturnal frontal lobe epilepsy," Nat. Genet., 11:201-203, 1995.

Stratagene Catalog 1991, "Gene characterization", p. 66.

Szabo et al., "Surface plasmon resonance and its use in biomolecular interaction analysis (BIA).," Curr. Opinion, Struct. Biol., 5:699-705, 1995.

Tamaskovic et al., "Enzyme-linked immunosorbent assay for the measurement of JNK activity in cell extracts," Biological Chemistry, 380:569-578, 1999.

Taylor et al., "Sodium channels and therapy of central nervous system diseases," Adv. Pharmacol., 39:47-98, 1997.

Tian et al., "Endogenous bursting due to altered sodium channel function in rat hippocampal CA1 neurons," Brain Res., 680:164-172, 1995.

Wallace et al., "Febrile seizures and generalized epilepsy associated with a mutation in the Na+-channel betal subunit gene SCNIB," Nature Genet., 19:366-370, 1998.

Wang, "Pharmacological targeting of long QT mutant sodium channels", 1997. J Clin Invest 99:1714-1720.

Xie et al., "Electrophysiological and pharmacological properties of the human brain type IIA Na+ channel expressed in a stable mammalian cell line." Pflügers Archiv 'European Journal Ofphysiology Jan. 2001 vol. 441, No. 4, pp. 425-433, XP009132588.

Kayano et al., "Primary structure of rat brain sodium channel III deduced from the cDNA sequence" (1988) 228 (1):187-194.

Suzuki et al., "Functional expression of cloned cDNA encoding sodium channel III" (1988) 228(1):195-200.

Zuchermann et al., "Discovery of nanomolar ligands for 7-transmembrane G-protein-coupled receptors from a diverse N-(substituted)glycine peptoid library," J. Med. Chem., 37:2678-2685, 1994.

Myers et al., 1999, "Visualization and Functional Analysis of a Maxi-K Channel (mSlo) Fused to Green Fluorescent Protein (GFP)", EJB Electronic Journal of Biotechnology, 2(3):140-151.

Meisler et al., 2005, "Sodium channel mutations in epilepsy and other neurological disorders", The Journal of Clinical Investigation, 115(8): 2010-2017.

Tarnawa et al., 2007, "Blockers of Voltage-Gated Sodium Channels for the Treatment of Central Nervous System Diseases", Recent Patents on CNS Drug Discovery, 2:57-78.

Schoonheim et al., 2010, "Optogenetic Localization and Genetic Perturbation of Saccade-Generating Neurons in Zebrafish", The Journal of Neuroscience, 30(20): 7111-7120.

Fletcher, 2011, "Alternative splicing in SCN1A: Biophysical consequences for NaV1.1 channels", A thesis submitted to University College London for the degree of Doctor of Philosophy, Department of Molecular Neuroscience Institute of Neurology, Queen Square, London, published online Mar. 2, 2011.

Alekov et al., 2001. "Short Communication: Enhanced inactivation and acceleration of activation of the sodium channel associated with epilepsy in man", European Journal of Neuroscience, 13:2171-2176.

"Decision of A Delegate of the Commissioner of Patents," issued in Australian Patent Application No. 18465/01, entitled 'Loci for idiopathic generalised epilepsy, mutations thereof and method using same to assess, diagnose, prognose or treatepilepsy,' dated Jan. 29, 2007.

"Molecular and Functional Diversity of Ion Channels and Receptors," Annals of the New York Academy of Sciences, 868: Table of Contents, 1999.

"Molecular and Functional Diversity of Ion Channels and Receptors. Proceedings of a conference. New York City, New York, USA. May 14-17, 1998." Ann. N.Y. Acad. Sci., 868:1, 1999 (PubMed Citation downloaded Nov. 14, 2006).

Ahmed et al., "Primary structure, chromosomal localization, and functional expression of a voltage-gated sodium channel from human brain," Proc. Natl. Acad. Sci. USA, 89:8220-8224, 1992.

Alberts et al. Molecular Biology of the Cell, 3rd Edition, 1994, pp. 98-104.

Andermann, E., Genetic Basis of the Epilepsies, Raven Press, New York, pp. 355-374, 1982.

Anderson et al., "Use of cyclosporin A in establishing Epstein-Barr virus-transformed human lymphoblastoid cell lines," In Vitro, 20:856-858, 1984.

Annegers et al., Genetic Basis of the Epilepsies, Raven Press, New York, pp. 151-159, 1982.

Avanzini et al., "Physiological properties of immature neocortical neurons relevant to pathophysiology of infantile epileptic encephalopathies," Prog Nat. Epileptogenesis (Epilepsy Res. Suppl.), 12:53-61, 1996.

Baker et al., "Cell proloferation kinetics of normal and tumor tissue in vitro: quiescent reproductive cells and the cycling reproductive fraction," Cell Prolif., 28:1-15, 1995.

Barker et al., "GABA actions on the excitability of cultured CNS neurons ," Neurosci. Lett., 47:313-318, 1984.

Barnard et al., "Molecular biology of the GABA(A) receptor: the receptor/channel superfamily", TINS, 10(12):502-509, 1987.

Bar-Sagi et al., "Negative modulation of sodium channels in cultured chick muscle cells by the channel activator batrachotoxin," J. Biol. Chem., 260:4740-4744, 1985.

Baulac et al., "A second locus for familial generalized epilepsy with febrile seizures plus maps to chromosome 2q21-q33," Am. J. Hum. Genet., 65:1078-1085, 1999.

Baunoch et al., "R-ELISA: repeated use of antigen-coated plates for ELISA and its application for testing of antibodies to HIV and other pathogens," Biotechniques, 12:412-417, 1992.

Berkovic et al., "Epilepsies in twins: genetics of the major epilepsy syndromes," Ann. Neurol., 43:435-445, 1998.

Biervert et al., "A potassium channel mutation in neonatal human epilepsy," Science, 279:403-406, 1998.

Birch et al., "Strategies to identify ion channel mosulators: current and novel approaches to target neuropathic pain," Drug Discovery Today, 9:410-418, 2004.

Bu et al., "The exon-intron organization of the genes (GAD1 and GAD2) encoding two human glutamate decarboxylases (GAD67 and GAD65) suggests that they derive from a common ancestral GAD," Genomics, 21:222-228, 1994.

Cardell et al., Agnew. Chem. Int. Ed. Engl., 33:2061-2063, 1994.

Charlier et al., "A pore mutation in a novel KQT-like potassium channel gene in an idiopathic epilepsy family," Nat. Genet, 18:53-55, 1998.

Cheviron et al., "The antiproliferative activity of the tetrapeptide Acetyl-N-SerAspLysPro, an inhibitor of haematopoietic stem cell proliferation, is not mediated by a thymosin beta 4-like effect on actin assembly," Cell Prolif., 29:437-446, 1996.

Chia et al., "Cytoskeletal association of an esterase in *Dictyostelium discoideum*," Exp.Cell Res., 244:340-348, 1998.

Cho et al., "An Unnatural Biopolymer," Science, 261:1303-1305, 1993.

Clare et al., "Cloning of Functional Analysis of the Type III Na+ Channel from Human Brain," Annals of the New York Academy of Sciences, 868:80-83, 1999.

Clare et al., "Voltage-gated sodium channels as therapeutic targets," Drug Discovery Today, 5:506-520, 2000.

Commission on classification and terminology of the international league against epilepsy, Epilepsia, 30:389-399, 1989.

Corey et al., "The occurrence of epilepsy and febrile seizures in Virginian and Norwegian twins," Neurology, 41:1433:1436, 1991.

Cossette et al., "Functional characterization of the D188V mutation in neuronal voltage-gated sodium channel causing generalized epilepsy with febrile seizures plus (GEFS).", Epilepsy Research 52:107-117, 2003.

Cull et al., "Screening for receptor ligands using large libraries of peptides linked to the C terminus of the lac repressor," Proc. Natl. Acad. Sci. USA, 89:1865-1869, 1992.

Database EMBL EBI; BAC-clone comprising SCN1A Sep. 14, 1999, XP007902202.

Database EMBL EBI; complete eDNA of SCN2A Oct. 7, 1992, XP007902201.

Database EMBL EBI; partial cDNA of SCN3A Dec. 9, 1997, XP007902200.

Davila, HM, "Molecular and Functional Diversity of Voltage-Gated Calcium Channels", Annals New York Academy of Sciences, pp. 102-117 Apr. 1999—vol. 868.

Denyer et al., "HTS approaches to voltage-gated ion channel drug discovery," Drug Discovery Today, 3:323-332, 1998.

DeWitt et al., ""Diversomers": an approach to nonpeptide, nonoligomeric chemical diversity," Proc. Natl. Acad. Sci. USA, 90:6909-6913, 1993.

Dupere et al., "The anticonvulsant BW534U87 depresses epileptiform activity in rat hippocampal slices by an adenosine-dependent mechanism and through inhibition of voltage-gated Na+ channels", British Journal of Pharmacology, vol. 128, No. 5, 1999, pp. 1011-1020.

Elliot et al., "Bin1 functionally interacts with Myc and inhibits cell proliferation via multiple mechanisms," Oncogene, 18:3564-3573, 1999.

Elmslie et al., "Genetic mapping of a major susceptibility locus for juvenile myoclonic epilepsy on chromosome 15q," Hum. Mol. Genet.,6:1329-1334, 1997.

Engel et al., Epilepsy: A Comprehensive Textbook, Lippincott-Raven, Phildelphia, 1-7 (1), 1997.

Erb et al., "Recursive deconvolution of combinatorial chemical libraries," Proc. Natl. Acad. Sci, USA, 91:11422-11426, 1994.

Escayg et al., "Mutations of SCN1A, encoding a neuronal sodium channel, in two families with GEFS+," Nat. Genet., 24:343-345, 2000.

Fodor et al., "Multiplexed biochemical assays with biological chips," Nature, 364:555-556, 1993.

Gallop et al., "Applications of combinatorial technologies to drug discovery. 1. Background and peptide combinatorial libraries," J. Med. Chem., 37:1233-1251, 1994.

Geibel et al., "Establishment of Cell-Free Electrophysiology for Ion Transporters: Application for Pharmacological Profiling", Journal of Biomolecular Screening 2006:262-268.

GenBank AAC29514, sequence from Aug. 10, 1998.

GenBank AF035685, sequence from Aug. 10, 1998.

Goldin, "Diversity of Mammalian Voltage-Gated Sodium Channels," Annals of the New York Academy of Sciences, 868:38-50, 1999.

Gonzalez et al., "Cell-based assays and instrumentation for screening ion-channel targets," Drug Discovery Today, 4:431-439, 1999.

* cited by examiner

Ch 2q23-q31

Centromere

| | | |
|---|---|---|
| 1cM | D2S142 | |
| 4cM | D2S284 | |
| 4cM | D2S156/ D2S354 | |
| | D2S111 | |
| 5cM | | |
| | D2S294 | |
| 2cM | | |
| | D2S335 | |
| 6cM | | IGE locus |
| | | 29 cM |
| 2cM | D2S324 | |
| 2cM | D2S384 | |
| | D2S152 | |
| 8cM | | |

Telomere

1Ax00.1
NaC-340 TGTGTTCTGCCCCAGTGAGACT,
NaC-341 CTTCCTGCTCTGCCCAAACTGAAT
257 bp 53.4C

1Ax00.2
NaC-342 GGCGATGTAATGTAAGGTGCTGTC,
NaC-343 GTGCCTTCAGTTGCAATTGTTCAG
259 bp 54.5C

1Ax01.1
NaC-268, TTAGGAATTTCATATGCAGAATAA,
NaC-269 TGGGCCATTTTCGTCGTC
201 bp 50.9C

1Ax01.2
NaC-270 GAAAGACGCATTGCAGAAGAAAGG,
NaC-271 CTATTGGCATGTGTTGGTGCTACA
277 bp 54.4C

1Ax02
NaC-45 GTGCTGGTTTCTCATTTAACTTTAC,
NaC-46 TTCCCAACTTAATTTGATATTTAGC
319 bp 49.9C

1Ax03
NaC-87, GCAGTTTGGGCTTTTCAATGTTAG,
NaC-88, GACACAGTTTCARAATCCCRAATG
234 bp 48.9C

1Ax04
NaC-63, TTAGGGCTACGTTTCATTTGTATG,
NaC-64, AGCACTGATGGAAAACCAAACTAT
338 bp 50.8C

1Ax05
NaC-164 AGCCCATGCAGTAATATAAATCCT,
NaC-165 TCCAGGCTGATAAGCTATGTCTAA
488 bp 52.8C

FIG. 2

1Ax06
NaC-276, CTGTGGCCTGCCTGAGCGTATT,
NaC-277 CCAATTCTACTTTTTAAGGAAATG
248 bp 50.3C

1Ax07
NaC-272, AAATACTTGTGCCTTTGAA,
NaC-273, GTACATACAATATACACAGATGC
240 bp 46.7C

1Ax08
Nac-89, AGGCAGCAGAACGACTTGTAATA,
NaC-90, ATCCGGTTTTAATTTCATAACTCA
267 bp 51.9C

1Ax09.2
NaC-217 GTTGAGCACCCTTAGTGAATAATA,
NaC-218 TCACACGCTCTAGACTACTTCTCT
337 bp 52.7C

1Ax10a NaC-29, TGCAAATACTTCAGCCCTTTCAAA,
NaC-30, TTCCCCACCAGACTGCTCTTTC
239 bp 55.1C

1Ax10a
NaC-31, GCAGCAGGCAGGCTCTCA,
NaC-32, TCTCCCATGTTTTAATTTTCAACC
293 bp 54.5C

1Ax10b
NaC-67, ATAATCTTGCAAAATGAAATCACA,
NaC-68, ATCCGGGATGACCTACTGG
307 bp 53.7C

1Ax10b
NaC-65, GATAACGAGAGCCGTAGAGATTCC,
NaC-66, AGCCAGCCATGCCTGAACTA
282 bp 56.4C

*Fig. 2 (cont'd)*

1Ax10c
NaC-39, TGTTTGCTTGTCATATTGCTCAA,
NaC-40, TGCACTATTCCCAACTCACAAA
286 bp 50.7C

1Ax11.1
NaC-69 AAGGGTGTCTCTGTAACAAAAATG,
NaC-70, GTGATGGCCAGGTCAACAAA
269 bp 50.8C

1Ax11.2
NaC-71 CTGGGACTGTTCTCCATATTGGTT,
NaC-72, TTTGCAGGGGCCAGGAAG
294 bp 53.3°C

1Ax12
NaC-41 CATTGTGGGAAAATAGCATAAGC,
NaC-42, GCAAGAACCCTGAATGTTAGAAA
334 bp 51.2C

1Ax13.1
NaC-92 TAATGCTTTTAAGAATCATACAAA,
NaC-93, CCAGCGTGGGAGTTGACAATC
256 bp 51.1C

1Ax13.2
NaC-75 CGGCATGCAGCTCTTTGGTA,
NaC-91, ATGTGCCATGCTGGTGTATTTC
277 bp 55.6C

1Ax14.1
NaC-79 CACCCATCTTCTAATCACTATGC,
NaC-80, CAGCAATTTGGAGATTATTCATT
254 bp 50.4C

1Ax14.2
NaC-81 GCAGCCACTGATGATGATAA,
NaC-82, CTGCCAGTTCCTATACCACTT
269 bp 49.4C

FIG. 2 (cont'd)

1Ax14.3
NaC-83 TACAGCAGAAATTGGGAAAGAT,
NaC-84, GTATTCATACCTACCCACACCTAT
269 bp 50.2C

1Ax15
NaC-202 TTCTTGGCAGGCAACTTATTACC,
NaC-203 TAAGCTGCACTCCAAATGAAAGAT
233 bp 53.1C

1Ax16.1
NaC-187, GGCTGAATGTTTCCACAACT,
NaC-168 GTTCAACTATTCGGAAACACG
277 bp 51.4C

1Ax16.2
NaC-188, AGGCAGAGGAAAACAATGG,
NaC-189, ACAAGGTGGGATAATTAAAAATG
234 bp 50.3C

1Ax17
NaC-143, GTTTCTCTGCCCTCCTATTCC,
NaC-144, AAGCTACCTTGAACAGAGACA
330 bp 48.8C

1Ax18
NaC-139, AATGATGATTCTGTTTATTA,
NaC-140, AATTTGCCATTCCTTTTG
272 bp 46.1C

1Ax19.1
NaC-219 TTGACATCGAAGACGTGAATAATC,
NaC-220 CCATCTGGGCTCATAAACTTGTA
285 bp 49.3C

1Ax20
NaC-338 CCCTTTGAAAATTATATCAGTAA,
NaC-339 ATTTGGTCGTTTATGCTTTATTC
230 bp 47.6C

FIG. 2 (cont'd)

1Ax21
NaC-252, TCCAGCACTAAAATGTATGGTAAT,
NaC-253, ATTTGGCAGAGAAAACACTCC
261 bp 49.8C

1Ax22
NaC-254, TTTTAGCCATCCATTTTCTATTTT,
NaC-255, TATTTTCCCCATATCATTTGA
223 bp 49.1C

1Ax23.1
NaC-256 TTTGCAAGAAACTAGAAAGTC,
NaC-257 TTGATGCGTGACAAAATGG
250 bp 48.3C

1Ax23.2
NaC-258 GACCAGAGTGAATATGTGACTACC,
NaC-259 CTGGGATGATCTTGAATCTAATC
246 bp 49.5C

1Ax24.1
NaC-221 GCAACTCAGTTCATGGAATTTGAA,
NaC-222 CTTGTTTTCGTTTTAAAGTAGTA
289 bp 56.1C

1Ax24.2
NaC-213 CAAAGATCACCCTGGAAGCTCAGTT,
NaC-223 TTCAAGCGCAGCTGCAAACTGAGAT
277 bp 55.8C

1Ax24.3
NaC-260 ACATCGGCCTCCTACTCTTCCTA,
NaC-261 ACAGATGGGTTCCCACAGTCC
268 bp 55.3C

1Ax24.4
NaC-262 TAACGCATGATTTCTTCACTGGTT,
NaC-263 ATCCCAAAGATGGCGTAGATGA
262 bp 54.9C

FIG. 2 (cont'd)

1Ax24.5
NaC-308, TGAGAAATAGGCTAAGGACCTCTA,
NaC-309 CCTAGGGGCTGGATTCC
244 bp 53.2C

1Ax24.6
NaC-310, AAGGGGTGCAAACCTGTGATTTT,
NaC-311 AGGGCCATGTGGTTGCCATAC
252 bp 53.4C

1Ax24.7
NaC-312 CTTCCGGTTTATGTTTTCATTTCT,
NaC-313 TCTTTATTAGTTTTGCACATTTTA
278 bp 48.4C

1Ax24.8
NaC-364 CAATCCTTCCAAGGTCTCCTATC,
NaC-365 TTTCATCTTTGCCTTCTTGCTCAT
326 bp 52.4C

1Ax24.9
NaC-366 CATGTCCACTGCAGCTTGTCCA,
NaC-367 TCCCCTTTACACAGAGTCACAGTT
292 bp 53.1C

FIG. 2 (cont'd)

a. Glu1238Asp:
normal: GCA TTT GAA GAT ATA;
patient R10191 with IGE: GCA TTT GAC GAT ATA.

b. Ser1773Tyr:
normal: ATC ATA TcC TTC CTG;
patient R9049 with IGE: ATC ATA TmC TTC CTG; TCC>TAC

FIG. 3

2Ax00.1 NaC-235 ATGGGTTGAATGACTTTCTGACAT, NaC-236,
AGGCATTTCCTGTACAGGGACTAC
266 bp 52.7C

2Ax00.2 NaC-237 ACAGGAAATGCCTCTTCTTACTTC, NaC-238,
TTTCCCCAAGGATTCTACTACTGT
277 bp 50.6C

2Ax01 NaC-100, AGTGCATGTAACTGACACAATCAC, NaC-101,
CTTGCGTTCCTGTTTGGGTCTCT
241 bp 53.7C

2Ax01 NaC-11 TCCGCTTCTTTACCAGGGAATC, NaC-102,
AGGCAGTGAAGGCAACTTGACTAA
259 bp 55.1C

2Ax02 NaC-96, CAGGGCAATATTTATAAATAATGG, NaC-97,
TTTGGAAAATGTGTAGCTCAATAA
289 bp 48.7C

2Ax03 NaC-43, AAGGCATGGTAGTGCATAAAAG, NaC-44,
ATGAAACATAAAGGGAGGTCAA
201 bp 49.3°C

2Ax04 NaC-47, AATGTGAGCTTGGCTATTGTCTCT, NaC-48,
ATAGGCTCCCACCAGTGATTTAC
213 bp 50.9°C

2Ax05 NaC-49, AGGCCCCTTATATCTCCAACTG, NaC-50,
CAACAAGGCTTCTGCACAAAAG
241 bp 53.9°C

2Ax05.2 NaC-110, CTTGGTGGCTTGCCTTGAC, NaC-111,
TCATGAGTGTCGCCATCAGC
223 bp 51.1C

FIG. 4

2Ax05.3 NaC-112, GGAAAGCTGATGGCGACACT, NaC-113,
CTGAGACATTGCCCAGGTCC
329 bp 53.0C

2Ax05.4 NaC-114, TTTTTACCCGTTGCTTTCTTTA, NaC-115,
TATCCCTTGCTCTTTCATTTATCT
224 bp 50.9C

2Ax06.1 NaC-169, GCCGGTAAAATAGCTGTTGAGTAG, NaC-170,
GCCATTGCAAACATTTATTTCGTA
206 bp 53.3C

2Ax06.2 NaC-171, GCGTGTTTGCGCTAATAG, NaC-172,
CTAAGTCACTTGATTCACATCTAA
295 bp 48.0C

2Ax07 Nac-196, ACAGGGTGGCTGAAGTGTTTTA, NaC-197,
GTGGGAGGTGGCAGGTTATT
199 bp 52.6C

2Ax08 NaC-118, CAATTAGCAGACTTGCCGTTATT, NaC-119,
TCTCTTGAGTTCGGTGTTTTATGA
252 bp 52.9C

2Ax09 NaC-120, ACCGAACTCAAGAGAATTGCTGTA, NaC-121,
AAAGGACCGTATGCTTGTTCACTA
334 bp 52.9C

2Ax10a.1 NaC-161 TATGAATGCGCATTTTACTCTTTG, NaC-156,
TGGAGCTCAACTTAGATGCTACTG
286 bp 52.1C

2Ax10a.2 NaC-13 GGTGCTGGTGGGATAGGAGTTTTT, NaC-162,
TCCATTAAATTCTGGCATATTCTT
316 bp 50.9C

2Ax10b.1 NaC-145 TCAGAGGGGTGCTTTCTTCCACAT, NaC-14,
CTTCGGCTGTCATTGTCCTCAAAG
298 bp 55.6C

FIG. 4 (cont'd)

2Ax10b.2 NaC-146,GCAAAGGACATTGGCTCTGAGAAT, NaC-147,
CTGCCTGCACCAGTCACAACTCT
324 bp 59.4C

2Ax10c NaC-190, TGGGCTTTGCTGCTTTCAA, NaC-191,
AGTAACTGTGACGCAGGACTTTTA
218 bp 51.5C

2Ax11.1 NaC-148, CCCTGTTCCTCCAGCAGATTA, NaC-70,
GTGATGGCCAGGTCAACAAA
283 bp 51.5C

2Ax11.2 NaC-149,TTTGATTTGGGACTGTTGTAAAC, NaC-150,
AAGGCAATTATAAACTCTTTCAAG
233 bp 52.0C

2Ax12 NaC-159, TGGGAGTTAAATTAAGTTGCTCAA, NaC-160,
ACATTTTATGAACACTCCCAGTTA
285 bp 50.4C

2Ax13.1 NaC-239 ATTAACACTGTTCTTGCTTTTAT, NaC-240,
GTGCCAGCGTGGGAGTTC
239 bp 51.1C

2Ax13.2 NaC-241 GTGGGGGCTCTAGGAAACCT, NaC-242,
TTTAATGAAAATGAGGAAAATGTT
324 bp 53.7C

2Ax14.1 NaC-134, GACCAAGCATTTTTATTTCATTC, NaC-135,
AGTGGCAGCAAGATTGTCA
234 bp 49.6C

2Ax14.2 NaC-136, GGCCTTGCTTTTGAGTTCC, NaC-137,
GGTCTTTGCCTATTTCTATGGTG
257 bp 51.1C

FIG. 4 (cont'd)

2Ax14.3 NaC-266, TTAAACCGCTTGAAGATCTAAATA, NaC-267,
TATACACCAAAATATCTCCTTAT
319 bp 48.5C

2Ax15 NaC-314 GGGGCACACCTAATTAATTTTTAT, NaC-315,
AAAGAGGATACTCAAGACCACATA
(247 bp) 51.5C

2Ax16 NaC-344 CCCACCAACACAAATATACCTAAT, NaC-345,
TGAAGGGAAGGGAAAAGATTT
283 bp 52.2C

2Ax17 NaC-346 TCCAGCCTTAGGCACCTGATAA, NaC-347,
ATAAAGCAGCAAAGTGCAGCATAC
310 bp 52.4C

2Ax18 NaC-348 AAGGCTGAACTGTGTAGACATTTT, NaC-349,
TGACATTTCCATGGTACAAAGTGT
262 bp 52.2C

2Ax19.1 NaC-350 TTTGTTGTTGGCTTTTCACTTAT, NaC-351,
CCACCTGGCAGTTTGATTG
268 bp 51.9C

2Ax19.2 NaC-352 TAAGCGTGGTCAACAACTACAGT, NaC-353,
ATTCTTGCCAGCATTTATTGTC
260 bp 50.2C

2Ax20 NaC-354 CAAAACATTGCCCCAAAAG, NaC-355,
TCAAACTAAACAATTTCCCTCTAA
239 bp 48.1C

2Ax21 NaC-306, GATAATTAAAAACTCACTGATGTA, NaC-307,
GGAGGCTAAAGGAAAGAGTATG
288 bp 46.6C

2Ax22 NaC-356 ATTTTATAGCCAGCAAAGAACAC, NaC-357,
CTAGAAATTCGGGCTGTGAA
230 bp 49.6C

FIG. 4 (cont'd)

2Ax23.1 NaC-358 CTGCTTTGTGACCTAAGGCAAGTT, NaC-359,
GTGACCATGTTAAGGCAGATGAGG
290 bp 51.4C

2Ax23.2 NaC-360 GGAATGGTCTTTGATTTTGTAACC, NaC-361,
TCCTTAACTGAATAAAAGCACCTC
290 bp 51.6C

2Ax24.1 NaC-207 TGGAACACCCATCAAAGAAGATACT, NaC-208,
GTGGGAGTCCTGTTGACACAAAC
278 bp 52.8C

2Ax24.2 NaC-209 AGCGATTCATGGCATCAAAC, NaC-210,
ACGTGGTGGAAGGCGTCATA
270 bp 52.9C

2Ax24.3 NaC-211 GCGACCCAGTTTATAGAGTTTGCC, NaC-212,
CTTGTTTGCGTTTCAACGTGGTC
289 bp 56.1C

2Ax24.4 NaC-213 CAAAGATCACCCTGGAAGCTCAGTT, NaC-214,
ATCCAGGGCATCTGCAAAATCAGAA
277 bp 55.8C

2Ax24.5 NaC-215 TGCCTATGTTAAGAGGGAAGTTGGG, NaC-216,
ATGACCGCGATGTACATGTTCAG
279 bp 55.3C

2Ax24.6 NaC-278 TCAATTGTTTACAGCCCGTGATG, NaC-279,
TTTATACAAAGGCAGACAACAT
302 bp 52.0C

2Ax24.7 NaC-280 AGGCGTAATGGCTACTCAGACGA, NaC-281,
GTAATCCCTCTCCCCGAACATAAAC
251 bp 53.8C

2Ax24.8 NaC-282 TTTGATTCACGGGTTGTTTACTCTTA, NaC-283,
TTCTATGGAACATTTACAGGCACATT
294 bp 52.1C

FIG. 4 (cont'd)

2Ax24.9 NaC-284 TAATGTGCCTGTAAATGTTCCATAGA, NaC-285,
CAGGCTTCTTAGAAAGGACTGATAGG
264 bp 50.6C

2Ax24.10 NaC-286 GTCCCAGCAGCATGACTATC, NaC-287,
CCCACTGGGTAAAATTACTAAC
249 bp 49.4C

2Ax24.11 NaC-288 TAGCCATCTTCTGCTCTTGGT, NaC-289,
TGGCTTCCCATATTAGACTTCTG
307 bp 51.3C

2Ax24.12 NaC-290 TCTTGCCTATGCTGCTGTATCTTA, NaC-291,
AGTCGGGCTTTTCATCATTGAG
207 bp 51.8C

2Ax24.13 NaC-292 TTCTTCATGTCATTAAGCAATAGG, NaC-293,
TTCAATTTAAAAGTGCTAGGAACA
299 bp 49.4C

2Ax24.14 NaC-294 CTTCAGGTGGATGTCACAGTCACTA, NaC-295,
ATTCAAGCAATGCCAAGAGTATCA
263 bp 51.5C

2Ax24.15 NaC-296 CTTTCAATAGTAATGCCTTATCAT, NaC-297,
TCCTGCATGCATTTCACCAAC
348 bp 49.6C

2Ax24.16 NaC-362 CTGTTCACATTTTGTAAAACTAAT, NaC-263,
ATCCCAAAGATGGCGTAGATGA
309 bp 50.8C

2Ax24.17 NaC-325 CACGCTGCTCTTTGCTTTGA, NaC-363,
GATCTTTGTCAGGGTCACAGTCT
269 bp 54.0C

FIG. 4 (cont'd)

a. Lys908Arg:
normal: TAC AAA GAA;
9782 (Patient with IGE): TAC AGA GAA;

b. leu768val, in individuals 8197, 9062 et 9822 (all IGE patients).

FIG. 5

3Ax00a.1 NaC-390 TGTGTCCGCCAGTAGATGG, NaC-391,
TTTTTGACCACAGAGGTTTACAA
233 bp 51.4C

3Ax00a.2 NaC-392 GAAGCGGAGGCATAAGCAGA, NaC-393,
GGTGCAGATAATGAAATGTTTTGT
253 bp 51.3C

3Ax00b NaC-394 CACCCCTATGCCAAATGTCAAAGA, NaC-395,
CAAAAACAAACTTATACCCAGAAG
293 bp 51.6C

3Ax00c NaC-396 CAAATATTGGGCAAACCCTAAT, NaC-397,
AAGGTGCCATCACAAAATCAT
225 bp 50.7C

3Ax01.1 NaC-51 ATCGCTTGCTTTCCTAACTCTTGT, NaC-52,
AAGTCACTATTTGGCTTGGTTG
260 bp 53.1C

3Ax01.2 NaC-53 AGAAGCCCAAAAAGGAACAAGATA, NaC-54,
GGCCCAGAAAAGTATATTACAGTT
231 bp 50.8C

3Ax02 NaC-85, TCCTTAAATAAGCCCATGTCTAAT, NaC-86,
TCTCAAAGAAATTTTACAGATACT
273 bp 47.3C

3Ax03 NaC-27, AATGGCCATGGTAACCTACTAACA, NaC-28,
CAGGCTATACCCACAAGGAGATT
212 bp 51.8C

3Ax04 NaC-94, TGTTAATTTTGGCTTGGATGTT, NaC-95,
TCACTCCTTTGCGCTTATCAA
198 bp 50.8C

3Ax05.1 NaC-247, AGGGCTCTATGTGCCAAACC, NaC-248,
AGGGGCCTACTACCTTACACCAG
213 bp 52.2C

FIG_8

3Ax05.2 NaC-249 TGTAATCCCAGGTAAGAAGAAAC, NaC-250,
TACCGGGATGAACTGTAATAATAA
304 bp 51.8C

3Ax06.1 NaC-192,TTCTGGCACTCTTCCTCAGGTAAC, NaC-193,
GTCCCATTTGAATCCATTGTGC
261 bp 55.4C

3Ax06.2 NaC-194,GGCCCCCAAGCGATTCTG, NaC-195,
TGTACACCCACAGTCTCAACTATT
209 bp 50.3C

3Ax07 NaC-204, ACAGCCACCTTTGTAAATAA, NaC-205,
TTTTTCGCAAAGAGTTCTAT
220 bp 46.6C

3Ax08 NaC-98, AAACTGACCCTACCTCCATTTCTC, NaC-99,
ACTCAGCCTATGCTTTTCATTTCA
247 bp 53.2C

3Ax09 NaC-37 CAGATATTTATTTGGGGACATTAT, NaC-38,
AAATCTTTGCKTTTATCACTCAGT
295 bp 52.0C

3Ax10a.1 NaC-198 TAGTGCCTGGCTTTGTTTTATGAC, NaC-199,
CGGATTTGGGAAAGCTGTCTCT
225 bp 54.3C

3Ax10a.2 NaC-200 AGAGCACCTTGAAGGAAACAACAA, NaC-274,
TCCCTCAACTGAAGTACAGATAGT
253 bp 51.2C

3Ax10b NaC-33, ATAATTGCGTTCTTCCCCTACCC, NaC-34,
AAGCCCTGGCACCATCCTG
301 bp 56.2°C

3Ax10c NaC-35, _TTTGCAAAGAAATGCTATGT, NaC-36,
CTGGGTAACAGACTTCAGTAAT
303 bp 51.4°C

FIG. 6 (cont'd)

3Ax11.1 NaC-122, ATGGGATTGTCTTCTCAAGTTTCT, NaC-123, GATGGCAAGATCAACAAATGGA
294 bp 50.3C

3Ax11.2 NaC-124, CTTGATCTGGGACTGCTGTGATG, NaC-125, AGGATATAATTTTTGGTTCAACA
284 bp 51.5C

3Ax12 NaC-61, TTTTCAGTGCTCTTGATAGTAGTG, NaC-62, GTGCCAATGAGCGACAGG
254 bp 50.7°C

3Ax13.1 NaC-73, CCACGTGTGGTTCTATGATACC, NaC-74, ACCGTGGGAGCGTACAGTCA
298 bp 52.3C

3Ax13.2 NaC-75, CGGCATGCAGCTCTTTGGTA, NaC-76, TGGCCACGTTCCTAGCTACTGTC
291 bp 55.9C

3Ax14.1 NaC-55, GAGTTCCCTTTTTAGGCTGTTATT, NaC-56, TCTTATTGCCTTCATGGATTTCTA
285 bp 50.5C

3Ax14.2 NaC-57, TGAAAAATAAGATGCGGGAGTG, NaC-58, GTGAGGCTGGGGTTGTTTATG
247 bp 51.7C

3Ax14.3 NaC-59, GAGATGGGAATGGAACCACCA, NaC-60, TTCGATAATGCATATAAGCACAA
297 bp 51.7C

3Ax15 NaC-318 AAGGGGGAAAATCACATCTTT, NaC-319, TTAAATGAGGCATATTCAGTCTCC
235 bp 51.8C

3Ax16 NaC-116, GGAAGTGGAGTGGGGAAGG, NaC-117, ATTCTTGCCAATATGCATTTCACT
271 bp 51.1C

FIG. 6 (cont'd)

3Ax17 NaC-157,TTCTTTTGTACTCACTATTATACTAA, NaC-158,
AAACTTGCCTCTTTTAAAAACAAT
317 bp 46.6C

3Ax18 NaC-374 TACCACACCCTATACCTTCAGTCA, NaC-375,
GAGTATGGCACCCTTTTCTATCTA
275 bp 51.4C

3Ax19.1 NaC-386 GCTATGTTCCCCTCGCTGTCT, NaC-387,
TGCTTGCCAAGAGCCTGAC
231 bp 53.6C

3Ax19.2 NaC-388 GCTGGCAAGTTCTACCACTGTG, NaC-389,
CAAACGAAGAACATCAGGGAAATA
247 bp 53.0C

3Ax20 NaC-376 TTCACAATATTGTACAAAAGTTA, NaC-377,
ATTACCACCAATATTCACCATAAG
230 bp 46.4C

3Ax21 NaC-378 TCAGGGTAAGGCAAAAGTAGCAC, NaC-379,
GAACCCCAGAATGAAGAAAGGTAA
294 bp 50.2C

3Ax22 NaC-380 TTTGTGAAAGTACTATTGGAACAC, NaC-381,
ACGCATGGCTTTGGAACAT
204 bp 49.6C

3Ax23.1 NaC-382 CCCGTATGTGGAAGGGCTTTAT, NaC-383,
CTAGGTTGATCCGGGACAAAACTA
246 bp 52.9C

3Ax23.2 NaC-384 AACGGATGACCAGGGCAAATAC, NaC-385,
CTAGAAGGTCCTGGGGCAACTG
234 bp 54.8C

3Ax24.1 NaC-317 AAGCCATCATGTAAAGTGAAAAG, NaC-320,
ATCCCAAAGATGGCATAGATA
274 bp 52.5C

FIG. 6 (cont'd)

3Ax24.2 NaC-325 CACGCTGCTCTTTGCTTTGA, NaC-326,
TGAGCTGCCAGGGTGAATTG
282 bp 54.9C

3Ax24.3 NaC-327 TTGCTAGCACCTATTCTTAATAGTGC NaC-328,
CCAGGGCAGCTGCAAAATCAGAG
318 bp 54.2C

3Ax24.4 NaC-329 CCCGATGCGACCCAGTTTA, NaC-330,
TGGAGGGGTTTGATGCCATA
250 bp 55.2C

3Ax24.5 NaC-331 GATGGATGCCCTTCGAATACAGA, NaC-332,
TTCCCATTTAGTTTGTCAATAATC
258 bp 50.6C

3Ax24.6 NaC-321 AAGGGGAGGATTGACTTACCTAT, NaC-333,
TTGGCATGGACCTCCTCTTGA
302 bp 51.5C

FIG. 8 (cont'd)

a. Asn43DEL:
9706 (allele 1; IGE patient): CAA GAT AAT GAT GAT GAG;
9632 (allele 2; patient has IGE): CAA GAT --- GAT GAT GAG;
allele 1 = 131/146 (0.90);
allele 2= 15/146 (0.10);
for IGE patients: homozygotes (22): 3958, 9632; heterozygotes (12): 9049, 9152, 9649, 9710, 9896, 10069, 10191, 10213, 9993, 10009, 10256 (note that 2 patients are homozygous for the rare allele; all patients have IGE); in controls: allele 1 = 45/154 (0.94); allele 2 = 9/154 (0.06) and no 22 homozygotes found.

b. normal:            tggtgtaaggtag,
10670 (IGE patient):  tggtataaggtag c. normal:            ccccttatatctccaac,
10250 (IGE patient):  ccccttatayctccaac;

d. Val1035Ile:
normal:               AAA TAC GTA ATC GAT,
9269 (IGE patient):   AAA TAC RTA ATC GAT; GTA>ATA = Val>Ile.

FIG_7

SEQUENCE LISTING

```
<160> NUMBER OF SEQ ID NOS: 440

<210> SEQ ID NO 1
<211> LENGTH: 8379
<212> TYPE: DNA
<213> ORGANISM: Homo sapiens

<400> SEQUENCE: 1
tactgcagag gtctctggtg catgtgtgta tgtgtgcgtt tgtgtgtgtt tgtgtgtctg      60
tgtgttctgc cccagtgaga ctgcagcccct tgtaaatact ttgacaccctt ttgcaagaag    120 gaatctgaac aattgcaact gaaggcacat tgttatcatc tcgtctttgg gtgatgctgt     180
tcctcactgc agatggataa ttttcctttt aatcaggaat ttcatatgca gaataaatgg     240
```

```
taattaaaat gtgcaggatg acaagatgga gcaaacagtg cttgtaccac caggacctga        300
cagcttcaac ttcttcacca gagaatctct tgcggctatt gaaagacgca ttgcagaaga        360
aaaggcaaag aatcccaaac cagacaaaaa agatgacgac gaaaatggcc caaagccaaa        420
tagtgacttg gaagctggaa agaaccttcc atttatttat ggagacattc ctccagagat        480
ggtgtcagag cccctggagg acctggaccc ctactatatc aataagaaaa cttttatagt        540
attgaataaa gggaaggcca tcttccggtt cagtgccacc tctgccctgt acattttaac        600
tcccttcaat cctcttagga aaatagctat taagattttg gtacattcat tattcagcat        660
gctaattatg tgcactattt tgacaaactg tgtgtttatg acaatgagta accctcctga        720
ttggacaaag aatgtagaat acaccttcac aggaatatat acttttgaat cacttataaa        780
aattattgca aggggattct gtttagaaga ttttactttc cttcgggatc catggaactg        840
gctcgatttc actgtcatta catttgcgta cgtcacagag tttgtggacc tgggcaatgt        900
ctcggcattg agaacattca gagttctccg agcattgaag acgatttcag tcattccagg        960
cctgaaaacc attgtgggag ccctgatcca gtctgtgaag aagctctcag atgtaatgat       1020
cctgactgtg ttctgtctga gcgtatttgc tctaattggg ctgcagctgt tcatgggcaa       1080
cctgaggaat aaatgtatac aatggcctcc caccaatgct tccttggagg aacatagtat       1140
agaaaagaat ataactgtga attataatgg tacacttata aatgaaactg tctttgagtt       1200
tgactggaag tcatatattc aagattcaag atatcattat ttcctggagg gttttttaga       1260
tgcactacta tgtggaaata gctctgatgc aggccaatgt ccagagggat atatgtgtgt       1320
gaaagctggt agaaatccca attatggcta cacaagcttt gataccttca gttgggcttt       1380
tttgtccttg tttcgactaa tgactcagga cttctgggaa aatctttatc aactgacatt       1440
acgtgctgct gggaaaacgt acatgatatt ttttgtattg gtcattttct tgggctcatt       1500
ctacctaata aatttgatcc tggctgtggt ggccatggcc tacgaggaac agaatcaggc       1560
caccttggaa gaagcagaac agaaagaggc cgaatttcag cagatgattg aacagcttaa       1620
aaagcaacag gaggcagctc agcaggcagc aacggcaact gcctcagaac attccagaga       1680
gcccagtgca gcaggcaggc tctcagacag ctcatctgaa gcctctaagt tgagttccaa       1740
gagtgctaag gaaagaagaa atcggaggaa gaaaagaaaa cagaaagagc agtctggtgg       1800
ggaagagaaa gatgaggatg aattccaaaa atctgaatct gaggacagca tcaggaggaa       1860
aggttttcgc ttctccattg aagggaaccg attgacatat gaaaagaggt actcctcccc       1920
acaccagtct ttgttgagca tccgtggctc cctattttca ccaaggcgaa atagcagaac       1980 aagcctttc agctttagag ggcgagcaaa ggatgtggga tctgagaacg acttcgcaga       2040
tgatgagcac agcaccttg aggataacga gagccgtaga gattccttgt tgtgccccg        2100 acgacacgga gagagacgca acagcaacct gagtcagacc agtaggtcat cccggatgct       2160
ggcagtgttt ccagcgaatg ggaagatgca cagcactgtg gattgcaatg gtgtggtttc       2220
cttggttggt ggaccttcag ttcctacatc gcctgttgga cagcttctgc cagaggtgat       2280
aatagataag ccagctactg atgacaatgg aacaaccact gaaactgaaa tgagaaagag       2340
aaggtcaagt tctttccacg tttccatgga cttctagaa gatccttccc aaaggcaacg       2400
agcaatgagt atagccagca ttctaacaaa tacagtagaa gaacttgaag aatccaggca       2460
gaaatgccca ccctgttggt ataaattttc caacatattc ttaatctggg actgttctcc       2520
atattggtta aaagtgaaac atgttgtcaa cctggttgtg atggaccat ttgttgacct       2580 ggccatcacc atctgtattg tcttaaatac tcttttcatg gccatggagc actatccaat       2640
```

```
gacggaccat tcaataatg tgcttacagt aggaaacttg gttttcactg ggatctttac    2700
agcagaaatg tttctgaaaa ttattgccat ggatccttac tattatttcc aagaaggctg    2760
gaatatcttt gacggtttta ttgtgacgct tagcctggta gaacttggac tcgccaatgt    2820
ggaaggatta tctgttctcc gttcatttcg attgctgcga gttttcaagt tggcaaaatc    2880
ttggccaacg ttaaatatgc taataaagat catcggcaat ccgtgggggg ctctgggaaa    2940
tttaaccctc gtcttggcca tcatcgtctt catttttgcc gtggtcggca tgcagctctt    3000
tggtaaaagc tacaaagatt gtgtctgcaa gatcgccagt gattgtcaac tcccacgctg    3060
gcacatgaat gacttcttcc actccttcct gattgtgttc cgcgtgctgt gtggggagtg    3120
gatagagacc atgtgggact gtatggaggt tgctggtcaa gccatgtgcc ttactgtctt    3180
catgatggtc atggtgattg aaacctagt ggtcctgaat ctctttctgg ccttgcttct    3240
gagctcattt agtgcagaca accttgcagc cactgatgat gataatgaaa tgaataatct    3300
ccaaattgct gtggatagga tgcacaaagg agtagccttt gtgaaaagaa aaatatatga    3360
atttattcaa cagtccttca ttaggaaaca aaagatttta gatgaaatta accacttga    3420 tgatctaaac aacaagaaag acagttgtat gtccaatcat acagcagaaa ttgggaaaga    3480
tcttgactat cttaaagatg taaatggaac tacaagtggt ataggaactg cagcagtgt    3540 tgaaaaatac attattgatg aaagtgatta catgtcattc ataaacaacc ccagtcttac    3600
tgtgactgta ccaattgctg taggagaatc tgactttgaa atttaaaaca cggaagactt    3660
tagtagtgaa tcggatctgg aagaaagcaa agagaaactg aatgaaagca gtagctcatc    3720
agaaggtagc actgtggaca tcggcgcacc tgtagaagaa cagcccgtag tggaacctga    3780
agaaactctt gaaccagaag cttgtttcac tgaaggctgt gtacaaagat tcaagtgttg    3840
tcaaatcaat gtggaagaag cagaggaaa caatggtgg aacctgagaa ggacgtgttt    3900
ccgaatagtt gaacataact ggtttgagac cttcattgtt ttcatgattc tccttagtag    3960
tggtgctctg gcatttgaag atatatatat tgatcagcga aagacgatta agacgatgtt    4020
ggaatatgct gacaaggttt tcacttacat ttttcattctg gaaatgcttc taaaatgggt    4080
ggcatatggc tatcaaacat atttccaccaa tgcctggtgt tggctggact tcttaattgt    4140
tgatgtttca ttggtcagtt taacagcaaa tgccttgggt tactcagaac ttggagccat    4200
caaatctctc aggacactaa gagctctgag acctctaaga gccttatctc gatttgaagg    4260
gatgagggtg gttgtgaatg ccctttagg agcaattcca tccatcatga atgtgcttct    4320
ggtttgtctt atattctggc taattttcag catcatgggc gtaaatttgt ttgctggcaa    4380
attctaccac tgtattaaca ccacaactgg tgacaggttt gacatcgaag acgtgaataa    4440
tcatactgat tgcctaaaac taatagaaag aaatgagact gctcgatgga aaaatgtgaa    4500
agtaaacttt gataatgtag gatttgggta tctctctttg cttcaagttg ccacattcaa    4560
aggatggatg gatataatgt atgcagcagt tgattccaga aatgtggaac tccagcctaa    4620
gtatgaagaa agtctgtaca tgtatcttta ctttgttatt ttcatcatct ttgggtcctt    4680
cttcaccttg aacctgttta ttggtgtcat catagataat ttcaaccagc agaaaaagaa    4740
gtttggaggt caagacatct ttatgacaga agaacagaag aaatactata atgcaatgaa    4800
aaaattagga tcgaaaaaac cgcaaaagcc tatcctcga ccaggaaaca aatttcaagg    4860
aatggtcttt gacttcgtaa ccagacaagt ttttgacata agcatcatga ttctcatctg    4920
tcttaacatg gtcacaatga tggtggaaac agatgaccag agtgaatatg tgactaccat    4980
tttgtcacgc atcaatctgg tgttcattgt gctatttact ggagagtgtg tactgaaact    5040
```

```
catctctcta cgccattatt attttaccat tggatggaat attttttgatt ttgtggttgt   5100
cattctctcc attgtaggta tgtttcttgc cgagctgata gaaaagtatt tcgtgtcccc   5160
taccctgttc cgagtgatcc gtcttgctag gattggccga atcctacgtc tgatcaaagg   5220
agcaaagggg atccgcacgc tgctctttgc tttgatgatg tcccttcctg cgttgtttaa   5280
catcggcctc ctactcttcc tagtcatgtt catctacgcc atctttggga tgtccaactt   5340
tgcctatgtt aagagggaag ttgggatcga tgacatgttc aactttgaga cctttggcaa   5400
cagcatgatc tgcctattcc aaattacaac ctctgctggc tgggatggat tgctagcacc   5460
cattctcaac agtaagccac ccgactgtga ccctaataaa gttaaccctg gaagctcagt   5520
taagggagac tgtgggaacc catctgttgg aattttcttt tttgtcagtt acatcatcat   5580
atccttcctg gttgtggtga acatgtacat cgcggtcatc ctggagaact tcagtgttgc   5640
tactgaagaa agtgcagagc ctctgagtga ggatgacttt gagatgttct atgaggtttg   5700
ggagaagttt gatcccgatg caactcagtt catggaattt gaaaaattat ctcagtttgc   5760
agctgcgctt gaaccgcctc tcaatctgcc acaaccaaac aaactccagc tcattgccat   5820
ggatttgccc atggtgagtg gtgaccggat ccactgtctt gatatcttat ttgcttttac   5880
aaagcgggtt ctaggagaga gtggagagat ggatgctcta cgaatacaga tggaagagcg   5940
attcatggct tccaatcctt ccaaggtctc ctatcagcca atcactacta ctttaaaacg   6000
aaaacaagag gaagtatctg ctgtcattat tcagcgtgct tacagacgcc acctttttaaa  6060
gcgaactgta aaacaagctt cctttacgta caataaaaac aaaatcaaag gtggggctaa   6120
tcttcttata aagaagaca tgataattga cagaataaat gaaaactcta ttacagaaaa    6180
aactgatctg accatgtcca ctgcagcttg tccaccttcc tatgaccggg tgacaaagcc   6240
aattgtggaa aaacatgagc aagaaggcaa agatgaaaaa gccaagggaa ataaatgaa    6300
aataaataaa ataattggg tgacaaattg tttacagcct gtgaaggtga tgtatttta    6360
tcaacaggac tcctttagga ggtcaatgcc aaactgactg ttttttacaca aatctcctta   6420
aggtcagtgc ctacaataag acagtgaccc cttgtcagca aactgtgact ctgtgtaaag   6480
gggagatgac cttgacagga ggttactgtt ctcactacca gctgacactg ctgaagataa   6540
gatgcacaat ggctagtcag actgtaggga ccagtttcaa ggggtgcaaa cctgtgattt   6600
tggggttgtt taacatgaaa cactttagtg tagtaattgt atccactgtt tgcatttcaa   6660
ctgccacatt tgtcacattt ttatggaatc tgttagtgga ttcatctttt tgttaatcca   6720
tgtgtttatt atatgtgact ttttttgtaa acgaagtttc tgttgagaaa taggctaagg   6780
acctctataa caggtatgcc acctgggggg tatggcaacc acatggccct cccagctaca   6840
caaagtcgtg gtttgcatga gggcatgctg cacttagaga tcatgcatga gaaaaagtca   6900
caagaaaaac aaattcttaa atttccacat atttctggga ggggtaattg ggtgataagt   6960
ggaggtgctt tgttgatctt gttttgcgaa atccagcccc tagaccaagt agattatttg   7020
tgggtaggcc agtaaatctt agcaggtgca aacttcattc aaatgtttgg agtcataaat   7080
gttatgtttc tttttgttgt attaaaaaaa aaacctgaat agtgaatatt gcccctcacc   7140
ctccaccgcc agaagactga attgaccaaa attactcttt ataaatttct gctttttcct   7200
gcactttgtt tagccatctt cggctctcag caaggttgac actgtatatg ttaatgaaat   7260
gctatttatt atgtaaatag tcattttacc ctgtggtgca cgtttgagca aacaaataat   7320
gacctaagca cagtatttat tgcatcaaat atgtaccaca agaaatgtag agtgcaagct   7380
ttacacaggt aataaaatgt attctgtacc atttatagat agtttggatg ctatcaatgc   7440
```

```
atgtttatat taccatgctg ctgtatctgg tttctctcac tgctcagaat ctcatttatg    7500
agaaaccata tgtcagtggt aaagtcaagg aaattgttca acagatctca tttatttaag    7560
tcattaagca atagtttgca gcactttaac agcttttTgg ttattTttac attttaagtg    7620
```

```
atgtttatat taccatgctg ctgtatctgg tttctctcac tgctcagaat ctcatttatg    7500
agaaaccata tgtcagtggt aaagtcaagg aaattgttca acagatctca tttatttaag    7560
tcattaagca atagtttgca gcactttaac agcttttTgg ttatttTTac attttaagtg    7620
gataacatat ggtatatagc cagactgtac agacatgttt aaaaaaacac actgcttaac    7680
ctattaaata tgtgtttaga attttataag caaatataaa tactgtaaaa agtcacttta    7740
ttttattttt cagcattatg tacataaata tgaagaggaa attatcttca ggttgatatc    7800
acaatcactt ttcttacttt ctgtccatag tactttttca tgaaagaaat ttgctaaata    7860
agacatgaaa acaagactgg gtagttgtag atttctgctt tttaaattac atttgctaat    7920
tttagattat ttcacaattt taaggagcaa aataggttca cgattcatat ccaaattatg    7980
ctttgcaatt ggaaaagggt ttaaaatttt atttatattt ctggtagtac ctgcactaac    8040
tgaattgaag gtagtgctta tgttattttt gttctttttt tctgacttcg gtttatgttt    8100
tcatttcttt ggagtaatgc tgctctagtt gttctaaata gaatgtgggc ttcataattt    8160
ttttttccac aaaaacagag tagtcaactt atatagtcaa ttacatcagg acattttgtg    8220
tttcttacag aagcaaacca taggctcctc ttttccttaa aactacttag ataaactgta    8280
ttcgtgaact gcatgctgga aaatgctact attatgctaa ataatgctaa ccaacattta    8340
aaatgtgcaa aactaataaa gattacattt tttatttta                           8379

<210> SEQ ID NO 2
<211> LENGTH: 8378
<212> TYPE: DNA
<213> ORGANISM: Homo sapiens

<400> SEQUENCE: 2
tactgcagag gtctctggtg catgtgtgta tgtgtgcgtt tgtgtgtgtt tgtgtgtctg      60
tgtgttctgc cccagtgaga ctgcagcct tgtaaatact ttgacacctt ttgcaagaag     120
gaatctgaac aattgcaact gaaggcacat tgttatcatc tcgtctttgg gtgatgctgt     180
tcctcactgc agatggataa ttttcctttt aatcaggaat tcatatgca gaataaatgg      240 taattaaaat gtgcaggatg acaagatgga gcaaacagtg cttgtaccac caggacctga     300
cagcttcaac ttcttcacca gagaatctct tgcggctatt gaaagacgca ttgcagaaga     360
aaaggcaaag aatcccaaac cagacaaaaa agatgacgac gaaaatggcc caaagccaaa     420
tagtgacttg gaagctggaa agaaccttcc atttatttat ggagacattc ctccagagat     480
ggtgtcagag cccctggagg acctggaccc ctactatatc aataagaaaa ctttttatagt    540 attgaataaa gggaaggcca tcttccggtt cagtgccacc tctgccctgt acattttaac     600
tcccttcaat cctcttagga aaatagctat taagattttg gtacattcat tattcagcat     660
gctaattatg tgcactattt tgacaaactg tgtgtttatg acaatgagta accctcctga     720
ttggacaaag aatgtagaat acaccttcac aggaatatat acttttgaat cacttataaa     780
aattattgca aggggattct gtttagaaga ttttactttc cttcgggatc catggaactg     840
gctcgatttc actgtcatta catttgcgtt tgtaacagaa tttgtaaacc taggcaattt     900
ttcagctctt cgcactttca gagtcttgag agctttgaaa actatttcgg taattccagg     960
cctgaaaacc attgtgggag ccctgatcca gtctgtgaag aagctctcag atgtaatgat    1020
cctgactgtg ttctgtctga gcgtatttgc tctaattggg ctgcagctgt tcatgggcaa    1080
cctgaggaat aaatgtatac aatggcctcc caccaatgct tccttggagg aacatagtat    1140
agaaaagaat ataactgtga attataatgg tacacttata aatgaaactg tctttgagtt    1200
```

```
tgactggaag tcatatattc aagattcaag atatcattat ttcctggagg gttttttaga   1260
tgcactacta tgtggaaata gctctgatgc aggccaatgt ccagagggat atatgtgtgt   1320
gaaagctggt agaaatccca attatggcta cacaagcttt gatacctcca gttgggcttt   1380
tttgtccttg tttcgactaa tgactcagga cttctgggaa aatctttatc aactgacatt   1440
acgtgctgct gggaaaacgt acatgatatt ttttgtattg gtcattttct tgggctcatt   1500
ctacctaata aatttgatcc tggctgtggt ggccatggcc tacgaggaac agaatcaggc   1560
caccttggaa gaagcagaac agaaagaggc cgaatttcag cagatgattg aacagcttaa   1620
aaagcaacag gaggcagctc agcaggcagc aacggcaact gcctcagaac attccagaga   1680
gcccagtgca gcaggcaggc tctcagacag ctcatctgaa gcctctaagt tgagttccaa   1740
gagtgctaag gaaagaagaa atcggaggaa gaaaagaaaa cagaaagagc agtctggtgg   1800
ggaagagaaa gatgaggatg aattccaaaa atctgaatct gaggacagca tcaggaggaa   1860
aggttttcgc ttctccattg aagggaaccg attgacatat gaaaagaggt actcctcccc   1920
acaccagtct tgttgagca tccgtggctc cctatttca ccaaggcgaa atagcagaac   1980 aagcctttc agctttagag ggcgagcaaa ggatgtggga tctgagaacg acttcgcaga   2040
tgatgagcca gcacctttga ggataacgag agccgtagag attccttgtt tgtgccccga   2100
cgacacggag agagacgcaa cagcaacctg agtcagacca gtaggtcatc ccggatgctg   2160
gcagtgtttc cagcgaatgg gaagatgcac agcactgtgg attgcaatgg tgtggtttcc   2220
ttggttggtg gaccttcagt tcctacatcg cctgttggac agcttctgcc agaggtgata   2280
atagataagc cagctactga tgacaatgga acaaccactg aaactgaaat gagaaagaga   2340
aggtcaagtt ctttccacgt ttccatggac tttctagaag atccttccca aaggcaacga   2400
gcaatgagta tagccagcat tctaacaaat acagtagaag aacttgaaga atccaggcag   2460
aaatgcccac cctgttggta taaattttcc aacatattct taatctggga ctgttctcca   2520
tattggttaa aagtgaaaca tgttgtcaac ctggttgtga tggacccatt tgttgacctg   2580
gccatcacca tctgtattgt cttaaatact cttttcatgg ccatggagca ctatccaatg   2640
acggaccatt tcaataatgt gcttacagta ggaaacttgg ttttcactgg gatctttaca   2700
gcagaaatgt ttctgaaaat tattgccatg gatccttact attatttcca agaaggctgg   2760
aatatctttg acggttttat tgtgacgctt agcctggtag aacttggact cgccaatgtg   2820
gaaggattat ctgttctccg ttcatttcga ttgctgcgag ttttcaagtt ggcaaaatct   2880
tggccaacgt taaatatgct aataaagatc atcggcaatt ccgtggggc tctgggaaat   2940 ttaaccctcg tcttggccat catcgtcttc attttgccg tggtcggcat gcagctcttt   3000
ggtaaaagct acaaagattg tgtctgcaag atcgccagtg attgtcaact cccacgctgg   3060
cacatgaatg acttcttcca ctccttcctg attgtgttcc gcgtgctgtg tggggagtgg   3120
atagagacca tgtgggactg tatggaggtt gctggtcaag ccatgtgcct tactgtcttc   3180
atgatggtca tggtgattgg aaacctagtg gtcctgaatc tctttctggc cttgcttctg   3240
agctcattta gtgcagacaa ccttgcagcc actgatgatg ataatgaaat gaataatctc   3300
caaattgctg tggataggat gcacaaagga gtagcttatg tgaaaagaaa aatatatgaa   3360
tttattcaac agtccttcat taggaaacaa aagatttag atgaaattaa accacttgat   3420
gatctaaaca acaagaaaga cagttgtatg tccaatcata cagcagaaat tgggaaagat   3480
cttgactatc ttaaagatgt aaatggaact acaagtggta taggaactgg cagcagtgtt   3540
gaaaaataca ttattgatga aagtgattac atgtcattca taaacaaccc cagtcttact   3600
```

```
gtgactgtac caattgctgt aggagaatct gactttgaaa atttaaacac ggaagacttt    3660
agtagtgaat cggatctgga agaaagcaaa gagaaactga atgaaagcag tagctcatca    3720
gaaggtagca ctgtggacat cggcgcacct gtagaagaac agcccgtagt ggaacctgaa    3780
gaaactcttg aaccagaagc ttgtttcact gaaggctgtg tacaaagatt caagtgttgt    3840
caaatcaatg tggaagaagg cagaggaaaa caatggtgga acctgagaag gacgtgtttc    3900
cgaatagttg aacataactg gtttgagacc ttcattgttt tcatgattct ccttagtagt    3960
ggtgctctgg catttgaaga tatatatatt gatcagcgaa agacgattaa gacgatgttg    4020
gaatatgctg acaaggtttt cacttacatt ttcattctgg aaatgcttct aaaatgggtg    4080
gcatatggct atcaaaatat ttcaccaatg cctggtgttg ctggacttc ttaattgttg     4140 atgtttcatt ggtcagttta acagcaaatg ccttgggtta ctcagaactt ggagccatca    4200
aatctctcag gacactaaga gctctgagac ctctaagagc cttatctcga tttgaaggga    4260
tgagggtggt tgtgaatgcc cttttaggag caattccatc catcatgaat gtgcttctgg    4320
tttgtcttat attctggcta attttcagca tcatgggcgt aaatttgttt gctggcaaat    4380
tctaccactg tattaacacc acaactggtg acaggtttga catcgaagac gtgaataatc    4440
atactgattg cctaaaacta atagaaagaa atgagactgc tcgatggaaa aatgtgaaag    4500
taaactttga taatgtagga tttgggtatc tctctttgct tcaagttgcc acattcaaag    4560
gatggatgga tataatgtat gcagcagttg attccagaaa tgtggaactc cagcctaagt    4620
atgaagaaag tctgtacatg tatctttact ttgttatttt catcatcttt gggtccttct    4680
tcaccttgaa cctgtttatt ggtgtcatca tagataattt caaccagcag aaaaagaagt    4740
ttggaggtca agacatcttt atgacagaag aacagaagaa atactataat gcaatgaaaa    4800
aattaggatc gaaaaaaccg caaaagccta tacctcgacc aggaaacaaa tttcaaggaa    4860
tggtctttga cttcgtaacc agacaagttt ttgacataag catcatgatt ctcatctgtc    4920
ttaacatggt cacaatgatg gtggaaacag atgaccagag tgaatatgtg actaccattt    4980
tgtcacgcat caatctggtg ttcattgtgc tatttactgg agagtgtgta ctgaaactca    5040
tctctctacg ccattattat tttaccattg gatggaatat ttttgatttt gtggttgtca    5100
ttctctccat tgtaggtatg tttccttgccg agctgataga aaagtatttc gtgtcccta     5160 ccctgttccg agtgatccgt cttgctagga ttggccgaat cctacgtctg atcaaaggag    5220
caaaggggat ccgcacgctg ctcttttgctt tgatgatgtc ccttcctgcg ttgtttaaca    5280
tcggcctcct actcttccta gtcatgttca tctacgccat ctttgggatg ccaactttg     5340 cctatgttaa gagggaagtt gggatcgatg acatgttcaa ctttgagacc tttggcaaca    5400
gcatgatctg cctattccaa attacaacct ctgctggctg ggatggattg ctagcaccca    5460
ttctcaacag taagccaccc gactgtgacc ctaataaagt taaccctgga agctcagtta    5520
agggagactg tgggaaccca tctgttggaa ttttcttttt tgtcagttac atcatcatat    5580
ccttcctggt tgtggtgaac atgtacatcg cggtcatcct ggagaacttc agtgttgcta    5640
ctgaagaaag tgcagagcct ctgagtgagg atgactttga tgttctat gaggtttggg      5700 agaagtttga tcccgatgca actcagttca tggaatttga aaattatct cagtttgcag     5760 ctgcgcttga accgcctctc aatctgccac aaccaaacaa actccagctc attgccatgg    5820 atttgccat ggtgagtggt gaccggatcc actgtcttga tatcttattt gcttttacaa     5880
agcgggttct aggagagagt ggagagatgg atgctctacg aatacagatg gaagagcgat    5940
tcatggcttc caatccttcc aaggtctcct atcagccaat cactactact ttaaaacgaa    6000
```

```
aacaagagga agtatctgct gtcattattc agcgtgctta cagacgccac ctttttaaagc    6060 gaactgtaaa acaagcttcc tttacgtaca ataaaaacaa atcaaaggt ggggctaatc      6120 ttcttataaa agaagacatg ataattgaca gaataaatga aaactctatt acagaaaaaa    6180
ctgatctgac catgtccact gcagcttgtc caccttccta tgaccgggtg acaaagccaa    6240
ttgtggaaaa acatgagcaa gaaggcaaag atgaaaaagc caagggaaa taatgaaaa      6300 taaataaaaa taattgggtg acaaattgtt tacagcctgt gaaggtgatg tatttttatc    6360
aacaggactc ctttaggagg tcaatgccaa actgactgtt tttacacaaa tctccttaag    6420
gtcagtgcct acaataagac agtgaccct tgtcagcaaa ctgtgactct gtgtaaaggg     6480
gagatgacct tgacaggagg ttactgttct cactaccagc tgacactgct gaagataaga    6540
tgcacaatgg ctagtcagac tgtagggacc agtttcaagg ggtgcaaacc tgtgattttg    6600
gggttgttta acatgaaaca ctttagtgta gtaattgtat ccactgtttg catttcaact    6660
gccacatttg tcacatttt atggaatctg ttagtggatt catcttttg ttaatccatg      6720 tgtttattat atgtgactat ttttgtaaac gaagtttctg ttgagaaata ggctaaggac    6780
ctctataaca ggtatgccac ctggggggta tggcaaccac atggccctcc cagctacaca    6840
aagtcgtggt ttgcatgagg gcatgctgca cttagagatc atgcatgaga aaagtcaca    6900 agaaaaacaa attcttaaat ttcaccatat ttctgggagg ggtaattggg tgataagtgg    6960
aggtgctttg ttgatcttgt tttgcgaaat ccagcccta gaccaagtag attatttgtg     7020
ggtaggccag taaatcttag caggtgcaaa cttcattcaa atgtttggag tcataaatgt    7080
tatgtttctt tttgttgtat taaaaaaaaa acctgaatag tgaatattgc ccctcaccct    7140
ccaccgccag aagactgaat tgaccaaaat tactcttat aaatttctgc ttttcctgc      7200 actttgttta gccatcttcg gctctcagca aggttgacac tgtatatgtt aatgaaatgc    7260
tatttattat gtaaatagtc attttacccct gtggtgcacg tttgagcaaa caataatga    7320 cctaagcaca gtatttattg catcaaatat gtaccacaag aaatgtagag tgcaagcttt    7380
acacaggtaa taaaatgtat tctgtaccat ttatagatag tttggatgct atcaatgcat    7440
gtttatatta ccatgctgct gtatctggtt tctctcactg ctcagaatct catttatgag    7500
aaaccatatg tcagtggtaa agtcaaggaa attgttcaac agatctcatt tatttaagtc    7560
attaagcaat agtttgcagc actttaacag ctttttggtt attttacat tttaagtgga    7620 taacatatgg tatatagcca gactgtacag acatgtttaa aaaacacac tgcttaacct     7680 attaaatatg tgtttagaat tttataagca aatataaata ctgtaaaaag tcactttatt    7740
ttatttttca gcattatgta cataaatatg aagaggaaat tatcttcagg ttgatatcac    7800
aatcactttt cttactttct gtccatagta ctttttcatg aaagaaattt gctaaataag    7860
acatgaaaac aagactgggt agttgtagat ttctgctttt taaattacat ttgctaatt     7920 tagattattt cacaattta aggagcaaaa taggttcacg attcatatcc aaattatgct    7980
ttgcaattgg aaaagggttt aaaatttat ttatatttct ggtagtacct gcactaactg     8040
aattgaaggt agtgcttatg ttattttttgt tctttttttc tgacttcggt ttatgttttc    8100
atttctttgg agtaatgctg ctctagattg ttctaaatag aatgtgggct tcataatttt    8160
tttttccaca aaacagagt agtcaactta tatagtcaat tacatcagga cattttgtgt     8220
ttcttacaga agcaaaccat aggctcctct tttccttaaa actacttaga taaactgtat    8280
tcgtgaactg catgctggaa aatgctacta ttatgctaaa taatgctaac caacatttaa    8340
aatgtgcaaa actaataaag attacatttt ttatttta                           8378
```

<210> SEQ ID NO 3
<211> LENGTH: 2009
<212> TYPE: PRT
<213> ORGANISM: Homo sapiens

<400> SEQUENCE: 3

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

```
Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
            405                 410                 415

Leu Ile Leu Ala Val Val Ala Met Ala Tyr Glu Glu Gln Asn Gln Ala
        420                 425                 430

Thr Leu Glu Glu Ala Glu Gln Lys Glu Ala Glu Phe Gln Gln Met Ile
    435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
        530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
        610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
            725                 730                 735

Cys Trp Tyr Lys Phe Ser Asn Ile Phe Leu Ile Trp Asp Cys Ser Pro
        740                 745                 750

Tyr Trp Leu Lys Val Lys His Val Asn Leu Val Val Met Asp Pro
    755                 760                 765

Phe Val Asp Leu Ala Ile Thr Ile Cys Ile Val Leu Asn Thr Leu Phe
        770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
```

-continued

```
                805                 810                 815
Leu Lys Ile Ile Ala Met Asp Pro Tyr Tyr Phe Gln Glu Gly Trp
        820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
        995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Ala Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215
```

-continued

```
Trp Phe Glu Thr Phe Ile Val Phe Met Ile Leu Leu Ser Ser Gly
1220                1225                1230

Ala Leu Ala Phe Glu Asp Ile Tyr Ile Asp Gln Arg Lys Thr Ile
1235                1240                1245

Lys Thr Met Leu Glu Tyr Ala Asp Lys Val Phe Thr Tyr Ile Phe
1250                1255                1260

Ile Leu Glu Met Leu Leu Lys Trp Val Ala Tyr Gly Tyr Gln Thr
1265                1270                1275

Tyr Phe Thr Asn Ala Trp Cys Trp Leu Asp Phe Leu Ile Val Asp
1280                1285                1290

Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Glu Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620
```

```
Leu Ile Glu Lys Tyr Phe Val Ser Pro Thr Leu Phe Arg Val Ile
    1625            1630            1635

Arg Leu Ala Arg Ile Gly Arg Ile Leu Arg Leu Ile Lys Gly Ala
    1640            1645            1650

Lys Gly Ile Arg Thr Leu Leu Phe Ala Leu Met Met Ser Leu Pro
    1655            1660            1665

Ala Leu Phe Asn Ile Gly Leu Leu Leu Phe Leu Val Met Phe Ile
    1670            1675            1680

Tyr Ala Ile Phe Gly Met Ser Asn Phe Ala Tyr Val Lys Arg Glu
    1685            1690            1695

Val Gly Ile Asp Asp Met Phe Asn Phe Glu Thr Phe Gly Asn Ser
    1700            1705            1710

Met Ile Cys Leu Phe Gln Ile Thr Thr Ser Ala Gly Trp Asp Gly
    1715            1720            1725

Leu Leu Ala Pro Ile Leu Asn Ser Lys Pro Pro Asp Cys Asp Pro
    1730            1735            1740

Asn Lys Val Asn Pro Gly Ser Ser Val Lys Gly Asp Cys Gly Asn
    1745            1750            1755

Pro Ser Val Gly Ile Phe Phe Phe Val Ser Tyr Ile Ile Ile Ser
    1760            1765            1770

Phe Leu Val Val Val Asn Met Tyr Ile Ala Val Ile Leu Glu Asn
    1775            1780            1785

Phe Ser Val Ala Thr Glu Glu Ser Ala Glu Pro Leu Ser Glu Asp
    1790            1795            1800

Asp Phe Glu Met Phe Tyr Glu Val Trp Glu Lys Phe Asp Pro Asp
    1805            1810            1815

Ala Thr Gln Phe Met Glu Phe Glu Lys Leu Ser Gln Phe Ala Ala
    1820            1825            1830

Ala Leu Glu Pro Pro Leu Asn Leu Pro Gln Pro Asn Lys Leu Gln
    1835            1840            1845

Leu Ile Ala Met Asp Leu Pro Met Val Ser Gly Asp Arg Ile His
    1850            1855            1860

Cys Leu Asp Ile Leu Phe Ala Phe Thr Lys Arg Val Leu Gly Glu
    1865            1870            1875

Ser Gly Glu Met Asp Ala Leu Arg Ile Gln Met Glu Glu Arg Phe
    1880            1885            1890

Met Ala Ser Asn Pro Ser Lys Val Ser Tyr Gln Pro Ile Thr Thr
    1895            1900            1905

Thr Leu Lys Arg Lys Gln Glu Glu Val Ser Ala Val Ile Ile Gln
    1910            1915            1920

Arg Ala Tyr Arg Arg His Leu Leu Lys Arg Thr Val Lys Gln Ala
    1925            1930            1935

Ser Phe Thr Tyr Asn Lys Asn Lys Ile Lys Gly Gly Ala Asn Leu
    1940            1945            1950

Leu Ile Lys Glu Asp Met Ile Ile Asp Arg Ile Asn Glu Asn Ser
    1955            1960            1965

Ile Thr Glu Lys Thr Asp Leu Thr Met Ser Thr Ala Ala Cys Pro
    1970            1975            1980

Pro Ser Tyr Asp Arg Val Thr Lys Pro Ile Val Glu Lys His Glu
    1985            1990            1995

Gln Glu Gly Lys Asp Glu Lys Ala Lys Gly Lys
    2000            2005
```

<210> SEQ ID NO 4
<211> LENGTH: 2009
<212> TYPE: PRT
<213> ORGANISM: Homo sapiens

<400> SEQUENCE: 4

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Phe Val Thr Glu Phe Val Asn
        195                 200                 205

Leu Gly Asn Phe Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
```

```
              385                 390                 395                 400
        Ile Phe Phe Val Leu Val Ile Phe Leu Gly Ser Phe Tyr Leu Ile Asn
                        405                 410                 415

Leu Ile Leu Ala Val Val Ala Met Ala Tyr Glu Glu Gln Asn Gln Ala
                        420                 425                 430

Thr Leu Glu Glu Ala Glu Gln Lys Glu Ala Glu Phe Gln Gln Met Ile
                    435                 440                 445

Glu Gln Leu Lys Lys Gln Glu Ala Ala Gln Ala Ala Thr Ala
                    450                 455                 460

Thr Ala Ser Glu His Ser Arg Glu Pro Ser Ala Ala Gly Arg Leu Ser
        465                 470                 475                 480

Asp Ser Ser Ser Glu Ala Ser Lys Leu Ser Ser Lys Ser Ala Lys Glu
                        485                 490                 495

Arg Arg Asn Arg Arg Lys Lys Arg Lys Gln Lys Glu Gln Ser Gly Gly
                        500                 505                 510

Glu Glu Lys Asp Glu Asp Glu Phe Gln Lys Ser Glu Ser Glu Asp Ser
                    515                 520                 525

Ile Arg Arg Lys Gly Phe Arg Phe Ser Ile Glu Gly Asn Arg Leu Thr
                530                 535                 540

Tyr Glu Lys Arg Tyr Ser Ser Pro His Gln Ser Leu Leu Ser Ile Arg
        545                 550                 555                 560

Gly Ser Leu Phe Ser Pro Arg Arg Asn Ser Arg Thr Ser Leu Phe Ser
                        565                 570                 575

Phe Arg Gly Arg Ala Lys Asp Val Gly Ser Glu Asn Asp Phe Ala Asp
                        580                 585                 590

Asp Glu His Ser Thr Phe Glu Asp Asn Glu Ser Arg Arg Asp Ser Leu
                    595                 600                 605

Phe Val Pro Arg Arg His Gly Glu Arg Arg Asn Ser Asn Leu Ser Gln
                610                 615                 620

Thr Ser Arg Ser Ser Arg Met Leu Ala Val Phe Pro Ala Asn Gly Lys
        625                 630                 635                 640

Met His Ser Thr Val Asp Cys Asn Gly Val Val Ser Leu Val Gly Gly
                        645                 650                 655

Pro Ser Val Pro Thr Ser Pro Val Gly Gln Leu Leu Pro Glu Val Ile
                        660                 665                 670

Ile Asp Lys Pro Ala Thr Asp Asp Asn Gly Thr Thr Thr Glu Thr Glu
                    675                 680                 685

Met Arg Lys Arg Arg Ser Ser Ser Phe His Val Ser Met Asp Phe Leu
                690                 695                 700

Glu Asp Pro Ser Gln Arg Gln Arg Ala Met Ser Ile Ala Ser Ile Leu
        705                 710                 715                 720

Thr Asn Thr Val Glu Glu Leu Glu Glu Ser Arg Gln Lys Cys Pro Pro
                        725                 730                 735

Cys Trp Tyr Lys Phe Ser Asn Ile Phe Leu Ile Trp Asp Cys Ser Pro
                        740                 745                 750

Tyr Trp Leu Lys Val Lys His Val Val Asn Leu Val Val Met Asp Pro
                    755                 760                 765

Phe Val Asp Leu Ala Ile Thr Ile Cys Ile Val Leu Asn Thr Leu Phe
                770                 775                 780

Met Ala Met Glu His Tyr Pro Met Thr Asp His Phe Asn Asn Val Leu
        785                 790                 795                 800

Thr Val Gly Asn Leu Val Phe Thr Gly Ile Phe Thr Ala Glu Met Phe
                        805                 810                 815
```

-continued

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
            850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
            885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
            930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
            965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
            995                 1000                1005

Met Asn Asn Leu Gln Ile Ala Val Asp Arg Met His Lys Gly Val
            1010                1015                1020

Ala Tyr Val Lys Arg Lys Ile Tyr Glu Phe Ile Gln Gln Ser Phe
            1025                1030                1035

Ile Arg Lys Gln Lys Ile Leu Asp Glu Ile Lys Pro Leu Asp Asp
            1040                1045                1050

Leu Asn Asn Lys Lys Asp Ser Cys Met Ser Asn His Thr Ala Glu
            1055                1060                1065

Ile Gly Lys Asp Leu Asp Tyr Leu Lys Asp Val Asn Gly Thr Thr
            1070                1075                1080

Ser Gly Ile Gly Thr Gly Ser Ser Val Glu Lys Tyr Ile Ile Asp
            1085                1090                1095

Glu Ser Asp Tyr Met Ser Phe Ile Asn Asn Pro Ser Leu Thr Val
            1100                1105                1110

Thr Val Pro Ile Ala Val Gly Glu Ser Asp Phe Glu Asn Leu Asn
            1115                1120                1125

Thr Glu Asp Phe Ser Ser Glu Ser Asp Leu Glu Glu Ser Lys Glu
            1130                1135                1140

Lys Leu Asn Glu Ser Ser Ser Ser Glu Gly Ser Thr Val Asp
            1145                1150                1155

Ile Gly Ala Pro Val Glu Glu Gln Pro Val Val Glu Pro Glu Glu
            1160                1165                1170

Thr Leu Glu Pro Glu Ala Cys Phe Thr Glu Gly Cys Val Gln Arg
            1175                1180                1185

Phe Lys Cys Cys Gln Ile Asn Val Glu Glu Gly Arg Gly Lys Gln
            1190                1195                1200

Trp Trp Asn Leu Arg Arg Thr Cys Phe Arg Ile Val Glu His Asn
            1205                1210                1215

Trp Phe Glu Thr Phe Ile Val Phe Met Ile Leu Leu Ser Ser Gly
            1220                1225                1230

```
Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
1250                1255                1260

Ile Leu Glu Met Leu Leu Lys Trp Val Ala Tyr Gly Tyr Gln Thr
1265                1270                1275

Tyr Phe Thr Asn Ala Trp Cys Trp Leu Asp Phe Leu Ile Val Asp
1280                1285                1290

Val Ser Leu Val Ser Leu Thr Ala Asn Ala Leu Gly Tyr Ser Glu
1295                1300                1305

Leu Gly Ala Ile Lys Ser Leu Arg Thr Leu Arg Ala Leu Arg Pro
1310                1315                1320

Leu Arg Ala Leu Ser Arg Phe Glu Gly Met Arg Val Val Val Asn
1325                1330                1335

Ala Leu Leu Gly Ala Ile Pro Ser Ile Met Asn Val Leu Leu Val
1340                1345                1350

Cys Leu Ile Phe Trp Leu Ile Phe Ser Ile Met Gly Val Asn Leu
1355                1360                1365

Phe Ala Gly Lys Phe Tyr His Cys Ile Asn Thr Thr Thr Gly Asp
1370                1375                1380

Arg Phe Asp Ile Glu Asp Val Asn Asn His Thr Asp Cys Leu Lys
1385                1390                1395

Leu Ile Glu Arg Asn Glu Thr Ala Arg Trp Lys Asn Val Lys Val
1400                1405                1410

Asn Phe Asp Asn Val Gly Phe Gly Tyr Leu Ser Leu Leu Gln Val
1415                1420                1425

Ala Thr Phe Lys Gly Trp Met Asp Ile Met Tyr Ala Ala Val Asp
1430                1435                1440

Ser Arg Asn Val Glu Leu Gln Pro Lys Tyr Glu Glu Ser Leu Tyr
1445                1450                1455

Met Tyr Leu Tyr Phe Val Ile Phe Ile Ile Phe Gly Ser Phe Phe
1460                1465                1470

Thr Leu Asn Leu Phe Ile Gly Val Ile Ile Asp Asn Phe Asn Gln
1475                1480                1485

Gln Lys Lys Lys Phe Gly Gly Gln Asp Ile Phe Met Thr Glu Glu
1490                1495                1500

Gln Lys Lys Tyr Tyr Asn Ala Met Lys Lys Leu Gly Ser Lys Lys
1505                1510                1515

Pro Gln Lys Pro Ile Pro Arg Pro Gly Asn Lys Phe Gln Gly Met
1520                1525                1530

Val Phe Asp Phe Val Thr Arg Gln Val Phe Asp Ile Ser Ile Met
1535                1540                1545

Ile Leu Ile Cys Leu Asn Met Val Thr Met Met Val Glu Thr Asp
1550                1555                1560

Asp Gln Ser Glu Tyr Val Thr Thr Ile Leu Ser Arg Ile Asn Leu
1565                1570                1575

Val Phe Ile Val Leu Phe Thr Gly Glu Cys Val Leu Lys Leu Ile
1580                1585                1590

Ser Leu Arg His Tyr Tyr Phe Thr Ile Gly Trp Asn Ile Phe Asp
1595                1600                1605

Phe Val Val Val Ile Leu Ser Ile Val Gly Met Phe Leu Ala Glu
1610                1615                1620

Leu Ile Glu Lys Tyr Phe Val Ser Pro Thr Leu Phe Arg Val Ile
```

```
                1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
    1955                1960                1965

Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys Ala Lys Gly Lys
    2000                2005

<210> SEQ ID NO 5
<211> LENGTH: 850
```

```
<212> TYPE: DNA
<213> ORGANISM: Homo sapiens

<400> SEQUENCE: 5
ctaaaataat gctaaagttt ttcaagtact acttgaaaat agctatattt actttcaaac      60
cttttcctct ttgagtcatt aggttcatga tattatatag caatagggaa tgaaagagaa     120
gcaaggagaa gcaatactgg gagattacag agaagaaagg aaaaaaggct gagagaaaag     180
aggttgagga agaaatcata aatctggatt gtgagaaagt gtttaatatt tagccactag     240
atggcgatgt aatgtaaggt gctgtcttga cttttttttt ttttttttga aacaagctat     300
ttgctgattt gtattaggta ccatagagtg aggcgaggat gaagccgaga agatactgca     360
gaggtctctg gtgcatgtgt gtatgtgtgc gtttgtgtgt gtttgtgtgt ctgtgtgttc     420
tgccccagtg agactgcagc ccttgtaaat actttgacac cttttgcaag aaggaatctg     480
aacaattgca actgaaggca cattgttatc atctcgtctt tgggtgatgc tgttcctcac     540
tgcagatgga taattttcct tttaatcagg taagccatct aattgtttca tcttgatttt     600
aagtttattc attccagtta ttcctttgga aaaagagtcc atggaaattc agtttgggca     660
gagcaggaag tccattttg tatgtgtatt cagaccaact gtcccctcc tcctctcct     720 cctcttcttg tcccctcccc cgcgccctcc tctctcaacc ttccatgaac tgaaatcagg     780
tttgttttgc agttcagcat tttgatagaa gatgggattc tttggcctga aatagcttgg     840
catctggcca                                                            850

<210> SEQ ID NO 6
<211> LENGTH: 483
<212> TYPE: DNA
<213> ORGANISM: Homo sapiens

<400> SEQUENCE: 6
acatctctta gtcctctctt aaatatctgt attccttta ttttaggaat ttcatatgca      60
gaataaatgg taattaaaat gtgcaggatg acaagatgga gcaaacagtg cttgtaccac     120
caggacctga cagcttcaac ttcttcacca gagaatctct tgcggctatt gaaagacgca     180
ttgcagaaga aaaggcaaag aatcccaaac cagacaaaaa aagatgacga cgaaaaatgg     240
cccaaagcaa atagtgactt ggaagctgga aagaaccttc catttattta tggagacatt     300
cctccagaga tggtgtcaga gccctggag gacctggacc cctactatat caataagaaa     360
gtgagtgttt ttttatcag gcatattttt gctgctaatt gcctactgca ttccttggac     420
tgttgtagca ccaacacatg ccaatagcac aaatctagta tctctgttag aatgaacaca     480
ttt                                                                   483

<210> SEQ ID NO 7
<211> LENGTH: 497
<212> TYPE: DNA
<213> ORGANISM: Homo sapiens

<400> SEQUENCE: 7
taagaagaga tccagtgaca gtttgttttc atggggcact ttaggaaatt gtgattgtgc      60
tggtttctca tttaacttta caataattta ttatgacaag taacagaaag tagataacag     120
agtttaagtg gtttatactt tcatacttct atgttgtgtt cctgtcttac agacttttat     180
agtattgaat aaagggaagg ccatcttccg gttcagtgcc acctctgccc tgtacatttt     240
aactcccttc aatcctctta ggaaaatagc tattaagatt ttggtacatt catatccttt     300
ttcaagtgat taatattaac tatttgtaca tgatctgtaa gcactttata gctaaatatc     360
```

| | |
|---|---:|
| aaattaagtt gggaaatgtc catattatat aggtttcatc actctcattt tgcatctttg | 420 |
| tcatattagc ctcattctta aagttcatta atcacataga cattactgaa acatgtactc | 480 |
| tttaacattt tatatat | 497 |

<210> SEQ ID NO 8
<211> LENGTH: 501
<212> TYPE: DNA
<213> ORGANISM: Homo sapiens

<400> SEQUENCE: 8

| | |
|---|---:|
| tcatatacat tacctcattt aatctataca aatactcagt gaaggtgata ttattaccca | 60 |
| catttttacac atgaagaaat tgaaatgtaa ggagattaga agacttgccc acaatgcatt | 120 |
| tatccctgaa ttttggctaa gctgcagttt gggcttttca atgttagctt tttgtaatat | 180 |
| aacacttgga ttttgatttt cttttgtgtg ttccttaaca ataacctaca ttattcagca | 240 |
| tgctaattat gtgcactatt ttgacaaact gtgtgtttat gacaatgagt aaccctcctg | 300 |
| attggacaaa gaatgtagag taagttcaac ttatattttt aataacatat atacattygg | 360 |
| gattytgaaa ctgtgtctta atgtagtctt aaaataaaac tgaagagcat tttattaaag | 420 |
| tcattcctag acaaaattac gcagcaagag gacaatgctc attggccctc aggcctgctg | 480 |
| gcgttatact gattatcact c | 501 |

<210> SEQ ID NO 9
<211> LENGTH: 563
<212> TYPE: DNA
<213> ORGANISM: Homo sapiens

<400> SEQUENCE: 9

| | |
|---|---:|
| gctaaataga tttcatatac cttgtatttc tcacactact cttaagacac tttacgaaac | 60 |
| aactctttgt gttaggaagc tgaatttaaa tttagggcta cgtttcattt gtatgaaatt | 120 |
| aaaatccatc tgcttagttt tctttttttag tatttatcta ttccactgat ggagtgataa | 180 |
| gaaattggta tgctatgaaa aaacactgtt actttatcaa atttttttgga tgcttgtttt | 240 |
| cagatacacc ttcacaggaa tatatacttt tgaatcactt ataaaaatta ttgcaagggg | 300 |
| attctgttta gaagatttta ctttccttcg ggatccatgg aactggctcg atttcactgt | 360 |
| cattacattt gcgtaagtgc ctttbytgaa actttaagag agaacatagt ttggttttcc | 420 |
| atcagtgctt atgctttta gaataggttt gctttacctg tagaatattt ttgtgtgatt | 480 |
| tatacattca aactctggat ttcaatttag cacaacaaag gtctaagtgg aatttcacta | 540 |
| tagcatgaag gctttgcagt agt | 563 |

<210> SEQ ID NO 10
<211> LENGTH: 253
<212> TYPE: DNA
<213> ORGANISM: Homo sapiens

<400> SEQUENCE: 10

| | |
|---|---:|
| cttataagcc catgcagtaa tataaatcct gctaaaatct tgaataattc tgatttaatt | 60 |
| ctacaggttt gtaacagaat tgtaaacct aggcaatttt tcagctcttc gcactttcag | 120 |
| agtcttgaga gctttgaaaa ctatttcggt aattccaggt aagaagtgat tagagtaaag | 180 |
| gataggctct ttgtacctac agcttttttct ttgtgtcctg tttttgtgtt tgtgtgtgaa | 240 |
| ctcccgctta cag | 253 |

```
<210> SEQ ID NO 11
<211> LENGTH: 340
<212> TYPE: DNA
<213> ORGANISM: Homo sapiens

<400> SEQUENCE: 11
gtaagaagtg attagagtaa aggataggct ctttgtacct acagcttttt ctttgtgtcc      60 tgttttgtg tttgtgtgtg aactcccgct tacaggtacg tcacagagtt tgtggacctg      120
ggcaatgtct cggcattgag aacattcaga gttctccgag cattgaagac gatttcagtc      180
attccaggtg agagcaaggt tagataatga gacggaccca tcatgtgatt cagcatcctt      240
ctctgcttga cattcagttt tacagaaaat caggaatcat aagactaggt gttcaaagaa      300
atgattatta tgttagacat agcttatcag cctggagtta                           340

<210> SEQ ID NO 12
<211> LENGTH: 409
<212> TYPE: DNA
<213> ORGANISM: Homo sapiens

<400> SEQUENCE: 12
cacgcgtgct tagccctcat agtaatagcc tcctaccttc aggcctgaaa accattgtgg      60
gagccctgat ccagtctgtg aagaagctct cagatgtaat gatcctgact gtgttctgtc      120
tgagcgtatt tgctctaatt gggctgcagc tgttcatggg caacctgagg aataaatgta      180
tacaatggcc tcccaccaat gcttccttgg aggaacatag tatagaaaag aatataactg      240
tgaattataa tggtacactt ataaatgaaa ctgtctttga gtttgactgg aagtcatata      300
ttcaagattc aagtaagaat tattgttatg tacatttcct taaaaagtag aattggattg      360
tttgtaacac aaaggataaa tacttgaggg gctggatatc ccattttac                 409

<210> SEQ ID NO 13
<211> LENGTH: 266
<212> TYPE: DNA
<213> ORGANISM: Homo sapiens

<400> SEQUENCE: 13
cgcgcaaata cttgtgcctt tgaatgaata atatatttaa aattactcaa taaacttaaa     60
agtagaacct gaccttcctg ttctctttga gtgttttaa caatgcaaat gttcagcata      120
cgactttctt ttttcaaaca ggatatcatt atttcctgga gggttttta gatgcactac     180 tatgtggaaa tagctctgat gcagggtaag tcaatattgt gtgcatctgt gtatattgta      240
tgtacacaat acatatgtgt atcttt                                          266

<210> SEQ ID NO 14
<211> LENGTH: 604
<212> TYPE: DNA
<213> ORGANISM: Homo sapiens

<400> SEQUENCE: 14
aggtgttgaa aatgcaaatt atcaacaaaa attattttgt aaaatattat tagaaatgct     60
gcaccatatt ttaatgatga caccaagtag ctaataagac tatatgcagt caaaagttgg     120
gaaatagatt agttacttat ttgtcaaact tttattttga ataccaaat ctttctgact      180 aggcaatatc atagcatagt atcagagtaa aaggcagca gaacgacttg taatactttc     240 ttttaccccca cttgcagcca atgtccagag ggatatatgt gtgtgacagc tggtagaaat     300
cccaattatg gctacacaag ctttgatacc ttcagttggg cttttttgtc cttgtttcga     360
ctaatgactc aggacttctg ggaaaatctt tatcaactgg tgagaactaa agagccacac     420
```

| | |
|---|---|
| tctccattta agtaaaagta tacaagaaaa ccaattgagt tatgaaatta aaaccggatg | 480 |
| ataatatagt agaaagagca gaacttgaca cgagacttga gttcctctat cctattgatt | 540 |
| ataacacata ctgagcagag tgatgccaag gattgcaatt ctctcccatt tcttcttggc | 600 |
| tcaa | 604 |

<210> SEQ ID NO 15
<211> LENGTH: 378
<212> TYPE: DNA
<213> ORGANISM: Homo sapiens

<400> SEQUENCE: 15

| | |
|---|---|
| ttatatctga gttttgctag ccacatgagt aaattgaaag ttgagcaccc ttagtgaata | 60 |
| atattgggaa ataattctga tatttttgtt tgcagacatt acgtgctgct gggaaaacgt | 120 |
| acatgatatt ttttgtattg gtcattttct tgggctcatt ctacctaata aatttgatcc | 180 |
| tggctgtggt ggccatggcc tacgaggaac agaatcaggc caccttggaa gaagcagaac | 240 |
| agaaagaggc cgaatttcag cagatgattg aacagcttaa aaagcaacag gaggcagctc | 300 |
| aggtaagctg ccctgctcat ggcactgacc tttatcgtct gatgtactat atgagagaag | 360 |
| tagtctagag cgtgtgat | 378 |

<210> SEQ ID NO 16
<211> LENGTH: 845
<212> TYPE: DNA
<213> ORGANISM: Homo sapiens

<400> SEQUENCE: 16

| | |
|---|---|
| caaccctaat taaataccaa tttttaaagt aaatcaaatc ccaaaaagta atgaatttat | 60 |
| tttcttgttg atacatgttg gatatttttg aatacgtggt ctgtggagca ttaacagaga | 120 |
| cataataaat gttaccatgg agcaaactaa attatctcca aaagccttca ttaggtagaa | 180 |
| agaaaaaaaa aatctcctct tatacttgca gagaatcttc tctgtgagat gatcttcagt | 240 |
| cagttcaata tattttttaa aagccatgca aatacttcag ccctttcaaa gaaagataca | 300 |
| gtctcttcag gtgctatgtt aaaatcattt ctcttcaata tagcaggcag caacggcaac | 360 |
| tgcctcagaa cattccagag agcccagtgc agcaggcagg ctctcagaca gctcatctga | 420 |
| agcctctaag ttgagttcca agagtgctaa ggaaagaaga aatcggagga agaaaagaaa | 480 |
| acagaaagag cagtctggtg gggaagagaa agatgaggat gaattccaaa aatctgaatc | 540 |
| tgaggacagc atcaggaggw aaggttttcg cttctccatt gaagggaacc ggttgacata | 600 |
| tgaaagagg tactcctccc cacaccaggt atggcactgc tgagtttact gatgcatggt | 660 |
| tgaaaattaa acatgggag agaggggag atttagaaaa tggactcagg aattttttatc | 720 |
| aactgaatca accactgttg tgttatattt aaacccatcc cttcttcaca tagttatgca | 780 |
| aaaactttac tccacagata tgtaagtcta cagctcggtg tagttaagat aacaccaagt | 840 |
| tgaca | 845 |

<210> SEQ ID NO 17
<211> LENGTH: 965
<212> TYPE: DNA
<213> ORGANISM: Homo sapiens

<400> SEQUENCE: 17

| | |
|---|---|
| cattgccata ttctaaggat gtttcccttt gaacttgaga aatggtcgtt cagggtgtgt | 60 |
| gtgtatgtgt gtgtgtgtgt gtttcaatat gttaaggttg caatctatct cctcattctt | 120 |

```
taatcccaag ggctagaaac tttcttttat caaggtaatt taatttaatg tgaatgcaca        180
taaaatgaga atgataatca aaaggaatga accatattct gttatgaatg ctgaaatctc        240
cttctacata atcttgcaaa atgaaatcac attcaaatgt ccatattaat atgactctat        300
ttgtbtgctc tttcaaactt ctagtctttg ttgagcatcc gtggctccct attttcacca        360
aggcgaaata gcagaacaag ccttttcagc tttagagggc gagcaaagga tgtgggatct        420
gagaacgact tcgcagatga tgagcacagc acctttgagg ataacgagag ccgtagagat        480
tccttgtttg tgccccgacg acacggagag agacgcaaca gcaacctgag tcagaccagt        540
aggtcatccc ggatgctggc agtgtttcca gcgaatggga agatgcacag cactgtggat        600
tgcaatggtg tgggttcctt ggttggtgga ccttcagttc ctacatcgcc tgttggacag        660
cttctgccag aggtgataat agataagcca gctactgatg acaatgtaag gaagtyttaa        720
atagttcagg catggctggc tcactattgc tgcaccagcc agtgtgtcta cagaacggca        780
accttgagaa tgattcctgg ttggtcacgc tgtgaatgca cctgcatctt gtaatatctt        840
tgatagacta accaactaaa acttaaaacc ttagcagtcg cctgcacaaa cctgaatgca        900
tttacttatt aaaagtgcta aggattgatt agacacaata attactgcct ccagttggag        960
gattt                                                                    965

<210> SEQ ID NO 18
<211> LENGTH: 641
<212> TYPE: DNA
<213> ORGANISM: Homo sapiens

<400> SEQUENCE: 18
aagagtttta tcaactatat taaaattatt ttgtatttta taaaattatg aaatcaggaa         60
gttaacatct tggttttgc tgtatgacta aatggttaac agtttgaaca ttccaggcta        120
atgatacaat aagtcagaaa tatctgccat caccaattga atatgaaagt gcatgatgca        180
tgtgtttcat gaaattcact gtgtcaccat ttggttgttt gcttgtcata ttgctcaaat        240
taattgttta atgcattagc atttttttt acagggaaca accactgaaa ctgaaatgag        300
aaagagaagg tcaagttctt tccacgtttc catggacttt ctagaagatc cttcccaaag        360
gcaacgagca atgagtatag ccagcattct aacaaataca gtagaaggtt ggtaacaaat        420
tctattttcg tttcaattat tttcaccaaa cttatattgt ctcatttcaa acaaatatat        480
ttgtgagttg ggaatagtgc attctaatga aaagacagtc taattcaaga gctgttattt        540
cttatatcta ctcagatatt ctagaagcct taacaattta ttttaaaatg agtgatattg        600
ggactaagac tgttttccta actgtgtagc aactctttga a                           641

<210> SEQ ID NO 19
<211> LENGTH: 818
<212> TYPE: DNA
<213> ORGANISM: Homo sapiens

<400> SEQUENCE: 19
gtgaggcggc acatgaaaga ccacccattt aacctgaggc caagtgctga gccacaatgg         60
cagtgcataa gacaaaaaac tacccattgt tacctgggcc ctatgtgtgt gtctgatgaa        120
ataaccttgg gaggtttaga gtaaactgta attttttaa caagtacaaa aaagggtgtc        180
tctgtaacaa aaatgtgttg attactgaaa ataagtttag tggatatgaa ataaatgtgt        240
gtgtataaag tawacctttt ggtgggtctt tttttttttt ttcttaatct agaacttgaa        300
gaatccaggc agaaatgccc accctgttgg tataaatttt ccaacatatt cttaatctgg        360
```

```
gactgttctc catattggtt aaaagtgaaa catgttgtca acctggttgt gatggaccca      420
tttgttgacc tggccatcac catctgtatt gtcttaaata ctcttttcat ggccatggag      480
cactatccaa tgacggacca tttcaataat gtgcttacag taggaaactt ggtaagcata      540
ttggaaggta aatgtgttta gtcttcaaat tttctgcttg aaaaactgtt tacatttaat      600
tgtgtatagc agtctttcaa ccatccttca tgcttcctgg cccctgcaaa atcgcaatta      660
tatttagctg gctatactct acttttttgc caaaaataat cacccttaat gtgctcacaa      720
aaactgagaa aggcataggc ctacagcact acttgaaaag tcaacagcaa tatttataat      780
ttttcaggat ccagaagtag ctcatagatt aagaacat                              818
```

<210> SEQ ID NO 20
<211> LENGTH: 645
<212> TYPE: DNA
<213> ORGANISM: Homo sapiens

<400> SEQUENCE: 20

```
caagccattt cacccatctg aagacctcag tttccttatc tgtaaagtaa taattgtata       60
ttatctactt cgcgttttcca caggataaa attaaataat gtatatgawa gtctttcatc      120
aactacaaat tgccatacaa atttaagtta gtaatagaat cattgtggga aaatagcata      180
agcattatgt tctaagagca aatcttatgt catgtatgtt attatctggt ggaattagat      240
taattttgtt ttgatcttag gttttcactg ggatctttac agcagaaatg tttctgaaaa      300
ttattgccat ggatccttac tattatttcc aagaaggctg gaatatcttt gacggtttta      360
ttgtgacgct tagcctggta gaacttggac tcgccaatgt ggaagggtta tctgttctcc      420
gttcatttcg attggtaaaa aaaaaaaaaa aaggaaccaa attcaaaaac ctttctaaca      480
ttcagggttc ttgcatagca ttgtcatagt ttttttgcca cacaaccatt aggcattgta      540 agttttttctg taacatttgc attgtcaaaa acttttccta catgggaata attctcaatt      600
attaggttac cttagttcaa gggcwaggtc ggaaaggtaa cggtt                     645
```

<210> SEQ ID NO 21
<211> LENGTH: 829
<212> TYPE: DNA
<213> ORGANISM: Homo sapiens

<400> SEQUENCE: 21

```
gaattctaat gaccatttct aggtaaagct caatatatat aatgctttta agaatcatac       60
aaatatatat taatctttca ttttccagct gcgagatttc aagttggcaa atcttggcc       120 aacgttaaat atgctaataa agatcatcgg caattccgtg ggggctctgg gaaatttaac      180
cctcgtcttg gccatcatcg tcttcatttt tgccgtggtc ggcatgcagc tctttggtaa      240
aagctacaaa gattgtgtct gcaagatcgc cagtgattgt caactcccac gctggcacat      300
gaatgacttc ttccactcck hcctgattgt gttccgcgtg ctgtgtgggg agtggataga      360
gaccatgtgg gactgtatgg aggttgctgg tcaagccatg tgccttactg tcttcatgat      420
ggtcatggtg attggaaacc tagcggtatg tacccactta agatatgcat tttggaaata      480
caccagcatg gcacatgtat acatatgtaa ctaacctgca cattgtgcac atgtacccta      540
aaacttaaag tataataaaa aaaagagta atttaatg gtgactgttt tgtcaaaaag        600
aaaaacaaac tatgattatt ggtttaaaag tccattacct tggatatatt atcactttaa      660
caacacagca atatabcagt gcccctgcat ttttatacc aaattctatt ttgtcagtca       720
ctttatcaca tttttttatgt gaattacaat agagtatcat attgagatga gcctaaaagg    780
```

```
atgtgctggg accattttat aaattcagag ccaaggaaga gagaagtct              829
```

```
<210> SEQ ID NO 22
<211> LENGTH: 909
<212> TYPE: DNA
<213> ORGANISM: Homo sapiens

<400> SEQUENCE: 22
gaattctcgt attgtacaca tataaatctg ttttcttcta ctcatacaat tttagagtta   60
acaaaacctt agattagctc attcaatttc actttacgaa tgggagaact tgagagcaac  120
agaaatcatg tctttgtcca aggatgtgct attgagccag tcacaaattc agatcaccca  180
tcttctaatc actatgctgt ggtgtttcct tctcatcaag ttttagaact tagagttttt  240
tccacactta aaagaaagaa taagtgattg taatctgctc ttccctacat tggtgtaaaa  300
ttataatcat gttttttgttg tttttaaggt cctgaatctc tttctggcct tgcttctgag  360
ctcatttagt gcagacaacc ttgcagccac tgatgatgat aatgaaatga ataatctcca  420
aattgctgtg gataggatgc acaaaggagt agcttatgtg aaaagaaaaa tatatgartt  480
tattcaacag tccttcatta ggaaacaaaa gattttagat gaaattaaac cacttgatga  540
tctaaacaac aagaaagaca gttgtatgtc caatcataca gcagaaattg ggaaagatct  600
tgactatctt aaagatgtaa atggaactac aagtggtata ggaactggca gcagtgttga  660
aaaatacatt attgatgaaa gtgattacat gtcattcata acaacccca gtcttactgt  720 gactgtacca attgctgtag gagaatctga ctttgaaaat ttaaacacgg aagactttag  780
tagtgaatcg gatctggaag aaagcaaaga ggtaagattc tataggtgtg ggtaggtatg  840
aatacatata catatataca tatacacaca tacagatgay cctcagctta atgatgtttt  900
tacttaaga                                                           909
```

```
<210> SEQ ID NO 23
<211> LENGTH: 516
<212> TYPE: DNA
<213> ORGANISM: Homo sapiens
<220> FEATURE:
<221> NAME/KEY: misc_feature
<222> LOCATION: (393)..(393)
<223> OTHER INFORMATION: n = a, c, t or g
<220> FEATURE:
<221> NAME/KEY: misc_feature
<222> LOCATION: (415)..(451)
<223> OTHER INFORMATION: N = a, c, t or g
<220> FEATURE:
<221> NAME/KEY: misc_feature
<222> LOCATION: (454)..(454)
<223> OTHER INFORMATION: N = a, c, t or g
<220> FEATURE:
<221> NAME/KEY: misc_feature
<222> LOCATION: (513)..(513)
<223> OTHER INFORMATION: n = a, c, t or g

<400> SEQUENCE: 23
aagcttacat tgtgaattat ggtaaaaggg ttagcacaga caatgatttt cttatttctt   60
ccccttattc aatctctctt tttctctaaa aatatctcta cctcaagaag aataaaaaac  120
aaattcatag taataatcct tcttggcagg caacttatta ccaaaattaa ggactttact  180
ttctatgtcc atctcactta cagaaactga atgaaagcag tagctcatca gaaggtagca  240
ctgtggacat cggcgcacct gtagaagaac agcccgtagt ggaacctgaa gaaactcttg  300
aacccgaagc ttgtttcact gaaggtaaag aaaagaatcc taatgttaat ctttcatttg  360
gagtgcagct tatttagctg ttggtcagct aanataaatc acatataata aaatngcact  420
```

```
ttgtaataga tataattcaa tcacctctaa tatnttgaca gacaaaaaaa cttaaagtct      480
agtgtcatgc tttgattata tctgcccaat atntgg                              516

<210> SEQ ID NO 24
<211> LENGTH: 640
<212> TYPE: DNA
<213> ORGANISM: Homo sapiens

<400> SEQUENCE: 24
ccatttaaat gtggctgaat gtttccacaa cttcacacag ctgatgaatg tgctcttact      60
actctaggct tagagagcta tgctagcaag acagagatga gcatagtaat aaaaagacaa     120
gacaaggaca ttgctaaagg atattatgga agcagagaca cttatctac ttttatttca      180 acactttctg caggctgtgt acaaagattc aagtgttgtc aaatcaatgt ggaagaaggc     240
agaggaaaac aatggtggaa cctgagaagg acgtgtttcc gaatagttga acataactgg    300
tttgagacct tcattgtttt catgattctc cttagtagtg gtgctctggt gagtgagatt    360
aagaaaaggt gatacagcac taattttag aacactctaa tactgatgac ttattaatcc    420
tttgtttcat tgtcttagta tccaatgcat ttttaattat cccaccttgt atcttctata    480
gatttactct ataactctat atttctggat taacttttac tatgtatgta aatataattt    540
taagaagcta atcattaatt tttgcttact attaaatagc ccagaaagtg tagcccttca    600
gcttattcat taacaccaaa ggatgtgaat attcaattac                          640

<210> SEQ ID NO 25
<211> LENGTH: 607
<212> TYPE: DNA
<213> ORGANISM: Homo sapiens

<400> SEQUENCE: 25
ccacatcagg atacaacatc aagaactatt tcctgactaa gtcaaattaa ttcattggaa      60
tcatactttt ctttttcttc caccaatagt ctttcccctg attaaataag taaaagacct    120
ttgcgaggaa aaaaaaaaag taacagtaac tactgtttct ctgccctcct attccaatga    180
aatgtcatat gcatatgatt aatttttta atagcttatg gagtataatt attttttgaaa   240 gctaataatg tgtaacattt tctttatagg catttgaaga tatatatatt gaycagcgaa    300
agacgattaa gacgatgttg gaatatgctg acaaggtttt cacttacatt ttcattctgg   360
aaatgcttct aaaatgggtg gcatatggct atcaaacata tttcaccaat gcctggagtt   420
ggctggactt cttaattgtt gatgtaggta tcgttcatat ttttgtctct gttcaaggta    480
gcttgtctta tttatattca aattctacaa tagtgagtct cagaccacta tgttatgttg    540
acagactata atarccacta aacgcatata tgcaatgaga gtgtcatttc tggaagacaa    600
gggctaa                                                              607

<210> SEQ ID NO 26
<211> LENGTH: 336
<212> TYPE: DNA
<213> ORGANISM: Homo sapiens

<400> SEQUENCE: 26
aaaaattata cttgtcgtat tatatagcaa ctacacattg aatgatgatt ctgtttatta      60
attgttatta ttcytgtgtg tgcaggtttc attggtcagt ttaacagcaa atgccttggg     120
ttactcagaa cttggagcct atcaatctct caggacacta agagctctga gacctctaag    180
agccttatct cgatttgaag ggatgagggt aagaaaaatg aaagaacctg aagtattgta    240
```

```
tatagccaaa attaaactaa attaaattta gaaaaaagga aaaatgtatg catgcaaaag    300
gaatggcaaa ttcttgcaaa atgctctttta ttgttt                              336
```

<210> SEQ ID NO 27
<211> LENGTH: 677
<212> TYPE: DNA
<213> ORGANISM: Homo sapiens

<400> SEQUENCE: 27

```
cttggttata ttgcctatag ttgttttcct aagtgtattg cttaagaaaa aaaaatgaat     60
tttaagattt ttttgaacct tgcttttaca tatcctagaa taaatagcat tgatagaaaa    120
aaagaatgga agaccagag attactaggg gaatttttttt tctttattaa cagataagaa    180
ttctgacttt tcttttttttc catttgtgta ttaggtggtt gtgaatgccc ttttaggagc    240
aattccatcc atcatgaatg tgcttctggt ttgtcttata ttctggctaa ttttcagcat    300
catgggcgta aatttgtttg ctggcaaatt ctaccactgt attaacacca caactggtga    360
caggtttgac atcgaagacg tgaataatca tactgattgc ctaaaactaa tagaaagaaa    420
tgagactgct cgatggaaaa atgtgaaagt aaactttgat aatgtaggat ttgggtatct    480
ctctttgctt caagttgtaa gtgaacacta ttttctctga atatttttat tgtttggaat    540
aataacaaaa taatgacata catctattat ttagttccta agaaaagta tatatttctt     600 tctatttaaa aaattcaat ttgttagtac aagtttatga gcccagatgg gtgaaaactt    660
tattacatgt aaggact                                                   677
```

<210> SEQ ID NO 28
<211> LENGTH: 457
<212> TYPE: DNA
<213> ORGANISM: Homo sapiens

<400> SEQUENCE: 28

```
aatggccatt ttgttcaata tgtgttctag aaatgaaaag ccatactaaa atactgtctt     60
ggtccaaaat ctgtgtaaaa tttgttttga aatgtctttc aaaaatattc ccttttgaaa    120
attatatcag taagaatatt tattaaacat caggtctaaa ttatttttac tccaaagtaa    180
aacatgcatg tccttcttaa taggccacat tcaaaggatg gatggatata atgtatgcag    240
cagttgattc cagaaatgta agtattcctt gtattctaag tcttttttaca atattgatca    300 ggtggtaaaa ttaatcgaat aaagcataaa cgaccaaatg aaatgattct atcttgattt    360
aaaatatttg ggaaaaagtg tgacaggtaa atattcaagc atagcaatgt ttatcagaaa    420
gatcttacta agataattca acacatgaat tattttg                             457
```

<210> SEQ ID NO 29
<211> LENGTH: 379
<212> TYPE: DNA
<213> ORGANISM: Homo sapiens
<220> FEATURE:
<221> NAME/KEY: misc_feature
<222> LOCATION: (43)..(43)
<223> OTHER INFORMATION: n = a, c, t or g

<400> SEQUENCE: 29

```
cagaaaaaaa aaaaatgctg acatattagt aagaataatt ttntctattg ttatgaaaaa     60
gcaccagtga cgattccag cactaaaatg tatggtaata ttttacaaaa tattccccctt    120 tggtaggtgg aactccagcc taagtatgaa gaaagtctgt acatgtatct ttactttgtt    180
attttcatca tctttgggtc cttcttcacc ttgaacctgt ttattggtgt catcatagat    240
```

```
aatttcaacc agcagaaaaa gaagataagt atttctaata ttttctctcc cactgagata    300
gaaaaattat tccttggagt gttttctctg ccaaatgagt acttgaattt agaacaaatg    360
ggagtatata ttataactg                                                 379

<210> SEQ ID NO 30
<211> LENGTH: 393
<212> TYPE: DNA
<213> ORGANISM: Homo sapiens

<400> SEQUENCE: 30
gtcattttga attatttagg gaattaaaat attatcatac ctaaagagta caatttttttt    60 tacattttaa atcccagata taattatact aatcagttga attttgtatt tctttttta    120 gccatccatt ttctatttta acattgaaaa aaatgtacaa aaggacacag ttttaaccag    180
tttgattttt cttttctata ctttggaggt caagacatct ttatgacaga agaacagaag   240
aaatactata atgcaatgaa aaattagga tcgaaaaaac cgcaaaagcc tatacctcga    300
ccaggagtaa aagtatcaa atgatatggg ggaaaataca aaaacaaaaa ctgcatgctt    360
gtctcacaaa aagaaaagt aagctaaaca ttt                                 393

<210> SEQ ID NO 31
<211> LENGTH: 539
<212> TYPE: DNA
<213> ORGANISM: Homo sapiens

<400> SEQUENCE: 31
ttttaacaat taattatgct ataaattcat tcttacaaaa atcatttgga atgactactt    60
tgcaagaaac tagaaagtca attaatgcag aaagtactta atgctaatgc acatgagaaa   120
aactcctttg ttgttaaaag catttctatt tctctacaga acaaatttca aggaatggtc    180
tttgacttcg taaccagaca agttttttgac ataagcatca tgattctcat ctgtcttaac   240
atggtcacaa tgatggtgga aacagatgac cagagtgaat atgtgactac cattttgtca    300
cgcatcaatc tggtgttcat tgtgctattt actggagagt gtgtactgaa actcatctct    360
ctacgccatt attattttac cattggatgg aatatttttg atttttgtggt tgtcattctc    420 tccattgtag gtaagaaata tttaaagttc ttaaattcag ttaaataaaa gtgaaagctg   480
aaacaatcaa gattagattc aagatcatcc cagcaatcag agataatcac tgtaaatat    539

<210> SEQ ID NO 32
<211> LENGTH: 3403
<212> TYPE: DNA
<213> ORGANISM: Homo sapiens

<400> SEQUENCE: 32
agtatatatt atatatagtt gtcatatttta atataactgg gttcaggact ctgaaccttta    60 ccttggagct ttagaagaaa catatgttta ttttaacgca tgatttcttc actggttggt   120
attctcattg tttattcata ggtatgttttc ttgccgagct gatagaaaag tatttcgtgt    180
cccctaccct gttccgagtg atccgtcttg ctaggattgg ccgaatccta cgtctgatca    240
aaggagcaaa ggggatccgc acgctgctct ttgctttgat gatgtccctt cctgcgttgt    300
ttaacatcgg cctcctactc ttcctagtca tgttcatcta cgccatcttt gggatgtcca    360
actttgccta tgttaagagg gaagttggga tcgatgacat gttcaacttt gagacctttg    420
gcaacagcat gatctgccta ttccaaatta caacctctgc tggctgggat ggattgctag    480
cacccattct caacagtaag ccacccgact gtgaccctaa taaagttaac cctggaagct    540
```

```
cagttaaggg agactgtggg aacccatctg ttggaattttt cttttttgtc agttacatca    600
tcatatcctt cctggttgtg gtgaacatgt acatcgcggt catcctggag aacttcagtg    660
ttgctactga agaaagtgca gagcctctga gtgaggatga ctttgagatg ttctatgagg    720
tttgggagaa gtttgatccc gatgcaactc agttcatgga atttgaaaaa ttatctcagt    780
ttgcagtgcg cttgaaccgc ctctcaatct gccacaacca aacaaactcc agctcattgc    840
catggatttg cccatggtga gtggtgaccg gatccactgt cttgatatct tatttgcttt    900
tacaaagcgg gttctaggag agagtggaga gatggatgct ctacgaatac agatggaaga    960
gcgattcatg gcttccaatc cttccaaggt ctcctatcag ccaatcacta ctactttaaa   1020
acgaaaacaa gaggaagtat ctgctgtcat tattcagcgt gcttacagac gccacctttt   1080
aaagcgaact gtaaaacaag cttcctttac gtacaataaa aacaaaatca aggtggggc    1140
taatcttctt ataaagaag acatgataat tgacagaata aatgaaaact ctattacaga   1200
aaaaactgat ctgaccatgt ccactgcagc ttgtccacct tcctatgacc gggtgacaaa   1260
gccaattgtg aaaaacatg agcaagaagg caaagatgaa aaagccaaag ggaaataaat    1320
gaaaataaat aaaaataatt gggtgacaaa ttgtttacag cctgtgaagg tgatgtattt   1380
ttatcaacag gactccttta ggaggtcaat gccaaactga ctgttttttac acaaatctcc   1440
ttaaggtcag tgcctacaat aagacagtga ccccttgtca gcaaactgtg actctgtgta   1500
aaggggagat gaccttgaca ggaggttact gttctcacta ccagctgaca ctgctgaaga   1560
taagatgcac aatggctagt cagactgtag ggaccagttt caaggggtgc aaacctgtga   1620
ttttggggtt gtttaacatg aaacacttta gtgtagtaat tgtatccact gtttgcattt   1680
caactgccac atttgtcaca ttttatgga atctgttagt ggattcatct tttgttaat    1740
ccatgtgttt attatatgtg actattttg taaacgaagt ttctgttgag aaataggcta   1800
aggacctcta taacaggtat gccacctggg gggtatggca accacatggc cctcccagct   1860
acacaaagtc gtggtttgca tgagggcatg ctgcacttag agatcatgca tgagaaaaag   1920
tcacaagaaa aacaaattct taaatttcac catatttctg ggagggtaa ttgggtgata   1980
agtggaggtg ctttgttgat cttgttttgc gaaatccagc ccctagacca agtagattat   2040
ttgtgggtag gccagtaaat cttagcaggt gcaaacttca ttcaaatgtt tggagtcata   2100
aatgttatgt ttcttttgt tgtattaaaa aaaaaacctg aatagtgaat attgcccctc   2160
accctccacc gccagaagac tgaattgacc aaaattactc tttataaatt tctgcttttt   2220
cctgcacttt gtttagccat cttcggctct cagcaaggtt gacactgtat atgttaatga   2280
aatgctattt attatgtaaa tagtcatttt ccctgtggt gcacgtttga gcaaacaaat   2340
aatgacctaa gcacagtatt tattgcatca aatatgtacc acaagaaatg tagagtgcaa   2400
gctttacaca ggtaataaaa tgtattctgt accatttata gatagtttgg atgctatcaa   2460
tgcatgttta tattaccatg ctgctgtatc tggtttctct cactgctcag aatctcattt   2520
atgagaaacc atatgtcagt ggtaaagtca aggaaattgt tcaacagatc tcatttattt   2580
aagtcattaa gcaatagttt gcagcacttt aacagctttt tggttatttt tacattttaa   2640
gtggataaca tatggtatat agccagactg tacagacatg tttaaaaaaa cacactgctt   2700
aacctattaa atatgtgttt agaatttat aagcaaatat aaatactgta aaagtcact    2760
ttatttatt tttcagcatt atgtacataa atatgaagag gaattatct tcaggttgat    2820
atcacaatca ctttttcttac tttctgtcca tagtacttt tcatgaaaga aatttgctaa   2880
ataagacatg aaaacaagac tgggtagttg tagatttctg cttttttaaat tacatttgct   2940
```

```
aattttagat tatttcacaa ttttaaggag caaaataggt tcacgattca tatccaaatt    3000
atgctttgca attggaaaag ggtttaaaat tttatttata tttctggtag tacctgcact    3060
aactgaattg aaggtagtgc ttatgttatt tttgttcttt ttttctgact tcggtttatg    3120
ttttcatttc tttggagtaa tgctgctcta gattgttcta aatagaatgt gggcttcata    3180
attttttttt ccacaaaaac agagtagtca acttatatag tcaattacat caggacattt    3240
tgtgtttctt acagaagcaa accataggct cctcttttcc ttaaaactac ttagataaac    3300
tgtattcgtg aactgcatgc tggaaaatgc tactattatg ctaaataatg ctaaccaaca    3360
tttaaaatgt gcaaaactaa taaagattac attttttatt tta                     3403

<210> SEQ ID NO 33
<211> LENGTH: 8349
<212> TYPE: DNA
<213> ORGANISM: Homo sapiens

<400> SEQUENCE: 33
ttcttggtgc cagcttatca atcccaaact ctgggtgtaa aagattctac agggcacttt      60
cttatgcaag gagctaaaca gtgattaaag gagcaggatg aaaagatggc acagtcagtg     120
ctggtaccgc caggacctga cagcttccgc ttctttacca gggaatccct tgctgctatt     180
gaacaacgca ttgcagaaga gaaagctaag agacccaaac aggaacgcaa ggatgaggat     240
gatgaaaatg gcccaaagcc aaacagtgac ttggaagcag gaaaatctct tccatttatt     300
tatggagaca ttcctccaga gatggtgtca gtgcccctgg aggatctgga cccctactat     360
atcaataaga aaacgtttat agtattgaat aaagggaaag caatctctcg attcagtgcc     420 accccctgccc tttacatttt aactcccttc aaccctatta gaaaattagc tattaagatt     480
ttggtacatt ctttattcaa tatgctcatt atgtgcacga ttcttaccaa ctgtgtatt     540 atgaccatga gtaaccctcc agactggaca agaatgtgg agtataactt tacaggaatt     600
tatacttttg aatcacttat taaaatactt gcaaggggct tttgtttaga agatttcaca     660
tttttacggg atccatggaa ttggttggat ttcacagtca ttacttttgc atatgtgaca     720
gagtttgtgg acctgggcaa tgtctcagcg ttgagaacat tcagagttct ccgagcattg     780
aaaacaattt cagtcattcc aggcctgaag accattgtgg gggccctgat ccagtcagtg     840
aagaagcttt ctgatgtcat gatcttgact gtgttctgtc taagcgtgtt tgcgctaata     900
ggattgcagt tgttcatggg caacctacga aataaatgtt tgcaatggcc tccagataat     960
tcttcctttg aaataaatat cacttccttc tttaacaatt cattggatgg gaatggtact    1020
actttcaata ggacagtgag catatttaac tgggatgaat atattgagga taaaagtcac    1080 ttttatttt tagagggca aaatgatgct ctgctttgtg gcaacagctc agatgcaggc    1140
cagtgtcctg aaggatacat ctgtgtgaag gctggtagaa accccaacta tggctacacg    1200
agctttgaca ccctttagttg ggccttttg tccttatttc gtctcatgac tcaagacttc    1260
tgggaaaacc tttatcaact gacactacgt gctgctggga aaacgtacat gatatttttt    1320
gtgctggtca ttttcttggg ctcattctat ctaataaatt tgatcttggc tgtggtggcc    1380
atggcctatg aggaacagaa tcaggccaca ttggaagagg ctgaacagaa ggaagctgaa    1440
tttcagcaga tgctcgaaca gttgaaaaag caacaagaag aagctcaggc ggcagctgca    1500
gccgcatctg ctgaatcaag agacttcagt ggtgctggtg ggataggagt ttttcagag    1560 agttcttcag tagcatctaa gttgagctcc aaaagtgaaa aagagctgaa aacagaaga    1620 aagaaaaaga acagaaaga acagtctgga gaagaagaga aaaatgacag agtcctaaaa    1680
```

| | |
|---|---|
| tcggaatctg aagacagcat aagaagaaaa ggtttccgtt tttccttgga aggaagtagg | 1740 |
| ctgacatatg aaaagagatt ttcttctcca caccagtcct tactgagcat ccgtggctcc | 1800 |
| cttttctctc caagacgcaa cagtagggcg agccttttca gcttcagagg tcagcaaag | 1860 |
| gacattggct ctgagaatga ctttgctgat gatgagcaca gcacctttga ggacaatgac | 1920 |
| agccgaagag actctctgtt cgtgccgcac agacatggag aacggcgcca cagcaatgtc | 1980 |
| agccaggcca gccgtgcctc cagggtgctc cccatcctgc ccatgaatgg gaagatgcat | 2040 |
| agcgctgtgg actgcaatgg tgtggtctcc ctggtcgggg gcccttctac cctcacatct | 2100 |
| gctgggcagc tcctaccaga gggcacaact actgaaacag aaataagaaa gagacggtcc | 2160 |
| agttcttatc atgtttccat ggatttattg gaagatccta catcaaggca aagagcaatg | 2220 |
| agtatagcca gtattttgac caacaccatg gaagaacttg aagaatccag acagaaatgc | 2280 |
| ccaccatgct ggtataaatt tgctaatatg tgtttgattt gggactgttg taaaccatgg | 2340 |
| ttaaaggtga aacaccttgt caacctggtt gtaatggacc catttgttga cctggccatc | 2400 |
| accatctgca ttgtcttaaa tacactcttc atggctatgg agcactatcc catgacggag | 2460 |
| cagttcagca gtgtactgtc tgttggaaac ctggtcttca cagggatctt cacagcagaa | 2520 |
| atgtttctca agataattgc catggatcca tattattact ttcaagaagg ctggaatatt | 2580 |
| tttgatggtt ttattgtgag ccttagttta atggaacttg gtttggcaaa tgtggaagga | 2640 |
| ttgtcagttc tccgatcatt ccggctgctc cgagttttca gttggcaaa atcttggcca | 2700 |
| actctaaata tgctaattaa gatcattggc aattctgtgg gggctctagg aaacctcacc | 2760 |
| ttggtattgg ccatcatcgt cttcatttt gctgtggtcg gcatgcagct ctttggtaag | 2820 |
| agctacaaag aatgtgtctg caagatttcc aatgattgtg aactcccacg ctggcacatg | 2880 |
| catgactttt tccactcctt cctgatcgtg ttccgcgtgc tgtgtggaga gtggatagag | 2940 |
| accatgtggg actgtatgga ggtcgctggc caaaccatgt gccttactgt cttcatgatg | 3000 |
| gtcatggtga ttggaaatct agtggttctg aacctcttct tggccttgct tttgagttcc | 3060 |
| ttcagttctg acaatcttgc tgccactgat gatgataacg aaatgaataa tctccagatt | 3120 |
| gctgtgggaa ggatgcagaa aggaatcgat tttgttaaaa gaaaaatacg tgaatttatt | 3180 |
| cagaaagcct tgttaggaa gcagaaagct ttagatgaaa ttaaaccgct tgaagatcta | 3240 |
| aataataaaa aagacagctg tatttccaac cataccacca tagaaatagg caaagacctc | 3300 |
| aattatctca aagacggaaa tggaactact agtggcatag gcagcagtgt agaaaaatat | 3360 |
| gtcgtggatg aaagtgatta catgtcattt ataaacaacc ctagcctcac tgtgacagta | 3420 |
| ccaattgctg ttggagaatc tgactttgaa aatttaaata ctgaagaatt cagcagcgag | 3480 |
| tcagatatgg aggaaagcaa agagaagcta aatgcaacta gttcatctga aggcagcacg | 3540 |
| gttgatattg gagctcccgc cgagggagaa cagcctgagg ttgaacctga ggaatccctt | 3600 |
| gaacctgaag cctgttttac agaagactgt gtacggaagt tcaagtgttg tcagataagc | 3660 |
| atagaagaag gcaaagggaa actctggtgg aatttgagga aaacatgcta taagatagtg | 3720 |
| gagcacaatt ggttcgaaac cttcattgtc ttcatgattc tgctgagcag tggggctctg | 3780 |
| gcctttgaag atatatacat tgagcagcga aaaccatta agaccatgtt agaatatgct | 3840 |
| gacaaggttt tcacttacat attcattctg gaaatgctgc taaagtgggt tgcatatggt | 3900 |
| tttcaagtgt attttaccaa tgcctggtgc tggctagact tcctgattgt tgatgtctca | 3960 |
| ctggttagct taactgcaaa tgccttgggt tactcagaac ttggtgccat caatccctc | 4020 |
| agaacactaa gagctctgag gccactgaga gctttgtccc ggtttgaagg aatgagggct | 4080 |

```
gttgtaaatg ctcttttagg agccattcca tctatcatga atgtacttct ggtttgtctg   4140
atcttttggc taatattcag tatcatggga gtgaatctct ttgctggcaa gttttaccat   4200
tgtattaatt acaccactgg agagatgttt gatgtaagcg tggtcaacaa ctacagtgag   4260
tgcaaagctc tcattgagag caatcaaact gccaggtgga aaaatgtgaa agtaaacttt   4320
gataacgtag gacttggata tctgtctcta cttcaagtag ccacgtttaa gggatggatg   4380
gatattatgt atgcagctgt tgattcacga aatgtagaat tacaacccaa gtatgaagac   4440
aacctgtaca tgtatcttta ttttgtcatc tttattattt ttggttcatt ctttaccttg   4500
aatcttttca ttggtgtcat catagataac ttcaaccaac agaaaagaa gtttggaggt   4560 caagacattt ttatgacaga agaacagaag aaatactaca atgcaatgaa aaaactgggt   4620
tcaaagaaac cacaaaaacc catacctcga cctgctaaca aattccaagg aatggtcttt   4680
gattttgtaa ccaaacaagt ctttgatatc agcatcatga tcctcatctg ccttaacatg   4740
gtcaccatga tggtggaaac cgatgaccag agtcaagaaa tgacaaacat tctgtactgg   4800
attaatctgg tgtttattgt tctgttcact ggagaatgtg tgctgaaact gatctctctt   4860
cgttactact atttcactat tggatggaat attttttgatt ttgtggtggt cattctctcc   4920
attgtaggaa tgtttctggc tgaactgata gaaaagtatt ttgtgtcccc taccctgttc   4980
cgagtgatcc gtcttgccag gattggccga atcctacgtc tgatcaaagg agcaaagggg   5040
atccgcacgc tgctctttgc tttgatgatg tcccttcctg cgttgtttaa catcggcctc   5100
cttcttttcc tggtcatgtt catctacgcc atctttggga tgtccaattt tgcctatgtt   5160
aagagggaag ttgggatcga tgacatgttc aactttgaga cctttggcaa cagcatgatc   5220
tgcctgttcc aaattacaac ctctgctggc tgggatggat tgctagcacc tattcttaat   5280
agtggacctc cagactgtga ccctgacaaa gatcaccctg gaagctcagt taaggagac   5340 tgtgggaacc catctgttgg gattttcttt tttgtcagtt acatcatcat atccttcctg   5400
gttgtggtga acatgtacat cgcggtcatc ctggagaact tcagtgttgc tactgaagaa   5460
agtgcagagc tctgagtga ggatgacttt gagatgttct atgaggtttg ggagaagttt   5520
gatcccgatg cgacccagtt tatagagttt gccaaacttt ctgattttgc agatgccctg   5580
gatcctcctc ttctcatagc aaaacccaac aaagtccagc tcattgccat ggatctgccc   5640
atggtgagtg gtgaccggat ccactgtctt gacatcttat ttgcttttac aaagcgtgtt   5700
ttgggtgaga gtggagagat ggatgccctt cgaatacaga tggaagagcg attcatggca   5760 tcaaaccct ccaaagtctc ttatgagccc attacgacca cgttgaaacg caaacaagag   5820
gaggtgtctg ctattattat ccagagggct tacagacgct acctcttgaa gcaaaaagtt   5880
aaaaaggtat caagtatata caagaaagac aaaggcaaag aatgtgatgg aacacccatc   5940
aaagaagata ctctcattga taaactgaat gagaattcaa ctccagagaa aaccgatatg   6000
acgccttcca ccacgtctcc accctcgtat gatagtgtga ccaaaccaga aaagaaaaa   6060 tttgaaaaag acaaatcaga aaaggaagac aaagggaaag atatcaggga agtaaaaag   6120 taaaagaaa ccaagaattt tccattttgt gatcaattgt ttacagcccg tgatggtgat   6180
gtgtttgtgt caacaggact cccacaggag gtctatgcca aactgactgt ttttacaaat   6240
gtatacttaa ggtcagtgcc tataacaaga cagagacctc tggtcagcaa actgaactc   6300 agtaaactgg agaaatagta tcgatgggag gtttctattt tcacaaccag ctgacactgc   6360
tgaagagcag aggcgtaatg gctactcaga cgataggaac caatttaaag ggggaggga   6420 agttaaattt ttatgtaaat tcaacatgtg acacttgata atagtaattg tcaccagtgt   6480
```

```
ttatgtttta actgccacac ctgccatatt tttacaaaac gtgtgctgtg aatttatcac    6540 ttttctttt aattcacagg ttgtttacta ttatatgtga ctattttgt aaatgggttt      6600 gtgtttgggg agaggggatta aagggaggga attctacatt tctctattgt attgtataac  6660
tggatatatt ttaaatggag gcatgctgca attctcattc acacataaaa aaatcacatc   6720
acaaaaggga agagtttact tcttgtttca ggatgttttt agattttttga ggtgcttaaa  6780 tagctattcg tattttttaag gtgtctcatc cagaaaaaat ttaatgtgcc tgtaaatgtt  6840
ccatagaatc acaagcatta aagagttgtt ttatttttac ataacccatt aaatgtacat   6900
gtatatatgt atatatgtat atgtgcgtgt atatacatat atatgtatac acacatgcac   6960
acacagagat atacacatac cattacattg tcattcacag tcccagcagc atgactatca   7020 cattttgat aagtgtcctt tggcataaaa taaaaatatc ctatcagtcc tttctaagaa    7080
gcctgaattg accaaaaaac atccccacca ccactttata aagttgattc tgctttatcc   7140
tgcagtattg tttagccatc ttctgctctt ggtaaggttg acatagtata tgtcaattta   7200
aaaaataaaa gtctgctttg taaatagtaa ttttacccag tggtgcatgt ttgagcaaac   7260
aaaaatgatg atttaagcac actacttatt gcatcaaata tgtaccacag taagtatagt   7320
ttgcaagctt tcaacaggta atatgatgta attggttcca ttatagtttg aagctgtcac   7380
tgctgcatgt ttatcttgcc tatgctgctg tatcttattc cttccactgt tcagaagtct   7440
aatatgggaa gccatatatc agtggtaaag tgaagcaaat tgttctacca agacctcatt   7500
cttcatgtca ttaagcaata ggttcagca aacaaggaag agcttcttgc tttttattct     7560 tccaaccttta attgaacact caatgatgaa aagcccgact gtacaaacat gttgcaagct  7620
gcttaaatct gtttaaaata tatggttaga gttttctaag aaaatataaa tactgtaaaa   7680
agttcatttt atttttatttt tcagccttttt gtacgtaaaa tgagaaatta aaagtatctt  7740
caggtggatg tcacagtcac tattgttagt ttctgttcct agcacttttta aattgaagca   7800 cttcacaaaa taagaagcaa ggactaggat gcagtgtagg tttctgctt tttattagta    7860 ctgtaaactt gcacacattt caatgtgaaa caaatctcaa actgagttca atgttttattt  7920 gctttcaata gtaatgcctt atcattgaaa gaggcttaaa gaaaaaaaaa atcagctgat   7980
actcttggca ttgcttgaat ccaatgtttc cacctagtct ttttattcag taatcatcag   8040
tcttttccaa tgtttgttta cacagataga tcttattgac ccatatggca ctagaactgt   8100
atcagatata atatgggatc ccagcttttt ttcctctccc acaaaaccag gtagtgaagt   8160
tatattacca gttacagcaa aatactttgt gtttcacaag caacaataaa tgtagattct   8220
ttatactgaa gctattgact tgtagtgtgt tggtgaatgc atgcaggaag atgctgttac   8280
cataaagaac ggtaaaccac attacaatca agccaaagaa taaaggttcg cttatgtata   8340
tgtatttaa                                                           8349
```

<210> SEQ ID NO 34
<211> LENGTH: 8349
<212> TYPE: DNA
<213> ORGANISM: Homo sapiens

<400> SEQUENCE: 34

```
ttcttggtgc cagcttatca atcccaaact ctgggtgtaa aagattctac agggcacttt     60
cttatgcaag gagctaaaca gtgattaaag gagcaggatg aaaagatggc acagtcagtg   120
ctggtaccgc caggacctga cagcttccgc ttctttacca gggaatccct tgctgctatt   180
gaacaacgca ttgcagaaga gaaagctaag agacccaaac aggaacgcaa ggatgaggat   240
```

```
gatgaaaatg gcccaaagcc aaacagtgac ttggaagcag gaaaatctct tccatttatt      300
tatggagaca ttcctccaga gatggtgtca gtgccctgg aggatctgga ccctactat       360 atcaataaga aaacgtttat agtattgaat aaagggaaag caatctctcg attcagtgcc     420
acccctgccc tttacatttt aactcccttc aaccctatta gaaaattagc tattaagatt    480
ttggtacatt ctttattcaa tatgctcatt atgtgcacga ttcttaccaa ctgtgtattt    540
atgaccatga gtaaccctcc agactggaca agaatgtgg agtataccta tacaggaatt    600 tatactttg aatcacttat taaaatactt gcaagggggct tttgtttaga agatttcaca   660
tttttacggg atccatggaa ttggttggat ttcacagtca ttacttttgc atatgtgaca   720
gagtttgtgg acctgggcaa tgtctcagcg ttgagaacat tcagagttct ccgagcattg   780
aaaacaattt cagtcattcc aggcctgaag accattgtgg gggccctgat ccagtcagtg   840
aagaagcttt ctgatgtcat gatcttgact gtgttctgtc taagcgtgtt tgcgctaata   900
ggattgcagt tgttcatggg caacctacga aataaatgtt tgcaatggcc tccagataat   960
tcttcctttg aaataaatat cacttccttc tttaacaatt cattggatgg gaatggtact   1020
actttcaata ggacagtgag catatttaac tgggatgaat atattgagga taaaagtcac   1080 ttttatttt tagaggggca aaatgatgct ctgctttgtg gcaacagctc agatgcaggc   1140
cagtgtcctg aaggatacat ctgtgtgaag gctggtagaa accccaacta tggctacacg   1200
agctttgaca cctttagttg ggcctttttg tccttatttc gtctcatgac tcaagacttc   1260
tgggaaaacc tttatcaact gacactacgt gctgctggga aaacgtacat gatattttt   1320 gtgctggtca ttttcttggg ctcattctat ctaataaatt tgatcttggc tgtggtggcc   1380
atggcctatg aggaacagaa tcaggccaca ttggaagagg ctgaacagaa ggaagctgaa   1440
tttcagcaga tgctcgaaca gttgaaaaag caacaagaag aagctcaggc ggcagctgca   1500
gccgcatctg ctgaatcaag agacttcagt ggtgctggtg ggataggagt tttttcagag   1560
agttcttcag tagcatctaa gttgagctcc aaaagtgaaa aagagctgaa aaacagaaga   1620
aagaaaaaga acagaaaga acagtctgga gaagaagaga aaatgacag agtcctaaaa   1680 tcggaatctg aagacagcat aagaagaaaa ggtttccgtt tttccttgga aggaagtagg   1740
ctgacatatg aaaagagatt ttcttctcca caccagtcct tactgagcat ccgtggctcc   1800 ctttttctctc caagacgcaa cagtagggcg agccttttca gcttcagagg tcgagcaaag   1860
gacattggct ctgagaatga ctttgctgat gatgagcaca gcacctttga ggacaatgac   1920
agccgaagag actctctgtt cgtgccgcac agacatggag aacggcgcca cagcaatgtc   1980
agccaggcca gccgtgcctc cagggtgctc cccatcctgc ccatgaatgg gaagatgcat   2040
agcgctgtgg actgcaatgg tgtggtctcc ctggtcgggg gccttctac cctcacatct   2100 gctgggcagc tcctaccaga gggcacaact actgaaacag aaataagaaa agacgtcc    2160 agttcttatc atgtttccat ggatttattg gaagatccta catcaaggca agagcaatg    2220 agtatagcca gtattttgac caacaccatg gaagaactg aagaatccag acagaaatgc   2280
ccaccatgct ggtataaatt tgctaatatg tgtttgattt gggactgttg taaaccatgg   2340
ttaaaggtga aacaccttgt caacctggtt gtaatggacc catttgttga cctggccatc   2400
accatctgca ttgtccttaaa tacactcttc atggctatgg agcactatcc catgacggag   2460
cagttcagca gtgtactgtc tgttggaaac ctggtcttca caggggatcttt cacagcagaa  2520 atgtttctca agataattgc catggatcca tattattact ttcaagaagg ctggaatatt    2580
tttgatggtt ttattgtgag ccttagttta atggaacttg gtttggcaaa tgtggaagga    2640
```

```
ttgtcagttc tccgatcatt ccggctgctc cgagttttca agttggcaaa atcttggcca   2700
actctaaata tgctaattaa gatcattggc aattctgtgg gggctctagg aaacctcacc   2760
ttggtattgg ccatcatcgt cttcattttt gctgtggtcg gcatgcagct ctttggtaag   2820
agctacaaag aatgtgtctg caagatttcc aatgattgtg aactcccacg ctggcacatg   2880
catgactttt tccactcctt cctgatcgtg ttccgcgtgc tgtgtggaga gtggatagag   2940
accatgtggg actgtatgga ggtcgctggc caaaccatgt gccttactgt cttcatgatg   3000
gtcatggtga ttggaaatct agtggttctg aacctcttct tggccttgct tttgagttcc   3060
ttcagttctg acaatcttgc tgccactgat gatgataacg aaatgaataa tctccagatt   3120
gctgtgggaa ggatgcagaa aggaatcgat tttgttaaaa gaaaaatacg tgaatttatt   3180
cagaaagcct ttgttaggaa gcagaaagct ttagatgaaa ttaaaccgct tgaagatcta   3240
aataataaaa aagacagctg tatttccaac cataccacca tagaaatagg caaagacctc   3300
aattatctca aagacggaaa tggaactact agtggcatag cagcagtgt agaaaaatat   3360
gtcgtggatg aaagtgatta catgtcattt ataacaacc ctagcctcac tgtgacagta   3420
ccaattgctg ttggagaatc tgactttgaa aatttaaata ctgaagaatt cagcagcgag   3480
tcagatatgg aggaaagcaa agagaagcta aatgcaacta gttcatctga aggcagcacg   3540
gttgatattg gagctcccgc cgagggagaa cagcctgagg ttgaacctga ggaatccctt   3600
gaacctgaag cctgttttac agaagactgt gtacggaagt tcaagtgttg tcagataagc   3660
atagaagaag gcaaagggaa actctggtgg aatttgagga aaacatgcta taagatagtg   3720
gagcacaatt ggttcgaaac cttcattgtc ttcatgattc tgctgagcag tggggctctg   3780
gcctttgaag atatatacat tgagcagcga aaaaccatta agaccatgtt agaatatgct   3840
gacaaggttt tcacttacat attcattctg gaaatgctgc taaagtgggt tgcatatggt   3900
tttcaagtgt attttaccaa tgcctggtgc tggctagact tcctgattgt tgatgtctca   3960
ctggttagct taactgcaaa tgccttgggt tactcagaac ttggtgccat caaatccctc   4020
agaacactaa gagctctgag gccactgaga gctttgtccc ggtttgaagg aatgagggct   4080
gttgtaaatg ctcttttagg agccattcca tctatcatga atgtacttct ggtttgtctg   4140
atcttttggc taatattcag tatcatggga gtgaatctct tgctggcaa gttttaccat   4200
tgtattaatt acaccactgg agagatgttt gatgtaagcg tggtcaacaa ctacagtgag   4260
tgcaaagctc tcattgagag caatcaaact gccaggtgga aaatgtgaa agtaaacttt   4320
gataacgtag gacttggata tctgtctcta cttcaagtag ccacgtttaa gggatggatg   4380
gatattatgt atgcagctgt tgattcacga aatgtagaat tacaacccaa gtatgaagac   4440
aacctgtaca tgtatctta tttgtcatc tttattattt ttggttcatt ctttaccttg   4500
aatctttttca ttggtgtcat catagataac ttcaaccaac agaaaaagaa gtttggaggt   4560
caagacattt ttatgacaga agaacagaag aaatactaca tgcaatgaa aaaactgggt   4620
tcaaagaaac cacaaaaacc catacctcga cctgctaaca aattccaagg aatggtcttt   4680
gattttgtaa ccaaacaagt ctttgatatc agcatcatga tcctcatctg ccttaacatg   4740
gtcaccatga tggtgaaaac cgatgaccag agtcaagaaa tgacaaacat tctgtactgg   4800
attaatctgg tgtttattgt tctgttcact ggagaatgtg tgctgaaact gatctctctt   4860
cgttactact atttcactat tggatggaat atttttgatt ttgtggtggt cattctctcc   4920
attgtaggaa tgtttctggc tgaactgata gaaaagtatt ttgtgtcccc taccctgttc   4980
cgagtgatcc gtcttgccag gattggccga atcctacgtc tgatcaaagg agcaaagggg   5040
```

```
atccgcacgc tgctctttgc tttgatgatg tcccttcctg cgttgtttaa catcggcctc    5100
cttcttttcc tggtcatgtt catctacgcc atctttggga tgtccaattt tgcctatgtt    5160
aagagggaag ttgggatcga tgacatgttc aactttgaga cctttggcaa cagcatgatc    5220
tgcctgttcc aaattacaac ctctgctggc tgggatggat tgctagcacc tattcttaat    5280
agtggacctc cagactgtga ccctgacaaa gatcaccctg gaagctcagt taaaggagac    5340
tgtgggaacc catctgttgg gatttttctt tttgtcagtt acatcatcat atccttcctg    5400
gttgtggtga acatgtacat cgcggtcatc ctggagaact tcagtgttgc tactgaagaa    5460
agtgcagagc ctctgagtga ggatgacttt gagatgttct atgaggtttg ggagaagttt    5520
gatcccgatg cgacccagtt tatagagttt gccaaacttt ctgattttgc agatgccctg    5580
gatcctcctc ttctcatagc aaaacccaac aaagtccagc tcattgccat ggatctgccc    5640
atggtgagtg gtgaccggat ccactgtctt gacatcttat ttgcttttac aaagcgtgtt    5700
ttgggtgaga gtggagagat ggatgccctt cgaatacaga tggaagagcg attcatggca    5760
tcaaacccct ccaaagtctc ttatgagccc attacgacca cgttgaaacg caaacaagag    5820
gaggtgtctg ctattattat ccagagggct tacagacgct acctcttgaa gcaaaaagtt    5880
aaaaaggtat caagtatata caagaaagac aaaggcaaag aatgtgatgg aacacccatc    5940
aaagaagata ctctcattga taaactgaat gagaattcaa ctccagagaa aaccgatatg    6000
acgccttcca ccacgtctcc accctcgtat gatagtgtga ccaaaccaga aaagaaaaa    6060 tttgaaaaag acaaatcaga aaggaagac aaagggaaag atatcaggga agtaaaaag    6120 taaaaagaaa ccaagaattt tccatttttgt gatcaattgt ttacagcccg tgatggtgat    6180
gtgtttgtgt caacaggact cccacaggag gtctatgcca aactgactgt ttttacaaat    6240
gtatacttaa ggtcagtgcc tataacaaga cagagacctc tggtcagcaa actggaactc    6300
agtaaactgg agaaatagta tcgatgggag gtttctattt tcacaaccag ctgacactgc    6360
tgaagagcag aggcgtaatg gctactcaga cgataggaac caatttaaag ggggaggga    6420 agttaaattt ttatgtaaat tcaacatgtg acacttgata atagtaattg tcaccagtgt    6480
ttatgtttta actgccacac ctgccatatt tttacaaaac gtgtgctgtg aatttatcac    6540
ttttcttttt aattcacagg ttgtttacta ttatatgtga ctattttgt aaatgggttt    6600 gtgtttgggg agagggatta aagggaggga attctacatt tctctattgt attgtataac    6660
tggatatatt ttaaatggag gcatgctgca attctcattc acacataaaa aaatcacatc    6720
acaaaaggga agagtttact tcttgtttca ggatgttttt agattttga ggtgcttaaa    6780 tagctattcg tattttaag gtgtctcatc cagaaaaaat ttaatgtgcc tgtaaatgtt    6840
ccatagaatc acaagcatta aagagttgtt ttatttttac ataacccatt aaatgtacat    6900
gtatatatgt atatatgtat atgtgcgtgt atatacatat atatgtatac acacatgcac    6960
acacagagat atacacatac cattacattg tcattcacag tcccagcagc atgactatca    7020 cattttgat aagtgtccctt tggcataaaa taaaaatatc ctatcagtcc tttctaagaa    7080
gcctgaattg accaaaaaaac atccccacca ccactttata aagttgattc tgctttatcc    7140
tgcagtattg tttagccatc ttctgctctt ggtaaggttg acatagtata tgtcaattta    7200
aaaaataaaa gtctgctttg taaatagtaa ttttacccag tggtgcatgt ttgagcaaac    7260
aaaaatgatg atttaagcac actacttatt gcatcaaata tgtaccacag taagtatagt    7320
ttgcaagctt tcaacaggta atatgatgta attggttcca ttatagtttg aagctgtcac    7380
tgctgcatgt ttatcttgcc tatgctgctg tatcttattc cttccactgt tcagaagtct    7440
```

-continued

```
aatatgggaa gccatatatc agtggtaaag tgaagcaaat tgttctacca agacctcatt    7500
cttcatgtca ttaagcaata ggttgcagca aacaaggaag agcttcttgc ttttattct    7560 tccaaccttta attgaacact caatgatgaa aagcccgact gtacaaacat gttgcaagct   7620
gcttaaatct gtttaaaata tatggttaga gttttctaag aaaatataaa tactgtaaaa   7680
agttcatttt atttttatttt tcagccttttt gtacgtaaaa tgagaaatta aaagtatctt  7740
caggtggatg tcacagtcac tattgttagt ttctgttcct agcacttta aattgaagca    7800 cttcacaaaa taagaagcaa ggactaggat gcagtgtagg tttctgcttt tttattagta   7860
ctgtaaactt gcacacattt caatgtgaaa caaatctcaa actgagttca atgtttattt   7920
gctttcaata gtaatgcctt atcattgaaa gaggcttaaa gaaaaaaaaa atcagctgat   7980
actcttggca ttgcttgaat ccaatgtttc cacctagtct ttttattcag taatcatcag   8040
tcttttccaa tgtttgttta cacagataga tcttattgac ccatatggca ctagaactgt   8100
atcagatata atatgggatc ccagcttttt ttcctctccc acaaaaccag gtagtgaagt   8160
tatattacca gttacagcaa aatactttgt gtttcacaag caacaataaa tgtagattct   8220
ttatactgaa gctattgact tgtagtgtgt tggtgaatgc atgcaggaag atgctgttac   8280
cataaagaac ggtaaaccac attacaatca agccaaagaa taaaggttcg cttatgtata   8340
tgtatttaa                                                           8349
```

<210> SEQ ID NO 35
<211> LENGTH: 2005
<212> TYPE: PRT
<213> ORGANISM: Homo sapiens

<400> SEQUENCE: 35

```
Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205
```

-continued

```
Asp Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
        275                 280                 285

Glu Ile Asn Ile Thr Ser Phe Phe Asn Asn Ser Leu Asp Gly Asn Gly
290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
        355                 360                 365

Thr Phe Ser Trp Ala Phe Leu Ser Leu Phe Arg Leu Met Thr Gln Asp
    370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
        435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Gln Lys Glu
            500                 505                 510

Gln Ser Gly Glu Glu Lys Asn Asp Arg Val Leu Lys Ser Glu Ser
        515                 520                 525

Glu Asp Ser Ile Arg Arg Lys Gly Phe Arg Phe Ser Leu Glu Gly Ser
    530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg His Ser Asn
    610                 615                 620

Val Ser Gln Ala Ser Arg Ala Ser Arg Val Leu Pro Ile Leu Pro Met
625                 630                 635                 640
```

```
Asn Gly Lys Met His Ser Ala Val Asp Cys Asn Gly Val Val Ser Leu
            645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Ser Ser Tyr
            675                 680                 685

His Val Ser Met Asp Leu Leu Glu Asp Pro Thr Ser Arg Gln Arg Ala
            690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
                740                 745                 750

Asn Leu Val Val Met Asp Pro Phe Val Asp Leu Ala Ile Thr Ile Cys
                755                 760                 765

Ile Val Leu Asn Thr Leu Phe Met Ala Met Glu His Tyr Pro Met Thr
            770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
                820                 825                 830

Leu Ser Leu Met Glu Leu Gly Leu Ala Asn Val Glu Gly Leu Ser Val
            835                 840                 845

Leu Arg Ser Phe Arg Leu Leu Arg Val Phe Lys Leu Ala Lys Ser Trp
            850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
                900                 905                 910

Lys Ile Ser Asn Asp Cys Glu Leu Pro Arg Trp His Met His Asp Phe
                915                 920                 925

Phe His Ser Phe Leu Ile Val Phe Arg Val Leu Cys Gly Glu Trp Ile
            930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990

Ala Thr Asp Asp Asp Asn Glu Met Asn Asn Leu Gln Ile Ala Val Gly
            995                 1000                1005

Arg Met Gln Lys Gly Ile Asp Phe Val Lys Arg Lys Ile Arg Glu
            1010                1015                1020

Phe Ile Gln Lys Ala Phe Val Arg Lys Gln Lys Ala Leu Asp Glu
            1025                1030                1035

Ile Lys Pro Leu Glu Asp Leu Asn Asn Lys Lys Asp Ser Cys Ile
            1040                1045                1050

Ser Asn His Thr Thr Ile Glu Ile Gly Lys Asp Leu Asn Tyr Leu
```

-continued

|         |         |         |         |         |         |         |         |         |         |         |         |
|---------|---------|---------|---------|---------|---------|---------|---------|---------|---------|---------|---------|
|         |         |         |         | 1055    |         |         | 1060    |         |         | 1065    |         |
| Lys     | Asp     | Gly     | Asn     | Gly     | Thr     | Thr     | Ser     | Gly     | Ile     | Gly     | Ser     | Ser | Val | Glu |
|         |         |         | 1070    |         |         |         | 1075    |         |         |         | 1080    |
| Lys     | Tyr     | Val     | Val     | Asp     | Glu     | Ser     | Asp     | Tyr     | Met     | Ser     | Phe     | Ile | Asn | Asn |
|         |         |         | 1085    |         |         |         | 1090    |         |         |         | 1095    |
| Pro     | Ser     | Leu     | Thr     | Val     | Thr     | Val     | Pro     | Ile     | Ala     | Val     | Gly     | Glu | Ser | Asp |
|         |         |         | 1100    |         |         |         | 1105    |         |         |         | 1110    |
| Phe     | Glu     | Asn     | Leu     | Asn     | Thr     | Glu     | Glu     | Phe     | Ser     | Glu     | Ser     | Asp | Met |
|         |         |         | 1115    |         |         |         | 1120    |         |         |         | 1125    |
| Glu     | Glu     | Ser     | Lys     | Glu     | Lys     | Leu     | Asn     | Ala     | Thr     | Ser     | Ser     | Ser | Glu | Gly |
|         |         |         | 1130    |         |         |         | 1135    |         |         |         | 1140    |
| Ser     | Thr     | Val     | Asp     | Ile     | Gly     | Ala     | Pro     | Ala     | Glu     | Gly     | Glu     | Gln | Pro | Glu |
|         |         |         | 1145    |         |         |         | 1150    |         |         |         | 1155    |
| Val     | Glu     | Pro     | Glu     | Glu     | Ser     | Leu     | Glu     | Pro     | Glu     | Ala     | Cys     | Phe | Thr | Glu |
|         |         |         | 1160    |         |         |         | 1165    |         |         |         | 1170    |
| Asp     | Cys     | Val     | Arg     | Lys     | Phe     | Lys     | Cys     | Cys     | Gln     | Ile     | Ser     | Ile | Glu | Glu |
|         |         |         | 1175    |         |         |         | 1180    |         |         |         | 1185    |
| Gly     | Lys     | Gly     | Lys     | Leu     | Trp     | Trp     | Asn     | Leu     | Arg     | Lys     | Thr     | Cys | Tyr | Lys |
|         |         |         | 1190    |         |         |         | 1195    |         |         |         | 1200    |
| Ile     | Val     | Glu     | His     | Asn     | Trp     | Phe     | Glu     | Thr     | Phe     | Ile     | Val     | Phe | Met | Ile |
|         |         |         | 1205    |         |         |         | 1210    |         |         |         | 1215    |
| Leu     | Leu     | Ser     | Ser     | Gly     | Ala     | Leu     | Ala     | Phe     | Glu     | Asp     | Ile     | Tyr | Ile | Glu |
|         |         |         | 1220    |         |         |         | 1225    |         |         |         | 1230    |
| Gln     | Arg     | Lys     | Thr     | Ile     | Lys     | Thr     | Met     | Leu     | Glu     | Tyr     | Ala     | Asp | Lys | Val |
|         |         |         | 1235    |         |         |         | 1240    |         |         |         | 1245    |
| Phe     | Thr     | Tyr     | Ile     | Phe     | Ile     | Leu     | Glu     | Met     | Leu     | Leu     | Lys     | Trp | Val | Ala |
|         |         |         | 1250    |         |         |         | 1255    |         |         |         | 1260    |
| Tyr     | Gly     | Phe     | Gln     | Val     | Tyr     | Phe     | Thr     | Asn     | Ala     | Trp     | Cys     | Trp | Leu | Asp |
|         |         |         | 1265    |         |         |         | 1270    |         |         |         | 1275    |
| Phe     | Leu     | Ile     | Val     | Asp     | Val     | Ser     | Leu     | Val     | Ser     | Leu     | Thr     | Ala | Asn | Ala |
|         |         |         | 1280    |         |         |         | 1285    |         |         |         | 1290    |
| Leu     | Gly     | Tyr     | Ser     | Glu     | Leu     | Gly     | Ala     | Ile     | Lys     | Ser     | Leu     | Arg | Thr | Leu |
|         |         |         | 1295    |         |         |         | 1300    |         |         |         | 1305    |
| Arg     | Ala     | Leu     | Arg     | Pro     | Leu     | Arg     | Ala     | Leu     | Ser     | Arg     | Phe     | Glu | Gly | Met |
|         |         |         | 1310    |         |         |         | 1315    |         |         |         | 1320    |
| Arg     | Ala     | Val     | Val     | Asn     | Ala     | Leu     | Leu     | Gly     | Ala     | Ile     | Pro     | Ser | Ile | Met |
|         |         |         | 1325    |         |         |         | 1330    |         |         |         | 1335    |
| Asn     | Val     | Leu     | Leu     | Val     | Cys     | Leu     | Ile     | Phe     | Trp     | Leu     | Ile     | Phe | Ser | Ile |
|         |         |         | 1340    |         |         |         | 1345    |         |         |         | 1350    |
| Met     | Gly     | Val     | Asn     | Leu     | Phe     | Ala     | Gly     | Lys     | Phe     | Tyr     | His     | Cys | Ile | Asn |
|         |         |         | 1355    |         |         |         | 1360    |         |         |         | 1365    |
| Tyr     | Thr     | Thr     | Gly     | Glu     | Met     | Phe     | Asp     | Val     | Ser     | Val     | Val     | Asn | Asn | Tyr |
|         |         |         | 1370    |         |         |         | 1375    |         |         |         | 1380    |
| Ser     | Glu     | Cys     | Lys     | Ala     | Leu     | Ile     | Glu     | Ser     | Asn     | Gln     | Thr     | Ala | Arg | Trp |
|         |         |         | 1385    |         |         |         | 1390    |         |         |         | 1395    |
| Lys     | Asn     | Val     | Lys     | Val     | Asn     | Phe     | Asp     | Asn     | Val     | Gly     | Leu     | Gly | Tyr | Leu |
|         |         |         | 1400    |         |         |         | 1405    |         |         |         | 1410    |
| Ser     | Leu     | Leu     | Gln     | Val     | Ala     | Thr     | Phe     | Lys     | Gly     | Trp     | Met     | Asp | Ile | Met |
|         |         |         | 1415    |         |         |         | 1420    |         |         |         | 1425    |
| Tyr     | Ala     | Ala     | Val     | Asp     | Ser     | Arg     | Asn     | Val     | Glu     | Leu     | Gln     | Pro | Lys | Tyr |
|         |         |         | 1430    |         |         |         | 1435    |         |         |         | 1440    |
| Glu     | Asp     | Asn     | Leu     | Tyr     | Met     | Tyr     | Leu     | Tyr     | Phe     | Val     | Ile     | Phe | Ile | Ile |
|         |         |         | 1445    |         |         |         | 1450    |         |         |         | 1455    |

```
Phe Gly Ser Phe Phe Thr Leu Asn Leu Phe Ile Gly Val Ile Ile
    1460                1465                1470

Asp Asn Phe Asn Gln Gln Lys Lys Phe Gly Gly Gln Asp Ile
    1475                1480                1485

Phe Met Thr Glu Glu Gln Lys Lys Tyr Tyr Asn Ala Met Lys Lys
    1490                1495                1500

Leu Gly Ser Lys Lys Pro Gln Lys Pro Ile Pro Arg Pro Ala Asn
    1505                1510                1515

Lys Phe Gln Gly Met Val Phe Asp Phe Val Thr Lys Gln Val Phe
    1520                1525                1530

Asp Ile Ser Ile Met Ile Leu Ile Cys Leu Asn Met Val Thr Met
    1535                1540                1545

Met Val Glu Thr Asp Asp Gln Ser Gln Glu Met Thr Asn Ile Leu
    1550                1555                1560

Tyr Trp Ile Asn Leu Val Phe Ile Val Leu Phe Thr Gly Glu Cys
    1565                1570                1575

Val Leu Lys Leu Ile Ser Leu Arg Tyr Tyr Tyr Phe Thr Ile Gly
    1580                1585                1590

Trp Asn Ile Phe Asp Phe Val Val Val Ile Leu Ser Ile Val Gly
    1595                1600                1605

Met Phe Leu Ala Glu Leu Ile Glu Lys Tyr Phe Val Ser Pro Thr
    1610                1615                1620

Leu Phe Arg Val Ile Arg Leu Ala Arg Ile Gly Arg Ile Leu Arg
    1625                1630                1635

Leu Ile Lys Gly Ala Lys Gly Ile Arg Thr Leu Leu Phe Ala Leu
    1640                1645                1650

Met Met Ser Leu Pro Ala Leu Phe Asn Ile Gly Leu Leu Leu Phe
    1655                1660                1665

Leu Val Met Phe Ile Tyr Ala Ile Phe Gly Met Ser Asn Phe Ala
    1670                1675                1680

Tyr Val Lys Arg Glu Val Gly Ile Asp Asp Met Phe Asn Phe Glu
    1685                1690                1695

Thr Phe Gly Asn Ser Met Ile Cys Leu Phe Gln Ile Thr Thr Ser
    1700                1705                1710

Ala Gly Trp Asp Gly Leu Leu Ala Pro Ile Leu Asn Ser Gly Pro
    1715                1720                1725

Pro Asp Cys Asp Pro Asp Lys Asp His Pro Gly Ser Ser Val Lys
    1730                1735                1740

Gly Asp Cys Gly Asn Pro Ser Val Gly Ile Phe Phe Phe Val Ser
    1745                1750                1755

Tyr Ile Ile Ile Ser Phe Leu Val Val Val Asn Met Tyr Ile Ala
    1760                1765                1770

Val Ile Leu Glu Asn Phe Ser Val Ala Thr Glu Glu Ser Ala Glu
    1775                1780                1785

Pro Leu Ser Glu Asp Asp Phe Glu Met Phe Tyr Glu Val Trp Glu
    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860
```

```
Arg Val Leu Gly Glu Ser Gly Glu Met Asp Ala Leu Arg Ile Gln
    1865             1870                 1875

Met Glu Glu Arg Phe Met Ala Ser Asn Pro Ser Lys Val Ser Tyr
    1880             1885                 1890

Glu Pro Ile Thr Thr Thr Leu Lys Arg Lys Gln Glu Glu Val Ser
    1895             1900                 1905

Ala Ile Ile Ile Gln Arg Ala Tyr Arg Arg Tyr Leu Leu Lys Gln
    1910             1915                 1920

Lys Val Lys Lys Val Ser Ser Ile Tyr Lys Lys Asp Lys Gly Lys
    1925             1930                 1935

Glu Cys Asp Gly Thr Pro Ile Lys Glu Asp Thr Leu Ile Asp Lys
    1940             1945                 1950

Leu Asn Glu Asn Ser Thr Pro Glu Lys Thr Asp Met Thr Pro Ser
    1955             1960                 1965

Thr Thr Ser Pro Pro Ser Tyr Asp Ser Val Thr Lys Pro Glu Lys
    1970             1975                 1980

Glu Lys Phe Glu Lys Asp Lys Ser Glu Lys Glu Asp Lys Gly Lys
    1985             1990                 1995

Asp Ile Arg Glu Ser Lys Lys
    2000             2005

<210> SEQ ID NO 36
<211> LENGTH: 2005
<212> TYPE: PRT
<213> ORGANISM: Homo sapiens

<400> SEQUENCE: 36

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
                20                  25                  30

Lys Ala Lys Arg Pro Lys Gln Glu Arg Lys Asp Glu Asp Asp Glu Asn
            35                  40                  45

Gly Pro Lys Pro Asn Ser Asp Leu Glu Ala Gly Lys Ser Leu Pro Phe
        50                  55                  60

Ile Tyr Gly Asp Ile Pro Pro Glu Met Val Ser Val Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
            115                 120                 125

Ser Leu Phe Asn Met Leu Ile Met Cys Thr Ile Leu Thr Asn Cys Val
        130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asn Leu Gly Asn Val Ser Ala Leu Arg Thr Phe Arg Val Leu Arg Ala
        210                 215                 220
```

-continued

```
Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
                260                 265                 270

Asn Leu Arg Asn Lys Cys Leu Gln Trp Pro Pro Asp Asn Ser Ser Phe
                275                 280                 285

Glu Ile Asn Ile Thr Ser Phe Phe Asn Asn Ser Leu Asp Gly Asn Gly
290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
                340                 345                 350

Cys Val Lys Ala Gly Arg Asn Pro Asn Tyr Gly Tyr Thr Ser Phe Asp
                355                 360                 365

Thr Phe Ser Trp Ala Phe Leu Ser Leu Phe Arg Leu Met Thr Gln Asp
                370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
                420                 425                 430

Gln Ala Thr Leu Glu Glu Ala Glu Gln Lys Glu Ala Glu Phe Gln Gln
                435                 440                 445

Met Leu Glu Gln Leu Lys Lys Gln Gln Glu Glu Ala Gln Ala Ala Ala
450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Gln Lys Glu
                500                 505                 510

Gln Ser Gly Glu Glu Lys Asn Asp Arg Val Leu Lys Ser Glu Ser
                515                 520                 525

Glu Asp Ser Ile Arg Arg Lys Gly Phe Arg Phe Ser Leu Glu Gly Ser
530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
                580                 585                 590

Phe Ala Asp Asp Glu His Ser Thr Phe Glu Asp Asn Asp Ser Arg Arg
                595                 600                 605

Asp Ser Leu Phe Val Pro His Arg His Gly Glu Arg Arg His Ser Asn
                610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
```

-continued

```
            645                 650                 655
Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Ser Ser Tyr
            675                 680             685

His Val Ser Met Asp Leu Leu Glu Asp Pro Thr Ser Arg Gln Arg Ala
            690                 695             700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
                740                 745             750

Asn Leu Val Val Met Asp Pro Phe Val Asp Leu Ala Ile Thr Ile Cys
                755                 760             765

Ile Val Leu Asn Thr Leu Phe Met Ala Met Glu His Tyr Pro Met Thr
770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
                820                 825             830

Leu Ser Leu Met Glu Leu Gly Leu Ala Asn Val Glu Gly Leu Ser Val
                835                 840             845

Leu Arg Ser Phe Arg Leu Leu Arg Val Phe Lys Leu Ala Lys Ser Trp
850                 855                 860

Pro Thr Leu Asn Met Leu Ile Lys Ile Ile Gly Asn Ser Val Gly Ala
865                 870                 875             880

Leu Gly Asn Leu Thr Leu Val Leu Ala Ile Ile Val Phe Ile Phe Ala
                885                 890             895

Val Val Gly Met Gln Leu Phe Gly Lys Ser Tyr Lys Glu Cys Val Cys
                900                 905                 910

Lys Ile Ser Asn Asp Cys Glu Leu Pro Arg Trp His Met His Asp Phe
915                 920                 925

Phe His Ser Phe Leu Ile Val Phe Arg Val Leu Cys Gly Glu Trp Ile
            930                 935             940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990

Ala Thr Asp Asp Asp Asn Glu Met Asn Asn Leu Gln Ile Ala Val Gly
            995                  1000                 1005

Arg Met Gln Lys Gly Ile Asp Phe Val Lys Arg Lys Ile Arg Glu
     1010                 1015                 1020

Phe Ile Gln Lys Ala Phe Val Arg Lys Gln Lys Ala Leu Asp Glu
     1025                 1030                 1035

Ile Lys Pro Leu Glu Asp Leu Asn Asn Lys Lys Asp Ser Cys Ile
     1040                 1045                 1050

Ser Asn His Thr Thr Ile Glu Ile Gly Lys Asp Leu Asn Tyr Leu
     1055                 1060                 1065
```

-continued

Lys Asp Gly Asn Gly Thr Thr Ser Gly Ile Gly Ser Ser Val Glu
1070                    1075                1080

Lys Tyr Val Val Asp Glu Ser Asp Tyr Met Ser Phe Ile Asn Asn
1085                    1090                1095

Pro Ser Leu Thr Val Thr Val Pro Ile Ala Val Gly Glu Ser Asp
1100                    1105                1110

Phe Glu Asn Leu Asn Thr Glu Glu Phe Ser Ser Glu Ser Asp Met
1115                    1120                1125

Glu Glu Ser Lys Glu Lys Leu Asn Ala Thr Ser Ser Ser Glu Gly
1130                    1135                1140

Ser Thr Val Asp Ile Gly Ala Pro Ala Glu Gly Glu Gln Pro Glu
1145                    1150                1155

Val Glu Pro Glu Glu Ser Leu Glu Pro Glu Ala Cys Phe Thr Glu
1160                    1165                1170

Asp Cys Val Arg Lys Phe Lys Cys Cys Gln Ile Ser Ile Glu Glu
1175                    1180                1185

Gly Lys Gly Lys Leu Trp Trp Asn Leu Arg Lys Thr Cys Tyr Lys
1190                    1195                1200

Ile Val Glu His Asn Trp Phe Glu Thr Phe Ile Val Phe Met Ile
1205                    1210                1215

Leu Leu Ser Ser Gly Ala Leu Ala Phe Glu Asp Ile Tyr Ile Glu
1220                    1225                1230

Gln Arg Lys Thr Ile Lys Thr Met Leu Glu Tyr Ala Asp Lys Val
1235                    1240                1245

Phe Thr Tyr Ile Phe Ile Leu Glu Met Leu Leu Lys Trp Val Ala
1250                    1255                1260

Tyr Gly Phe Gln Val Tyr Phe Thr Asn Ala Trp Cys Trp Leu Asp
1265                    1270                1275

Phe Leu Ile Val Asp Val Ser Leu Val Ser Leu Thr Ala Asn Ala
1280                    1285                1290

Leu Gly Tyr Ser Glu Leu Gly Ala Ile Lys Ser Leu Arg Thr Leu
1295                    1300                1305

Arg Ala Leu Arg Pro Leu Arg Ala Leu Ser Arg Phe Glu Gly Met
1310                    1315                1320

Arg Ala Val Val Asn Ala Leu Leu Gly Ala Ile Pro Ser Ile Met
1325                    1330                1335

Asn Val Leu Leu Val Cys Leu Ile Phe Trp Leu Ile Phe Ser Ile
1340                    1345                1350

Met Gly Val Asn Leu Phe Ala Gly Lys Phe Tyr His Cys Ile Asn
1355                    1360                1365

Tyr Thr Thr Gly Glu Met Phe Asp Val Ser Val Val Asn Asn Tyr
1370                    1375                1380

Ser Glu Cys Lys Ala Leu Ile Glu Ser Asn Gln Thr Ala Arg Trp
1385                    1390                1395

Lys Asn Val Lys Val Asn Phe Asp Asn Val Gly Leu Gly Tyr Leu
1400                    1405                1410

Ser Leu Leu Gln Val Ala Thr Phe Lys Gly Trp Met Asp Ile Met
1415                    1420                1425

Tyr Ala Ala Val Asp Ser Arg Asn Val Glu Leu Gln Pro Lys Tyr
1430                    1435                1440

Glu Asp Asn Leu Tyr Met Tyr Leu Tyr Phe Val Ile Phe Ile Ile
1445                    1450                1455

Phe Gly Ser Phe Phe Thr Leu Asn Leu Phe Ile Gly Val Ile Ile
1460                    1465                1470

```
Asp Asn Phe Asn Gln Gln Lys Lys Lys Phe Gly Gly Gln Asp Ile
    1475                1480                1485

Phe Met Thr Glu Glu Gln Lys Lys Tyr Tyr Asn Ala Met Lys Lys
    1490                1495                1500

Leu Gly Ser Lys Lys Pro Gln Lys Pro Ile Pro Arg Pro Ala Asn
    1505                1510                1515

Lys Phe Gln Gly Met Val Phe Asp Phe Val Thr Lys Gln Val Phe
    1520                1525                1530

Asp Ile Ser Ile Met Ile Leu Ile Cys Leu Asn Met Val Thr Met
    1535                1540                1545

Met Val Glu Thr Asp Asp Gln Ser Gln Glu Met Thr Asn Ile Leu
    1550                1555                1560

Tyr Trp Ile Asn Leu Val Phe Ile Val Leu Phe Thr Gly Glu Cys
    1565                1570                1575

Val Leu Lys Leu Ile Ser Leu Arg Tyr Tyr Tyr Phe Thr Ile Gly
    1580                1585                1590

Trp Asn Ile Phe Asp Phe Val Val Val Ile Leu Ser Ile Val Gly
    1595                1600                1605

Met Phe Leu Ala Glu Leu Ile Glu Lys Tyr Phe Val Ser Pro Thr
    1610                1615                1620

Leu Phe Arg Val Ile Arg Leu Ala Arg Ile Gly Arg Ile Leu Arg
    1625                1630                1635

Leu Ile Lys Gly Ala Lys Gly Ile Arg Thr Leu Leu Phe Ala Leu
    1640                1645                1650

Met Met Ser Leu Pro Ala Leu Phe Asn Ile Gly Leu Leu Leu Phe
    1655                1660                1665

Leu Val Met Phe Ile Tyr Ala Ile Phe Gly Met Ser Asn Phe Ala
    1670                1675                1680

Tyr Val Lys Arg Glu Val Gly Ile Asp Asp Met Phe Asn Phe Glu
    1685                1690                1695

Thr Phe Gly Asn Ser Met Ile Cys Leu Phe Gln Ile Thr Thr Ser
    1700                1705                1710

Ala Gly Trp Asp Gly Leu Leu Ala Pro Ile Leu Asn Ser Gly Pro
    1715                1720                1725

Pro Asp Cys Asp Pro Asp Lys Asp His Pro Gly Ser Ser Val Lys
    1730                1735                1740

Gly Asp Cys Gly Asn Pro Ser Val Gly Ile Phe Phe Phe Val Ser
    1745                1750                1755

Tyr Ile Ile Ile Ser Phe Leu Val Val Val Asn Met Tyr Ile Ala
    1760                1765                1770

Val Ile Leu Glu Asn Phe Ser Val Ala Thr Glu Glu Ser Ala Glu
    1775                1780                1785

Pro Leu Ser Glu Asp Asp Phe Glu Met Phe Tyr Glu Val Trp Glu
    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
```

```
                1865                1870                1875
Met Glu Glu Arg Phe Met Ala Ser Asn Pro Ser Lys Val Ser Tyr
    1880                1885                1890
Glu Pro Ile Thr Thr Thr Leu Lys Arg Lys Gln Glu Glu Val Ser
    1895                1900                1905
Ala Ile Ile Ile Gln Arg Ala Tyr Arg Arg Tyr Leu Leu Lys Gln
    1910                1915                1920
Lys Val Lys Lys Val Ser Ser Ile Tyr Lys Lys Asp Lys Gly Lys
    1925                1930                1935
Glu Cys Asp Gly Thr Pro Ile Lys Glu Asp Thr Leu Ile Asp Lys
    1940                1945                1950
Leu Asn Glu Asn Ser Thr Pro Glu Lys Thr Asp Met Thr Pro Ser
    1955                1960                1965
Thr Thr Ser Pro Pro Ser Tyr Asp Ser Val Thr Lys Pro Glu Lys
    1970                1975                1980
Glu Lys Phe Glu Lys Asp Lys Ser Glu Lys Glu Asp Lys Gly Lys
    1985                1990                1995
Asp Ile Arg Glu Ser Lys Lys
    2000                2005

<210> SEQ ID NO 37
<211> LENGTH: 912
<212> TYPE: DNA
<213> ORGANISM: Homo sapiens

<400> SEQUENCE: 37
gaattcttta tatgggttga atgactttct gacatagcaa ataaaaagca tgaggagaag    60
cattatctgt taacaaaatt aacacttaaa atcaacaaag ttttaatgtt tcgttccaag   120
aaaagcctgt ggaagatcag ttccacaact gagagctttg ggctgcttca gacatatgtc   180
tgtgtgtacg ctgtgaaggt gtttctcttc acagttcccc gccctctagt ggtagttaca   240
ataatgccat tttgtagtcc ctgtacagga aatgcctctt cttacttcag ttaccagaat   300
ccttttacag gaagttaggt gtggtctttg aaggagaatt aaaaaaaaaa aaaaaaaaa    360 aaaaaagatt ttttttttt taaagcatga tggaatttta gctgcagtct tcttggggcc   420
agcttatcaa tcccaaactc tgggggtaaa agattctaca ggggtaatgt tttattattc   480
ttattatgct tattctctgt gatgcttctc tacctttaca gtagtagaat ccttggggaa   540
atctgcagag ggaccacttt catttttgaag ctgctggctg catgttttag catgtctctt   600
ctattagaga atccaggcat ggcagtttcc tcccccagtg tgcaaggacc atcttcatgc   660
ctatgtctgt cgctaggcat gagggtctct aggaatgggt gaaaaaaatg agggatgttt   720
tggaggcact ataatactgg ggagggcagt ctgctagctg gtagctgaaa ggtcctggtt   780
tacttcaaca tttttttaa ataaaactgt gcagtagttt tgttatttt agggttccct    840 ctgttttatc tggtgtatgc tgcagaagtg aactgcataa cacatttcac tcttagaaat   900
gcattccata ta                                                       912

<210> SEQ ID NO 38
<211> LENGTH: 722
<212> TYPE: DNA
<213> ORGANISM: Homo sapiens

<400> SEQUENCE: 38
ctcagtgcat gtaactgaca caatcacctc tatctaatgg tcatgcttct tacctcctgt    60
tctgtagcac tttcttatgc aaggagctaa acagtgatta aaggagcagg atgaaaagat   120
```

```
ggcacagtca gtgctggtac cgccaggacc tgacagcttc cgcttcttta ccagggaatc    180
ccttgctgct attgaacaac gcattgcaga agagaaagct aagagaccca acaggaacg     240 caaggatgag gatgatgaaa atggcccaaa gccaaacagt gacttggaag cagsaaaatc    300
tcttccattt atttatggag acattcctcc agagatggtg tcagtgcccc tggaggatct    360 ggaccoctac tatatcaata agaaagtgag ttcttagtca agttgccttc actgcctatt    420
tactaattgg ttctgggcta gtcccaggga tgatggtgaa aaggctggc ctccttccct     480 ctgtctaaag tatcactaag atgctggatg ggcctgaccg tgtaatggac caatgatcct    540
agaagtcttt tggaagcact catttgaacc tgcatttgtg agacaggcag agaactggtg    600
aggcatcctc cagcgcggga attaaggaag acaaaagcc tattcacctt cttgaataca     660
aattatatgc ttaaaccagt gtaaattgac cctgattccc aataatgtt gagaagcaaa     720 aa                                                                   722

<210> SEQ ID NO 39
<211> LENGTH: 561
<212> TYPE: DNA
<213> ORGANISM: Homo sapiens

<400> SEQUENCE: 39
cctatggcat tgatcacaaa ttttcttaat aatcctcatg tcatttatca aatttaggaa    60
agtttatagt gctcagaaaa aaaaagcatc tatcttcatg tcatatgatg gtaattatta   120
tgttatacac tattttacag ggcaatattt ataataatg gttttactt tctcttaaaa    180 tattcttaat atatattcta agttttgttt tatgtgttgt gttttctttt tcagacgttt   240
atagtattga ataaagggaa agcaatctct cgattcagtg ccacccctgc cctttacatt   300
ttaactccct tcaaccctat tagaaaatta gctattaaga ttttggtaca ttcatatcct   360
ttttcaaatc gtcacttaat atgatttct tctttgacca agttattgag ctacacattt    420
tccaaaatat ctgtggttgg caatgttatg tgttctttct ttttctttcc ttttactcaa   480
tcgttagcat gttgcaaaat gagatcacag gtaagtgaat tactttcccc cgtcttctaa   540
gtgtttcttc tctacccaac t                                             561

<210> SEQ ID NO 40
<211> LENGTH: 510
<212> TYPE: DNA
<213> ORGANISM: Homo sapiens

<400> SEQUENCE: 40
acctaaatag cctcaaaata gttgatggct tggcctgaag acaagatcta aatatgaggt    60
tgctgagtta tagaaatggc aaaaaaaagg gtcaataata gaataataag caacaaaata   120
atagtaagca ctaaagtttt aaacttcatg tggtgaagg catggtagtg cataaaagta    180
agatttttcc attgaacttt gtcttccttg acgatattct actttattca atatgctcat   240
tatgtgcacg attcttacca actgtgtatt tatgaccatg agtaaccctc cagactggac   300
aaagaatgtg gagtaagtat aaatattttt caatattgac ctcccttat gtttcatatt    360 gtgcttttaa caccttgaga cctcctcaat ttctttaaca aatcatgcta gctactgtta   420
accagaccct gattcaaatt catttctgtc actaaatgtc ttctaggaca aagcttgtag   480
tgggctcact tagttgtgta aattactgca                                    510

<210> SEQ ID NO 41
<211> LENGTH: 370
```

<212> TYPE: DNA
<213> ORGANISM: Homo sapiens
<220> FEATURE:
<221> NAME/KEY: misc_feature
<222> LOCATION: (293)..(293)
<223> OTHER INFORMATION: n= a, c, t or g

<400> SEQUENCE: 41

```
taagatatgt acttgtaaat taaccactag atttttaatg tgagcttggc tattgtctct      60
caggtatacc tttacaggaa tttatacttt tgaatcactt attaaaatac ttgcaagggg     120
cttttgttta gaagatttca cattttacg ggatccatgg aattggttgg atttcacagt     180
cattactttt gcgtaagtat cttaatacat tttctatcct ggaagagtaa atcactggtg     240
ggagcctata ctatattttc cttggtggct tgccttgaca gaccaagcat ttntcttagt     300
aatcatagtt ttcttccaat caaattatcc agtttggaga aattaggaac tatcatagta     360
aattacatgg                                                            370
```

<210> SEQ ID NO 42
<211> LENGTH: 370
<212> TYPE: DNA
<213> ORGANISM: Homo sapiens
<220> FEATURE:
<221> NAME/KEY: misc_feature
<222> LOCATION: (133)..(133)
<223> OTHER INFORMATION: n = a, c, t or g

<400> SEQUENCE: 42

```
caattagcac tgtaaagtaa taaagtttcc caaataacag agattatgat tgatgacaat      60
gccatttcc tcttaattgg gaaagctgat ggcgacactc atgaaattaa aaaggtcttg     120
atgaaagacc aangaagacg tagatttccc taaattctga ataactctga tttaattcta     180
caggtatgta acagaatttg taaacctagg caatgtttca gctcttcgaa ctttcagagt     240
cttgagagct ttgaaaacta tttctgtaat tccaggtaag aagaaaatgg tataaggtgg     300
taggccccctt atatctccaa ctgtttcttg tgttctgtca ttgtgtttgt gtgtgaaccc     360
cctattacag                                                            370
```

<210> SEQ ID NO 43
<211> LENGTH: 410
<212> TYPE: DNA
<213> ORGANISM: Homo sapiens

<400> SEQUENCE: 43

```
gtaagaagaa aatggtataa ggtggtaggc cccttatatc tccaactgtt tcttgtgttc      60
tgtcattgtg tttgtgtgtg aaccccctat tacagatatg tgacagagtt tgtggacctg     120
ggcaatgtct cagcgttgag aacattcaga gttctccgag cattgaaaac aatttcagtc     180
attccaggtg agagctaggt taaacaccga ggctgacttt agctacagtg gtgctacaat     240
cacagcttt gtgcagaagc cttgttgcta gttgcatatt gcaataaat atgtaaaaaa     300
gcaagaattg gtacatcatt ttttggatgg atttgattct ttgcttttta cccgttgctt     360
tctttaaaac tattctaaat cagcctttga gtttaacaag tgttgcatga                410
```

<210> SEQ ID NO 44
<211> LENGTH: 1066
<212> TYPE: DNA
<213> ORGANISM: Homo sapiens
<220> FEATURE:
<221> NAME/KEY: misc_feature
<222> LOCATION: (229)..(229)
<223> OTHER INFORMATION: n = a, c, t or g

<400> SEQUENCE: 44

```
aaagagtgtt tggaaataca catttggttc atttccattc acagttttct aatgaacata      60
caagttctgc tttcattcat tttcaccagc tagtaggctt ttcatgaaaa tgttattcaa     120
tcacaaacat taaactaata ttgttggcat tctgcatgac attttttattt tccaggccaa    180
gctcatgata tttttgccgg taaaatagct gttgagtagt atatttaant tccccttct      240
gatttgttt gtaggcctga agaccattgt gggggccctg atccagtcag tgaagaagct      300
ttctgatgtc atgatcttga ctgtgttctg tctaagcgtg tttgcgctaa taggattgca     360
gttgttcatg ggcaacctac gaaataaatg tttgcaatgg cctccagata attcttcctt    420
tgaaataaat atcacttcct tctttaacaa ttcattggat gggaatggta ctactttcaa    480
taggacagtg agcatattta actgggatga atatattgag gataaaagta agatatactc    540
tataaaccat taagttgttt agttctctaa atattaaata ttatatataa tggaaattat    600
ctcaatttag atgtgaatca agtgacttag actaatttaa gatgatttaa tacatataaa    660
agagatatca aaggatacct tattctattt tsttatctg tccattgata tagtaaaagt     720
tctcatttga aaatgtgttg tcttatactc atgttgaaag taatttcata ttatgccata    780
ttaaaaaagg tttatttggt agacattaat caggttttc agtcatttta ataaataagt     840
cagtagtttg aactattcmg cgtattccac tgaaatgtcg ttaagaagac tgaggggaaa    900
taatttggcc ctatttggtt gatgcaacat atgtattgag tacatatgct atatctgaaa    960
ctagagaaac catttatcaa gatgaaataa gaatttgtgt gctcctcaga aggttaagta   1020
accctgattt agccattcac ttcatccata ttctaattag tccctt                   1066
```

<210> SEQ ID NO 45  
<211> LENGTH: 385  
<212> TYPE: DNA  
<213> ORGANISM: Homo sapiens

<400> SEQUENCE: 45

```
gttcaattat tgtgaaaaat cttctttagc catatatatt tattagttta tccatctcat      60
tatgattgaa acatttgtg agctttgcca cctaaacagg gtggctgaag tgttttacag     120
gattttaatg attcttttcta ttcctttctc tttaaatagg tcacttttat tttttacagg   180
ggcaaaatga tgctctgctt tgtggcaaca gctcagatgc agggtaagtg tatgcttcct    240
actgagtttc agtccacact gctccatcag tgtcaataac ctgccacctc ccactcatcc    300
agtcccacca ctcctcactc aaaaccctcc ataaattcta cttcacggtg actctcagaa    360
tgaccaggat aagtgtagat tctca                                           385
```

<210> SEQ ID NO 46  
<211> LENGTH: 430  
<212> TYPE: DNA  
<213> ORGANISM: Homo sapiens

<400> SEQUENCE: 46

```
tataataatg acaattatga atcacagagg aatccacaaa gtagaccttaa tagattctgt     60
cattatataa atcagtccac ttagtgctga gttaagtact gggtaaggtg agagaaatcg    120
gcttttttct agtgcctgta taaaacagac attggcatat attaaaacag gaaaccaat    180
tagcagactt gccgttattg actycctctc tttcctctaa cctaattaca gccagtgtcc    240
tgaaggatac atctgtgtga aggctggtag aaacccaac tatggctaca cgagctttga    300
cacctttagt tgggcctttt tgtccttatt tcgtctcatg actcaagact tctgggaaaa    360
```

```
cctttatcaa ctggtgagaa cagataaaat cattttctg agaatcataa aacaccgaac    420
tcaagagaat                                                          430

<210> SEQ ID NO 47
<211> LENGTH: 646
<212> TYPE: DNA
<213> ORGANISM: Homo sapiens

<400> SEQUENCE: 47
tgctgtagaa tattttatta cttagagtgt aagtttgtaa catcctatat aaaatttatt     60
aaaatctctc ttccattttg cagacactac gtgctgctgg gaaaacgtac atgatatttt   120
ttgtgctggt cattttcttg ggctcattct atctaataaa tttgatcttg gctgtggtgg   180
ccatggccta tgaggaacag aatcaggcca cattggaaga ggctgaacag aaggaagctg   240
aatttcagca gatgctcgaa cagttgaaaa agcaacaaga agaagctcag gtatagtgaa   300
caagcatacg gtcctttgtt tttctgtatc taaattcttt aacctaaatg ttgaggtcag   360
tggcaaggta gttgacatta gaaataggtc atatgtgttt ggtaagtgct aggagcctgt   420
ttggttatta agaagttatt actttattgc aatgatctct gtcaatagtg tcaatagtaa   480
tggcatcaaa aatggataa ttataattgc tttactgaca ttttttctc ccttgtgact    540 ccttgaggaa attaatgatt aacaaaggcc tcatgtactc aaacttgcag agtagataaa   600
cctacatgtc ctcagttgaa gtattttctt aggggaagag gaattc                  646

<210> SEQ ID NO 48
<211> LENGTH: 711
<212> TYPE: DNA
<213> ORGANISM: Homo sapiens
<220> FEATURE:
<221> NAME/KEY: misc_feature
<222> LOCATION: (164)..(164)
<223> OTHER INFORMATION: n = a, c, t or g

<400> SEQUENCE: 48
tatgtatcat cttccatatg aatgcgcatt ttactctttg attggtctaa taacagtgta     60
ctgtgttcta aaacacagaa taaaatggag aattgttttt caagattatc ttcatgatat   120
tgaagctcaa ttaagcagta acatgataat tattttttaa gatnatatgc aacttcccac   180
atactttgcg cccttctagg cggcagctgc agccgcatct gctgaatcaa gagacttcag   240
tggtgctggt gggataggag ttttttcaga gagttcttca gtagcatcta agttgagctc   300
caaaagtgaa aaagagctga aaacagaag aaagaaaag aaacagaaag aacagtctgg   360
agaagaagag aaaatgaca gagtcctaaa atcggaatct gaagcagca taagaagaaa    420 aggtttccgt ttttccttgg aaggaagtag gctgacatat gaaaagagat tttcttctcc   480
acaccaggta aaaatattaa attacatgaa ttgtgttctc ataaatttt taaaagaata   540 tgccagaatt taatggagag aaaaccgcct tccacctgga tggcacaatg ctttcagagt   600
agtgatgatt atcaagtgtt ttggctatca cttcagagaa tttgtgagtt ttgcaacttt   660
ttggaatccc aggaaggaaa ttttagatcc ctctgggttt ggaaaaattt g            711

<210> SEQ ID NO 49
<211> LENGTH: 1026
<212> TYPE: DNA
<213> ORGANISM: Homo sapiens

<400> SEQUENCE: 49
ttatggggac acttctgact atgttgaggt gtgggtaaag taggagaaaa gagagcagaa     60
```

```
gatggaaaat ggaggaagga gaaaaagcga gagtgaaata gaaaaggtga accttgtaga    120
aagtgccaaa atgccaccag cagtcatcag aggggtgctt tcttccacat gtccaatgac    180
ttatccttga gtaagtcaat gactatgaca caatgaatca aattctgttt ttcagaatgc    240
cagctcttaa ctctcttcat ctcattttg tttcttttct tgttattcat agtccttact     300
gagcatccgt ggctcccttt tctctccaag acgcaacagt agggcgagcc ttttcagctt    360
cagaggtcga gcaaaggaca ttggctctga gaatgacttt gctgatgatg agcacagcac    420
ctttgaggac aatgacagcc gaagagactc tctgttcgtg ccgcacagac atggagaacg    480
gcgccacagc aatgtcagcc aggccagccg tgcctccagg gtgctcccca tcctgcccat    540
gaatgggaag atgcatagcg ctgtggactg caatggtgtg gtctccctgg tcggggccc     600 ttctaccctc acatctgctg ggcagctcct accagaggtg aggccaacyy magattgcag    660
ctgatgtgaa gagagttgtg actggtgcag gcaggagtgy ttttccattt mcacatctaa    720
gaatttkttg agtttsttgc ccaaaggctg ggagtttgtt caatcaagct gttaactgtc    780
ttgtgaaact sttctattca gactttycta caaagtaatt aaaaacctag gttggctgtc    840
agagaatata attagamgtm atctttcatc ayyattacta tggtatgaaa ctcgccaaaa    900
agcaaagcaa caatttatca agcataatgt tygaytaata tagttaaatt aaatccaagg    960
aaattaatgc tcacaaatta aataaatact taaggatttt gtgattgttg ttcatttaaa    1020
aggaga                                                               1026

<210> SEQ ID NO 50
<211> LENGTH: 601
<212> TYPE: DNA
<213> ORGANISM: Homo sapiens

<400> SEQUENCE: 50
ataggaaagc ccaccttgac aaacccaggg ctccccaaaa gctgaaaatc tgacagactt     60
taaacaaccc ccaaataatt atcattccaa caatatctta gtgagctttt tacatctgag    120
aaagcatggt gtatatttag ttaaataaca cctgttgtag gaatgctttg ggctttgctg    180 cttttcaaaaa tagtggttat ttcatctgaa attctacttc tagggcacaa ctactgaaac    240
agaaataaga aagagacggt ccagttctta tcatgtttcc atggattat tggaagatcc     300 tacatcaagg caaagagcaa tgagtatagc cagtattttg accaacacca tggaaggtat    360
gttaaaagtc ctgcgtcaca gttacttggt gctttcctaa tgatgaaaaa cacttcataa    420
atttcaataa aatacttcct gacttgatat tgtatcatta ttacacattt tactaaataa    480
cagtaaaatc cgtgcataac tcatggattc atatattcca cagattttt ttttttatat     540 ttagcctgta gaaagctgct gcaaatgtaa ggtatatttg aacaccactt tcataactta    600
a                                                                     601

<210> SEQ ID NO 51
<211> LENGTH: 645
<212> TYPE: DNA
<213> ORGANISM: Homo sapiens

<400> SEQUENCE: 51
gcttactagc ctttctgtac tgatcctttc tatgacagca aacccattgt aaaatttcc      60 ctgttcctcc agcagattaa cccataatat cttttaacaa ctttagattt tttaaattcc    120
ttttaattta aaccaaatct gcttaataga aagtaagcag ttttcatgag gattctaact    180 tttttcttc cagaacttga agaatccaga cagaaatgcc caccatgctg gtataaattt     240
```

```
gctaatatgt gtttgatttg ggactgttgt aaaccatggt taaaggtgaa acaccttgtc    300
aacctggttg taatggaccc atttgttgac ctggccatca ccatctgcat tgtcttaaat    360
acactcttca tggctatgga gcactatccc atgacggagc agttcagcag tgtactgtct    420
gttggaaacc tggtaagcct cactgagagt ttctcttcct cttgaaagag tttataattg    480
ccttagtgaa ttttacatat tgctctcaaa ttaaatatca actaattggc catgtatatc    540
ttgacatcaa atgtttagca tccctttttaa ataacaaaaa aatgttgcta ccatagtgca    600
aaagagtcaa agaatttatg tacaatttga tttagaattg aattt                    645

<210> SEQ ID NO 52
<211> LENGTH: 485
<212> TYPE: DNA
<213> ORGANISM: Homo sapiens

<400> SEQUENCE: 52
tggcccaaac caattttaa atcaggaatt taatttwtat attgttggga gttaaattaa     60
gttgctcaat aattattcgt gtttcaakas tatttgctca tataatgaac tacacttctc    120
atttaggtct tcacagggat cttcacagca gaaatgtttc tcaagataat tgccatggat    180
ccatattatt actttcaaga aggctggaat attttgatg gttttattgt gagccttagt     240
ttaatggaac ttggtttggc aaatgtggaa ggattgtcag ttctccgatc attccggctg    300
gtaaattaac tgggagtgtt cataaaatgt actttrtaat taattagtct tcattctcat    360
ctagtaaaaa tggcaagatt tcccatcatt ataatatatt tgaatacctt ctaaaacaga    420
ttggattgcc ataccaccaa atggtagttt cttcttcatc atagctttaa taaagttcac    480
ttaaa                                                                485

<210> SEQ ID NO 53
<211> LENGTH: 602
<212> TYPE: DNA
<213> ORGANISM: Homo sapiens

<400> SEQUENCE: 53
acagatttcc tcctgtgtcc atgtgactaa cccattgtgc acatgtaccc taaaaattag    60
tatataataa taaataaaa taaaaataaa aataaaaaaa taaaaataaa ataaaattgc     120 agatttttt agaaatgcag agattaacac tgttcttgct tttatttcca gctccgagtt     180
ttcaagttgg caaatcttg gccaactcta aatatgctaa ttaagatcat tggcaattct    240
gtgggggctc taggaaacct caccttggta ttggccatca tcgtcttcat ttttgctgtg    300
gtcggcatgc agctctttgg taagagctac aaagaatgtg tctgcaagat ttccaatgat    360
tgtgaactcc cacgctggca catgcatgac ttttttccact ccttcctgat cgtgttccgc    420
gtgctgtgtg gagagtggat agagaccatg tgggactgta tggaggtcgc tggccaaacc    480
atgtgcctta ctgtcttcat gatggtcatg gtgattggaa atctagtggt atgtagcaaa    540
aacattttcc tcattttcat taaaaataat gtaatcatta aaaagtgttc aactgaagaa    600
ta                                                                   602

<210> SEQ ID NO 54
<211> LENGTH: 803
<212> TYPE: DNA
<213> ORGANISM: Homo sapiens

<400> SEQUENCE: 54
gtttcattta gcaatgattt cagtattttc tgcaatgact aataagcaaa tagtgataat    60
```

```
agtattattt tatattgacc aagcatttt atttcattca cttttttca gaatagtgta    120 tcatgaatta gcagaaatgc atgttagaat aaaataaggt gtcaagaaca atcttagaaa   180
actaatgatg gaaagcaatt gaagcaatag aatgttttga tcacctgttt ttcctgctgt   240
gtttcaggtt ctgaacctct tcttggcctt gcttttgagt tccttcagtt ctgacaatct   300
tgctgccact gatgatgata acgaaatgaa taatctccag attgctgtgg gaaggatgca   360
gaaaggaatc gattttgtta aaagaaaaat acgtgaattt attcagaaag cctttgttag   420
gaagcagaaa gctttagatg aaattaaacc gcttgaagat ctaaataata aaaaagacag   480
ctgtatttcc aaccatacca ccatagaaat aggcaaagac ctcaattatc tcaaagacgg   540
aaatggaact actagtggca taggcagcag tgtagaaaaa tatgtcgtgg atgaaagtga   600
ttacatgtca tttataaaca accctagcct cactgtgaca gtaccaattg ctgttggaga   660
atctgacttt gaaaatttaa atactgaaga attcagcagc gagtcagata tggaggaaag   720
caaagaggta aaatgttaaa taggagata ttttggtgta tataatctgt gttaaatatc    780
aggtgtttaa tgcgtgtctc tgt                                           803
```

<210> SEQ ID NO 55
<211> LENGTH: 615
<212> TYPE: DNA
<213> ORGANISM: Homo sapiens
<220> FEATURE:
<221> NAME/KEY: misc_feature
<222> LOCATION: (90)..(90)
<223> OTHER INFORMATION: n = a, c, t or g
<220> FEATURE:
<221> NAME/KEY: misc_feature
<222> LOCATION: (378)..(386)
<223> OTHER INFORMATION: n = a, c, t or g

<400> SEQUENCE: 55

```
atctctatac taggctcaaa cagaagttat ttccgttgtt agcaccatat ttttaaaaga    60
aaaaaaaata ctatggtgtt gtatctaatn ttgtgacccc tgacctttac caaagcggat   120
tggcattatg tttaagttct taattacaga tcaagaaaaa tgcatacaga agatggggg   180 gggcacacct aattaatttt tatatttaga ttaaagaaaa taattaaatg tgttttttg    240 tgggattgat tttcagaagc taaatgcaac tagttcatct gaaggcagca cggttgatat   300
tggagctccc gccgagggag aacagcctga ggttgaacct gaggaatccc ttgaacctga   360
agcctgtttt acagaagnnn nnnnnaagc aaaacaataa catatgtggt cttgagtatc    420
ctcttttcta cccatttttt cctatttatt taaatgtctg tttatttgtc taccatctag   480
ttcatctatc tatctgtatc tatctatcta tctatctatc tagtaatcat ctatacctat   540
ccaacaactg tacatttatt tgttttttt ttttgcattt gctgtttgaa aaaaatgca     600 acgttttaaa ggcaa                                                    615
```

<210> SEQ ID NO 56
<211> LENGTH: 400
<212> TYPE: DNA
<213> ORGANISM: Homo sapiens

<400> SEQUENCE: 56

```
gatagctttt gtaagcggaa gctatcttaa aaattaatgt tatttacaat gtattatcag    60
gtaataatgt aaatgaatct cccaccaaca caaatatacc taatcaaaga gtaatttttt   120
gtcttcattt ttttcccaca tattttagac tgtgtacgga agttcaagtg ttgtcagata   180
agcatagaag aaggcaaagg gaaactctgg tggaatttga ggaaaacatg ctataagata   240
```

```
gtggagcaca attggttcga aaccttcatt gtcttcatga ttctgctgag cagtggggct    300
ctggtaggtg atgcatgatc cactccttca cctttcatct gaaatctttt cccttttccct   360 tcaatcaact catattaccc acttttaaat taaggtgttt                          400
```

```
<210> SEQ ID NO 57
<211> LENGTH: 560
<212> TYPE: DNA
<213> ORGANISM: Homo sapiens

<400> SEQUENCE: 57
aaattactga aacccttggt tgactgaaat gcccagtcag cagtcattta tgatcagata    60
atgataaagt aaaattcagc catgggaaac attaaacctt ccagccttag gcacctgata   120
agagcttgca tcgtttcctt ttttaagaaa tcatcaatta gagactgttt ctgatcataa   180
aatttaatag aattttttga cttacaggcc tttgaagata tatacattga gcagcgaaaa   240
accattaaga ccatgttaga atatgctgac aaggttttca cttacatatt cattctggaa   300
atgctgctaa agtgggttgc atatggtttt caagtgtatt ttaccaatgc tggtgctgg    360 ctagacttcc tgattgttga tgtgagtatg ctgcactttg ctgctttatt cattggcata   420
tatgtaatag ttctagcaat ggtgcctgac acagtgtagg cactcagtaa cactgtatca   480
gcccaaatat aaattatgtt tctcatttca cagtgagagg atgcctcaaa acatttttta   540
ccaatttaaa tacatataca                                               560
```

```
<210> SEQ ID NO 58
<211> LENGTH: 480
<212> TYPE: DNA
<213> ORGANISM: Homo sapiens

<400> SEQUENCE: 58
aaattcttag gccttttcccc aaacttacta agtcagactc tgctattggt gtttttaaca   60
agacccctgg gtgattttga aactcatgaa agttcgagaa ttactgattc attgcataga   120
gcaaggctga actgtgtaga catttttata tgtaaataag aaaattgtgt tgcttttttct  180 gtataggtct cactggttag cttaactgca aatgccttgg gttactcaga acttggtgcc   240
atcaaatccc tcagaacact aagagctctg aggccactga gagctttgtc ccggtttgaa   300
ggaatgaggg taagactgaa tgccttagag tttgtcagaa ttattattga gagcagactg   360
acactttgta ccatggaaat gtcaaattta tggagaattt gtgtcttaca cattcatact   420
gacatagcta atcaatcaaa ataatatttt accagatgcc cataatactt ggcactgctg   480
```

```
<210> SEQ ID NO 59
<211> LENGTH: 640
<212> TYPE: DNA
<213> ORGANISM: Homo sapiens

<400> SEQUENCE: 59
taattttaaa attcttagtt ggagctacca gagtctagtt tctacccaat attcaacttt    60
gaaacagatt ttttttaatca tttgactgtt cttttaataa tgtttaaaaa taagtaaata   120
tttgttgttg gcttttcact tatttttcct tctcatcctg tgccaggttg ttgtaaatgc   180
tcttttagga gccattccat ctatcatgaa tgtacttctg gtttgtctga tcttttggct   240
aatattcagt atcatgggag tgaatctctt tgctggcaag ttttaccatt gtattaatta   300
caccactgga gagatgtttg atgtaagcgt ggtcaacaac tacagtgagt gcaaagctct   360
cattgagagc aatcaaactg ccaggtggaa aaatgtgaaa gtaaactttg ataacgtagg   420
```

```
acttggatat ctgtctctac ttcaagtagt aagtaatcac tttattattt tccatgatgt      480
gtaattaaaa tgagtctaaa gttttcttc ctcataatga gatatccacc tgttagaatg       540
gctattatca aacagataaa tgacaataaa tgctggcaag aatgtgaaga aaagggaacc      600
cttgtacatt gttggcaggg atgtaaatta gtatagcttt                            640

<210> SEQ ID NO 60
<211> LENGTH: 480
<212> TYPE: DNA
<213> ORGANISM: Homo sapiens

<400> SEQUENCE: 60
atttgaagta ttttcaatgc atatcgcaaa acattgcccc aaaagtgaat acaaatttca       60
agcttattta tatgcctgta ttgaatacat gtcaaataga attttgatca attattcaat      120 ttatttcta aaattataat tttgggaaaa agaaaatga tatgactttt cttacaggcc        180
acgtttaagg gatggatgga tattatgtat gcagctgttg attcacgaaa tgtaagtcta      240
gttagaggga aattgtttag tttgattaaa tgtatatttc tacaatattg taatttagtg      300
atattgtcaa taaaataaaa ttatgtgctt aatttataaa acccatctat attataagga      360
taaaatattt aatcatacta tttctttcaa aattatcata ggatgatttt ctctaatcac      420
tctgtatctt ttaacatatc tttctagta tttagcaagg cacctgacac aaaactttat      480

<210> SEQ ID NO 61
<211> LENGTH: 366
<212> TYPE: DNA
<213> ORGANISM: Homo sapiens

<400> SEQUENCE: 61
taaaacatgc ttagataatt aaaaactcac tgatgtactt tttgtgaaac aagtactaga       60
tataatggtt acaattcttc atattcttta ggtagaatta caacccaagt atgaagacaa      120
cctgtacatg tatctttatt ttgtcatctt tattatttt ggttcattct ttaccttgaa       180
tcttttcatt ggtgtcatca tagataactt caaccaacag aaaaagaaga taagtatatt      240
aaaacttcat ccttgctctg aaatatgaac taaatatttc atactctttc ctttagcctc      300
caaaatgcaa tcaccaaaaa aagaatataa aattcagaaa ttattttgag acatttgata      360
atcgat                                                                 366

<210> SEQ ID NO 62
<211> LENGTH: 560
<212> TYPE: DNA
<213> ORGANISM: Homo sapiens

<400> SEQUENCE: 62
tcgataagct tttaagcaat taataattca gatagcatgt ttttgatatt tttagtctag       60
aaatatgact aatatggcat aatttatata ttgaataaag gcatctctat aaatacagat      120
attagtaaca atagaatgaa atgtgggagc caatttttcac atgattacta aggtggattt     180
tatagccagc aaagaacaca atttaacaa gtgttgcttt catttcttta ctttggaggt      240
caagacattt ttatgacaga agaacagaag aaatactaca atgcaatgaa aaaactgggt     300
tcaaagaaac cacaaaaacc catacctcga cctgctgtaa gaataacata tttcattgc      360 ctgttaaaac tatattacct aaccgtttca cagcccgaat ttctagaaac tagttatttt    420
tgtggatttg taacacaaag ttttttacct taacaatggg actagctagc ctaaatagct    480
tgaaaaatgt actttacata tataatatgt ataaattata taatgcataa catatttat     540
```

```
atgtaaacat ataaaataca                                            560

<210> SEQ ID NO 63
<211> LENGTH: 650
<212> TYPE: DNA
<213> ORGANISM: Homo sapiens

<400> SEQUENCE: 63
gttttgcaag gaattttttt ttttgtaaaa tgttgtgagg attaaagatg tgtttttata    60
aaagctacat tttttgttgc tttcttaaaa tcagaagaat tgaattcgat ttttttttaag  120 gtttctaatg gaacttttac atattatttg ttccagaaca aattccaagg aatggtcttt  180
gattttgtaa ccaaacaagt ctttgatatc agcatcatga tcctcatctg ccttaacatg  240
gtcaccatga tggtggaaac cgatgaccag agtcaagaaa tgacaaacat tctgtactgg  300
attaatctgg tgtttattgt tctgttcact ggagaatgtg tgctgaaact gatctctctt  360
cgttactact atttcactat tggatggaat attttttgatt ttgtggtggt cattctctcc  420
attgtaggta agaagaggtg ctttttattca gttaaggaat atagtggtaa aaatatgtgt  480
tttaaaactt tagaggtgtt tttcactaat cttttctcatt catcccaaac tcccaaataa  540
aaatctaata gtccattgtt ttagttttag tttgccatttt ctctaattgc atgctgtgct  600
tgaaatgatg agtggaatac aaggaattta tattttcagc tttcatttat              650

<210> SEQ ID NO 64
<211> LENGTH: 3700
<212> TYPE: DNA
<213> ORGANISM: Homo sapiens

<400> SEQUENCE: 64
aatgttataa caccaaacat accagtttca ttttgctcaa caaacattgc agattatttg    60
catatataca tgtacctaac tgtcctgttc acattttgta aaactaatgt acttatgtaa  120
actttcattt gctactatta agtataacaa tattttttgtt atttgttgat tttctacagg  180
aatgtttctg gctgaactga tagaaaagta ttttgtgtcc cctaccctgt tccgagtgat  240
ccgtcttgcc aggattggcc gaatcctacg tctgatcaaa ggagcaaagg ggatccgcac  300
gctgctcttt gctttgatga tgtcccttcc tgcgttgttt aacatcggcc tcttctttt  360 cctggtcatg ttcatctacg ccatctttgg gatgtccaat tttgcctatg ttaagaggga  420
agttgggatc gatgacatgt tcaactttga gacctttggc aacagcatga tctgcctgtt  480
ccaaattaca acctctgctg gctgggatgg attgctagca cctattctta atagtggacc  540
tccagactgt gaccctgaca agatcacccc tggaagctca gttaaaggag actgtgggaa  600
cccatctgtt gggattttct tttttgtcag ttacatcatc atatccttcc tggttgtggt  660
gaacatgtac atcgcggtca tcctggagaa cttcagtgtt gctactgaag aaagtgcaga  720
gcctctgagt gaggatgact tgagatgtt ctatgaggtt gggagaagt tgatcccga    780 tgcgacccag tttatagagt ttgccaaact ttctgatttt gcagatgccc tggatcctcc  840
tcttctcata gcaaaaccca acaaagtcca gctcattgcc atggatctgc ccatggtgag  900
tggtgaccgg atccactgtc ttgacatctt atttgctttt acaaagcgtg ttttgggtga  960
gagtggagag atggatgccc ttcgaataca gatggaagag cgattcatgg catcaaaccc 1020
ctccaaagtc tcttatgagc ccattacgac cacgttgaaa cgcaaacaag aggaggtgtc 1080
tgctattatt atccagagggg cttacagacg ctacctcttg aagcaaaaag ttaaaaaggt 1140
atcaagtata tacaagaaag acaaaggcaa agaatgtgat ggaacaccca tcaaagaaga 1200
```

```
tactctcatt gataaactga atgagaattc aactccagag aaaaccgata tgacgccttc   1260
caccacgtct ccaccctcgt atgatagtgt gaccaaacca gaaaagaaa aatttgaaaa    1320 agacaaatca gaaaaggaag acaaagggaa agatatcagg gaaagtaaaa agtaaaaaga   1380
aaccaagaat tttccatttt gtgatcaatt gtttacagcc cgtgatggtg atgtgtttgt   1440
gtcaacagga ctcccacagg aggtctatgc caaactgact gttttttacaa atgtatactt  1500 aaggtcagtg cctataacaa gacagagacc tctggtcagc aaactggaac tcagtaaact   1560
ggagaaatag tatcgatggg aggtttctat tttcacaacc agctgacact gctgaagagc   1620
agaggcgtaa tggctactca gacgatagga accaatttaa aggggggagg gaagttaaat   1680
ttttatgtaa attcaacatg tgacacttga aatagtaat tgtcaccagt gtttatgttt    1740
taactgccac acctgccata tttttacaaa acgtgtgctg tgaatttatc acttttcttt   1800
ttaattcaca ggttgtttac tattatatgt gactatttt gtaaatgggt tgtgtttgg     1860 ggagagggat taaagggagg gaattctaca tttctctatt gtattgtata actggatata   1920
ttttaaatgg aggcatgctg caattctcat tcacacataa aaaaatcaca tcacaaaagg   1980
gaagagttta cttcttgttt caggatgttt ttagattttt gaggtgctta aatagctatt   2040
cgtattttta aggtgtctca tccagaaaaa atttaatgtg cctgtaaatg ttccatagaa   2100
tcacaagcat taaagagttg ttttattttt acataaccca ttaaatgtac atgtatatat    2160
gtatatatgt atatgtgcgt gtatatacat atatatgtat acacacatgc acacacagag   2220
atatacacat accattacat tgtcattcac agtcccagca gcatgactat cacattttg    2280 ataagtgtcc tttggcataa aataaaaata tcctatcagt cctttctaag aagcctgaat   2340
tgaccaaaaa acatccccac caccacttta taaagttgat tctgctttat cctgcagtat   2400
tgtttagcca tcttctgctc ttggtaaggt tgacatagta tatgtcaatt taaaaaataa   2460
aagtctgctt tgtaaatagt aattttaccc agtggtgcat gtttgagcaa acaaaaatga   2520
tgatttaagc acactactta ttgcatcaaa tatgtaccac agtaagtata gtttgcaagc   2580
tttcaacagg taatatgatg taattggttc cattatagtt tgaagctgtc actgctgcat   2640
gtttatcttg cctatgctgc tgtatcttat tccttccact gttcagaagt ctaatatggg   2700
aagccatata tcagtggtaa agtgaagcaa attgttctac caagacctca ttcttcatgt   2760
cattaagcaa taggttgcag caaacaagga agagcttctt gctttttatt cttccaacct   2820
taattgaaca ctcaatgatg aaaagcccga ctgtacaaac atgttgcaag ctgcttaaat   2880
ctgtttaaaa tatatggtta gagttttcta agaaaatata aatactgtaa aaagttcatt   2940
ttattttatt tttcagcctt ttgtacgtaa aatgagaaat taaagtatc ttcaggtgga    3000 tgtcacagtc actattgtta gtttctgttc ctagcacttt taaattgaag cacttcacaa   3060
aataagaagc aaggactagg atgcagtgta ggtttctgct tttttattag tactgtaaac   3120
ttgcacacat ttcaatgtga aacaaatctc aaactgagtt caatgtttat ttgctttcaa   3180
tagtaatgcc ttatcattga aagaggctta aagaaaaaaa aaatcagctg atactcttgg   3240
cattgcttga atccaatgtt tccacctagt cttttattc agtaatcatc agtcttttcc    3300
aatgtttgtt tacacagata gatcttattg acccatatgg cactagaact gtatcagata   3360
taatatggga tcccagcttt ttttcctctc ccacaaaacc aggtagtgaa gttatattac   3420
cagttacagc aaaatacttt gtgtttcaca agcaacaata aatgtagatt ctttatactg   3480
aagctattga cttgtagtgt gttggtgaat gcatgcagga agatgctgtt accataaaga   3540 acggtaaaacc acattacaat caagccaaag aataaaggtt cgcttatgta tatgtattta   3600
```

```
attgttgtct tgtttctat ctttgaaatg ccatttaaag gtagatttct atcatgtaaa    3660
aataatctat ctgaaaaaca aatgtaaaga acacacatta                        3700

<210> SEQ ID NO 65
<211> LENGTH: 9112
<212> TYPE: DNA
<213> ORGANISM: Homo sapiens

<400> SEQUENCE: 65
accatagagt gaatctcaga acaggaagcg gaggcataag cagagaggat tctggaaagg     60
tctctttgtt ttcttatcca cagagaaaga aagaaaaaaa attgtaacta atttgtaaac    120
ctctgtggtc aaaaaaaaaa aaaaaaaaaa aagctgaaca gctgcagagg aagacacgtt    180 atacccctaac catcttggat gctgggcttt gttatgctgt aattcataag gctctgtttt    240
atcagagatt atggagcaag aaaactgaag ccaagccaca tcaaggtttg acagggatga    300
gatacctgtc aaggattcat agtagagtgg cttactggga aaggagcaaa gaatctcttc    360
tagggatatt gtaagaataa atgagataat tcacagaagg gacctggagc ttttccggaa    420
aaaggtgctg tgactatcta aggggaaaag ctgagagtct ggaactagcc tatcttccga    480
ggacttagag acaacagtat gggaatttca acgagacgtt tttactttct tttgaccaag    540
attcaaattc tttattccag cccttgataa gtaaataaga aggtaattcg tatgcaagaa    600
gctacacgta attaaatgtg caggatgaaa agatggcaca ggcactgttg gtaccccag    660 gacctgaaag cttccgcctt tttactagag aatctcttgc tgctatcgaa aaacgtgctg    720
cagaagagaa agccaagaag cccaaaaagg aacaagataa tgatgatgag aacaaaccaa    780 agccaaaatag tgacttggaa gctggaaaga accttccatt tatttatgga gacattcctc    840
cagagatggt gtcagagccc tggaggaccc tggatcccta ctatatcaat aagaaaactt    900
ttatagtaat gaataaagga aaggcaattt cccgattcag tgccacctct gccttgtata    960
ttttaactcc actaaaccct gttaggaaaa ttgctabsaa gattttggta cattctttat   1020
tcagcatgct tatcatgtgc actattttga ccaactgtgt attatgacc ttgagcaacc   1080 ctcctgactg gacaaagaat gtagagtaca cattcactgg aatctatacc tttgagtcac   1140
ttataaaaat cttggcaaga gggttttgct tagaagattt tacgtttctt cgtgatccat   1200
ggaactggct ggatttcagt gtcattgtga tggcatatgt gacagagttt gtggacctgg   1260
gcaatgtctc agcgttgaga acattcagag ttctccgagc actgaaaaca atttcagtca   1320
ttccaggttt aaagaccatt gtggggccc tgatccagtc ggtaaagaag ctttctgatg   1380
tgatgatcct gactgtgttc tgtctgagcg tgtttgctct cattgggctg cagctgttca   1440
tgggcaatct gaggaataaa tgtttgcagt ggccccaag cgattctgct tttgaaacca   1500
acaccacttc ctactttaat ggcacaatgg attcaaatgg gacatttgtt aatgtaacaa   1560
tgagcacatt taactggaag gattacattg gagatgacag tcactttta gttttggatg   1620 ggcaaaaaga cccttactc tgtgaaaatg gctcagatgc aggccagtgt ccagaaggat   1680
acatctgtgt gaaggctggt cgaaacccca actatggcta cacaagcttt gacaccttta   1740
gctgggcttt cctgtctcta tttcgactca tgactcaaga ctactgggaa aatctttacc   1800
agttgacatt acgtgctgct gggaaaacat acatgatatt ttttgtcctg gtcatttct   1860 tgggctcatt ttatttggtg aatttgatcc tggctgtggt ggccatggcc tatgaggggc   1920
agaatcaggc caccttggaa gaagcagaac aaaaagaggc cgaatttcag cagatgctcg   1980
aacagcttaa aaagcaacag gaagaagctc aggcagttgc ggcagcatca gctgcttcaa   2040
```

```
gagatttcag tggaataggt gggttaggag agctgttgga aagttcttca gaagcatcaa    2100
agttgagttc caaaagtgct aaagaatgga ggaaccgaag gaagaaaaga agacagagag    2160
agcaccttga aggaaacaac aaaggagaga gagacagctt tcccaaatcc gaatctgaag    2220
acagcgtcaa aagaagcagc ttccttttct ccatggatgg aaacagactg accagtgaca    2280
aaaaattctg ctcccctcat cagtctctct tgagtatccg tggctccctg ttttccccaa    2340
gacgcaatag caaaacaagc attttcagtt tcagaggtcg ggcaaaggat gttggatctg    2400
aaaatgactt tgctgatgat gaacacagca catttgaaga cagcgaaagc aggagagact    2460
cactgtttgt gccgcacaga catggagagc gacgcaacag taacggcacc accactgaaa    2520
cggaagtcag aaagagaagg ttaagctctt accagatttc aatggagatg ctggaggatt    2580
cctctggaag gcaaagagcc gtgagcatag ccagcattct gaccaacaca atggaagaac    2640
ttgaagaatc tagacagaaa tgtccgccat gctggtatag atttgccaat gtgttcttga    2700
tctgggactg ctgtgatgca tggttaaaag taaaacatct tgtgaattta attgttatgg    2760
atccatttgt tgatcttgcc atcactattt gcattgtctt aaatacccctc tttatggcca    2820 tggagcacta ccccatgact gagcaattca gtagtgtgtt gactgtagga aacctggtct    2880
ttactgggat ttttacagca gaaatggttc tcaagatcat tgccatggat ccttattact    2940
atttccaaga aggctggaat atctttgatg gaattattgt cagcctcagt ttaatggagc    3000
ttggtctgtc aaatgtggag ggattgtctg tactgcgatc attcagactg cttagagttt    3060
tcaagttggc aaaatcctgg cccacactaa atatgctaat taagatcatt ggcaattctg    3120
tgggggctct aggaaacctc accttggtgt tggccatcat cgtcttcatt tttgctgtgg    3180
tcggcatgca gctcttttgg aagagctaca agaatgtgt ctgcaagatc aatgatgact    3240
gtacgctccc acggtggcac atgaacgact tcttccactc cttcctgatt gtgttccgcg    3300
tgctgtgtgg agagtggata gagaccatgt gggactgtat ggaggtcgct ggccaaacca    3360
tgtgccttat tgttttcatg ttggtcatgg tcattggaaa ccttgtggtt ctgaacctct    3420 ttctggccttt attgttgagt tcatttagct cagacaacct tgctgctact gatgatgaca    3480
atgaaatgaa taatctgcag attgcagtag gaagaatgca aagggaatt gattatgtga    3540 aaaataagat gcgggagtgt ttccaaaaag ccttttttag aaagccaaaa gttatagaaa    3600
tccatgaagg caataagata gacagctgca tgtccaataa tactggaatt gaaataagca    3660
aagagcttaa ttatcttaga gatgggaatg gaaccaccag tggtgtaggt actggaagca    3720
gtgttgaaaa atacgtaatc gatgaaaatg attatatgtc attcataaac aaccccagcc    3780
tcaccgtcac agtgccaatt gctgttggag agtctgactt tgaaaactta aatactgaag    3840
agttcagcag tgagtcagaa ctagaagaaa gcaaggagaa attaaatgca accagctcat    3900
ctgaaggaag cacagttgat gttgttctac cccgagaagg tgaacaagct gaaactgaac    3960
ccgaagaaga ccttaaaccg gaagcttgtt ttactgaagg atgtattaaa aagtttccat    4020
tctgtcaagt aagtacagaa gaaggcaaag ggaagatctg gtggaatctt cgaaaaacct    4080
gctacagtat tgttgagcac aactggttg agactttcat tgtgttcatg atccttctca    4140
gtagtggtgc attggccttt gaagatatat acattgaaca gcgaaagact atcaaaacca    4200
tgctagaata tgctgacaaa gtcttttacct atatattcat tctggaaatg cttctcaaat    4260
gggttgctta tggatttcaa acatatttca ctaatgcctg gtgctggcta gatttcttga    4320
tcgttgatgt ttctttggtt agcctggtag ccaatgctct tggctactca gaactcggtg    4380
ccatcaaatc attacggaca ttaagagctt taagacctct aagagcctta tcccggtttg    4440
```

```
aaggcatgag ggtggttgtg aatgctcttg ttggagcaat tccctctatc atgaatgtgc   4500
tgttggtctg tctcatcttc tggttgatct ttagcatcat gggtgtgaat ttgtttgctg   4560
gcaagttcta ccactgtgtt aacatgacaa cgggtaacat gtttgacatt agtgatgtta   4620
acaatttgag tgactgtcag gctcttggca agcaagctcg gtggaaaaac gtgaaagtaa   4680
actttgataa tgttggcgct ggctatcttg cactgcttca agtggccaca tttaaaggct   4740
ggatggatat tatgtatgca gctgttgatt cacgagatgt taaacttcag cctgtatatg   4800
aagaaaatct gtacatgtat ttatactttg tcatctttat catctttggg tcattcttca   4860
ctctgaatct attcattggt gtcatcatag ataacttcaa ccagcagaaa aagaagtttg   4920
gaggtcaaga catctttatg acagaggaac agaaaaaata ttacaatgca atgaagaaac   4980
ttggatccaa gaaacctcag aaacccatac ctcgcccagc aaacaaattc caaggaatgg   5040
tctttgattt tgtaaccaga caagtctttg atatcagcat catgatcctc atctgcctca   5100
acatggtcac catgatggtg gaaacggatg accaggggcaa atacatgacc ctagttttgt   5160
cccggatcaa cctagtgttc attgttctgt tcactggaga atttgtgctg aagctcgtct   5220
ccctcagaca ctactacttc actataggct ggaacatctt tgactttgtg gtggtgattc   5280
tctccattgt aggtatgttt ctggctgaga tgatagaaaa gtattttgtg tcccctacct   5340
tgttccgagt gatccgtctt gccaggattg gccgaatcct acgtctgatc aaaggagcaa   5400
aggggatccg cacgctgctc tttgctttga tgatgtccct tcctgcgttg tttaacatcg   5460
gcctcctgct cttcctggtc atgtttatct atgccatctt gggatgtcc aactttgcct   5520 atgttaaaaa ggaagctgga attgatgaca tgttcaactt tgagaccttt ggcaacagca   5580
tgatctgctt gttccaaatt acaacctctg ctggatggga tggattgcta gcacctattc   5640
ttaatagtgc accacccgac tgtgaccctg acacaattca ccctggcagc tcagttaagg   5700
gagactgtgg gaacccatct gttgggattt tcttttttgt cagttacatc atcatatcct   5760
tcctggtggt ggtgaacagt tacatcgcgg tcatcctgga aacttcagt gttgctactg   5820 aagaaagtgc agagccctg agtgaggatg actttgagat gttctatgag gtttgggaaa   5880
agtttgatcc cgatgcgacc cagtttatag agttctctaa actctctgat tttgcagctg   5940
ccctggatcc tcctcttctc atagcaaaac ccaacaaagt ccagcttatt gccatggatc   6000
tgcccatggt cagtggtgac cggatccact gtcttgatat tttatttgcc tttacaaagc   6060 gtgtttggg tgagagtgga gagatggatg ccccttcgaat acagatggaa gacaggttta   6120
tggcatcaaa cccctccaaa gtctcttatg agcctattac aaccactttg aaacgtaaac   6180
aagaggaggt gtctgccgct atcattcagc gtaatttcag atgttatctt ttaaagcaaa   6240
ggttaaaaaa tatatcaagt aactataaca agaggcaat aaagggggagg attgacttac   6300 ctataaaaca agacatgatt attgacaaac tgaatgggaa ctccactcca gaaaaaacag   6360
atgggagttc ctctaccacc tctcctcctt cctatgatag tgtaacaaaa ccagacaagg   6420
aaaagtttga gaaagacaaa ccagaaaaag aaagcaaagg aaaagaggtc agagaaaatc   6480
aaaagtaaaa agaaacaaag aattatcttt gtgatcaatt gtttacagcc tatgaaggta   6540
aagtatatgt gtcaactgga cttcaagagg aggtccatgc caaactgact gttttaacaa   6600
atactcatag tcagtgccta tacaagacag tgaagtgacc tctctgtcac tgcaactctg   6660
tgaagcaggg tatcaacatt gacaagaggt tgctgttttt attaccagct gacactgctg   6720
aggagaaacc caatggctac ctagactata gggatagttg tgcaaagtga acattgtaac   6780
tacaccaaac acctttagta cagtccttgc atccattcta tttttaactt ccatatctgc   6840
```

```
catattttta caaaatttgt tctagtgcat ttccatggtc cccaattcat agtttattca    6900
taatgctatg tcactatttt tgtaaatgag gtttacgttg aagaaacagt atacaagaac    6960
cctgtctctc aaatgatcag acaaaggtgt tttgccagag agataaaatt tttgctcaaa    7020
accagaaaaa gaattgtaat ggctacagtt tcagttactt ccattttcta gatggcttta    7080
attttgaaag tattttagtc tgttatgttt gtttctatct gaacagttat gtgcctgtaa    7140
agtctcctct aatatttaaa ggattatttt tatgcaaagt attctgtttc agcaagtgca    7200
aattttattc taagtttcag agctctatat ttaatttagg tcaaatgctt tccaaaaagt    7260
aatctaataa atccattcta gaaaaatata tctaaagtat tgctttagaa tagttgttcc    7320
actttctgct gcagtattgc tttgccatct tctgctctca gcaaagctga tagtctatgt    7380
caattaaata ccctatgtta tgtaaatagt tattttatcc tgtggtgcat gtttgggcaa    7440
atatatatat agcctgataa acaacttcta ttaaatcaaa tatgtaccac agtgtatgtg    7500
tcttttgcaa gcttccaaca gggatgtatc ctgtatcatt cattaaacat agtttaaagg    7560
ctatcactaa tgcatgttaa tattgcctat gctgctctat tttactcaat ccattcttca    7620
caagtcttgg ttaaagaatg tcacatattg gtgatagaat gaattcaacc tgctctgtcc    7680
attatgtcaa gcagaataat ttgaagctat ttacaaacac ctttactttt gcacttttaa    7740
ttcaacatga gtatcatatg gtatctctct agatttcaag gaaacacact ggatactgcc    7800
tactgacaaa acctattctt catattttgc taaaaatatg tctaaaactt gcgcaaatat    7860
aaataatgta aaaatataat caactttatt tgtcagcatt ttgtacataa gaaaattatt    7920
ttcaggttga tgacatcaca atttatttta ctttatgctt ttgcttttga tttttaatca    7980
caattccaaa cttttgaatc cataagattt ttcaatggat aatttcctaa aataaaagtt    8040
agataatggg ttttatggat ttctttgtta taatatattt tctaccattc caataggaga    8100
tacattggtc aaacactcaa acctagatca ttttctacca actatggttg cctcaatata    8160
acctttatt catagatgtt tttttttatt caacttttgt agtatttacg tatgcagact    8220
agtcttattt ttttaattcc tgctgcacta aagctattac aaatataaca tggactttgt    8280
tcttttagc catgaacaaa gtggcaaagt tgtgcaatta cctaacatga tataaatttt    8340
tgttttttgc acaaaccaaa agtttaatgt taattctttt tacaaaacta tttactgtag    8400
tgtattgaag aactgcatgc agggaattgc tattgctaaa aagaatggtg agctacgtca    8460
ttattgagcc aaaagaataa atttcatttt ttattgcatt tcacttattg gcctctgggg    8520
ttttttgttt ttgttttttg ctgttggcag tttaaaatat atataattaa taaaacctgt    8580
gcttgatctg acatttgtat acataaaagt ttacatgaat tttacaacag actagtgcat    8640
gattcaccaa gcagtactac agaacaaagg caaatgaaaa gcagctttgt gcacttttat    8700
gtgtgcaaag gatcaagttc acatgttcca actttcaggt ttgataataa tagtagtaac    8760
cacctacaat agctttcaat ttcaattaac tcccttggct ataagcatct aaactcatct    8820
tctttcaata taattgatgc tatctcctaa ttacttggtg gctaataaat gttacattct    8880
ttgttactta aatgcattat ataaactcct atgtatacat aaggtattaa tgatatagtt    8940
attgagaatt tatattaact ttttttttcaa gaacccttgg atttatgtga ggtcaaaacc    9000
aaactcttat tctcagtgga aaactccagt tgtaatgcat attttttaaag acaatttgga    9060
tctaaatatg tatttcataa ttctcccata ataaattata taaggtggct aa             9112
```

<210> SEQ ID NO 66
<211> LENGTH: 9112

<212> TYPE: DNA
<213> ORGANISM: Homo sapiens

<400> SEQUENCE: 66

```
accatagagt gaatctcaga acaggaagcg gaggcataag cagagaggat tctggaaagg    60
tctctttgtt ttcttatcca cagagaaaga aagaaaaaaa attgtaacta atttgtaaac   120
ctctgtggtc aaaaaaaaaa aaaaaaaaaa aagctgaaca gctgcagagg aagacacgtt   180
atacccctaac catcttggat gctgggcttt gttatgctgt aattcataag gctctgtttt   240
atcagagatt atggagcaag aaaactgaag ccaagccaca tcaaggtttg acagggatga   300
gatacctgtc aaggattcat agtagagtgg cttactggga aaggagcaaa gaatctcttc   360
tagggatatt gtaagaataa atgagataat tcacagaagg gacctggagc ttttccggaa   420
aaaggtgctg tgactatcta aggggaaaag ctgagagtct ggaactagcc tatcttccga   480
ggacttagag acaacagtat ggaatttca acgagacgtt tttactttct tttgaccaag   540
attcaaattc tttattccag cccttgataa gtaaataaga aggtaattcg tatgcaagaa   600
gctacacgta attaaatgtg caggatgaaa agatggcaca ggcactgttg gtaccccag   660
gacctgaaag cttccgcctt tttactagag aatctcttgc tgctatcgaa aaacgtgctg   720
cagaagagaa agccaagaag cccaaaaagg aacaagataa tgatgatgag aacaaaccaa   780
agccaaatag tgacttggaa gctggaaaga accttccatt tatttatgga gacattcctc   840
cagagatggt gtcagagccc ctggaggacc tggatcccta ctatatcaat aagaaaactt   900
ttatagtaat gaataaagga aaggcaattt cccgattcag tgccacctct gccttgtata   960
ttttaactcc actaaaccct gttaggaaaa ttgctabsaa gattttggta cattctttat  1020
tcagcatgct tatcatgtgc actatttga ccaactgtgt atttatgacc ttgagcaacc  1080
ctcctgactg gacaaagaat gtagagtaca cattcactgg aatctatacc tttgagtcac  1140
ttataaaaat cttggcaaga gggttttgct tagaagattt tacgtttctt cgtgatccat  1200
ggaactggct ggatttcagt gtcattgtga tggcgtatgt aacagaattt gtaagcctag  1260
gcaatgtttc agcccttcga actttcagag tcttgagagc tctgaaaact atttctgtaa  1320
tcccaggttt aaagaccatt gtgggggccc tgatccagtc ggtaaagaag ctttctgatg  1380
tgatgatcct gactgtgttc tgtctgagcg tgtttgctct cattgggctg cagctgttca  1440
tgggcaatct gaggaataaa tgtttgcagt ggccccaag cgattctgct tttgaaacca  1500
acaccacttc ctactttaat ggcacaatgg attcaaatgg acatttgtt aatgtaacaa  1560
tgagcacatt taactggaag gattacattg gagatgacag tcactttat gttttggatg  1620
ggcaaaaaga ccctttactc tgtggaaatg gctcagatgc aggccagtgt ccagaaggat  1680
acatctgtgt gaaggctggt cgaaacccca actatggcta cacaagcttt gacacctta  1740
gctgggcttt cctgtctcta tttcgactca tgactcaaga ctactgggaa aatctttacc  1800
agttgacatt acgtgctgct gggaaaacat acatgatatt ttttgtcctg gtcatttct  1860
tgggctcatt ttatttggtg aatttgatcc tggctgtggt ggccatggcc tatgaggggc  1920
agaatcaggc caccttggaa gaagcagaac aaaaagaggc cgaatttcag cagatgctcg  1980
aacagcttaa aaagcaacag gaagaagctc aggcagttgc ggcagcatca gctgcttcaa  2040
gagatttcag tggaataggt gggttaggag agctgttgga aagttcttca gaagcatcaa  2100
agttgagttc caaagtgctc aaagaatgga ggaaccgaag gaagaaaaga agacagagag  2160
agcaccttga aggaaacaac aaaggagaga gagacagctt tcccaaatcc gaatctgaag  2220
acagcgtcaa aagaagcagc ttccttttct ccatggatgg aaacagactg accagtgaca  2280
```

```
aaaaattctg ctccoctcat cagtctctct tgagtatccg tggctccctg ttttccccaa    2340
gacgcaatag caaaacaagc attttcagtt tcagaggtcg ggcaaaggat gttggatctg    2400
aaaatgactt tgctgatgat gaacacagca catttgaaga cagcgaaagc aggagagact    2460
cactgtttgt gccgcacaga catggagagc gacgcaacag taacggcacc accactgaaa    2520
cggaagtcag aaagagaagg ttaagctctt accagatttc aatggagatg ctggaggatt    2580
cctctggaag gcaaagagcc gtgagcatag ccagcattct gaccaacaca atggaagaac    2640
ttgaagaatc tagacagaaa tgtccgccat gctggtatag atttgccaat gtgttcttga    2700
tctgggactg ctgtgatgca tggttaaaag taaacatct tgtgaattta attgttatgg     2760
atccatttgt tgatcttgcc atcactattt gcattgtctt aaatacctc tttatggcca    2820 tggagcacta ccccatgact gagcaattca gtagtgtgtt gactgtagga aacctggtct    2880
ttactgggat ttttacagca gaaatggttc tcaagatcat tgccatggat ccttattact    2940
atttccaaga aggctggaat atctttgatg gaattattgt cagcctcagt ttaatggagc    3000
ttggtctgtc aaatgtggag ggattgtctg tactgcgatc attcagactg cttagagttt    3060
tcaagttggc aaaatcctgg cccacactaa atatgctaat taagatcatt ggcaattctg    3120
tgggggctct aggaaacctc accttggtgt tggccatcat cgtcttcatt tttgctgtgg    3180
tcggcatgca gctcttttgg aagagctaca agaatgtgt ctgcaagatc aatgatgact    3240
gtacgctccc acggtggcac atgaacgact tcttccactc cttcctgatt gtgttccgcg    3300
tgctgtgtgg agagtggata gagaccatgt gggactgtat ggaggtcgct ggccaaacca    3360
tgtgccttat tgttttcatg ttggtcatgg tcattggaaa ccttgtggtt ctgaacctct    3420
ttctggcctt attgttgagt tcatttagct cagacaacct tgctgctact gatgatgaca    3480
atgaaatgaa taatctgcag attgcagtag aagaatgca aaagggaatt gattatgtga    3540
aaaataagat gcgggagtgt ttccaaaag cctttttag aaagccaaaa gttatagaaa     3600
tccatgaagg caataagata gacagctgca tgtccaataa tactggaatt gaaataagca    3660
aagagcttaa ttatcttaga gatgggaatg gaaccaccag tggtgtaggt actggaagca    3720
gtgttgaaaa atacgtaatc gatgaaaatg attatatgtc attcataaac aaccccagcc    3780
tcaccgtcac agtgccaatt gctgttggag agtctgactt tgaaaactta atactgaag    3840 agttcagcag tgagtcagaa ctagaagaaa gcaaggagaa attaaatgca accagctcat    3900
ctgaaggaag cacagttgat gttgttctac cccgagaagg tgaacaagct gaaactgaac    3960
ccgaagaaga ccttaaaccg gaagcttgtt ttactgaagg atgtattaaa aagtttccat    4020
tctgtcaagt aagtacagaa gaaggcaaag ggaagatctg gtggaatctt cgaaaaacct    4080
gctacagtat tgttgagcac aactggttg agactttcat tgtgttcatg atccttctca    4140
gtagtggtgc attggccttt gaagatatat acattgaaca gcgaaagact atcaaaacca    4200
tgctagaata tgctgacaaa gtctttacct atatattcat tctggaaatg cttctcaaat    4260
gggttgctta tggatttcaa acatatttca ctaatgcctg gtgctggcta gatttcttga    4320
tcgttgatgt ttctttggtt agcctggtag ccaatgctct tggctactca gaactcggtg    4380
ccatcaaatc attacggaca ttaagagctt taagacctct aagagcctta tcccggtttg    4440
aaggcatgag ggtggttgtg aatgctcttg ttggagcaat tccctctatc atgaatgtgc    4500
tgttggtctg tctcatcttc tggttgatct ttagcatcat gggtgtgaat ttgtttgctg    4560
gcaagttcta ccactgtgtt aacatgacaa cgggtaacat gtttgacatt agtgatgtta    4620
acaatttgag tgactgtcag gctcttggca agcaagctcg gtggaaaaac gtgaaagtaa    4680
```

```
actttgataa tgttggcgct ggctatcttg cactgcttca agtggccaca tttaaaggct    4740
ggatggatat tatgtatgca gctgttgatt cacgagatgt taaacttcag cctgtatatg    4800
aagaaaatct gtacatgtat ttatactttg tcatctttat catctttggg tcattcttca    4860
ctctgaatct attcattggt gtcatcatag ataacttcaa ccagcagaaa agaagtttg     4920 gaggtcaaga catctttatg acagaggaac agaaaaaata ttacaatgca atgaagaaac    4980
ttggatccaa gaaacctcag aaacccatac ctcgcccagc aaacaaattc caaggaatgg    5040
tctttgattt tgtaaccaga caagtctttg atatcagcat catgatcctc atctgcctca    5100
acatggtcac catgatggtg gaaacggatg accagggcaa atacatgacc ctagttttgt    5160
cccggatcaa cctagtgttc attgttctgt tcactggaga atttgtgctg aagctcgtct    5220
ccctcagaca ctactacttc actataggct ggaacatctt tgactttgtg gtggtgattc    5280
tctccattgt aggtatgttt ctggctgaga tgatagaaaa gtattttgtg tccctacct    5340 tgttccgagt gatccgtctt gccaggattg ccgaatcct acgtctgatc aaaggagcaa    5400
aggggatccg cacgctgctc tttgctttga tgatgtccct tcctgcgttg tttaacatcg    5460
gcctcctgct cttcctggtc atgtttatct atgccatctt gggatgtcc aactttgcct    5520 atgttaaaaa ggaagctgga attgatgaca tgttcaactt tgagaccttt ggcaacagca    5580
tgatctgctt gttccaaatt acaacctctg ctggatggga tggattgcta gcacctattc    5640
ttaatagtgc accacccgac tgtgaccctg acacaattca ccctggcagc tcagttaagg    5700
gagactgtgg gaacccatct gttgggattt tctttttgt cagttacatc atcatatcct    5760
tcctggtggt ggtgaacagt tacatcgcgg tcatcctgga aacttcagt gttgctactg    5820 aagaaagtgc agagccctg agtgaggatg actttgagat gttctatgag gtttgggaaa    5880
agtttgatcc cgatgcgacc cagtttatag agttctctaa actctctgat tttgcagctg    5940
ccctggatcc tcctcttctc atagcaaaac ccaacaaagt ccagcttatt gccatggatc    6000
tgcccatggt cagtggtgac cggatccact gtcttgatat tttatttgcc tttacaaagc    6060
gtgttttggg tgagagtgga gagatggatg cccttcgaat acagatggaa acaggtttta    6120
tggcatcaaa cccctccaaa gtctcttatg agcctattac aaccactttg aaacgtaaac    6180
aagaggaggt gtctgccgct atcattcagc gtaattcag atgttatctt ttaaagcaaa    6240
ggttaaaaaa tatatcaagt aactataaca agaggcaat aaaggggagg attgacttac    6300
ctataaaaca agcatgatt attgacaaac tgaatgggaa ctccactcca gaaaaaacag    6360
atgggagttc ctctaccacc tctcctcctt cctatgatag tgtaacaaaa ccagacaagg    6420
aaaagtttga aaagacaaa ccagaaaaag aaagcaaagg aaaagaggtc agagaaaatc    6480
aaaagtaaaa agaaacaaag aattatcttt gtgatcaatt gtttacagcc tatgaaggta    6540
aagtatatgt gtcaactgga cttcaagagg aggtccatgc caaactgact gtttttaacaa    6600 atactcatag tcagtgccta tacaagacag tgaagtgacc tctctgtcac tgcaactctg    6660
tgaagcaggg tatcaacatt gacaagaggt tgctgtttttt attaccagct gacactgctg    6720
aggagaaacc caatggctac ctagactata gggatagttg tgcaaagtga acattgtaac    6780
tacaccaaac acctttagta cagtccttgc atccattcta ttttaactt ccatatctgc    6840 catatttta caaatttgt tctagtgcat ttccatggtc cccaattcat agtttattca    6900
taatgctatg tcactatttt tgtaaatgag gtttacgttg aagaaacagt atacaagaac    6960
cctgtctctc aaatgatcag acaaaggtgt tttgccagag agataaaatt tttgctcaaa    7020
accagaaaaa gaattgtaat ggctacagtt tcagttactt ccatttttcta gatggcttta    7080
```

```
attttgaaag tattttagtc tgttatgttt gtttctatct gaacagttat gtgcctgtaa   7140
agtctcctct aatatttaaa ggattatttt tatgcaaagt attctgtttc agcaagtgca   7200
aattttattc taagtttcag agctctatat ttaatttagg tcaaatgctt tccaaaaagt   7260
aatctaataa atccattcta gaaaaatata tctaaagtat tgctttagaa tagttgttcc   7320
actttctgct gcagtattgc tttgccatct tctgctctca gcaaagctga tagtctatgt   7380
caattaaata ccctatgtta tgtaaatagt tattttatcc tgtggtgcat gtttgggcaa   7440
atatatatat agcctgataa acaacttcta ttaaatcaaa tatgtaccac agtgtatgtg   7500
tcttttgcaa gcttccaaca gggatgtatc ctgtatcatt cattaaacat agtttaaagg   7560
ctatcactaa tgcatgttaa tattgcctat gctgctctat tttactcaat ccattcttca   7620
caagtcttgg ttaaagaatg tcacatattg gtgatagaat gaattcaacc tgctctgtcc   7680
attatgtcaa gcagaataat ttgaagctat ttacaaacac ctttactttt gcacttttaa   7740
ttcaacatga gtatcatatg gtatctctct agatttcaag gaaacacact ggatactgcc   7800
tactgacaaa acctattctt catattttgc taaaaatatg tctaaaactt gcgcaaatat   7860
aaataatgta aaaatataat caactttatt tgtcagcatt ttgtacataa gaaaattatt   7920
ttcaggttga tgacatcaca atttatttta ctttatgctt ttgcttttga ttttaatca    7980 caattccaaa cttttgaatc cataagattt ttcaatggat aatttcctaa aataaaagtt   8040
agataatggg ttttatggat ttctttgtta taatatattt tctaccattc caataggaga   8100
tacattggtc aaacactcaa acctagatca ttttctacca actatggttg cctcaatata   8160 acctttatt catagatgtt ttttttttatt caacttttgt agtatttacg tatgcagact   8220
agtcttattt ttttaattcc tgctgcacta aagctattac aaatataaca tggactttgt   8280 tcttttagc catgaacaaa gtggcaaagt tgtgcaatta cctaacatga tataaatttt   8340
tgttttttgc acaaaccaaa agtttaatgt taattctttt tacaaaacta tttactgtag   8400
tgtattgaag aactgcatgc agggaattgc tattgctaaa aagaatggtg agctacgtca   8460
ttattgagcc aaaagaataa atttcatttt ttattgcatt tcacttattg gcctctgggg   8520 tttttttgttt ttgttttttg ctgttggcag tttaaaatat atataattaa taaaacctgt   8580
gcttgatctg acatttgtat acataaaagt ttacatgaat tttacaacag actagtgcat   8640
gattcaccaa gcagtactac agaacaaagg caaatgaaaa gcagctttgt gcacttttat   8700
gtgtgcaaag gatcaagttc acatgttcca actttcaggt ttgataataa tagtagtaac   8760
cacctacaat agctttcaat ttcaattaac tcccttggct ataagcatct aaactcatct   8820
tctttcaata taattgatgc tatctcctaa ttacttggtg gctaataaat gttacattct   8880
ttgttactta aatgcattat ataaactcct atgtatacat aaggtattaa tgatatagtt   8940
attgagaatt tatattaact ttttttttcaa gaacccttgg atttatgtga ggtcaaaacc   9000
aaactcttat tctcagtgga aaactccagt tgtaatgcat attttttaaag acaatttgga   9060 tctaaatatg tatttcataa ttctcccata ataaattata taaggtggct aa            9112
```

<210> SEQ ID NO 67
<211> LENGTH: 1951
<212> TYPE: PRT
<213> ORGANISM: Homo sapiens
<220> FEATURE:
<221> NAME/KEY: MISC_FEATURE
<222> LOCATION: (122)..(122)
<223> OTHER INFORMATION: Xaa = any amino acid

<400> SEQUENCE: 67

```
Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Glu Asn Lys
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65              70                  75                      80

Asp Pro Tyr Tyr Ile Asn Lys Lys Thr Phe Ile Val Met Asn Lys Gly
                85                  90                  95

Lys Ala Ile Ser Arg Phe Ser Ala Thr Ser Ala Leu Tyr Ile Leu Thr
            100                 105                 110

Pro Leu Asn Pro Val Arg Lys Ile Ala Xaa Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190

Leu Asp Phe Ser Val Ile Val Met Ala Tyr Val Thr Glu Phe Val Asp
    195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
    275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
    355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Gly Gln Asn Gln
```

```
                420             425             430
Ala Thr Leu Glu Glu Ala Glu Gln Lys Glu Ala Glu Phe Gln Gln Met
            435                 440                 445
Leu Glu Gln Leu Lys Lys Gln Gln Glu Glu Ala Gln Ala Val Ala Ala
        450                 455                 460
Ala Ser Ala Ala Ser Arg Asp Phe Ser Gly Ile Gly Gly Leu Gly Glu
465                 470                 475                 480
Leu Leu Glu Ser Ser Ser Glu Ala Ser Lys Leu Ser Ser Lys Ser Ala
                485                 490                 495
Lys Glu Trp Arg Asn Arg Arg Lys Lys Arg Arg Gln Arg Glu His Leu
            500                 505                 510
Glu Gly Asn Asn Lys Gly Glu Arg Asp Ser Phe Pro Lys Ser Glu Ser
        515                 520                 525
Glu Asp Ser Val Lys Arg Ser Ser Phe Leu Phe Ser Met Asp Gly Asn
530                 535                 540
Arg Leu Thr Ser Asp Lys Lys Phe Cys Ser Pro His Gln Ser Leu Leu
545                 550                 555                 560
Ser Ile Arg Gly Ser Leu Phe Ser Pro Arg Arg Asn Ser Lys Thr Ser
                565                 570                 575
Ile Phe Ser Phe Arg Gly Arg Ala Lys Asp Val Gly Ser Glu Asn Asp
            580                 585                 590
Phe Ala Asp Asp Glu His Ser Thr Phe Glu Asp Ser Glu Ser Arg Arg
        595                 600                 605
Asp Ser Leu Phe Val Pro His Arg His Gly Glu Arg Arg Asn Ser Asn
        610                 615                 620
Gly Thr Thr Thr Glu Thr Glu Val Arg Lys Arg Arg Leu Ser Ser Tyr
625                 630                 635                 640
Gln Ile Ser Met Glu Met Leu Glu Asp Ser Ser Gly Arg Gln Arg Ala
                645                 650                 655
Val Ser Ile Ala Ser Ile Leu Thr Asn Thr Met Glu Glu Leu Glu Glu
            660                 665                 670
Ser Arg Gln Lys Cys Pro Pro Cys Trp Tyr Arg Phe Ala Asn Val Phe
        675                 680                 685
Leu Ile Trp Asp Cys Cys Asp Ala Trp Leu Lys Val Lys His Leu Val
        690                 695                 700
Asn Leu Ile Val Met Asp Pro Phe Val Asp Leu Ala Ile Thr Ile Cys
705                 710                 715                 720
Ile Val Leu Asn Thr Leu Phe Met Ala Met Glu His Tyr Pro Met Thr
                725                 730                 735
Glu Gln Phe Ser Ser Val Leu Thr Val Gly Asn Leu Val Phe Thr Gly
            740                 745                 750
Ile Phe Thr Ala Glu Met Val Leu Lys Ile Ile Ala Met Asp Pro Tyr
        755                 760                 765
Tyr Tyr Phe Gln Glu Gly Trp Asn Ile Phe Asp Gly Ile Ile Val Ser
        770                 775                 780
Leu Ser Leu Met Glu Leu Gly Leu Ser Asn Val Glu Gly Leu Ser Val
785                 790                 795                 800
Leu Arg Ser Phe Arg Leu Leu Arg Val Phe Lys Leu Ala Lys Ser Trp
                805                 810                 815
Pro Thr Leu Asn Met Leu Ile Lys Ile Ile Gly Asn Ser Val Gly Ala
            820                 825                 830
Leu Gly Asn Leu Thr Leu Val Leu Ala Ile Ile Val Phe Ile Phe Ala
        835                 840                 845
```

```
Val Val Gly Met Gln Leu Phe Gly Lys Ser Tyr Lys Glu Cys Val Cys
850                 855                 860

Lys Ile Asn Asp Asp Cys Thr Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
                900                 905                 910

Ile Val Phe Met Leu Val Met Val Ile Gly Asn Leu Val Val Leu Asn
                915                 920                 925

Leu Phe Leu Ala Leu Leu Leu Ser Ser Phe Ser Ser Asp Asn Leu Ala
930                 935                 940

Ala Thr Asp Asp Asp Asn Glu Met Asn Asn Leu Gln Ile Ala Val Gly
945                 950                 955                 960

Arg Met Gln Lys Gly Ile Asp Tyr Val Lys Asn Lys Met Arg Glu Cys
                965                 970                 975

Phe Gln Lys Ala Phe Phe Arg Lys Pro Lys Val Ile Glu Ile His Glu
                980                 985                 990

Gly Asn Lys Ile Asp Ser Cys Met Ser Asn Thr Gly Ile Glu Ile
                995                 1000                1005

Ser Lys Glu Leu Asn Tyr Leu Arg Asp Gly Asn Gly Thr Thr Ser
1010                1015                1020

Gly Val Gly Thr Gly Ser Ser Val Glu Lys Tyr Val Ile Asp Glu
1025                1030                1035

Asn Asp Tyr Met Ser Phe Ile Asn Asn Pro Ser Leu Thr Val Thr
1040                1045                1050

Val Pro Ile Ala Val Gly Glu Ser Asp Phe Glu Asn Leu Asn Thr
1055                1060                1065

Glu Glu Phe Ser Ser Glu Ser Glu Leu Glu Glu Ser Lys Glu Lys
1070                1075                1080

Leu Asn Ala Thr Ser Ser Ser Glu Gly Ser Thr Val Asp Val Val
1085                1090                1095

Leu Pro Arg Glu Gly Glu Gln Ala Glu Thr Glu Pro Glu Glu Asp
1100                1105                1110

Leu Lys Pro Glu Ala Cys Phe Thr Glu Gly Cys Ile Lys Lys Phe
1115                1120                1125

Pro Phe Cys Gln Val Ser Thr Glu Glu Gly Lys Gly Lys Ile Trp
1130                1135                1140

Trp Asn Leu Arg Lys Thr Cys Tyr Ser Ile Val Glu His Asn Trp
1145                1150                1155

Phe Glu Thr Phe Ile Val Phe Met Ile Leu Leu Ser Ser Gly Ala
1160                1165                1170

Leu Ala Phe Glu Asp Ile Tyr Ile Glu Gln Arg Lys Thr Ile Lys
1175                1180                1185

Thr Met Leu Glu Tyr Ala Asp Lys Val Phe Thr Tyr Ile Phe Ile
1190                1195                1200

Leu Glu Met Leu Leu Lys Trp Val Ala Tyr Gly Phe Gln Thr Tyr
1205                1210                1215

Phe Thr Asn Ala Trp Cys Trp Leu Asp Phe Leu Ile Val Asp Val
1220                1225                1230

Ser Leu Val Ser Leu Val Ala Asn Ala Leu Gly Tyr Ser Glu Leu
1235                1240                1245

Gly Ala Ile Lys Ser Leu Arg Thr Leu Arg Ala Leu Arg Pro Leu
1250                1255                1260
```

```
Arg Ala Leu Ser Arg Phe Glu Gly Met Arg Val Val Asn Ala
    1265            1270                1275
Leu Val Gly Ala Ile Pro Ser Ile Met Asn Val Leu Leu Val Cys
    1280            1285                1290
Leu Ile Phe Trp Leu Ile Phe Ser Ile Met Gly Val Asn Leu Phe
    1295            1300                1305
Ala Gly Lys Phe Tyr His Cys Val Asn Met Thr Thr Gly Asn Met
    1310            1315                1320
Phe Asp Ile Ser Asp Val Asn Asn Leu Ser Asp Cys Gln Ala Leu
    1325            1330                1335
Gly Lys Gln Ala Arg Trp Lys Asn Val Lys Val Asn Phe Asp Asn
    1340            1345                1350
Val Gly Ala Gly Tyr Leu Ala Leu Leu Gln Val Ala Thr Phe Lys
    1355            1360                1365
Gly Trp Met Asp Ile Met Tyr Ala Ala Val Asp Ser Arg Asp Val
    1370            1375                1380
Lys Leu Gln Pro Val Tyr Glu Glu Asn Leu Tyr Met Tyr Leu Tyr
    1385            1390                1395
Phe Val Ile Phe Ile Ile Phe Gly Ser Phe Phe Thr Leu Asn Leu
    1400            1405                1410
Phe Ile Gly Val Ile Ile Asp Asn Phe Asn Gln Gln Lys Lys Lys
    1415            1420                1425
Phe Gly Gly Gln Asp Ile Phe Met Thr Glu Glu Gln Lys Lys Tyr
    1430            1435                1440
Tyr Asn Ala Met Lys Lys Leu Gly Ser Lys Lys Pro Gln Lys Pro
    1445            1450                1455
Ile Pro Arg Pro Ala Asn Lys Phe Gln Gly Met Val Phe Asp Phe
    1460            1465                1470
Val Thr Arg Gln Val Phe Asp Ile Ser Ile Met Ile Leu Ile Cys
    1475            1480                1485
Leu Asn Met Val Thr Met Met Val Glu Thr Asp Asp Gln Gly Lys
    1490            1495                1500
Tyr Met Thr Leu Val Leu Ser Arg Ile Asn Leu Val Phe Ile Val
    1505            1510                1515
Leu Phe Thr Gly Glu Phe Val Leu Lys Leu Val Ser Leu Arg His
    1520            1525                1530
Tyr Tyr Phe Thr Ile Gly Trp Asn Ile Phe Asp Phe Val Val Val
    1535            1540                1545
Ile Leu Ser Ile Val Gly Met Phe Leu Ala Glu Met Ile Glu Lys
    1550            1555                1560
Tyr Phe Val Ser Pro Thr Leu Phe Arg Val Ile Arg Leu Ala Arg
    1565            1570                1575
Ile Gly Arg Ile Leu Arg Leu Ile Lys Gly Ala Lys Gly Ile Arg
    1580            1585                1590
Thr Leu Leu Phe Ala Leu Met Met Ser Leu Pro Ala Leu Phe Asn
    1595            1600                1605
Ile Gly Leu Leu Leu Phe Leu Val Met Phe Ile Tyr Ala Ile Phe
    1610            1615                1620
Gly Met Ser Asn Phe Ala Tyr Val Lys Lys Glu Ala Gly Ile Asp
    1625            1630                1635
Asp Met Phe Asn Phe Glu Thr Phe Gly Asn Ser Met Ile Cys Leu
    1640            1645                1650
Phe Gln Ile Thr Thr Ser Ala Gly Trp Asp Gly Leu Leu Ala Pro
```

```
                 1655                1660                1665

Ile Leu Asn Ser Ala Pro Pro Asp Cys Asp Pro Asp Thr Ile His
        1670                1675                1680

Pro Gly Ser Ser Val Lys Gly Asp Cys Gly Asn Pro Ser Val Gly
        1685                1690                1695

Ile Phe Phe Phe Val Ser Tyr Ile Ile Ile Ser Phe Leu Val Val
        1700                1705                1710

Val Asn Ser Tyr Ile Ala Val Ile Leu Glu Asn Phe Ser Val Ala
        1715                1720                1725

Thr Glu Glu Ser Ala Glu Pro Leu Ser Glu Asp Phe Glu Met
        1730                1735                1740

Phe Tyr Glu Val Trp Glu Lys Phe Asp Pro Asp Ala Thr Gln Phe
        1745                1750                1755

Ile Glu Phe Ser Lys Leu Ser Asp Phe Ala Ala Ala Leu Asp Pro
        1760                1765                1770

Pro Leu Leu Ile Ala Lys Pro Asn Lys Val Gln Leu Ile Ala Met
        1775                1780                1785

Asp Leu Pro Met Val Ser Gly Asp Arg Ile His Cys Leu Asp Ile
        1790                1795                1800

Leu Phe Ala Phe Thr Lys Arg Val Leu Gly Glu Ser Gly Glu Met
        1805                1810                1815

Asp Ala Leu Arg Ile Gln Met Glu Asp Arg Phe Met Ala Ser Asn
        1820                1825                1830

Pro Ser Lys Val Ser Tyr Glu Pro Ile Thr Thr Thr Leu Lys Arg
        1835                1840                1845

Lys Gln Glu Glu Val Ser Ala Ala Ile Ile Gln Arg Asn Phe Arg
        1850                1855                1860

Cys Tyr Leu Leu Lys Gln Arg Leu Lys Asn Ile Ser Ser Asn Tyr
        1865                1870                1875

Asn Lys Glu Ala Ile Lys Gly Arg Ile Asp Leu Pro Ile Lys Gln
        1880                1885                1890

Asp Met Ile Ile Asp Lys Leu Asn Gly Asn Ser Thr Pro Glu Lys
        1895                1900                1905

Thr Asp Gly Ser Ser Ser Thr Thr Ser Pro Pro Ser Tyr Asp Ser
        1910                1915                1920

Val Thr Lys Pro Asp Lys Glu Lys Phe Glu Lys Asp Lys Pro Glu
        1925                1930                1935

Lys Glu Ser Lys Gly Lys Glu Val Arg Glu Asn Gln Lys
        1940                1945                1950

<210> SEQ ID NO 68
<211> LENGTH: 1951
<212> TYPE: PRT
<213> ORGANISM: Homo sapiens
<220> FEATURE:
<221> NAME/KEY: MISC_FEATURE
<222> LOCATION: (122)..(122)
<223> OTHER INFORMATION: Xaa = any amino acid

<400> SEQUENCE: 68

Met Ala Gln Ala Leu Leu Val Pro Pro Gly Pro Glu Ser Phe Arg Leu
1               5                   10                  15

Phe Thr Arg Glu Ser Leu Ala Ala Ile Glu Lys Arg Ala Ala Glu Glu
            20                  25                  30

Lys Ala Lys Lys Pro Lys Lys Glu Gln Asp Asn Asp Asp Glu Asn Lys
        35                  40                  45
```

```
Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Met Asn Lys Gly
                85                  90                  95

Lys Ala Ile Ser Arg Phe Ser Ala Thr Ser Ala Leu Tyr Ile Leu Thr
            100                 105                 110

Pro Leu Asn Pro Val Arg Lys Ile Ala Xaa Lys Ile Leu Val His Ser
            115                 120                 125

Leu Phe Ser Met Leu Ile Met Cys Thr Ile Leu Thr Asn Cys Val Phe
        130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190

Leu Asp Phe Ser Val Ile Val Met Ala Tyr Val Thr Glu Phe Val Ser
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Leu Gln Trp Pro Pro Ser Asp Ser Ala Phe Glu
        275                 280                 285

Thr Asn Thr Thr Ser Tyr Phe Asn Gly Thr Met Asp Ser Asn Gly Thr
    290                 295                 300

Phe Val Asn Val Thr Met Ser Thr Phe Asn Trp Lys Asp Tyr Ile Gly
305                 310                 315                 320

Asp Asp Ser His Phe Tyr Val Leu Asp Gly Gln Lys Asp Pro Leu Leu
                325                 330                 335

Cys Gly Asn Gly Ser Asp Ala Gly Gln Cys Pro Glu Gly Tyr Ile Cys
            340                 345                 350

Val Lys Ala Gly Arg Asn Pro Asn Tyr Gly Tyr Thr Ser Phe Asp Thr
        355                 360                 365

Phe Ser Trp Ala Phe Leu Ser Leu Phe Arg Leu Met Thr Gln Asp Tyr
    370                 375                 380

Trp Glu Asn Leu Tyr Gln Leu Thr Leu Arg Ala Ala Gly Lys Thr Tyr
385                 390                 395                 400

Met Ile Phe Phe Val Leu Val Ile Phe Leu Gly Ser Phe Tyr Leu Val
                405                 410                 415

Asn Leu Ile Leu Ala Val Val Ala Met Ala Tyr Glu Gly Gln Asn Gln
            420                 425                 430

Ala Thr Leu Glu Glu Ala Glu Gln Lys Glu Ala Glu Phe Gln Gln Met
        435                 440                 445

Leu Glu Gln Leu Lys Lys Gln Gln Glu Glu Ala Gln Ala Val Ala Ala
    450                 455                 460

Ala Ser Ala Ala Ser Arg Asp Phe Ser Gly Ile Gly Gly Leu Gly Glu
465                 470                 475                 480
```

```
Leu Leu Glu Ser Ser Ser Glu Ala Ser Lys Leu Ser Ser Lys Ser Ala
                485                 490                 495
Lys Glu Trp Arg Asn Arg Arg Lys Arg Arg Gln Arg Glu His Leu
            500                 505                 510
Glu Gly Asn Asn Lys Gly Glu Arg Asp Ser Phe Pro Lys Ser Glu Ser
                515                 520                 525
Glu Asp Ser Val Lys Arg Ser Ser Phe Leu Phe Ser Met Asp Gly Asn
        530                 535                 540
Arg Leu Thr Ser Asp Lys Lys Phe Cys Ser Pro His Gln Ser Leu Leu
545                 550                 555                 560
Ser Ile Arg Gly Ser Leu Phe Ser Pro Arg Arg Asn Ser Lys Thr Ser
                565                 570                 575
Ile Phe Ser Phe Arg Gly Arg Ala Lys Asp Val Gly Ser Glu Asn Asp
                580                 585                 590
Phe Ala Asp Asp Glu His Ser Thr Phe Glu Asp Ser Glu Ser Arg Arg
            595                 600                 605
Asp Ser Leu Phe Val Pro His Arg His Gly Glu Arg Arg Asn Ser Asn
        610                 615                 620
Gly Thr Thr Thr Glu Thr Glu Val Arg Lys Arg Leu Ser Ser Tyr
625                 630                 635                 640
Gln Ile Ser Met Glu Met Leu Glu Asp Ser Ser Gly Arg Gln Arg Ala
                645                 650                 655
Val Ser Ile Ala Ser Ile Leu Thr Asn Thr Met Glu Glu Leu Glu Glu
                660                 665                 670
Ser Arg Gln Lys Cys Pro Pro Cys Trp Tyr Arg Phe Ala Asn Val Phe
            675                 680                 685
Leu Ile Trp Asp Cys Cys Asp Ala Trp Leu Lys Val Lys His Leu Val
        690                 695                 700
Asn Leu Ile Val Met Asp Pro Phe Val Asp Leu Ala Ile Thr Ile Cys
705                 710                 715                 720
Ile Val Leu Asn Thr Leu Phe Met Ala Met Glu His Tyr Pro Met Thr
                725                 730                 735
Glu Gln Phe Ser Ser Val Leu Thr Val Gly Asn Leu Val Phe Thr Gly
            740                 745                 750
Ile Phe Thr Ala Glu Met Val Leu Lys Ile Ile Ala Met Asp Pro Tyr
        755                 760                 765
Tyr Tyr Phe Gln Glu Gly Trp Asn Ile Phe Asp Gly Ile Ile Val Ser
        770                 775                 780
Leu Ser Leu Met Glu Leu Gly Leu Ser Asn Val Glu Gly Leu Ser Val
785                 790                 795                 800
Leu Arg Ser Phe Arg Leu Leu Arg Val Phe Lys Leu Ala Lys Ser Trp
                805                 810                 815
Pro Thr Leu Asn Met Leu Ile Lys Ile Ile Gly Asn Ser Val Gly Ala
            820                 825                 830
Leu Gly Asn Leu Thr Leu Val Leu Ala Ile Ile Val Phe Ile Phe Ala
        835                 840                 845
Val Val Gly Met Gln Leu Phe Gly Lys Ser Tyr Lys Glu Cys Val Cys
        850                 855                 860
Lys Ile Asn Asp Asp Cys Thr Leu Pro Arg Trp His Met Asn Asp Phe
865                 870                 875                 880
Phe His Ser Phe Leu Ile Val Phe Arg Val Leu Cys Gly Glu Trp Ile
                885                 890                 895
Glu Thr Met Trp Asp Cys Met Glu Val Ala Gly Gln Thr Met Cys Leu
```

```
                      900             905             910
Ile Val Phe Met Leu Val Met Val Ile Gly Asn Leu Val Leu Asn
        915                 920                 925
Leu Phe Leu Ala Leu Leu Leu Ser Ser Phe Ser Ser Asp Asn Leu Ala
        930                 935                 940
Ala Thr Asp Asp Asp Asn Glu Met Asn Asn Leu Gln Ile Ala Val Gly
945                 950                 955                 960
Arg Met Gln Lys Gly Ile Asp Tyr Val Lys Asn Lys Met Arg Glu Cys
                965                 970                 975
Phe Gln Lys Ala Phe Phe Arg Lys Pro Lys Val Ile Glu Ile His Glu
            980                 985                 990
Gly Asn Lys Ile Asp Ser Cys Met Ser Asn Asn Thr Gly Ile Glu Ile
        995                 1000                1005
Ser Lys Glu Leu Asn Tyr Leu Arg Asp Gly Asn Gly Thr Thr Ser
    1010                1015                1020
Gly Val Gly Thr Gly Ser Ser Val Glu Lys Tyr Val Ile Asp Glu
    1025                1030                1035
Asn Asp Tyr Met Ser Phe Ile Asn Asn Pro Ser Leu Thr Val Thr
    1040                1045                1050
Val Pro Ile Ala Val Gly Glu Ser Asp Phe Glu Asn Leu Asn Thr
    1055                1060                1065
Glu Glu Phe Ser Ser Glu Ser Glu Leu Glu Glu Ser Lys Glu Lys
    1070                1075                1080
Leu Asn Ala Thr Ser Ser Ser Glu Gly Ser Thr Val Asp Val Val
    1085                1090                1095
Leu Pro Arg Glu Gly Glu Gln Ala Glu Thr Glu Pro Glu Glu Asp
    1100                1105                1110
Leu Lys Pro Glu Ala Cys Phe Thr Glu Gly Cys Ile Lys Lys Phe
    1115                1120                1125
Pro Phe Cys Gln Val Ser Thr Glu Glu Gly Lys Gly Lys Ile Trp
    1130                1135                1140
Trp Asn Leu Arg Lys Thr Cys Tyr Ser Ile Val Glu His Asn Trp
    1145                1150                1155
Phe Glu Thr Phe Ile Val Phe Met Ile Leu Leu Ser Ser Gly Ala
    1160                1165                1170
Leu Ala Phe Glu Asp Ile Tyr Ile Glu Gln Arg Lys Thr Ile Lys
    1175                1180                1185
Thr Met Leu Glu Tyr Ala Asp Lys Val Phe Thr Tyr Ile Phe Ile
    1190                1195                1200
Leu Glu Met Leu Leu Lys Trp Val Ala Tyr Gly Phe Gln Thr Tyr
    1205                1210                1215
Phe Thr Asn Ala Trp Cys Trp Leu Asp Phe Leu Ile Val Asp Val
    1220                1225                1230
Ser Leu Val Ser Leu Val Ala Asn Ala Leu Gly Tyr Ser Glu Leu
    1235                1240                1245
Gly Ala Ile Lys Ser Leu Arg Thr Leu Arg Ala Leu Arg Pro Leu
    1250                1255                1260
Arg Ala Leu Ser Arg Phe Glu Gly Met Arg Val Val Val Asn Ala
    1265                1270                1275
Leu Val Gly Ala Ile Pro Ser Ile Met Asn Val Leu Leu Val Cys
    1280                1285                1290
Leu Ile Phe Trp Leu Ile Phe Ser Ile Met Gly Val Asn Leu Phe
    1295                1300                1305
```

-continued

```
Ala Gly Lys Phe Tyr His Cys Val Asn Met Thr Thr Gly Asn Met
1310                1315                1320

Phe Asp Ile Ser Asp Val Asn Asn Leu Ser Asp Cys Gln Ala Leu
1325                1330                1335

Gly Lys Gln Ala Arg Trp Lys Asn Val Lys Val Asn Phe Asp Asn
1340                1345                1350

Val Gly Ala Gly Tyr Leu Ala Leu Leu Gln Val Ala Thr Phe Lys
1355                1360                1365

Gly Trp Met Asp Ile Met Tyr Ala Ala Val Asp Ser Arg Asp Val
1370                1375                1380

Lys Leu Gln Pro Val Tyr Glu Glu Asn Leu Tyr Met Tyr Leu Tyr
1385                1390                1395

Phe Val Ile Phe Ile Ile Phe Gly Ser Phe Phe Thr Leu Asn Leu
1400                1405                1410

Phe Ile Gly Val Ile Ile Asp Asn Phe Asn Gln Gln Lys Lys Lys
1415                1420                1425

Phe Gly Gly Gln Asp Ile Phe Met Thr Glu Glu Gln Lys Lys Tyr
1430                1435                1440

Tyr Asn Ala Met Lys Lys Leu Gly Ser Lys Lys Pro Gln Lys Pro
1445                1450                1455

Ile Pro Arg Pro Ala Asn Lys Phe Gln Gly Met Val Phe Asp Phe
1460                1465                1470

Val Thr Arg Gln Val Phe Asp Ile Ser Ile Met Ile Leu Ile Cys
1475                1480                1485

Leu Asn Met Val Thr Met Met Val Glu Thr Asp Asp Gln Gly Lys
1490                1495                1500

Tyr Met Thr Leu Val Leu Ser Arg Ile Asn Leu Val Phe Ile Val
1505                1510                1515

Leu Phe Thr Gly Glu Phe Val Leu Lys Leu Val Ser Leu Arg His
1520                1525                1530

Tyr Tyr Phe Thr Ile Gly Trp Asn Ile Phe Asp Phe Val Val Val
1535                1540                1545

Ile Leu Ser Ile Val Gly Met Phe Leu Ala Glu Met Ile Glu Lys
1550                1555                1560

Tyr Phe Val Ser Pro Thr Leu Phe Arg Val Ile Arg Leu Ala Arg
1565                1570                1575

Ile Gly Arg Ile Leu Arg Leu Ile Lys Gly Ala Lys Gly Ile Arg
1580                1585                1590

Thr Leu Leu Phe Ala Leu Met Met Ser Leu Pro Ala Leu Phe Asn
1595                1600                1605

Ile Gly Leu Leu Leu Phe Leu Val Met Phe Ile Tyr Ala Ile Phe
1610                1615                1620

Gly Met Ser Asn Phe Ala Tyr Val Lys Lys Glu Ala Gly Ile Asp
1625                1630                1635

Asp Met Phe Asn Phe Glu Thr Phe Gly Asn Ser Met Ile Cys Leu
1640                1645                1650

Phe Gln Ile Thr Thr Ser Ala Gly Trp Asp Gly Leu Leu Ala Pro
1655                1660                1665

Ile Leu Asn Ser Ala Pro Pro Asp Cys Asp Pro Asp Thr Ile His
1670                1675                1680

Pro Gly Ser Ser Val Lys Gly Asp Cys Gly Asn Pro Ser Val Gly
1685                1690                1695

Ile Phe Phe Phe Val Ser Tyr Ile Ile Ile Ser Phe Leu Val Val
1700                1705                1710
```

| | | | | | | | | | | |
|---|---|---|---|---|---|---|---|---|---|---|
| Val | Asn | Ser | Tyr | Ile | Ala | Val | Ile | Leu | Glu | Asn | Phe | Ser | Val | Ala |
| | 1715 | | | | 1720 | | | | 1725 | |

Val Asn Ser Tyr Ile Ala Val Ile Leu Glu Asn Phe Ser Val Ala
        1715                1720                1725

Thr Glu Glu Ser Ala Glu Pro Leu Ser Glu Asp Asp Phe Glu Met
    1730                1735                1740

Phe Tyr Glu Val Trp Glu Lys Phe Asp Pro Asp Ala Thr Gln Phe
1745                1750                1755

Ile Glu Phe Ser Lys Leu Ser Asp Phe Ala Ala Ala Leu Asp Pro
    1760                1765                1770

Pro Leu Leu Ile Ala Lys Pro Asn Lys Val Gln Leu Ile Ala Met
1775                1780                1785

Asp Leu Pro Met Val Ser Gly Asp Arg Ile His Cys Leu Asp Ile
    1790                1795                1800

Leu Phe Ala Phe Thr Lys Arg Val Leu Gly Glu Ser Gly Glu Met
1805                1810                1815

Asp Ala Leu Arg Ile Gln Met Glu Asp Arg Phe Met Ala Ser Asn
    1820                1825                1830

Pro Ser Lys Val Ser Tyr Glu Pro Ile Thr Thr Thr Leu Lys Arg
1835                1840                1845

Lys Gln Glu Glu Val Ser Ala Ala Ile Ile Gln Arg Asn Phe Arg
    1850                1855                1860

Cys Tyr Leu Leu Lys Gln Arg Leu Lys Asn Ile Ser Ser Asn Tyr
1865                1870                1875

Asn Lys Glu Ala Ile Lys Gly Arg Ile Asp Leu Pro Ile Lys Gln
    1880                1885                1890

Asp Met Ile Ile Asp Lys Leu Asn Gly Asn Ser Thr Pro Glu Lys
1895                1900                1905

Thr Asp Gly Ser Ser Ser Thr Thr Ser Pro Pro Ser Tyr Asp Ser
    1910                1915                1920

Val Thr Lys Pro Asp Lys Glu Lys Phe Glu Lys Asp Lys Pro Glu
1925                1930                1935

Lys Glu Ser Lys Gly Lys Glu Val Arg Glu Asn Gln Lys
    1940                1945                1950

<210> SEQ ID NO 69
<211> LENGTH: 1380
<212> TYPE: DNA
<213> ORGANISM: Homo sapiens

<400> SEQUENCE: 69 aatgtatttta tttaattgat gataaactgt aataaaatca tagttgtttg ctctaaagta      60
gatatgaaag gtcagatgaa acaataacat acatctggat tgagaaatat cttaataact     120
gatggattat ttttattttc tttatgtatt gtgtgcttca atatcctaat aaataatatt     180
agctaggttc actgatgtat agaatctttt tctacattta gatatttctt gcaaatgttt     240
taccagaaag caacacaaaa atactatcag tgagtatgtg tttacactgt tctctaagga     300
gtcaaattcc tcaccttgaa ataattcat cccaggaaga gaaaaggttt tcaaaagact     360
agagcaggcc acaagggagc tttcgcaaaa ctctacacgt aaagggtaat gtaaacttaa     420
aacctatttt tcaaacagta atttatatat ctttttaattt tagtagttta tgtgtgaaac     480
aatcatgcaa acaacaaag tgataaaatt ttttaaaaaa attagtgaga tgcaaataac     540
tgaatatgta aaaggtctca tacatattta tatgtagtag ataagttaca tttttttagt     600
gtgttgggaa attttagctc acatcaccctc tctactgtca tcttggggca ctttcatgac     660
tacccatgct tcatgcaggt ttactttcct ccctgtgaca gaggataatg ggaatgtttt     720

```
ttctttggct caattttgtg tgtgtccgcc agtagatggc gtaccacttt gagtgcgatc      780 ggccttttt  tctttcttt  tttttttcct caaagctgtt ttctgatata tgttgggtac      840
catagagtga atctcagaac aggaagcgga ggcataagca gagaggattc tggaaaggtc      900
tctttgtttt cttatccaca gagaaagaaa gaaaaaaat  tgtaactaat ttgtaaacct      960
ctgtggtcaa aaaaaaaaaa aaaaaaaaaa gctgaacagc tgcagaggaa gacacgttat     1020
accctaacca tcttggatgc tgggctttgt tatgctgtaa ttcataaggc tctgttttat     1080
caggtaagct gacaaaacat ttcattatct gcaccataga acctagctac caggtcattt     1140
tccttacttt aaaatcatct tcatgctgct attttaacc  cagtgttgtt taaatgtaaa     1200
ttacaggaac caaaggcatc gtttgatgtg taaactgctt actatttctt tatctttcaa     1260
agaaaataga gcctgtctgg aaatggtgat ttatggtaca tactaggcat caatggtctt     1320 gtgttttgt  agatgcttat gattaattgt attcagaaaa aatattttt  attatactta     1380
```

<210> SEQ ID NO 70
<211> LENGTH: 840
<212> TYPE: DNA
<213> ORGANISM: Homo sapiens

<400> SEQUENCE: 70

```
agggaagaac agaaggatgc tcaggagtgc cagcatgcct tcagaaagac taaatggatc       60
aaggctgcca agaaggggg  agcacccctg tcccaaccct aggatcctgg cagtggttcc      120
tggtcccatt cttcctaaat catgctaggg catgctttta acaagggtca aatatcttgc      180
tttgcatcat ccttgctttc tcgatccagg gccataaaaa aaaaggaat  aaaacccaga      240 cacagagcca gagcacccct atgccaaatg tcaaagatta taggctaatt tcacctgtat      300
tctctttcta cagagattat ggagcaagaa aactgaagcc aagccacatc aaggtttgac      360
agggatgaga tacctgtcaa ggattcatag tagagtggct tactgggaaa ggagcaaaga      420
atctcttcta gggatattgt aagaataaat gagataattc acagaaggga cctggagctt      480
ttccggaaaa aggtgctgtg actatctaag gtaactaaac aacttctggg tataagtttg      540
tttttgtgga aaataaacta aaatctctac tatttaacaa ggacagctgt atcaggacca      600
aaagaaggca gaggggtgtt tcttccttc  ctctaccagt ttgttcttcc aaagaggcaa      660
atacatacag ggagacatag cacagatgac cttagggaat ggaatgatgc caaaggctgt      720
tgatgtaaga aagagagatt aactcagttt ttttttttgtt tttgtttttt tgttgttgtt      780
gttgttgttt tgagacagag tctctctctg tcgcccaggc tggagtgcag tggcatgaac      840
```

<210> SEQ ID NO 71
<211> LENGTH: 780
<212> TYPE: DNA
<213> ORGANISM: Homo sapiens

<400> SEQUENCE: 71

```
gatatattaa attttatgta ttttaataaa ttataatgtg catataatca ttaataatat       60
atatattcca caccaaggca tcagtaagaa ttaatttta  aagtctgctc taatgtgaat      120
ataaaattat gtaagaactc tgtataataa gctcacagag tacaagaaag gagaggaaaa      180
aagtaaaaga gaactgcgaa agaactatga gggatttcca acagcaaaa  ttgtcattga      240 agccatgaga aactctactc actaaattct ttaatttctc agcctaccca aatattgggc      300
aaaccctaat tctcttgcag gggaaaagct gagagtctgg aactagccta tcttccgagg      360
acttagagac aacagtatgg gaatttcaac gagacgtttt tactttcttt tgaccaagat      420
```

```
tcaaattctt tattccagcc cttgataagt aaataagaag gtaaaggact atttatttgt      480
aaaaagtttt tcatgatttt gtgatggcac cttgttccat atcatctcag ataaatcaga      540
ataatttgtg aaaattactc ggtgatttcc acattagata tttttaaacct aatgttatttt    600 ctaaaacaaa aaccaaccag gagaatccaa ttaagtaaaa tgtatgtatt aatataaatt     660
agctattccc atctggaaaa gggcagccat ttctgtgttg aggtgcctca atgatactga     720
ggctgagaca ggttagatga tacaggcata ccattagcag cagactcaat actaacccag    780
```

```
<210> SEQ ID NO 72
<211> LENGTH: 1025
<212> TYPE: DNA
<213> ORGANISM: Homo sapiens

<400> SEQUENCE: 72
acaaagttat gaaaaggcgg ggggcaggat gcagaataat taagcaattt tattgacaaa      60
ctthactggc attactcttt tgctgaaagt atactatatt ttggcttaca gtgtcaaaac     120 agaattttt aaatgctttt aaaaaatgga caaaattata gatattcttg agtttaaata     180
taatgtttat atattatata tactgtacat tgtagaatgg ctaaatcaaa ctaattaaca     240
ttaagtacag acttttgata gatttatgaa cttggcttat tgagaatgag gttgaatgat     300
gatgttttca agttcaaatg tgtagtgcag tactaaaagc atgacttaat gtttatagct     360
ttaaaaagtt actaaagaat gacattttgg ttgatgttct tatgcccaat cgcttgcttt     420
cctaactctt gtgcaatttt tcttttttatt gcaggtaatt cgtatgcaag aagctacacg    480
taattaaatg tgcaggatga aaagatggca caggcactgt tggtaccccc aggacctgaa     540
agcttccgcc tttttactag agaatctctt gctgctatcg aaaaacgtgc tgcagaagag    600
aaagccaaga agcccaaaaa ggaacaagat aatgatgatg agaacaaacc aaagccaaat    660
agtgacttgg aagctggaaa gaaccttcca tttatttatg gagacattcc tccagagatg     720
gtgtcagagc ccctggagga cctggatccc tactatatca ataagaaagt gagtattgat    780
tttagacttc taataaatct ttaatgaaac tcttaactgt aatatacttt tctgggcctt     840
atatacagca tcacaatttt tcttctgtta aagatttat aatactcttc actgtcactt     900 attttttatca caatataata aaacaaacat ttataagaaa tgaagtcaag agttggttac    960
agtcaggaaa tatgaataga tgaatgattt ctacaatttc acagtgataa ttcagatagt   1020
caaaa                                                                1025
```

```
<210> SEQ ID NO 73
<211> LENGTH: 433
<212> TYPE: DNA
<213> ORGANISM: Homo sapiens

<400> SEQUENCE: 73
tgtaacyata tgttaattta aacatctaac atgtttgtag ttatgatata tcaactggtt      60
taaacaaacc agtttgaaca aacaaattcy atttttaaa aaggtcctca tgtatgtaag    120
ctccttaaat aagcccatgt ctaatttagt aattttactc gtattttctg tttcagactt    180
ttatagtaat gaataaagga aaggcaattt cccgattcag tgccacctct gccttgtata    240
ttttaactcc actaaaccct gttaggaaaa ttgctabsaa gattttggta cattcatatc    300
cttttaatgt gaattgccta aatgctattt ctaacagttg attttaaaga aaatgtcagt    360
tatattttca agtatctgta aaatttcttt gagattaatg gtaacattgt tagtttaatt    420
catttatttg cat                                                       433
```

<210> SEQ ID NO 74
<211> LENGTH: 450
<212> TYPE: DNA
<213> ORGANISM: Homo sapiens

<400> SEQUENCE: 74

```
gagtgcacca aggccatatc acaggctttg aagtttctta ttattttatc attgttttaa      60
aacaaataat attaatttca cagttttttgc atcgataaac ttttttgtgt gttttggatc     120
atttataaat ggccatggta acctactaac atttattcct taactataat ctactttatt    180
cagcatgctt atcatgtgca ctattttgac caactgtgta tttatgacct tgagcaaccc     240
tcctgactgg acaaagaatg tagagtaagt aggaataact tctgggaatg agaaatgcac     300
actcaaattc tctagcaatc tccttgtggg tatagcctga cttatggttt ccacttctgt     360
ctaagaaaag ttattttcat aatatgcagc cggtaaggga ggtctttcgg gggagctatt    420
cttctacgag gtaagtattt tcccacaaaa                                      450
```

<210> SEQ ID NO 75
<211> LENGTH: 701
<212> TYPE: DNA
<213> ORGANISM: Homo sapiens

<400> SEQUENCE: 75

```
aaaatttacc atttgyggct ttccattaca tttctatcag ataactctgc gctagtaggt      60
caaactagat gattatccat aagatacatg aaactattat tctaaaaccc aaatagttaa    120
accagattag attcctaaag aatatatttt ctcttcagtt taactctttg ctcaggcttg    180
taaaactaac taaatgaata gattatttgg taaatagaag taaggaacaa tattttaatg    240
aattgaaaaa ccacaaaagg ataggatttg ctatgattga aaacatttat tttaacagtt    300
caagcaaaat tgttaatttt ggcttggatg ttttttcctag gtacacattc actggaatct    360
ataccttga gtcacttata aaaatcttgg caagagggtt ttgcttagaa gattttacgt     420
ttcttcgtga tccatggaac tggctggatt tcagtgtcat tgtgatggcg tgagtaactt    480
tgaaaatttg ataagcgcaa aggagtgaaa atagtcatag tacaaacaag gtctttgtgt    540
catatattaa atgtagagct ttcttgttag tcaagttaac tatatgggtt gtgtattttc    600
agaatacata ttagaataca tattgcaatg taaatatatc cagtaaatga tcaataaatg    660
gggttatctt catgtcatat agtctttctc ttcatcaaaa t                        701
```

<210> SEQ ID NO 76
<211> LENGTH: 286
<212> TYPE: DNA
<213> ORGANISM: Homo sapiens

<400> SEQUENCE: 76

```
atttgttaaa ctcacagggc tctatgtgcc aaacccagca ttaagtcctt atttagtata      60
aactttgcca aaactatcag taactctgat ttaattctgc aggtatgtaa cagaatttgt    120
aagcctaggc aatgtttcag cccttcgaac tttcagagtc ttgagagctc tgaaaactat    180
ttctgtaatc ccaggtaaga agaaactggt gtaaggtagt aggcccctta tatctccaac    240
ttttcttgtg tgttattgtg tttgtgtgtg aactccccta ttacag                  286
```

<210> SEQ ID NO 77
<211> LENGTH: 515
<212> TYPE: DNA
<213> ORGANISM: Homo sapiens

<400> SEQUENCE: 77

```
gtaagaagaa actggtgtaa ggtagtaggc cccttatatc tccaactttt cttgtgtgtt      60
attgtgtttg tgtgtgaact cccctattac agatatgtga cagagtttgt ggacctgggc     120
aatgtctcag cgttgagaac attcagagtt ctccgagcac tgaaaacaat ttcagtcatt     180
ccaggtgaga gctaggttaa acaccgaggt tgactttaat tattgagttt gaaatcaatt     240
tatatgactt acagcattag ccttgttgct tattattaca gttcatcccg gtaaataatg     300
ccaaatgatg tttcaatgtc agtttagctc ctaaaatttt ataaattaca tgcgtattta     360
taaagtcagc ctttgagttt aacagaaaat tgcatgagac atcttcaaaa aatgctaatt     420
tgggcctctt gcgctctctc tctctctttt tcactaccat ggctttacta acagatttgg     480
attttaccat tcgctgcaga tgtagttcaa aaatg                                515
```

<210> SEQ ID NO 78
<211> LENGTH: 564
<212> TYPE: DNA
<213> ORGANISM: Homo sapiens

<400> SEQUENCE: 78

```
aaacttcctg actagatatt taaaccttca tattgaattt ccagcaagca cactgttcat      60
gtgtaaaatc tgctgttcat ctatttccca aatcatcagg ctatccatac agctttggtg     120
tctaaatagt caagcaatca tttatggggg aaagagaatg tgtgtgacta ttaagaaatc     180
atgatttctg gcactcttcc tcaggtaacc tatagttctc tctctgcagg tttaaagacc     240
attgtggggg ccctgatcca gtcggtaaag aagctttctg atgtgatgat cctgactgtg     300
ttctgtctga gcgtgtttgc tctcattggg ctgcagctgt tcatgggcaa tctgaggaat     360
aaatgtttgc agtggccccc aagcgattct gcttttgaaa ccaacaccac ttcctacttt     420
aatggcacaa tggattcaaa tgggacattt gttaatgtaa caatgagcac atttaactgg     480
aaggataaca ttggagatga cagtaagaag tattacatta tgttaacctt agtgttgctg     540
aatgaatttt caactataaa tagt                                            564
```

<210> SEQ ID NO 79
<211> LENGTH: 497
<212> TYPE: DNA
<213> ORGANISM: Homo sapiens

<400> SEQUENCE: 79

```
tgagactgtg ggtgtacagc cacctttgta aataactgaa atagtccaac tctgatttat      60
tactaatact aatgtgaata ggattaatat gaaataaaat gggttttttt ttgtattaac     120
aggtcacttt tatgttttgg atgggcaaaa agacccttta ctctgtggaa atggttcaga     180
tgcagggtaa gaaacataat atatattttt aagatataga actctttgcg aaaaaaaaaa     240
gtaggtagga aaacaactac atggttatat gtgtagcctt accatgtatg caataaagag     300
cagtgctgct cccctaggaa gtgccttgtc tgccttaccg gattgccact ggtcctaaac     360
tcacagcaat taaaaattat ccctttgtga agacctttcc ccaaaatttc acagttaaga     420
tgttcttaaa ttgatgctcc aatgtgtgaa ggcccagagt ctgtctttgc tgtacatcta     480
tcagagctgt taggaaa                                                    497
```

<210> SEQ ID NO 80
<211> LENGTH: 501
<212> TYPE: DNA
<213> ORGANISM: Homo sapiens

<400> SEQUENCE: 80

```
aaagagtaaa aatatggtaa ggtcagagcc aaaagtgtgt ggttgctagc tttctgccat    60
tctaaatgtc trwaaawatt tatttgcatc taaattttct atcggtcttc ctagtgaatt   120
tcatctgata agtttcacgg tgggcaatca cctaaagtgt tctggaaatt aaagcaagat   180
aattcgtcac agatagcagc tttgggtttt gaaaattcct ataagtcaaa taaattgaaa   240
ttgctgtaat ttctaaactg accctacctc catttctctc tcttatagcc agtgtccaga   300
aggatacatc tgtgtgaagg ctggtcgaaa ccccaactat ggctacacaa gctttgacac   360
ctttagctgg gctttcctgt ctctatttcg actcatgact caagactact gggaaaatct   420
ttaccagttg gtaaggtcca aatgagcatg cataacattt atttttatag acatgtatga   480
aatgaaaagc ataggctgag t                                              501
```

<210> SEQ ID NO 81
<211> LENGTH: 432
<212> TYPE: DNA
<213> ORGANISM: Homo sapiens

<400> SEQUENCE: 81

```
agctaattag tctactgact atctaactgt ggtaatcaga tatttatttg gggacattat    60
actaaaatac tgatggaatt atcccccatt tccctagac attacgtgct gctgggaaaa    120
catacatgat atttttgtc ctggtcattt tcttgggctc atttatttg gtgaatttga    180
tcctggctgt ggtggccatg gcctatgagg ggcagaatca ggccaccttg aagaagcag    240
aacaaaaaga ggccgaattt cagcagatgc tcgaacagct taaaaagcaa caggaagaag    300
ctcaggtact gagtgataaa mgcaaagatt tatcattatt attmttagtt tctaagtaga   360
aatagtgtta tactatagag ggtagattgg aactgctttt tcattttata tatmggcatt   420
gtcattagac ac                                                         432
```

<210> SEQ ID NO 82
<211> LENGTH: 489
<212> TYPE: DNA
<213> ORGANISM: Homo sapiens

<400> SEQUENCE: 82

```
tgcaaactgt tttcaaagct ctgtgttcta aatagtgcct ggctttgttt tatgacaggc    60
agttgcggca gcatcagctg cttcaagaga tttcagtgga ataggtgggt taggagagct   120
gttggaaagt tcttcagaag catcaaagtt gagttccaaa agtgctaaag aatggaggaa    180
ccgaaggaag aaaagaagac agagagagca ccttgaagga acaacaaag gagagagaga    240
cagctttccc aaatccgaat ctgaagacag cgtcaaaaga agcagcttcc ttttctccat   300
ggatggaaac agactgacca gtgacaaaaa attctgctcc cctcatcagg tatgattttc   360
tactaagtgc tctggtttct ttgtcattgc tattgctttt tagttttttgt attttgtttt   420
ggtacacttt tgtactatct gtacttcagt tgagggacag ggaactaaca tttaatatag   480
ttgtttaaa                                                             489
```

<210> SEQ ID NO 83
<211> LENGTH: 653
<212> TYPE: DNA
<213> ORGANISM: Homo sapiens

<400> SEQUENCE: 83

```
gtgaagacta aatgaagtgg ttgtatactt agtaaattgc aaatcagtat tgttagtcag    60
```

```
aaaaacactc tttgtactta aatttgcttt aataaaaata tcaaaatata tgtgtcctct      120
ataaatttga ttatccatgt ttaagggcaa gagtatacta actccaaaga aaacagatcc      180
tttaatatta atatttatta aataattgcg ttcttcccct accccatcc cattcctttc       240 cttttttgctt tctctgcagt ctctcttgag tatccgtggc tccctgtttt ccccaagacg     300
caatagcaaa acaagcattt tcagtttcag aggtcgggca aaggatgttg atctgaaaa      360 tgactttgct gatgatgaac acagcacatt tgaagacagc gaaagcagga gagactcact    420
gtttgtgccg cacagacatg gagagcgacg caacagtaac gttagtcagg ccagtatgtc      480
atccaggatg gtgccagggc ttccagcaaa tggggaagat gcacagcact gtggattgca     540
atggtgtggt ttccttggtg ggtggaccct cagctctaac gtcacctact gggcaacttc      600
cccagaggtg ataatagatg acctagctgc tactgacatt attcaccaat ttg             653
```

```
<210> SEQ ID NO 84
<211> LENGTH: 566
<212> TYPE: DNA
<213> ORGANISM: Homo sapiens
<220> FEATURE:
<221> NAME/KEY: misc_feature
<222> LOCATION: (477)..(477)
<223> OTHER INFORMATION: n = a, c, t or g

<400> SEQUENCE: 84
gaattctctt aaaggtacta cctgtgatac tttttttaaa aaaaaactgt ttataactta      60 gcataattc aatatttat tcttgaaatt cttacctgga aaattgcatg tagcatgatt       120
tgcaaagaaa tgctatgtgg tgttgtatta cttattggga agagtggttt gagccatcag     180
tatttggttt gcagggcacc accactgaaa cggaagtcag aaagagaagg ttaagctctt     240
accagatttc aatggagatg ctggaggatt cctctggaag gcaagagcc gtgagcatag      300 ccagcattct gaccaacaca atggaaggta agagcaggtc atggaacagc caactttctg    360
tgattatgtg ctttgtgaac tattccttct tttcatagaa ttactgaagt ctgttaccca    420
gatcgaacta tatattagac ctaagaatgt gatatatggt gtacattatc acattgntta     480
caaaactaat attggcctta ttcttttga cttgggtcct taccttactt gcagagtgat     540
atttcaacac ttgatattat atcaat                                           566
```

```
<210> SEQ ID NO 85
<211> LENGTH: 748
<212> TYPE: DNA
<213> ORGANISM: Homo sapiens

<400> SEQUENCE: 85
tagtcatttt aaaagcaaaa tattaaattc aaagtgctta ttttctgtat tcaaaagaga     60
aaaaagtcga tctatatgac attttaatta acattttctg aaaatattta atgggattgt     120
cttctcaagt ttcttaagta atatgaactt ctattttcaa atataagcat caattttgtt    180
aaataatgta aaatctacta gcaataataa ctcattttg ttgttatta ctactcttcc     240 ttgttattgt ccctccagaa cttgaagaat ctagacagaa atgtccgcca tgctggtata    300
gatttgccaa tgtgttcttg atctgggact gctgtgatgc atggttaaaa gtaaaacatc    360
ttgtgaattt aattgttatg gatccatttg ttgatcttgc catcactatt tgcattgtct    420 taaatacct ctttatggcc atggagcact accccatgac tgagcaattc agtagtgtgt     480
tgactgtagg aaacctggta agtacatttg aagtttactt atttacttg gtagatgtgg     540 gagagataga ccaaagggaa agatgtattt gtgctgtgtt gaacccaaaa attatatcct    600
```

```
ctttcctcat agaaagaaat atctaaggaa tattacaggg aatctcagag atacagccta      660
aaactcaact ggtatgaatg ctgattgttt aggccaatgt ctgtgctgat tgatcatggt      720
gtcttaccag ttgtaaacgt ctcaaaat                                         748
```

<210> SEQ ID NO 86
<211> LENGTH: 664
<212> TYPE: DNA
<213> ORGANISM: Homo sapiens

<400> SEQUENCE: 86

```
ctaagacttg aattgatttg tcactattct ctcactttaa attttagata tttttattcc       60
tgtctaatgt tcttctttat aaattcgtgt agcatcagtg ttttcagtgc tcttgatagt      120
agtgctgatc tctaattttt taggtcttta ctgggatttt tacagcagaa atggttctca      180
agatcattgc catggatcct tattactatt ccaagaagg  ctggaatatc tttgatggaa      240
ttattgtcag cctcagttta atggagcttg gtctgtcaaa tgtggaggga ttgtctgtac      300
tgcgatcatt cagactggta tctatttata tatatccctg tcgctcattg gcacaacatt      360
tattttgaaa ttgaatcaat gtatatttat ataattatta attttaattt taaatttaca      420
tcaatatgtg acattctaag aaaacatgta aacatccyct ttaaagctaa accattttct      480
aagaatgatg aaagcattca aaatactcta taatgattag gtatgtaggg cacattagaa      540
aacctacaag tactttctaa aactgtgttt taagtttatg aagcttttt  ggccttacag      600 tctgtaaaga tacgcaaata aaaatttaga ccccagttaa ttttagcttt ttattaaccc      660
tact                                                                   664
```

<210> SEQ ID NO 87
<211> LENGTH: 750
<212> TYPE: DNA
<213> ORGANISM: Homo sapiens

<400> SEQUENCE: 87

```
tattttattt tttgcactta aatgatatta tgaccagatt tacaattcta atattgttaa       60 cactatttt  tctggatttg aaattgaatc agttcagtat attttgagtt tttacatcta      120
ccacgtgtgg ttctatgata ccacatacta ataaaataat gtctaaaatt atattatgat      180
tactactaac agcatctttt cacttgatta cagcttagag ttttcaagtt ggcaaaatcc      240
tggcccacac taaatatgct aattaagatc attggcaatt ctgtggggc  tctaggaaac      300 ctcaccttgg tgttggccat catcgtcttc attttt gctg tggtcggcat gcagctcttt      360
ggtaagagct acaaagaatg tgtctgcaag atcaatgatg actgtacgct cccacgtgg       420 cacatgaacg acttcttcca ctccttcctg attgtgttcc gcgtgctgtg tggagagtgg      480
atagagacca tgtgggactg tatggaggtc gctggccaaa ccatgtgcct tattgttttc      540
atgttggtca tggtcattgg aaaccttgtg gtatgtatgt agtacaaatg ctcataaatt      600
agaacaagag cagacagtag ctaggaacgt ggccagatgt agtaaacata tctctggttt      660
atagtaagtg gcctagactg aaatccccct attagcactc agagaataag caagttattt      720
aacttctcct gggctctggt ttcccatttt                                       750
```

<210> SEQ ID NO 88
<211> LENGTH: 768
<212> TYPE: DNA
<213> ORGANISM: Homo sapiens

<400> SEQUENCE: 88

```
ccttagagca ggatattagg tcctttaaag agtgtgtgac ttagacatgg catctgaaat        60
atagtaagca ttcaataaac atttgttgaa ataattttag caaagatcta tgagttccct       120
ttttaggctg ttatttaaat gcatatttca atattaarat aggcattttt ctttttttct       180
tttaggttct gaacctcttt ctggccttat tgttgagttc atttagctca gacaaccttg       240
ctgctactga tgatgacaat gaaatgaata atctgcagat tgcagtagga agaatgcaaa       300
agggaattga ttatgtgaaa ataagatgc gggagtgttt ccaaaaagcc ttttttagaa        360
agccaaaagt tatagaaatc catgaaggca ataagataga cagctgcatg tccaataata       420
ctggaattga aataagcaaa gagcttaatt atcttagaga tgggaatgga accaccagtg       480
gtgtaggtac tggaagcagt gttgaaaaat acgtaatcga tgaaaatgat tatatgtcat       540
tcataaacaa ccccagcctc accgtcacag tgccaattgc tgttggagag tctgactttg       600
aaaacttaaa tactgaagag ttcagcagtg agtcagaact agaagaaagc aaggaggtaa       660
ggaatgcttt taaattttttt gttccatttc ctatgataac catgtactac agttatttac       720
tattttcatt gtgcttatat gcattatcga aaagcaatga ttgtaagt                    768

<210> SEQ ID NO 89
<211> LENGTH: 471
<212> TYPE: DNA
<213> ORGANISM: Homo sapiens

<400> SEQUENCE: 89
taattattag tacataatga tcagtaatgc taatagagtt aaatgctatc actacatttt       60
ttttcacaca atgacacagt atttcccagt tagttaaata aagggggaa atcacatct        120 ttgaaatggg attttgtttc cagaaattaa atgcaaccag ctcatctgaa ggaagcacag      180
ttgatgttgt tctaccccga gaaggtgaac aagctgaaac tgaacccgaa gaagaccta      240 aaccggaagc ttgttttact gaaggtaaac aagctctgat gtgattaaat acaatctccc      300
cttgttcttt acggagactg aatatgcctc atttaaaaaa aaaatttag caaacgaggt      360 gtggtggctt atgcctgtaa ccccaaaatt tggggaggct acggtaggag gattgcttga      420
ccccaggagt ttgagaccac cctgggaaat gtagtaaggc tttgcctcta c              471

<210> SEQ ID NO 90
<211> LENGTH: 623
<212> TYPE: DNA
<213> ORGANISM: Homo sapiens

<400> SEQUENCE: 90
gaattctaag tagctggctg agtatataag tctgagaata attcattata caggagggat       60
gctgacgata actaggaaat gaaggagatg gttaccctat gaaatgatta cctggaagtg      120
gagtggggaa ggggcaagaa agtttatttt ttcctattta agattaaaat atatttttta      180
attaactata tttsatttt aggatgtatt aaaaagtttc cattctgtca agtaagtaca      240
gaagaaggca aagggaagat ctggtggaat cttcgaaaaa cctgctacag tattgttgag      300
cacaactggt ttgagacttt cattgtgttc atgatccttc tcagtagtgg tgcattggta      360
agtgaaatgc atattggcaa gaatcagatt ctggtgaaat agtttattct ccaaaattac      420
cagatgcaaa cactgagctt cagaatcaaa agaaaaggca tatctgtgtc ttgcagagct      480
tggcacccaa ggtttaacga tgcaaaattc agttctgaac aaatcagcac catgaaacag      540
ccagatggaa tttctcatct ggtgtttatc taacagatgt tttcctcact gagacaacca      600
tttgcagaga cattctgtaa cca                                               623
```

```
<210> SEQ ID NO 91
<211> LENGTH: 520
<212> TYPE: DNA
<213> ORGANISM: Homo sapiens

<400> SEQUENCE: 91
ctagttagtc tttagatttg tctcatgttc aatgtttatg taaaatatca ataatcaaaa      60
ttattctttt gtactcacta ttatactaag caattttttc aaatatttag aagaagcaag     120
ccatttaagt aaaataaaat attttttgatt cataggcctt tgaagatata tacattgaac    180
agcgaaagac tatcaaaacc atgctagaat atgctgacaa agtctttacc tatatattca    240
ttctggaaat gcttctcaaa tgggttgctt atggatttca acatatttc actaatgcct     300 ggtgctggct agatttcttg atcgttgatg taagtatttt aagtgatttt tataaaattg    360 ttttaaaag aggcaagttt gacatttcat atgtttctgt tattaaaact ttcactaata    420
atgacataat tatgcagtta tttaaacaaa actgtaacat atgcaacaat gaggaatatc    480
tcatgggaaa gagtagagga ggtcctaaac atgggcagtg                          520

<210> SEQ ID NO 92
<211> LENGTH: 595
<212> TYPE: DNA
<213> ORGANISM: Homo sapiens

<400> SEQUENCE: 92
ctaactaata atttaagcac acatccatga aggatctggc attgaactca atcctgaatt      60
atcagtggta tatgcacaag ttgaaaaggg gtccatggta taaaatatct aactggagat    120
attgacacgt gttgataaat atgggcaagt attctggttt cattggttaa aaaaaagcaa    180
tagtatgaga tgagactggc aatataagat daccccacta tgtggaagat gaaagttgcc    240
aaggtatgtc caaattagta tttagtctgc attaaataga taccacaccc tataccttca    300
gtcaacagtt tatttcttgg tgaactaatt aattttttt tccttttgta ggtttctttg      360
gttagcctgg tagccaatgc tcttggctac tcagaactcg gtgccatcaa atcattacgg    420
acattaagag cttaagacc tctaagagcc ttatcccggt ttgaaggcat gagggtaaga    480
agaatagaca ctctaattat tcatgtcaaa aattacatgt aggtaatgat ttagatagaa    540
aagggtgcca tactcttctg atatttattt caatagaaat tacagaatta gaagc         595

<210> SEQ ID NO 93
<211> LENGTH: 787
<212> TYPE: DNA
<213> ORGANISM: Homo sapiens

<400> SEQUENCE: 93
ccagcataca aacattttct gactccatct tactatacca ggtttttaat gatttctttt      60
catactgtag catattttgc tttccttaaa accttagctc tttagttgtg tcattgtttg    120
ttttccttca aatatgtgct agaaaaatta gaagaaacaa cttgtccacc tagattttta    180
tttaactctt ttcaagcaca tattaatact aaacaaatac attgaaggaa tggtttccat    240
tcaaaaggtt tgtaagctat gttcccctcg ctgtctcttc taggtggttg tgaatgctct    300
tgttggagca attccctcta tcatgaatgt gctgttggtc tgtctcatct tctggttgat    360
ctttagcatc atgggtgtga atttgtttgc tggcaagttc taccactgtg ttaacatgac    420
aacgggtaac atgtttgaca ttagtgatgt taacaatttg agtgactgtc aggctcttgg    480
caagcaagct cggtggaaaa acgtgaaagt aaactttgat aatgttggcg ctggctatct    540
```

| | |
|---|---:|
| tgcactgctt caagtggtaa gtggctactg tacgagtttt gaaaaagttt tcaagatgtt | 600 |
| tcaaggaaga ttatttccct gatgttcttc gtttgaatga ctaacatttg acagcatgaa | 660 |
| aaaaagttaa tgataacacc tataatatca gcttgaattg atcataaaaa agatgttaca | 720 |
| attattttat aatgtatttt ccttagtgtt aagcttttag tatgttttaa tgtgatttta | 780 |
| tatttct | 787 |

<210> SEQ ID NO 94
<211> LENGTH: 438
<212> TYPE: DNA
<213> ORGANISM: Homo sapiens

<400> SEQUENCE: 94

| | |
|---|---:|
| aaaggaaaca agttccagac tttaaataca aatgtttttc tatttcaatt ttatttcaat | 60 |
| ctcttgatat gaaatttcac aatattgtac aaaaagttat tgttataat actgtcagat | 120 |
| tttcatctgg ttaaatgtca ttgttaggtg aaattttat gaacaattca atatatgtt | 180 |
| atttacaggc cacatttaaa ggctggatgg atattatgta tgcagctgtt gattcacgag | 240 |
| atgtaagtat cactcaaata ttatttatag gttctagatt tcttatggtg aatattggtg | 300 |
| gtaatttaaa cactgataca tccaaaattc tatattagaa catttaatat tgcatataaa | 360 |
| aaatgaacag tctgcttcaa tatagatgat gcttgattaa tgtgtgccta atatacaata | 420 |
| tgtagctaat atgaaacg | 438 |

<210> SEQ ID NO 95
<211> LENGTH: 637
<212> TYPE: DNA
<213> ORGANISM: Homo sapiens

<400> SEQUENCE: 95

| | |
|---|---:|
| gtaaggcaca atgggaaaag agaatcaaga acaatcataa aacttgcaaa ccttcatttt | 60 |
| actagatcat actagttta aaaaattgtt tttgtagaac aatatctcag ggtaaggcaa | 120 |
| aagtagcact gtattaagta acagcactca ataaattact gatttagtgt aagtatttat | 180 |
| agtattttc atattattta atattttcaa tatcatttag gttaaacttc agcctgtata | 240 |
| tgaagaaaat ctgtacatgt atttatactt tgtcatctttt atcatctttg ggtcattctt | 300 |
| cactctgaat ctattcattg gtgtcatcat agataacttc aaccagcaga aaaagaagat | 360 |
| aagtattctt tagcttttac cttctttcat tctggggttc tgtctgttaa tacagccaaa | 420 |
| taaccagaat acctgtggtc atgacagact taaatcatgt ttatattatt ttcagttgcc | 480 |
| catgtggtta tttaagctgc agggattcca gcctctagtc agtggctcct ctcaaagttt | 540 |
| atctattgga tagcttttctg acccaaaaat gtgtccactc cttcggaccc atccaacggg | 600 |
| tctccagtgc tttagcttgg cttacagagc cttttcag | 637 |

<210> SEQ ID NO 96
<211> LENGTH: 637
<212> TYPE: DNA
<213> ORGANISM: Homo sapiens

<400> SEQUENCE: 96

| | |
|---|---:|
| acccttgtgc ctacttttaa acatagtata atcaaattag gatcctgtag cgatcagagt | 60 |
| tttatgtacg taaggatttt gcataatatt aagatattca gaatttcaca taaatgggaa | 120 |
| aagcaggata aatgtatatg taggaggata atatccactt aaaaattaga aaagattaaa | 180 |
| ggaaagacaa atatttttg tgaaagtact attggaacac agaattgtaa ccagttttat | 240 |

```
actatgtctt tactttggag gtcaagacat ctttatgaca gaggaacaga aaaaatatta      300
caatgcaatg aagaaacttg gatccaagaa acctcagaaa cccatacctc gcccagcagt      360
aagaattact tgtctccttt aatgttccaa agccatgcgt ccatatggtc aaattgagca      420
atgctctgga gcagaacata ttaggtgata tcaccaatat tgagccctaa ttataaagtt      480
catattttgc atcataattc acaacttctg cactcattag gagttaccac attccaaaaa      540
aaggaggtaa tgttctttat aatttgtgag ttgaaaactt ctagctcagg gttcctaata      600
aatacttcca agcaaggtt cactttcctg ctaccaa                                637
```

<210> SEQ ID NO 97
<211> LENGTH: 759
<212> TYPE: DNA
<213> ORGANISM: Homo sapiens

<400> SEQUENCE: 97

```
tatataaacc aaatatgctt tgtttagcta tataaatttt ttttccatttt tttttaacat      60 gaagagaaaa aaagcacaca aaattgtttg gggtaatatg aggagggtgc acatccatcc     120
cgtatgtgga agggctttat ctacaatttt actgcattat tctttatgaa atatatatag     180
taaccttatt tctcttctct cactttctag aacaaattcc aaggaatggt ctttgatttt     240
gtaaccagac aagtctttga tatcagcatc atgatcctca tctgcctcaa catggtcacc     300
atgatggtgg aaacggatga ccagggcaaa tacatgaccc agttttgtc ccggatcaac     360 ctagtgttca ttgttctgtt cactggagaa tttgtgctga agctcgtctc cctcagacac     420
tactacttca ctataggctg gaacatcttt gactttgtgg tggtgattct ctccattgta     480
ggtaagaaca gcttaattac caagaggtat agttacagag aaacagttgc cccaggacct     540
tctagctgat taacatggaa attaggtctg agaataataa tgcatataga gtaaagttc     600 aacactagca tatttgaata aaaactctga aacctgggtt tattcacaaa gctaactagt     660
tagaaaccat gttaggaata ccagatttgg gaaagaggtg aagaagacag gaaataaaca     720
ttatcaggta ctctcctaat cttaaaccaa ggtcacagg                            759
```

<210> SEQ ID NO 98
<211> LENGTH: 3975
<212> TYPE: DNA
<213> ORGANISM: Homo sapiens

<400> SEQUENCE: 98

```
aatctgtaat gctaatgcag ggagtggatc caaatatta taaaggctc atattcataa        60 caagtttgtt gtgttcatag accttaaaaa agataaagcc atcatgtaaa gtgaaaagat     120
attatctgtt tagctgtgtt ctatgttttc cataggtatg tttctggctg agatgataga     180
aaagtatttt gtgtcccta ccttgttccg agtgatccgt cttgccagga ttggccgaat     240
cctacgtctg atcaaaggag caaggggat ccgcacgctg ctctttgctt tgatgatgtc     300
ccttcctgcg ttgtttaaca tcggcctcct gctcttcctg gtcatgttta tctatgccat     360
ctttgggatg tccaactttg cctatgttaa aaaggaagct ggaattgatg acatgttcaa     420
ctttgagacc tttggcaaca gcatgatctg cttgttccaa attacaacct ctgctggatg     480
ggatggattg ctagcaccta ttcttaatag tgcaccaccc gactgtgacc ctgacacaat     540
tcaccctggc agctcagtta agggagactg tgggaaccca tctgttggga ttttctttt     600 tgtcagttac atcatcatat ccttcctggt ggtggtgaac agttacatcg cggtcatcct     660
ggagaacttc agtgttgcta ctgaagaaag tgcagagccc ctgagtgagg atgactttga     720
```

```
gatgttctat gaggtttggg aaaagtttga tcccgatgcg acccagtttta tagagttctc    780 taaactctct gattttgcag ctgccctgga tcctcctctt ctcatagcaa aacccaacaa    840
agtccagctt attgccatgg atctgcccat ggtcagtggt gaccggatcc actgtcttga    900 tattttatt gcctttacaa agcgtgtttt gggtgagagt ggagagatgg atgcccttcg    960
aatacagatg gaagacaggt ttatggcatc aaaccctcc aaagtctctt atgagcctat    1020
tacaaccact ttgaaacgta acaagagga ggtgtctgcc gctatcattc agcgtaattt    1080
cagatgttat cttttaaagc aaaggttaaa aaatatatca agtaactata acaaagaggc    1140 aataagggg aggattgact tacctataaa acaagacatg attattgaca aactgaatgg    1200
gaactccact ccagaaaaaa cagatgggag ttcctctacc acctctcctc cttcctatga    1260
tagtgtaaca aaaccagaca aggaaaagtt tgagaaagac aaaccagaaa aagaaagcaa    1320
aggaaaagag gtcagagaaa atcaaaagta aaagaaaca aagaattatc tttgtgatca    1380
attgtttaca gcctatgaag gtaaagtata tgtgtcaact ggacttcaag aggaggtcca    1440
tgccaaactg actgttttaa caaatactca tagtcagtgc ctatacaaga cagtgaagtg    1500
acctctctgt cactgcaact ctgtgaagca gggtatcaac attgacaaga ggttgctgtt    1560
tttattacca gctgacactg ctgaggagaa acccaatggc tacctagact atagggatag    1620
ttgtgcaaag tgaacattgt aactacacca aacaccttta gtacagtcct tgcatccatt    1680 ctattttaa cttccatatc tgccatattt ttacaaaatt tgttctagtg catttccatg    1740
gtccccaatt catagtttat tcataatgct atgtcactat ttttgtaaat gaggtttacg    1800
ttgaagaaac agtatacaag aaccctgtct ctcaaatgat cagacaaagg tgttttgcca    1860
gagagataaa attttgctc aaaaccagaa aaagaattgt aatggctaca gtttcagtta    1920
cttccatttt ctagatggct ttaattttga aagtatttta gtctgttatg tttgtttcta    1980
tctgaacagt tatgtgcctg taaagtctcc tctaatattt aaaggattat ttttatgcaa    2040
agtattctgt ttcagcaagt gcaaatttta ttctaagttt cagagctcta tatttaattt    2100
aggtcaaatg ctttccaaaa agtaatctaa taaatccatt ctagaaaaat atatctaaag    2160
tattgcttta gaatagttgt tccacttct gctgcagtat tgctttgcca tcttctgctc    2220
tcagcaaagc tgatagtcta tgtcaattaa ataccctatg ttatgtaaat agttatttta    2280
tcctgtggtg catgtttggg caaatatata tatagcctga taaacaactt ctattaaatc    2340
aaatatgtac cacagtgtat gtgtcttttg caagcttcca acagggatgt atcctgtatc    2400
attcattaaa catagtttaa aggctatcac taatgcatgt taatattgcc tatgctgctc    2460
tattttactc aatccattct tcacaagtct tggttaaaga atgtcacata ttggtgatag    2520
aatgaattca acctgctctg tccattatgt caagcagaat aatttgaagc tatttacaaa    2580 caccttact tttgcacttt taattcaaca tgagtatcat atggtatctc tctagatttc    2640
aaggaaacac actggatact gcctactgac aaaacctatt cttcatattt tgctaaaaat    2700
atgtctaaaa cttgcgcaaa tataaataat gtaaaaatat aatcaacttt atttgtcagc    2760
attttgtaca taagaaaatt attttcaggt tgatgacatc acaatttatt ttactttatg    2820
cttttgcttt tgattttaa tcacaattcc aaactttga atccataaga ttttcaatg    2880 gataatttcc taaataaaa gttagataat gggtttatg gatttctttg ttataatata    2940
ttttctacca ttccaatagg agatacattg gtcaaacact caaacctaga tcattttcta    3000
ccaactatgg ttgcctcaat ataacctttt attcatagat gtttttttt attcaacttt    3060 tgtagtattt acgtatgcag actagtctta tttttttaat tcctgctgca ctaaagctat    3120
```

-continued

```
tacaaatata acatggactt tgttcttttt agccatgaac aaagtggcaa agttgtgcaa    3180
ttacctaaca tgatataaat ttttgttttt tgcacaaacc aaaagtttaa tgttaattct    3240
ttttacaaaa ctatttactg tagtgtattg aagaactgca tgcagggaat tgctattgct    3300
aaaaagaatg gtgagctacg tcattattga gccaaaagaa taaatttcat tttttattgc    3360
atttcactta ttggcctctg gggtttttg tttttgtttt ttgctgttgg cagtttaaaa    3420
tatatataat taataaaacc tgtgcttgat ctgacatttg tatacataaa agtttacatg    3480
aattttacaa cagactagtg catgattcac caagcagtac tacagaacaa aggcaaatga    3540
aaagcagctt tgtgcacttt tatgtgtgca aaggatcaag ttcacatgtt ccaactttca    3600
ggtttgataa taatagtagt aaccacctac aatagctttc aatttcaatt aactcccttg    3660
gctataagca tctaaactca tcttctttca atataattga tgctatctcc taattacttg    3720
gtggctaata aatgttacat tctttgttac ttaaatgcat tatataaact cctatgtata    3780
cataaggtat taatgatata gttattgaga atttatatta acttttttt caagaacct     3840 tggatttatg tgaggtcaaa accaaactct tattctcagt ggaaaactcc agttgtaatg    3900
catattttta aagacaattt ggatctaaat atgtatttca taattctccc ataataaatt    3960
atataaggtg gctaa                                                    3975
```

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 99
tgtgttctgc cccagtgaga ct                                              22

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 100
cttcctgctc tgcccaaact gaat                                            24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 101
ggcgatgtaa tgtaaggtgc tgtc                                            24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 102
gtgccttcag ttgcaattgt tcag                                              24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 103
ttaggaattt catatgcaga ataa                                              24

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 104
tgggccattt ttcgtcgtc                                                    19

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 105
gaaagacgca ttgcagaaga aaagg                                             25

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 106
ctattggcat gtgttggtgc taca                                              24

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 107
gtgctggttt ctcatttaac tttac                                             25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 108
ttcccaactt aatttgatat ttagc                                             25

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 109
gcagtttggg cttttcaatg ttag                                          24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 110
gacacagttt caraatcccr aatg                                          24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 111
ttagggctac gtttcatttg tatg                                          24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 112
agcactgatg gaaaaccaaa ctat                                          24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 113
agcccatgca gtaatataaa tcct                                          24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 114
tccaggctga taagctatgt ctaa                                          24

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 115
ctgtggcctg cctgagcgta tt                                      22

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 116
ccaattctac tttttaagga aatg                                    24

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 117
aaatacttgt gcctttgaa                                          19

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 118
gtacatacaa tatacacaga tgc                                     23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 119
aggcagcaga acgacttgta ata                                     23

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 120
atccggtttt aatttcataa ctca                                    24

<210> SEQ ID NO 121
<211> LENGTH: 24

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 121
gttgagcacc cttagtgaat aata                                          24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 122
tcacacgctc tagactactt ctct                                          24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 123
tgcaaatact tcagcccttt caaa                                          24

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 124
ttccccacca gactgctctt tc                                            22

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 125
gcagcaggca ggctctca                                                 18

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 126
tctcccatgt tttaattttc aacc                                          24

<210> SEQ ID NO 127
<211> LENGTH: 24
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 127
ataatcttgc aaaatgaaat caca                                              24

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 128
atccgggatg acctactgg                                                    19

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 129
gataacgaga gccgtagaga ttcc                                              24

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 130
agccagccat gcctgaacta                                                   20

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 131
tgtttgcttg tcatattgct caa                                               23

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 132
tgcactattc ccaactcaca aa                                                22

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 133
aagggtgtct ctgtaacaaa aatg                                              24

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 134
gtgatggcca ggtcaacaaa                                                   20

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 135
ctgggactgt tctccatatt ggtt                                              24

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 136
tttgcagggg ccaggaag                                                     18

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 137
cattgtggga aaatagcata agc                                               23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 138
gcaagaaccc tgaatgttag aaa                                               23

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 139
taatgctttt aagaatcata caaa            24

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 140
ccagcgtggg agttgacaat c            21

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 141
cggcatgcag ctctttggta            20

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 142
atgtgccatg ctggtgtatt tc            22

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 143
cacccatctt ctaatcacta tgc            23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 144
cagcaatttg gagattattc att            23

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 145
gcagccactg atgatgataa                                             20

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 146
ctgccagttc ctataccact t                                           21

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 147
tacagcagaa attgggaaag at                                          22

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 148
gtattcatac ctacccacac ctat                                        24

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 149
ttcttggcag gcaacttatt acc                                         23

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 150
taagctgcac tccaaatgaa agat                                        24

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 151
ggctgaatgt ttccacaact                                             20

```
<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 152
gttcaactat tcggaaacac g                                             21

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 153
aggcagagga aaacaatgg                                                19

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 154
acaaggtggg ataattaaaa atg                                           23

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 155
gtttctctgc cctcctattc c                                             21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 156
aagctacctt gaacagagac a                                             21

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 157
aatgatgatt ctgtttatta                                               20

<210> SEQ ID NO 158
```

-continued

```
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 158
aatttgccat tccttttg                                                       18

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 159
ttgacatcga agacgtgaat aatc                                                24

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 160
ccatctgggc tcataaactt gta                                                 23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 161
ccctttgaaa attatatcag taa                                                 23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 162
atttggtcgt ttatgcttta ttc                                                 23

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 163
tccagcacta aaatgtatgg taat                                                24

<210> SEQ ID NO 164
<211> LENGTH: 21
<212> TYPE: DNA
```

<213> ORGANISM: Artificial Sequence
<220> FEATURE:
<223> OTHER INFORMATION: Description of Artificial Sequence: synthetic
      oligonucleotide

<400> SEQUENCE: 164
atttggcaga gaaaacactc c                                      21

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 165
ttttagccat ccattttcta tttt                                   24

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 166
tattttcccc catatcattt ga                                     22

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 167
tttgcaagaa actagaaagt c                                      21

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 168
ttgatgcgtg acaaaatgg                                         19

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 169
gaccagagtg aatatgtgac tacc                                   24

<210> SEQ ID NO 170
<211> LENGTH: 23
<212> TYPE: DNA
<213> ORGANISM: Artificial Sequence
<220> FEATURE:

```
<223> OTHER INFORMATION: Description of Artificial Sequence: synthetic
      oligonucleotide

<400> SEQUENCE: 170
ctgggatgat cttgaatcta atc                                             23

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 171
gcaactcagt tcatggaatt tgaa                                            24

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 172
cttgttttcg ttttaaagta gta                                             23

<210> SEQ ID NO 173
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 173
caaagatcac cctggaagct cagtt                                           25

<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 174
ttcaagcgca gctgcaaact gagat                                           25

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 175
acatcggcct cctactcttc cta                                             23

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide
```

```
<400> SEQUENCE: 176
acagatgggt tcccacagtc c                                              21

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 177
taacgcatga tttcttcact ggtt                                           24

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 178
atcccaaaga tggcgtagat ga                                             22

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 179
tgagaaatag gctaaggacc tcta                                           24

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 180
cctaggggct ggattcc                                                   17

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 181 aagggggtgca aacctgtgat ttt                                           23

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 182
```

```
agggccatgt ggttgccata c                                       21
```

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 183

```
cttccggttt atgttttcat ttct                                    24
```

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 184

```
tctttattag ttttgcacat ttta                                    24
```

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 185

```
caatccttcc aaggtctcct atc                                     23
```

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 186

```
tttcatcttt gccttcttgc tcat                                    24
```

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 187

```
catgtccact gcagcttgtc ca                                      22
```

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 188

```
tcccctttac acagagtcac agtt                                    24
```

```
<210> SEQ ID NO 189
<211> LENGTH: 15
<212> TYPE: DNA
<213> ORGANISM: Homo sapiens

<400> SEQUENCE: 189
gcatttgaag atata                                                      15

<210> SEQ ID NO 190
<211> LENGTH: 15
<212> TYPE: DNA
<213> ORGANISM: Homo sapiens

<400> SEQUENCE: 190
gcatttgacg atata                                                      15

<210> SEQ ID NO 191
<211> LENGTH: 15
<212> TYPE: DNA
<213> ORGANISM: Homo sapiens

<400> SEQUENCE: 191
atcatatcct tcctg                                                      15

<210> SEQ ID NO 192
<211> LENGTH: 15
<212> TYPE: DNA
<213> ORGANISM: Homo sapiens

<400> SEQUENCE: 192
atcatatmct tcctg                                                      15

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 193
atgggttgaa tgactttctg acat                                            24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 194
aggcatttcc tgtacaggga ctac                                            24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 195
acaggaaatg cctcttctta cttc                                            24
```

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 196
tttccccaag gattctacta ctgt                                          24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 197
agtgcatgta actgacacaa tcac                                          24

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 198
cttgcgttcc tgtttgggtc tct                                           23

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 199
tccgcttctt taccagggaa tc                                            22

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 200
aggcagtgaa ggcaacttga ctaa                                          24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 201
cagggcaata tttataaata atgg                                          24

<210> SEQ ID NO 202

```
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 202
tttggaaaat gtgtagctca ataa                                              24

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 203
aaggcatggt agtgcataaa ag                                                22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 204
atgaaacata aagggaggtc aa                                                22

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 205
aatgtgagct tggctattgt ctct                                              24

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 206
ataggctccc accagtgatt tac                                               23

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 207
aggcccctta tatctccaac tg                                                22

<210> SEQ ID NO 208
<211> LENGTH: 22
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 208
caacaaggct tctgcacaaa ag                                              22

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 209
cttggtggct tgccttgac                                                  19

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 210
tcatgagtgt cgccatcagc                                                 20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 211
ggaaagctga tggcgacact                                                 20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 212
ctgagacatt gcccaggtcc                                                 20

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 213
tttttacccg ttgctttctt ta                                              22

<210> SEQ ID NO 214
<211> LENGTH: 24
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 214
tatcccttgc tctttcattt atct                                              24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 215
gccggtaaaa tagctgttga gtag                                              24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 216
gccattgcaa acatttattt cgta                                              24

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 217
gcgtgtttgc gctaatag                                                     18

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 218
ctaagtcact tgattcacat ctaa                                              24

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 219
acagggtggc tgaagtgttt ta                                                22

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide
```

```
<400> SEQUENCE: 220
gtgggaggtg gcaggttatt                                              20

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 221
caattagcag acttgccgtt att                                          23

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 222
tctcttgagt tcggtgtttt atga                                         24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 223
accgaactca agagaattgc tgta                                         24

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 224
aaaggaccgt atgcttgttc acta                                         24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 225
tatgaatgcg cattttactc tttg                                         24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 226
```

```
tggagctcaa cttagatgct actg                                              24
```

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 227

```
ggtgctggtg ggataggagt tttt                                              24
```

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 228

```
tccattaaat tctggcatat tctt                                              24
```

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 229

```
tcagaggggt gctttcttcc acat                                              24
```

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 230

```
cttcggctgt cattgtcctc aaag                                              24
```

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 231

```
gcaaaggaca ttggctctga gaat                                              24
```

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 232

```
ctgcctgcac cagtcacaac tct                                               23
```

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 233
tgggctttgc tgctttcaa                                                    19

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 234
agtaactgtg acgcaggact ttta                                              24

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 235
ccctgttcct ccagcagatt a                                                 21

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 236
gtgatggcca ggtcaacaaa                                                   20

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 237
tttgatttgg gactgttgta aac                                               23

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 238
aaggcaatta taaactcttt caag                                              24

```
<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 239
tgggagttaa attaagttgc tcaa                                              24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 240
acattttatg aacactccca gtta                                              24

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 241
attaacactg ttcttgcttt tat                                               23

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 242
gtgccagcgt gggagttc                                                     18

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 243
gtgggggctc taggaaacct                                                   20

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 244
tttaatgaaa atgaggaaaa tgtt                                              24

<210> SEQ ID NO 245
<211> LENGTH: 23
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 245
gaccaagcat ttttatttca ttc                                           23

<210> SEQ ID NO 246
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 246
agtggcagca agattgtca                                                19

<210> SEQ ID NO 247
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 247
ggccttgctt ttgagttcc                                                19

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 248
ggtctttgcc tatttctatg gtg                                           23

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 249
ttaaaccgct tgaagatcta aata                                          24

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 250
tatacaccaa aatatctcct tat                                           23

<210> SEQ ID NO 251
<211> LENGTH: 24
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 251
ggggcacacc taattaattt ttat                                          24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 252
aaagaggata ctcaagacca cata                                          24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 253
cccaccaaca caaatatacc taat                                          24

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 254
tgaagggaaa gggaaaagat tt                                            22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 255
tccagcctta ggcacctgat aa                                            22

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 256
ataaagcagc aaagtgcagc atac                                          24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 257
aaggctgaac tgtgtagaca tttt                                          24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 258
tgacatttcc atggtacaaa gtgt                                          24

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 259
tttgttgttg gcttttcact tat                                           23

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 260
ccacctggca gtttgattg                                                19

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 261
taagcgtggt caacaactac agt                                           23

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 262
attcttgcca gcatttattg tc                                            22

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 263
caaaacattg ccccaaaag                                           19

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 264
tcaaactaaa caatttccct ctaa                                     24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 265
gataattaaa aactcactga tgta                                     24

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 266
ggaggctaaa ggaaagagta tg                                       22

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 267
attttatagc cagcaaagaa cac                                      23

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 268
ctagaaattc gggctgtgaa                                          20

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 269
```
ctgctttgtg acctaaggca agtt                                          24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 270
gtgaccatgt taaggcagat gagg                                          24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 271
ggaatggtct ttgattttgt aacc                                          24

<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 272
tccttaactg aataaaagca cctc                                          24

<210> SEQ ID NO 273
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 273
tggaacaccc atcaaagaag atact                                         25

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 274
gtgggagtcc tgttgacaca aac                                           23

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 275
agcgattcat ggcatcaaac                                               20

```
<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 276
acgtggtgga aggcgtcata                                                    20

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 277
gcgacccagt ttatagagtt tgcc                                               24

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 278
cttgtttgcg tttcaacgtg gtc                                                23

<210> SEQ ID NO 279
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 279
caaagatcac cctggaagct cagtt                                              25

<210> SEQ ID NO 280
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 280
atccagggca tctgcaaaat cagaa                                              25

<210> SEQ ID NO 281
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 281
tgcctatgtt aagagggaag ttggg                                              25

<210> SEQ ID NO 282
```

```
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 282
atgaccgcga tgtacatgtt cag                                            23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 283
tcaattgttt acagcccgtg atg                                            23

<210> SEQ ID NO 284
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 284
tttatacaaa ggcagacaac at                                             22

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 285
aggcgtaatg gctactcaga cga                                            23

<210> SEQ ID NO 286
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 286
gtaatccctc tccccgaaca taaac                                          25

<210> SEQ ID NO 287
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 287
tttgattcac gggttgttta ctctta                                         26

<210> SEQ ID NO 288
<211> LENGTH: 26
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 288
ttctatggaa catttacagg cacatt                                          26

<210> SEQ ID NO 289
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 289
taatgtgcct gtaaatgttc cataga                                          26

<210> SEQ ID NO 290
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 290
caggcttctt agaaaggact gatagg                                          26

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 291
gtcccagcag catgactatc                                                 20

<210> SEQ ID NO 292
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 292
cccactgggt aaaattacta ac                                              22

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 293
tagccatctt ctgctcttgg t                                               21

<210> SEQ ID NO 294
<211> LENGTH: 23
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 294
tggcttccca tattagactt ctg                                            23

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 295
tcttgcctat gctgctgtat ctta                                           24

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 296
agtcgggctt ttcatcattg ag                                             22

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 297
ttcttcatgt cattaagcaa tagg                                           24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 298
ttcaatttaa aagtgctagg aaca                                           24

<210> SEQ ID NO 299
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 299
cttcaggtgg atgtcacagt cacta                                          25

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide
```

<400> SEQUENCE: 300
attcaagcaa tgccaagagt atca                                          24

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 301
ctttcaatag taatgcctta tcat                                          24

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 302
tcctgcatgc atttcaccaa c                                             21

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 303
ctgttcacat tttgtaaaac taat                                          24

<210> SEQ ID NO 304
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 304
atcccaaaga tggcgtagat ga                                            22

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 305
cacgctgctc tttgctttga                                               20

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 306

```
gatctttgtc agggtcacag tct                                              23
```

<210> SEQ ID NO 307
<211> LENGTH: 9
<212> TYPE: DNA
<213> ORGANISM: Homo sapiens

<400> SEQUENCE: 307

```
tacaaagaa                                                               9
```

<210> SEQ ID NO 308
<211> LENGTH: 9
<212> TYPE: DNA
<213> ORGANISM: Homo sapiens

<400> SEQUENCE: 308

```
tacagagaa                                                               9
```

<210> SEQ ID NO 309
<211> LENGTH: 9
<212> TYPE: DNA
<213> ORGANISM: Homo sapiens

<400> SEQUENCE: 309

```
tacagagaa                                                               9
```

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 310

```
tgtgtccgcc agtagatgg                                                   19
```

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 311

```
tttttgacca cagaggttta caa                                              23
```

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 312

```
gaagcggagg cataagcaga                                                  20
```

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 313
ggtgcagata atgaaatgtt ttgt                                              24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 314 caccccatatg ccaaatgtca aaga                                             24

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 315
caaaaacaaa cttataccca gaag                                              24

<210> SEQ ID NO 316
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 316
caaatattgg gcaaaccta at                                                 22

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 317
aaggtgccat cacaaaatca t                                                 21

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 318
atcgcttgct ttcctaactc ttgt                                              24

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 319
```

```
aagtcactat ttggctttgg ttg                                           23

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 320
agaagcccaa aaggaacaa gata                                           24

<210> SEQ ID NO 321
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 321
ggcccagaaa agtatattac agtt                                          24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 322
tccttaaata agcccatgtc taat                                          24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 323
tctcaaagaa attttacaga tact                                          24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 324
aatggccatg gtaacctact aaca                                          24

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 325
caggctatac ccacaaggag att                                           23
```

<210> SEQ ID NO 326
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 326 tgttaattttt ggcttggatg tt                                            22

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 327
tcactccttt gcgcttatca a                                              21

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 328
agggctctat gtgccaaacc                                                20

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 329
aggggcctac taccttacac cag                                            23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 330
tgtaatccca ggtaagaaga aac                                            23

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 331
taccgggatg aactgtaata ataa                                           24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 332
ttctggcact cttcctcagg taac                                              24

<210> SEQ ID NO 333
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 333
gtcccatttg aatccattgt gc                                                22

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 334
ggcccccaag cgattctg                                                     18

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 335
tgtacaccca cagtctcaac tatt                                              24

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 336
acagccacct ttgtaaataa                                                   20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 337
tttttcgcaa agagttctat                                                   20

<210> SEQ ID NO 338
<211> LENGTH: 24

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 338
aaactgaccc tacctccatt tctc                                          24

<210> SEQ ID NO 339
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 339
actcagccta tgcttttcat ttca                                          24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 340
cagatattta tttggggaca ttat                                          24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 341
aaatctttgc ktttatcact cagt                                          24

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 342
tagtgcctgg ctttgtttta tgac                                          24

<210> SEQ ID NO 343
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 343
cggatttggg aaagctgtct ct                                            22

<210> SEQ ID NO 344
<211> LENGTH: 24
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 344
agagcacctt gaaggaaaca acaa                                              24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 345
tccctcaact gaagtacaga tagt                                              24

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 346
ataattgcgt tcttcccta ccc                                                23

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 347
aagccctggc accatcctg                                                    19

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 348
tttgcaaaga aatgctatgt                                                   20

<210> SEQ ID NO 349
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 349
ctgggtaaca gacttcagta at                                                22

<210> SEQ ID NO 350
<211> LENGTH: 24
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 350
atgggattgt cttctcaagt ttct                                            24

<210> SEQ ID NO 351
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 351
gatggcaaga tcaacaaatg ga                                              22

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 352
cttgatctgg gactgctgtg atg                                             23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 353
aggatataat ttttggttca aca                                             23

<210> SEQ ID NO 354
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 354
ttttcagtgc tcttgatagt agtg                                            24

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 355
gtgccaatga gcgacagg                                                   18

<210> SEQ ID NO 356
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 356
ccacgtgtgg ttctatgata cc                                              22

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 357
accgtgggag cgtacagtca                                                 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 358
cggcatgcag ctctttggta                                                 20

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 359
tggccacgtt cctagctact gtc                                             23

<210> SEQ ID NO 360
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 360
gagttccctt tttaggctgt tatt                                            24

<210> SEQ ID NO 361
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 361
tcttattgcc ttcatggatt tcta                                            24

<210> SEQ ID NO 362
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 362
```
tgaaaaataa gatgcgggag tg                                                   22

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 363
gtgaggctgg ggttgtttat g                                                    21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 364
gagatgggaa tggaaccacc a                                                    21

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 365
ttcgataatg catataagca caa                                                  23

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 366 aaggggggaaa atcacatctt t                                                   21

<210> SEQ ID NO 367
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 367
ttaaatgagg catattcagt ctcc                                                 24

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 368
ggaagtggag tggggaagg                                                       19

<210> SEQ ID NO 369
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 369
attcttgcca atatgcattt cact                                          24

<210> SEQ ID NO 370
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 370
ttcttttgta ctcactatta tactaa                                        26

<210> SEQ ID NO 371
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 371
aaacttgcct cttttaaaaa caat                                          24

<210> SEQ ID NO 372
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 372
taccacaccc tataccttca gtca                                          24

<210> SEQ ID NO 373
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 373
gagtatggca ccctttttcta tcta                                         24

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 374
gctatgttcc cctcgctgtc t                                             21

<210> SEQ ID NO 375

```
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 375
tgcttgccaa gagcctgac                                                  19

<210> SEQ ID NO 376
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 376
gctggcaagt tctaccactg tg                                              22

<210> SEQ ID NO 377
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 377
caaacgaaga acatcaggga aata                                            24

<210> SEQ ID NO 378
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 378
ttcacaatat tgtacaaaaa gtta                                            24

<210> SEQ ID NO 379
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 379
attaccacca atattcacca taag                                            24

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 380
tcagggtaag gcaaaagtag cac                                             23

<210> SEQ ID NO 381
<211> LENGTH: 24
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 381 gaacccaga atgaagaaag gtaa                                              24

<210> SEQ ID NO 382
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 382
tttgtgaaag tactattgga acac                                             24

<210> SEQ ID NO 383
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 383
acgcatggct ttggaacat                                                   19

<210> SEQ ID NO 384
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 384
cccgtatgtg gaagggcttt at                                               22

<210> SEQ ID NO 385
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 385
ctaggttgat ccgggacaaa acta                                             24

<210> SEQ ID NO 386
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 386
aacggatgac cagggcaaat ac                                               22

<210> SEQ ID NO 387
<211> LENGTH: 22
<212> TYPE: DNA
<213> ORGANISM: Artificial Sequence
<220> FEATURE:
```

<223> OTHER INFORMATION: Description of Artificial Sequence: synthetic
      oligonucleotide

<400> SEQUENCE: 387
ctagaaggtc ctggggcaac tg                                              22

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 388
aagccatcat gtaaagtgaa aag                                             23

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 389
atcccaaaga tggcatagat a                                               21

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 390
cacgctgctc tttgctttga                                                 20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 391
tgagctgcca gggtgaattg                                                 20

<210> SEQ ID NO 392
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 392
ttgctagcac ctattcttaa tagtgc                                          26

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 393
ccagggcagc tgcaaaatca gag                                              23

<210> SEQ ID NO 394
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 394
cccgatgcga cccagttta                                                   19

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 395
tggaggggtt tgatgccata                                                  20

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 396
gatggatgcc cttcgaatac aga                                              23

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 397
ttcccattta gtttgtcaat aatc                                             24

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 398 aagggagga ttgacttacc tat                                               23

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 399
```

```
ttggcatgga cctcctcttg a                                          21

<210> SEQ ID NO 400
<211> LENGTH: 13
<212> TYPE: DNA
<213> ORGANISM: Homo sapiens

<400> SEQUENCE: 400
tggtataagg tag                                                   13

<210> SEQ ID NO 401
<211> LENGTH: 18
<212> TYPE: DNA
<213> ORGANISM: Homo sapiens

<400> SEQUENCE: 401
caagataatg atgatgag                                              18

<210> SEQ ID NO 402
<211> LENGTH: 15
<212> TYPE: DNA
<213> ORGANISM: Homo sapiens

<400> SEQUENCE: 402
caagatgatg atgag                                                 15

<210> SEQ ID NO 403
<211> LENGTH: 13
<212> TYPE: DNA
<213> ORGANISM: Homo sapiens

<400> SEQUENCE: 403
tggtgtaagg tag                                                   13

<210> SEQ ID NO 404
<211> LENGTH: 17
<212> TYPE: DNA
<213> ORGANISM: Homo sapiens

<400> SEQUENCE: 404
ccccttatat ctccaac                                               17

<210> SEQ ID NO 405
<211> LENGTH: 17
<212> TYPE: DNA
<213> ORGANISM: Homo sapiens

<400> SEQUENCE: 405
ccccttatay ctccaac                                               17

<210> SEQ ID NO 406
<211> LENGTH: 15
<212> TYPE: DNA
<213> ORGANISM: Homo sapiens

<400> SEQUENCE: 406
aaatacgtaa tcgat                                                 15

<210> SEQ ID NO 407
<211> LENGTH: 15
<212> TYPE: DNA
<213> ORGANISM: Homo sapiens

<400> SEQUENCE: 407
```
aaatacataa tcgat                                                    15

<210> SEQ ID NO 408
<211> LENGTH: 15
<212> TYPE: DNA
<213> ORGANISM: Homo sapiens

<400> SEQUENCE: 408
aaatacrtaa tcgat                                                    15

<210> SEQ ID NO 409
<211> LENGTH: 2009
<212> TYPE: PRT
<213> ORGANISM: Homo sapiens

<400> SEQUENCE: 409

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Val Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320
```

```
Ser Arg Tyr His Tyr Phe Leu Glu Gly Phe Leu Asp Ala Leu Leu Cys
            325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
            355                 360                 365

Ser Trp Ala Phe Leu Ser Leu Phe Arg Leu Met Thr Gln Asp Phe Trp
            370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
            405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
            435                 440                 445

Glu Gln Leu Lys Lys Gln Gln Glu Ala Ala Gln Ala Ala Thr Ala
            450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
            485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
            530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
            565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
            610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
            645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
            690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
            725                 730                 735

Cys Trp Tyr Lys Phe Ser Asn Ile Phe Leu Ile Trp Asp Cys Ser Pro
```

```
                      740               745               750
Tyr Trp Leu Lys Val Lys His Val Val Asn Leu Val Val Met Asp Pro
            755               760               765
Phe Val Asp Leu Ala Ile Thr Ile Cys Ile Val Leu Asn Thr Leu Phe
    770               775               780
Met Ala Met Glu His Tyr Pro Met Thr Asp His Phe Asn Asn Val Leu
785               790               795               800
Thr Val Gly Asn Leu Val Phe Thr Gly Ile Phe Thr Ala Glu Met Phe
                805               810               815
Leu Lys Ile Ile Ala Met Asp Pro Tyr Tyr Tyr Phe Gln Glu Gly Trp
            820               825               830
Asn Ile Phe Asp Gly Phe Ile Val Thr Leu Ser Leu Val Glu Leu Gly
        835               840               845
Leu Ala Asn Val Glu Gly Leu Ser Val Leu Arg Ser Phe Arg Leu Leu
    850               855               860
Arg Val Phe Lys Leu Ala Lys Ser Trp Pro Thr Leu Asn Met Leu Ile
865               870               875               880
Lys Ile Ile Gly Asn Ser Val Gly Ala Leu Gly Asn Leu Thr Leu Val
                885               890               895
Leu Ala Ile Ile Val Phe Ile Phe Ala Val Val Gly Met Gln Leu Phe
            900               905               910
Gly Lys Ser Tyr Lys Asp Cys Val Cys Lys Ile Ala Ser Asp Cys Gln
        915               920               925
Leu Pro Arg Trp His Met Asn Asp Phe Phe His Ser Phe Leu Ile Val
    930               935               940
Phe Arg Val Leu Cys Gly Glu Trp Ile Glu Thr Met Trp Asp Cys Met
945               950               955               960
Glu Val Ala Gly Gln Ala Met Cys Leu Thr Val Phe Met Met Val Met
                965               970               975
Val Ile Gly Asn Leu Val Val Leu Asn Leu Phe Leu Ala Leu Leu Leu
            980               985               990
Ser Ser Phe Ser Ala Asp Asn Leu  Ala Ala Thr Asp  Asp Asn Glu
        995               1000              1005
Met Asn  Asn Leu Gln Ile Ala  Val Asp Arg Met His  Lys Gly Val
    1010              1015              1020
Ala Tyr  Val Lys Arg Lys Ile  Tyr Glu Phe Ile Gln  Gln Ser Phe
    1025              1030              1035
Ile Arg  Lys Gln Lys Ile Leu  Asp Glu Ile Lys Pro  Leu Asp Asp
    1040              1045              1050
Leu Asn  Asn Lys Lys Asp Ser  Cys Met Ser Asn His  Thr Ala Glu
    1055              1060              1065
Ile Gly  Lys Asp Leu Asp Tyr  Leu Lys Asp Val Asn  Gly Thr Thr
    1070              1075              1080
Ser Gly  Ile Gly Thr Gly Ser  Ser Val Glu Lys Tyr  Ile Ile Asp
    1085              1090              1095
Glu Ser  Asp Tyr Met Ser Phe  Ile Asn Asn Pro Ser  Leu Thr Val
    1100              1105              1110
Thr Val  Pro Ile Ala Val Gly  Glu Ser Asp Phe Glu  Asn Leu Asn
    1115              1120              1125
Thr Glu  Asp Phe Ser Ser Glu  Ser Asp Leu Glu Glu  Ser Lys Glu
    1130              1135              1140
Lys Leu  Asn Glu Ser Ser Ser  Ser Ser Glu Gly Ser  Thr Val Asp
    1145              1150              1155
```

-continued

Ile Gly Ala Pro Val Glu Glu Gln Pro Val Val Glu Pro Glu Glu
1160                    1165                    1170

Thr Leu Glu Pro Glu Ala Cys Phe Thr Glu Gly Cys Val Gln Arg
1175                    1180                    1185

Phe Lys Cys Cys Gln Ile Asn Val Glu Glu Gly Arg Gly Lys Gln
1190                    1195                    1200

Trp Trp Asn Leu Arg Arg Thr Cys Phe Arg Ile Val Glu His Asn
1205                    1210                    1215

Trp Phe Glu Thr Phe Ile Val Phe Met Ile Leu Leu Ser Ser Gly
1220                    1225                    1230

Ala Leu Ala Phe Glu Asp Ile Tyr Ile Asp Gln Arg Lys Thr Ile
1235                    1240                    1245

Lys Thr Met Leu Glu Tyr Ala Asp Lys Val Phe Thr Tyr Ile Phe
1250                    1255                    1260

Ile Leu Glu Met Leu Leu Lys Trp Val Ala Tyr Gly Tyr Gln Thr
1265                    1270                    1275

Tyr Phe Thr Asn Ala Trp Cys Trp Leu Asp Phe Leu Ile Val Asp
1280                    1285                    1290

Val Ser Leu Val Ser Leu Thr Ala Asn Ala Leu Gly Tyr Ser Glu
1295                    1300                    1305

Leu Gly Ala Ile Lys Ser Leu Arg Thr Leu Arg Ala Leu Arg Pro
1310                    1315                    1320

Leu Arg Ala Leu Ser Arg Phe Glu Gly Met Arg Val Val Val Asn
1325                    1330                    1335

Ala Leu Leu Gly Ala Ile Pro Ser Ile Met Asn Val Leu Leu Val
1340                    1345                    1350

Cys Leu Ile Phe Trp Leu Ile Phe Ser Ile Met Gly Val Asn Leu
1355                    1360                    1365

Phe Ala Gly Lys Phe Tyr His Cys Ile Asn Thr Thr Thr Gly Asp
1370                    1375                    1380

Arg Phe Asp Ile Glu Asp Val Asn Asn His Thr Asp Cys Leu Lys
1385                    1390                    1395

Leu Ile Glu Arg Asn Glu Thr Ala Arg Trp Lys Asn Val Lys Val
1400                    1405                    1410

Asn Phe Asp Asn Val Gly Phe Gly Tyr Leu Ser Leu Leu Gln Val
1415                    1420                    1425

Ala Thr Phe Lys Gly Trp Met Asp Ile Met Tyr Ala Ala Val Asp
1430                    1435                    1440

Ser Arg Asn Val Glu Leu Gln Pro Lys Tyr Glu Glu Ser Leu Tyr
1445                    1450                    1455

Met Tyr Leu Tyr Phe Val Ile Phe Ile Ile Phe Gly Ser Phe Phe
1460                    1465                    1470

Thr Leu Asn Leu Phe Ile Gly Val Ile Ile Asp Asn Phe Asn Gln
1475                    1480                    1485

Gln Lys Lys Lys Phe Gly Gly Gln Asp Ile Phe Met Thr Glu Glu
1490                    1495                    1500

Gln Lys Lys Tyr Tyr Asn Ala Met Lys Lys Leu Gly Ser Lys Lys
1505                    1510                    1515

Pro Gln Lys Pro Ile Pro Arg Pro Gly Asn Lys Phe Gln Gly Met
1520                    1525                    1530

Val Phe Asp Phe Val Thr Arg Gln Val Phe Asp Ile Ser Ile Met
1535                    1540                    1545

Ile Leu Ile Cys Leu Asn Met Val Thr Met Met Val Glu Thr Asp
1550                    1555                    1560

-continued

```
Asp Gln Ser Glu Tyr Val Thr Thr Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800

Asp Phe Glu Met Phe Tyr Glu Val Trp Glu Lys Phe Asp Pro Asp
    1805                1810                1815

Ala Thr Gln Phe Met Glu Phe Glu Lys Leu Ser Gln Phe Ala Ala
    1820                1825                1830

Ala Leu Glu Pro Pro Leu Asn Leu Pro Gln Pro Asn Lys Leu Gln
    1835                1840                1845

Leu Ile Ala Met Asp Leu Pro Met Val Ser Gly Asp Arg Ile His
    1850                1855                1860

Cys Leu Asp Ile Leu Phe Ala Phe Thr Lys Arg Val Leu Gly Glu
    1865                1870                1875

Ser Gly Glu Met Asp Ala Leu Arg Ile Gln Met Glu Glu Arg Phe
    1880                1885                1890

Met Ala Ser Asn Pro Ser Lys Val Ser Tyr Gln Pro Ile Thr Thr
    1895                1900                1905

Thr Leu Lys Arg Lys Gln Glu Glu Val Ser Ala Val Ile Ile Gln
    1910                1915                1920

Arg Ala Tyr Arg Arg His Leu Leu Lys Arg Thr Val Lys Gln Ala
    1925                1930                1935

Ser Phe Thr Tyr Asn Lys Asn Lys Ile Lys Gly Gly Ala Asn Leu
    1940                1945                1950

Leu Ile Lys Glu Asp Met Ile Ile Asp Arg Ile Asn Glu Asn Ser
```

```
                    1955                1960                1965

Ile Thr  Glu Lys Thr Asp Leu  Thr Met Ser Thr Ala  Ala Cys Pro
    1970                1975                1980

Pro Ser  Tyr Asp Arg Val Thr  Lys Pro Ile Val Glu  Lys His Glu
    1985                1990                1995

Gln Glu  Gly Lys Asp Glu Lys  Ala Lys Gly Lys
    2000                2005

<210> SEQ ID NO 410
<211> LENGTH: 2009
<212> TYPE: PRT
<213> ORGANISM: Homo sapiens

<400> SEQUENCE: 410

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
```

```
                    325                 330                 335
Gly Asn Ser Ser Asp Ala Gly Gln Cys Pro Glu Gly Tyr Met Cys Val
                340                 345                 350

Lys Ala Gly Arg Asn Pro Asn Tyr Gly Tyr Thr Ser Phe Asp Thr Phe
                355                 360                 365

Ser Trp Ala Phe Leu Ser Leu Phe Arg Leu Met Thr Gln Asp Phe Trp
            370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
                420                 425                 430

Thr Leu Glu Glu Ala Glu Gln Lys Glu Ala Glu Phe Gln Gln Met Ile
            435                 440                 445

Glu Gln Leu Lys Lys Gln Gln Glu Ala Ala Gln Ala Ala Thr Ala
                450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
                500                 505                 510

Glu Glu Lys Asp Glu Asp Glu Phe Gln Lys Ser Glu Ser Glu Asp Ser
            515                 520                 525

Ile Arg Arg Lys Gly Phe Arg Phe Ser Ile Glu Gly Asn Arg Leu Thr
            530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
                580                 585                 590

Asp Glu His Ser Thr Phe Glu Asp Asn Glu Ser Arg Arg Asp Ser Leu
            595                 600                 605

Phe Val Pro Arg Arg His Gly Glu Arg Arg Asn Ser Asn Leu Ser Gln
            610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
                660                 665                 670

Ile Asp Lys Pro Ala Thr Asp Asp Asn Gly Thr Thr Thr Glu Thr Glu
            675                 680                 685

Met Arg Lys Arg Arg Ser Ser Ser Phe His Val Ser Met Asp Phe Leu
            690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
                740                 745                 750
```

-continued

```
Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
                820                 825                 830

Asn Ile Phe Asp Gly Phe Ile Val Thr Leu Ser Leu Val Glu Leu Gly
                835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
                915                 920                 925

Leu Pro Arg Trp His Met Asn Asp Phe Phe His Ser Phe Leu Ile Val
930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu Ala Ala Thr Asp Asp Asp Asn Glu
                995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Ala Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170
```

-continued

```
Thr Leu Glu Pro Glu Ala Cys Phe Thr Glu Gly Cys Val Gln Arg
    1175                1180                1185

Phe Lys Cys Cys Gln Ile Asn Val Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Asp Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275

Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
```

-continued

```
          1565                1570                1575

Val Phe  Ile Val Leu Phe  Thr Gly Glu Cys  Val Leu Lys Leu Ile
    1580                1585                1590

Ser Leu  Arg His Tyr Tyr  Phe Thr Ile Gly  Trp Asn Ile Phe Asp
    1595                1600                1605

Phe Val  Val Val Ile Leu  Ser Ile Val Gly  Met Phe Leu Ala Glu
    1610                1615                1620

Leu Ile  Glu Lys Tyr Phe  Val Ser Pro Thr  Leu Phe Arg Val Ile
    1625                1630                1635

Arg Leu  Ala Arg Ile Gly  Arg Ile Leu Arg  Leu Ile Lys Gly Ala
    1640                1645                1650

Lys Gly  Ile Arg Thr Leu  Leu Phe Ala Leu  Met Met Ser Leu Pro
    1655                1660                1665

Ala Leu  Phe Asn Ile Gly  Leu Leu Leu Phe  Leu Val Met Phe Ile
    1670                1675                1680

Tyr Ala  Ile Phe Gly Met  Ser Asn Phe Ala  Tyr Val Lys Arg Glu
    1685                1690                1695

Val Gly  Ile Asp Asp Met  Phe Asn Phe Glu  Thr Phe Gly Asn Ser
    1700                1705                1710

Met Ile  Cys Leu Phe Gln  Ile Thr Thr Ser  Ala Gly Trp Asp Gly
    1715                1720                1725

Leu Leu  Ala Pro Ile Leu  Asn Ser Lys Pro  Pro Asp Cys Asp Pro
    1730                1735                1740

Asn Lys  Val Asn Pro Gly  Ser Ser Val Lys  Gly Asp Cys Gly Asn
    1745                1750                1755

Pro Ser  Val Gly Ile Phe  Phe Phe Val Ser  Tyr Ile Ile Ile Ser
    1760                1765                1770

Phe Leu  Val Val Val Asn  Met Tyr Ile Ala  Val Ile Leu Glu Asn
    1775                1780                1785

Phe Ser  Val Ala Thr Glu  Glu Ser Ala Glu  Pro Leu Ser Glu Asp
    1790                1795                1800

Asp Phe  Glu Met Phe Tyr  Glu Val Trp Glu  Lys Phe Asp Pro Asp
    1805                1810                1815

Ala Thr  Gln Phe Met Glu  Phe Glu Lys Leu  Ser Gln Phe Ala Ala
    1820                1825                1830

Ala Leu  Glu Pro Pro Leu  Asn Leu Pro Gln  Pro Asn Lys Leu Gln
    1835                1840                1845

Leu Ile  Ala Met Asp Leu  Pro Met Val Ser  Gly Asp Arg Ile His
    1850                1855                1860

Cys Leu  Asp Ile Leu Phe  Ala Phe Thr Lys  Arg Val Leu Gly Glu
    1865                1870                1875

Ser Gly  Glu Met Asp Ala  Leu Arg Ile Gln  Met Glu Glu Arg Phe
    1880                1885                1890

Met Ala  Ser Asn Pro Ser  Lys Val Ser Tyr  Gln Pro Ile Thr Thr
    1895                1900                1905

Thr Leu  Lys Arg Lys Gln  Glu Glu Val Ser  Ala Val Ile Ile Gln
    1910                1915                1920

Arg Ala  Tyr Arg Arg His  Leu Leu Lys Arg  Thr Val Lys Gln Ala
    1925                1930                1935

Ser Phe  Thr Tyr Asn Lys  Asn Lys Ile Lys  Gly Gly Ala Asn Leu
    1940                1945                1950

Leu Ile  Lys Glu Asp Met  Ile Ile Asp Arg  Ile Asn Glu Asn Ser
    1955                1960                1965
```

```
Ile Thr Glu Lys Thr Asp Leu Thr Met Ser Thr Ala Ala Cys Pro
    1970                1975                1980

Pro Ser Tyr Asp Arg Val Thr Lys Pro Ile Val Glu Lys His Glu
    1985                1990                1995

Gln Glu Gly Lys Asp Glu Lys  Ala Lys Gly Lys
    2000                2005

<210> SEQ ID NO 411
<211> LENGTH: 2009
<212> TYPE: PRT
<213> ORGANISM: Homo sapiens

<400> SEQUENCE: 411

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335
```

-continued

```
Gly Asn Ser Ser Asp Ala Gly Gln Cys Pro Glu Gly Tyr Met Cys Val
            340                 345                 350
Lys Ala Gly Arg Asn Pro Asn Tyr Gly Tyr Thr Ser Phe Asp Thr Phe
            355                 360                 365
Ser Trp Ala Phe Leu Ser Leu Phe Arg Leu Met Thr Gln Asp Phe Trp
370                 375                 380
Glu Asn Leu Tyr Gln Leu Thr Leu Arg Ala Ala Gly Lys Thr Tyr Met
385                 390                 395                 400
Ile Phe Phe Val Leu Val Ile Phe Leu Gly Ser Phe Tyr Leu Ile Asn
                405                 410                 415
Leu Ile Leu Ala Val Val Ala Met Ala Tyr Glu Glu Gln Asn Gln Ala
            420                 425                 430
Thr Leu Glu Glu Ala Glu Gln Lys Glu Ala Glu Phe Gln Gln Met Ile
            435                 440                 445
Glu Gln Leu Lys Lys Gln Gln Glu Ala Ala Gln Ala Ala Thr Ala
            450                 455                 460
Thr Ala Ser Glu His Ser Arg Glu Pro Ser Ala Ala Gly Arg Leu Ser
465                 470                 475                 480
Asp Ser Ser Ser Glu Ala Ser Lys Leu Ser Ser Lys Ser Ala Lys Glu
                485                 490                 495
Arg Arg Asn Arg Arg Lys Lys Arg Lys Gln Lys Glu Gln Ser Gly Gly
            500                 505                 510
Glu Glu Lys Asp Glu Asp Glu Phe Gln Lys Ser Glu Ser Glu Asp Ser
            515                 520                 525
Ile Arg Arg Lys Gly Phe Arg Phe Ser Ile Glu Gly Asn Arg Leu Thr
            530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                565                 570                 575
Phe Arg Gly Arg Ala Lys Asp Val Gly Ser Glu Asn Asp Phe Ala Asp
            580                 585                 590
Asp Glu His Ser Thr Phe Glu Asp Asn Glu Ser Arg Arg Asp Ser Leu
            595                 600                 605
Phe Val Pro Arg Arg His Gly Glu Arg Arg Asn Ser Asn Leu Ser Gln
            610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                645                 650                 655
Pro Ser Val Pro Thr Ser Pro Val Gly Gln Leu Leu Pro Glu Val Ile
            660                 665                 670
Ile Asp Lys Pro Ala Thr Asp Asp Asn Gly Thr Thr Thr Glu Thr Glu
            675                 680                 685
Met Arg Lys Arg Arg Ser Ser Ser Phe His Val Ser Met Asp Phe Leu
            690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                725                 730                 735
Cys Trp Tyr Lys Phe Ser Asn Ile Phe Leu Ile Trp Asp Cys Ser Pro
            740                 745                 750
Tyr Trp Leu Lys Val Lys His Val Val Asn Leu Val Val Met Asp Pro
            755                 760                 765
```

Phe Val Asp Leu Ala Ile Thr Ile Cys Ile Val Leu Asn Thr Leu Phe
770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
            805                 810                 815

Leu Lys Ile Ile Ala Met Asp Pro Tyr Tyr Tyr Phe Gln Glu Gly Trp
        820                 825                 830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
            885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
            965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
        995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Ala Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg

-continued

```
            1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275

Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335

Ala Leu Leu Gly Ala Ile Pro Ser Ile Met Asn Val Leu Leu Val
    1340                1345                1350

Cys Leu Ile Phe Trp Leu Ile Phe Ser Ile Met Gly Val Asn Leu
    1355                1360                1365

Phe Ala Gly Lys Phe Tyr His Cys Ile Asn Thr Thr Thr Gly Asp
    1370                1375                1380

Arg Phe Asp Ile Glu Asp Val Asn Asn His Thr Asp Cys Leu Lys
    1385                1390                1395

Leu Ile Glu Arg Asn Glu Thr Ala Arg Trp Lys Asn Val Lys Val
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Glu Tyr Val Thr Thr Ile Leu Ser Arg Ile Asn Leu
    1565                1570                1575
```

-continued

```
Val Phe Ile Val Leu Phe Thr Gly Glu Cys Val Leu Lys Leu Ile
    1580            1585                1590

Ser Leu Arg His Tyr Tyr Phe Thr Ile Gly Trp Asn Ile Phe Asp
    1595            1600                1605

Phe Val Val Val Ile Leu Ser Ile Val Gly Met Phe Leu Ala Glu
    1610            1615                1620

Leu Ile Glu Lys Tyr Phe Val Ser Pro Thr Leu Phe Arg Val Ile
    1625            1630                1635

Arg Leu Ala Arg Ile Gly Arg Ile Leu Arg Leu Ile Lys Gly Ala
    1640            1645                1650

Lys Gly Ile Arg Thr Leu Leu Phe Ala Leu Met Met Ser Leu Pro
    1655            1660                1665

Ala Leu Phe Asn Ile Gly Leu Leu Leu Phe Leu Val Met Phe Ile
    1670            1675                1680

Tyr Ala Ile Phe Gly Met Ser Asn Phe Ala Tyr Val Lys Arg Glu
    1685            1690                1695

Val Gly Ile Asp Asp Met Phe Asn Phe Glu Thr Phe Gly Asn Ser
    1700            1705                1710

Met Ile Cys Leu Phe Gln Ile Thr Thr Ser Ala Gly Trp Asp Gly
    1715            1720                1725

Leu Leu Ala Pro Ile Leu Asn Ser Lys Pro Pro Asp Cys Asp Pro
    1730            1735                1740

Asn Lys Val Asn Pro Gly Ser Ser Val Lys Gly Asp Cys Gly Asn
    1745            1750                1755

Pro Ser Val Gly Ile Phe Phe Phe Val Ser Tyr Ile Ile Ile Tyr
    1760            1765                1770

Phe Leu Val Val Val Asn Met Tyr Ile Ala Val Ile Leu Glu Asn
    1775            1780                1785

Phe Ser Val Ala Thr Glu Glu Ser Ala Glu Pro Leu Ser Glu Asp
    1790            1795                1800

Asp Phe Glu Met Phe Tyr Glu Val Trp Glu Lys Phe Asp Pro Asp
    1805            1810                1815

Ala Thr Gln Phe Met Glu Phe Glu Lys Leu Ser Gln Phe Ala Ala
    1820            1825                1830

Ala Leu Glu Pro Pro Leu Asn Leu Pro Gln Pro Asn Lys Leu Gln
    1835            1840                1845

Leu Ile Ala Met Asp Leu Pro Met Val Ser Gly Asp Arg Ile His
    1850            1855                1860

Cys Leu Asp Ile Leu Phe Ala Phe Thr Lys Arg Val Leu Gly Glu
    1865            1870                1875

Ser Gly Glu Met Asp Ala Leu Arg Ile Gln Met Glu Glu Arg Phe
    1880            1885                1890

Met Ala Ser Asn Pro Ser Lys Val Ser Tyr Gln Pro Ile Thr Thr
    1895            1900                1905

Thr Leu Lys Arg Lys Gln Glu Glu Val Ser Ala Val Ile Ile Gln
    1910            1915                1920

Arg Ala Tyr Arg Arg His Leu Leu Lys Arg Thr Val Lys Gln Ala
    1925            1930                1935

Ser Phe Thr Tyr Asn Lys Asn Lys Ile Lys Gly Gly Ala Asn Leu
    1940            1945                1950

Leu Ile Lys Glu Asp Met Ile Ile Asp Arg Ile Asn Glu Asn Ser
    1955            1960                1965

Ile Thr Glu Lys Thr Asp Leu Thr Met Ser Thr Ala Ala Cys Pro
    1970            1975                1980
```

```
Pro Ser Tyr Asp Arg Val Thr Lys Pro Ile Val Glu Lys His Glu
    1985                1990                1995
Gln Glu Gly Lys Asp Glu Lys Ala Lys Gly Lys
    2000                2005

<210> SEQ ID NO 412
<211> LENGTH: 6030
<212> TYPE: DNA
<213> ORGANISM: Homo sapiens

<400> SEQUENCE: 412
atggagcaaa cagtgcttgt accaccagga cctgacagct tcaacttctt caccagagaa     60
tctcttgcgg ctattgaaag acgcattgca gaagaaaagg caaagaatcc caaaccagac    120
aaaaaagatg acgacgaaaa tggcccaaag ccaaatagtg acttggaagc tggaagaac     180 cttccattta tttatggaga cattcctcca gagatggtgt cagagcccct ggaggacctg    240 gaccectact atatcaataa gaaaactttt atagtattga ataaagggaa ggccatcttc    300
cggttcagtg ccacctctgc cctgtacatt ttaactccct tcaatcctct taggaaaata    360
gctattaaga ttttggtaca ttcattattc agcatgctaa ttatgtgcac tattttgaca    420
aactgtgtgt ttatgacaat gagtaaccct cctgattgga caaagaatgt agaatacacc    480
ttcacaggaa tatatacttt tgaatcactt ataaaaatta ttgcaagggg attctgttta    540
gaagatttta ctttccttcg ggatccatgg aactggctcg atttcactgt cattacattt    600
gcgtacgtca cagagtttgt ggacctgggc aatgtctcgg cattgagaac attcagagtt    660
ctccgagcat tgaagacgat ttcagtcatt ccaggcctga aaccattgt gggagccctg    720 atccagtctg tgaagaagct ctcagatgta atgatcctga ctgtgttctg tctgagcgta    780
tttgctctaa ttgggctgca gctgttcatg ggcaacctga gaataaatg tatacaatgg    840 cctcccacca atgcttcctt ggaggaacat agtatagaaa agaatataac tgtgaattat    900
aatggtacac ttataaatga aactgtcttt gagtttgact ggaagtcata tattcaagat    960
tcaagatatc attatttcct ggagggtttt ttagatgcac tactatgtgg aaatagctct   1020
gatgcaggcc aatgtccaga gggatatatg tgtgtgaaag ctggtagaaa tcccaattat   1080
ggctacacaa gctttgatac cttcagttgg gcttttttgt ccttgtttcg actaatgact   1140
caggacttct gggaaaatct ttatcaactg acattacgtg ctgctgggaa aacgtacatg   1200
atattttttg tattggtcat tttcttgggc tcattctacc taataaattt gatcctggct   1260
gtggtggcca tggcctacga ggaacagaat caggccacct tggaagaagc agaacagaaa   1320
gaggccgaat tcagcagat gattgaacag cttaaaaagc aacaggaggc agctcagcag   1380
gcagcaacgg caactgcctc agaacattcc agagagccca gtgcagcagg caggctctca   1440
gacagctcat ctgaagcctc taagttgagt tccaagagtg ctaaggaaag aagaaatcgg   1500
aggaagaaaa gaaaacagaa agagcagtct ggtgggaag agaaagatga ggatgaattc   1560
caaaaatctg aatctgagga cagcatcagg aggaaaggtt ttcgcttctc cattgaaggg   1620
aaccgattga catatgaaaa gaggtactcc tccccacacc agtctttgtt gagcatccgt   1680
ggctccctat tttccaccaag gcgaaatagc agaacaagcc ttttcagctt tagagggcga   1740
gcaaaggatg tgggatctga aacgacttca gcagatgatg agcacagcac ctttgaggat   1800
aacgagagcc gtagagattc cttgtttgtg ccccgacgac acggagagag acgcaacagc   1860
aacctgagtc agaccagtag gtcatccgg atgctggcag tgtttccagc gaatgggaag   1920
atgcacagca ctgtggattg caatggtgtg gttccttgg ttggtggacc ttcagttcct   1980
```

```
acatcgcctg ttggacagct tctgccagag gtgataatag ataagccagc tactgatgac   2040
aatggaacaa ccactgaaac tgaaatgaga aagagaaggt caagttcttt ccacgtttcc   2100
atggactttc tagaagatcc ttcccaaagg caacgagcaa tgagtatagc cagcattcta   2160
acaaatacag tagaagaact tgaagaatcc aggcagaaat gcccaccctg ttggtataaa   2220
ttttccaaca tattcttaat ctgggactgt tctccatatt ggttaaaagt gaaacatgtt   2280
gtcaacctgg ttgtgatgga cccatttgtt gacctggcca tcaccatctg tattgtctta   2340
aatactcttt tcatggccat ggagcactat ccaatgacgg accatttcaa taatgtgctt   2400
acagtaggaa acttggtttt cactgggatc tttacagcag aaatgtttct gaaaattatt   2460
gccatggatc cttactatta tttccaagaa ggctggaata tctttgacgg ttttattgtg   2520
acgcttagcc tggtagaact tggactcgcc aatgtggaag gattatctgt tctccgttca   2580
tttcgattgc tgcgagtttt caagttggca aaatcttggc caacgttaaa tatgctaata   2640
aagatcatcg gcaattccgt gggggctctg ggaaatttaa ccctcgtctt ggccatcatc   2700
gtcttcattt tgccgtggt cggcatgcag ctctttggta aaagctacaa agattgtgtc   2760
tgcaagatcg ccagtgattg tcaactccca cgctggcaca tgaatgactt cttccactcc   2820
ttcctgattg tgttccgcgt gctgtgtggg gagtggatag agaccatgtg ggactgtatg   2880
gaggttgctg gtcaagccat gtgccttact gtcttcatga tggtcatggt gattggaaac   2940
ctagtggtcc tgaatctctt tctggccttg cttctgagct catttagtgc agacaacctt   3000
gcagccactg atgatgataa tgaaatgaat aatctccaaa ttgctgtgga taggatgcac   3060
aaaggagtag cttatgtgaa aagaaaaata tatgaattta ttcaacagtc cttcattagg   3120
aaacaaaaga ttttagatga aattaaacca cttgatgatc taaacaacaa gaaagacagt   3180
tgtatgtcca atcatacagc agaaattggg aaagatcttg actatcttaa agatgtaaat   3240
ggaactacaa gtggtatagg aactggcagc agtgttgaaa aatacattat tgatgaaagt   3300
gattacatgt cattcataaa caaccccagt cttactgtga ctgtaccaat tgctgtagga   3360
gaatctgact ttgaaaattt aaacacggaa gactttagta gtgaatcgga tctggaagaa   3420
agcaaagaga aactgaatga aagcagtagc tcatcagaag gtagcactgt ggacatcggc   3480
gcacctgtag aagaacagcc cgtagtggaa cctgaagaaa ctcttgaacc agaagcttgt   3540
ttcactgaag gctgtgtaca agattcaag tgttgtcaaa tcaatgtgga agaaggcaga   3600
ggaaaacaat ggtggaacct gagaaggacg tgtttccgaa tagttgaaca taactggttt   3660
gagaccttca ttgttttcat gattctcctt agtagtggtg ctctggcatt tgaagatata   3720
tatattgatc agcgaaagac gattaagacg atgttggaat atgctgacaa ggttttcact   3780 tacatttta ttctggaaat gcttctaaaa tgggtggcat atggctatca aacatatttc   3840
accaatgcct ggtgttggct ggacttctta attgttgatg tttcattggt cagtttaaca   3900
gcaaatgcct tgggttactc agaacttgga gccatcaaat ctctcaggac actaagagct   3960
ctgagacctc taagagcctt atctcgattt gaagggatga gggtggttgt gaatgcccct   4020
ttaggagcaa ttccatccat catgaatgtg cttctggttt gtcttatatt ctggctaatt   4080
ttcagcatca tgggcgtaaa tttgtttgct ggcaaattct accactgtat taacaccaca   4140
actggtgaca ggtttgacat cgaagacgtg aataatcata ctgattgcct aaaactaata   4200
gaaagaaatg agactgctcg atggaaaaat gtgaaagtaa actttgataa tgtaggattt   4260
gggtatctct ctttgcttca agttgccaca ttcaaaggat ggatggatat aatgtatgca   4320
gcagttgatt ccagaaatgt ggaactccag cctaagtatg aagaaagtct gtacatgtat   4380
```

```
ctttactttg ttattttcat catctttggg tccttcttca ccttgaacct gtttattggt    4440
gtcatcatag ataatttcaa ccagcagaaa aagaagtttg gaggtcaaga catctttatg    4500
acagaagaac agaagaaata ctataatgca atgaaaaaat taggatcgaa aaaaccgcaa    4560
aagcctatac ctcgaccagg aaacaaattt caaggaatgg tctttgactt cgtaaccaga    4620 caagttttg acataagcat catgattctc atctgtctta acatggtcac aatgatggtg     4680
gaaacagatg accagagtga atatgtgact accattttgt cacgcatcaa tctggtgttc    4740
attgtgctat ttactggaga gtgtgtactg aaactcatct ctctacgcca ttattatttt    4800
accattggat ggaatatttt tgattttgtg gttgtcattc tctccattgt aggtatgttt    4860
cttgccgagc tgatagaaaa gtatttcgtg tcccctaccc tgttccgagt gatccgtctt    4920
gctaggattg gccgaatcct acgtctgatc aaggagcaa aggggatccg cacgctgctc     4980
tttgctttga tgatgtccct tcctgcgttg tttaacatcg gcctcctact cttcctagtc    5040
atgttcatct acgccatctt tgggatgtcc aactttgcct atgttaagag ggaagttggg    5100
atcgatgaca tgttcaactt tgagaccttt ggcaacagca tgatctgcct attccaaatt    5160
acaacctctg ctggctggga tggattgcta gcacccattc tcaacagtaa gccacccgac    5220
tgtgacccta ataaagttaa ccctggaagc tcagttaagg gagactgtgg gaacccatct    5280
gttgaatttt tcttttttgt cagttacatc atcatatcct tcctggttgt ggtgaacatg    5340
tacatcgcgg tcatcctgga gaacttcagt gttgctactg aagaaagtgc agagcctctg    5400
agtgaggatg acttttgagat gttctatgag gtttgggaga gtttgatcc cgatgcaact     5460 cagttcatgg aatttgaaaa attatctcag tttgcagctg cgcttgaacc gcctctcaat    5520
ctgccacaac caaacaaact ccagctcatt gccatggatt tgcccatggt gagtggtgac    5580
cggatccact gtcttgatat cttatttgct tttacaaagc gggttctagg agagagtgga    5640
gagatggatg ctctacgaat acagatggaa gagcgattca tggcttccaa tccttccaag    5700
gtctcctatc agccaatcac tactacttta aaacgaaaac aagaggaagt atctgctgtc    5760
attattcagc gtgcttacag acgccacctt ttaaagcgaa ctgtaaaaca agcttccttt    5820
acgtacaata aaaacaaaat caaaggtggg gctaatcttc ttataaaaga agacatgata    5880
attgacagaa taaatgaaaa ctctattaca gaaaaaactg atctgaccat gtccactgca    5940
gcttgtccac cttcctatga ccgggtgaca aagccaattg tggaaaaaca tgagcaagaa    6000
ggcaaagatg aaaaagccaa agggaaataa                                     6030
```

<210> SEQ ID NO 413
<211> LENGTH: 216
<212> TYPE: DNA
<213> ORGANISM: Homo sapiens

<400> SEQUENCE: 413

```
tactgcagag gtctctggtg catgtgtgta tgtgtgcgtt tgtgtgtgtt tgtgtgtctg      60
tgtgttctgc cccagtgaga ctgcagccct tgtaaatact ttgacacctt ttgcaagaag    120
gaatctgaac aattgcaact gaaggcacat tgttatcatc tcgtctttgg gtgatgctgt    180
tcctcactgc agatggataa ttttccttt aatcag                               216
```

<210> SEQ ID NO 414
<211> LENGTH: 146
<212> TYPE: DNA
<213> ORGANISM: Homo sapiens

<400> SEQUENCE: 414

```
gaatttcata tgcagaataa atggtaatta aaatgtgcag gatgacaaga tggagcaaac      60
agtgcttgta ccaccaggac ctgacagctt caacttcttc accagagaat ctcttgcggc     120
tattgaaaga cgcattgcag aagaaa                                          146

<210> SEQ ID NO 415
<211> LENGTH: 119
<212> TYPE: DNA
<213> ORGANISM: Homo sapiens

<400> SEQUENCE: 415
acttttatag tattgaataa agggaaggcc atcttccggt tcagtgccac ctctgccctg      60
tacattttaa ctcccttcaa tcctcttagg aaaatagcta ttaagatttt ggtacattc     119

<210> SEQ ID NO 416
<211> LENGTH: 90
<212> TYPE: DNA
<213> ORGANISM: Homo sapiens

<400> SEQUENCE: 416
attattcagc atgctaatta tgtgcactat tttgacaaac tgtgtgttta tgacaatgag      60
taaccctcct gattggacaa agaatgtaga                                       90

<210> SEQ ID NO 417
<211> LENGTH: 129
<212> TYPE: DNA
<213> ORGANISM: Homo sapiens

<400> SEQUENCE: 417
atacaccttc acaggaatat atactttga atcacttata aaaattattg caaggggatt      60
ctgtttagaa gattttactt tccttcggga tccatggaac tggctcgatt tcactgtcat    120
tacatttgc                                                            129

<210> SEQ ID NO 418
<211> LENGTH: 92
<212> TYPE: DNA
<213> ORGANISM: Homo sapiens

<400> SEQUENCE: 418
gtttgtaaca gaatttgtaa acctaggcaa tttttcagct cttcgcactt tcagagtctt      60
gagagctttg aaaactattt cggtaattcc ag                                   92

<210> SEQ ID NO 419
<211> LENGTH: 92
<212> TYPE: DNA
<213> ORGANISM: Homo sapiens

<400> SEQUENCE: 419
gtacgtcaca gagtttgtgg acctgggcaa tgtctcggca ttgagaacat tcagagttct      60
ccgagcattg aagacgattt cagtcattcc ag                                   92

<210> SEQ ID NO 420
<211> LENGTH: 270
<212> TYPE: DNA
<213> ORGANISM: Homo sapiens

<400> SEQUENCE: 420
gcctgaaaac cattgtggga gccctgatcc agtctgtgaa gaagctctca gatgtaatga      60
tcctgactgt gttctgtctg agcgtatttg ctctaattgg gctgcagctg ttcatgggca    120
```

```
acctgaggaa taaatgtata caatggcctc ccaccaatgc ttccttggag gaacatagta    180
tagaaaagaa tataactgtg aattataatg gtacacttat aaatgaaact gtctttgagt    240
ttgactggaa gtcatatatt caagattcaa                                    270

<210> SEQ ID NO 421
<211> LENGTH: 64
<212> TYPE: DNA
<213> ORGANISM: Homo sapiens

<400> SEQUENCE: 421
gatatcatta tttcctggag ggttttttag atgcactact atgtggaaat agctctgatg     60
cagg                                                                 64

<210> SEQ ID NO 422
<211> LENGTH: 142
<212> TYPE: DNA
<213> ORGANISM: Homo sapiens

<400> SEQUENCE: 422
ccaatgtcca gagggatata tgtgtgtgac agctggtaga aatcccaatt atggctacac     60
aagctttgat accttcagtt gggctttttt gtccttgttt cgactaatga ctcaggactt    120
ctgggaaaat ctttatcaac tg                                            142

<210> SEQ ID NO 423
<211> LENGTH: 207
<212> TYPE: DNA
<213> ORGANISM: Homo sapiens

<400> SEQUENCE: 423
acattacgtg ctgctgggaa aacgtacatg atatttttg tattggtcat tttcttgggc     60
tcattctacc taataaattt gatcctggct gtggtggcca tggcctacga ggaacagaat    120
caggccacct tggaagaagc agaacagaaa gaggccgaat tcagcagat gattgaacag    180 cttaaaaagc aacaggaggc agctcag                                       207

<210> SEQ ID NO 424
<211> LENGTH: 285
<212> TYPE: DNA
<213> ORGANISM: Homo sapiens

<400> SEQUENCE: 424
caggcagcaa cggcaactgc ctcagaacat tccagagagc ccagtgcagc aggcaggctc     60
tcagacagct catctgaagc ctctaagttg agttccaaga gtgctaagga aagaagaaat    120
cggaggaaga aaagaaaaca gaaagagcag tctggtgggg aagagaaaga tgaggatgaa    180
ttccaaaaat ctgaatctga ggacagcatc aggaggwaag gttttcgctt ctccattgaa    240
gggaaccggt tgacatatga aaagaggtac tcctccccac accag                   285

<210> SEQ ID NO 425
<211> LENGTH: 381
<212> TYPE: DNA
<213> ORGANISM: Homo sapiens

<400> SEQUENCE: 425
tctttgttga gcatccgtgg ctccctattt tcaccaaggc gaaatagcag aacaagcctt     60
ttcagcttta gagggcgagc aaaggatgtg ggatctgaga cgacttcgc agatgatgag    120 cacagcacct tgaggataa cgagagccgt agagattcct tgtttgtgcc ccgacgacac    180
```

```
ggagagagac gcaacagcaa cctgagtcag accagtaggt catcccggat gctggcagtg    240
tttccagcga atgggaagat gcacagcact gtggattgca atggtgtggg ttccttggtt    300
ggtggacctt cagttcctac atcgcctgtt ggacagcttc tgccagaggt gataatagat    360
aagccagcta ctgatgacaa t                                              381

<210> SEQ ID NO 426
<211> LENGTH: 133
<212> TYPE: DNA
<213> ORGANISM: Homo sapiens

<400> SEQUENCE: 426
ggaacaacca ctgaaactga aatgagaaag agaaggtcaa gttctttcca cgtttccatg     60
gactttctag aagatccttc ccaaaggcaa cgagcaatga gtatagccag cattctaaca    120
aatacagtag aag                                                       133

<210> SEQ ID NO 427
<211> LENGTH: 239
<212> TYPE: DNA
<213> ORGANISM: Homo sapiens

<400> SEQUENCE: 427
aacttgaaga atccaggcag aaatgcccac cctgttggta taaatttttcc aacatattct    60 taatctggga ctgttctcca tattggttaa aagtgaaaca tgttgtcaac ctggttgtga   120
tggacccatt tgttgacctg ccatcaccac tctgtattgt cttaaatact cttttcatgg   180
ccatggagca ctatccaatg acggaccatt tcaataatgt gcttacagta ggaaacttg     239

<210> SEQ ID NO 428
<211> LENGTH: 174
<212> TYPE: DNA
<213> ORGANISM: Homo sapiens

<400> SEQUENCE: 428
gttttcactg ggatctttac agcagaaatg tttctgaaaa ttattgccat ggatccttac    60
tattatttcc aagaaggctg gaatatcttt gacggtttta ttgtgacgct tagcctggta   120
gaacttggac tcgccaatgt ggaagggtta tctgttctcc gttcatttcg attg          174

<210> SEQ ID NO 429
<211> LENGTH: 357
<212> TYPE: DNA
<213> ORGANISM: Homo sapiens

<400> SEQUENCE: 429
ctgcgagatt tcaagttggc aaaatcttgg ccaacgttaa atatgctaat aaagatcatc    60
ggcaattccg tgggggctct gggaaattta accctcgtct tggccatcat cgtcttcatt   120
tttgccgtgg tcggcatgca gctctttggt aaaagctaca agattgtgt ctgcaagatc    180 gccagtgatt gtcaactccc acgctggcac atgaatgact tcttccactc ckhcctgatt   240
gtgttccgcg tgctgtgtgg ggagtggata gagaccatgt gggactgtat ggaggttgct   300
ggtcaagcca tgtgccttac tgtcttcatg atggtcatgg tgattggaaa cctagcg      357

<210> SEQ ID NO 430
<211> LENGTH: 483
<212> TYPE: DNA
<213> ORGANISM: Homo sapiens

<400> SEQUENCE: 430
```

```
gtcctgaatc tctttctggc cttgcttctg agctcattta gtgcagacaa ccttgcagcc      60
actgatgatg ataatgaaat gaataatctc caaattgctg tggataggat gcacaaagga     120
gtagcttatg tgaaaagaaa aatatatgar tttattcaac agtccttcat taggaaacaa     180
aagattttag atgaaattaa accacttgat gatctaaaca acaagaaaga cagttgtatg     240
tccaatcata cagcagaaat tgggaaagat cttgactatc ttaaagatgt aaatggaact     300
acaagtggta taggaactgg cagcagtgtt gaaaaataca ttattgatga aagtgattac     360
atgtcattca taaacaaccc cagtcttact gtgactgtac caattgctgt aggagaatct     420
gactttgaaa atttaaacac ggaagacttt agtagtgaat cggatctgga agaaagcaaa     480
gag                                                                  483
```

<210> SEQ ID NO 431
<211> LENGTH: 121
<212> TYPE: DNA
<213> ORGANISM: Homo sapiens

<400> SEQUENCE: 431

```
aaactgaatg aaagcagtag ctcatcagaa ggtagcactg tggacatcgg cgcacctgta      60
gaagaacagc ccgtagtgga acctgaagaa actcttgaac ccgaagcttg tttcactgaa     120
g                                                                    121
```

<210> SEQ ID NO 432
<211> LENGTH: 155
<212> TYPE: DNA
<213> ORGANISM: Homo sapiens

<400> SEQUENCE: 432

```
gctgtgtaca aagattcaag tgttgtcaaa tcaatgtgga agaaggcaga ggaaaacaat      60
ggtggaacct gagaaggacg tgtttccgaa tagttgaaca taactggttt gagaccttca     120
ttgttttcat gattctcctt agtagtggtg ctctg                                155
```

<210> SEQ ID NO 433
<211> LENGTH: 174
<212> TYPE: DNA
<213> ORGANISM: Homo sapiens

<400> SEQUENCE: 433

```
gcatttgaag atatatatat tgaycagcga aagacgatta agacgatgtt ggaatatgct      60
gacaaggttt tcacttacat tttcattctg gaaatgcttc taaaatgggt ggcatatggc     120
tatcaaacat atttcaccaa tgcctggagt tggctggact tcttaattgt tgat           174
```

<210> SEQ ID NO 434
<211> LENGTH: 123
<212> TYPE: DNA
<213> ORGANISM: Homo sapiens

<400> SEQUENCE: 434

```
gtttcattgg tcagtttaac agcaaatgcc ttgggttact cagaacttgg agcctatcaa      60
tctctcagga cactaagagc tctgagacct ctaagagcct tatctcgatt tgaagggatg     120
agg                                                                  123
```

<210> SEQ ID NO 435
<211> LENGTH: 282
<212> TYPE: DNA
<213> ORGANISM: Homo sapiens

```
<400> SEQUENCE: 435
gtggttgtga atgccctttt aggagcaatt ccatccatca tgaatgtgct tctggtttgt      60
cttatattct ggctaatttt cagcatcatg ggcgtaaatt tgtttgctgg caaattctac    120
cactgtatta acaccacaac tggtgacagg tttgacatcg aagacgtgaa taatcatact    180
gattgcctaa aactaataga agaaatgag actgctcgat ggaaaaatgt gaaagtaaac    240
tttgataatg taggatttgg gtatctctct ttgcttcaag tt                       282

<210> SEQ ID NO 436
<211> LENGTH: 54
<212> TYPE: DNA
<213> ORGANISM: Homo sapiens

<400> SEQUENCE: 436
gccacattca aaggatggat ggatataatg tatgcagcag ttgattccag aaat           54

<210> SEQ ID NO 437
<211> LENGTH: 138
<212> TYPE: DNA
<213> ORGANISM: Homo sapiens

<400> SEQUENCE: 437
gtggaactcc agcctaagta tgaagaaagt ctgtacatgt atctttactt tgttattttc     60
atcatctttg ggtccttctt caccttgaac ctgtttattg gtgtcatcat agataatttc   120
aaccagcaga aaaagaag                                                  138

<210> SEQ ID NO 438
<211> LENGTH: 105
<212> TYPE: DNA
<213> ORGANISM: Homo sapiens

<400> SEQUENCE: 438
tttggaggtc aagacatctt tatgacagaa gaacagaaga aatactataa tgcaatgaaa     60
aaattaggat cgaaaaaacc gcaaaagcct atacctcgac cagga                    105

<210> SEQ ID NO 439
<211> LENGTH: 271
<212> TYPE: DNA
<213> ORGANISM: Homo sapiens

<400> SEQUENCE: 439
aacaaatttc aaggaatggt cttttgacttc gtaaccagac aagtttttga cataagcatc    60
atgattctca tctgtcttaa catggtcaca atgatggtgg aaacagatga ccagagtgaa   120
tatgtgacta ccattttgtc acgcatcaat ctggtgttca ttgtgctatt tactggagag   180
tgtgtactga aactcatctc tctacgccat tattatttta ccattggatg gaatattttt   240
gattttgtgg ttgtcattct ctccattgta g                                  271

<210> SEQ ID NO 440
<211> LENGTH: 3262
<212> TYPE: DNA
<213> ORGANISM: Homo sapiens

<400> SEQUENCE: 440 gtatgttct tgccgagctg atagaaaagt atttcgtgtc ccctaccctg ttccgagtga     60
tccgtcttgc taggattggc cgaatcctac gtctgatcaa aggagcaaag gggatccgca    120
cgctgctctt tgctttgatg atgtcccttc ctgcgttgtt taacatcggc ctcctactct   180
```

-continued

```
tcctagtcat gttcatctac gccatctttg ggatgtccaa ctttgcctat gttaagaggg      240
aagttgggat cgatgacatg ttcaactttg agacctttgg caacagcatg atctgcctat      300
tccaaattac aacctctgct ggctgggatg gattgctagc acccattctc aacagtaagc      360
cacccgactg tgaccctaat aaagttaacc ctggaagctc agttaaggga gactgtggga      420
acccatctgt tggaattttc tttttgtca gttacatcat catatccttc ctggttgtgg       480
tgaacatgta catcgcggtc atcctggaga acttcagtgt tgctactgaa gaaagtgcag      540
agcctctgag tgaggatgac tttgagatgt tctatgaggt ttgggagaag tttgatcccg      600
atgcaactca gttcatggaa tttgaaaaat tatctcagtt tgcagtgcgc ttgaaccgcc      660
tctcaatctg ccacaaccaa acaaactcca gctcattgcc atggatttgc ccatggtgag      720
tggtgaccgg atccactgtc ttgatatctt atttgctttt acaaagcggg ttctaggaga      780
gagtggagag atggatgctc tacgaataca gatggaagag cgattcatgg cttccaatcc      840
ttccaaggtc tcctatcagc caatcactac tactttaaaa cgaaaacaag aggaagtatc      900
tgctgtcatt attcagcgtg cttacagacg ccacctttta aagcgaactg taaaacaagc      960
ttcctttacg tacaataaaa acaaaatcaa aggtggggct aatcttctta aaaagaaga     1020 catgataatt gacagaataa atgaaaactc tattacagaa aaaactgatc tgaccatgtc     1080
cactgcagct tgtccacctt cctatgaccg ggtgacaaag ccaattgtgg aaaaacatga     1140
gcaagaaggc aaagatgaaa aagccaaagg gaaataaatg aaaataaata aaataattg     1200 ggtgacaaat tgtttacagc ctgtgaaggt gatgtatttt tatcaacagg actccttag     1260 gaggtcaatg ccaaactgac tgttttaca caaatctcct taaggtcagt gcctacaata     1320
agacagtgac cccttgtcag caaactgtga ctctgtgtaa aggggagatg accttgacag     1380
gaggttactg ttctcactac cagctgacac tgctgaagat aagatgcaca atggctagtc     1440
agactgtagg gaccagtttc aagggtgca aacctgtgat tttggggttg tttaacatga     1500
aacactttag tgtagtaatt gtatccactg tttgcatttc aactgccaca tttgtcacat     1560
ttttatggaa tctgttagtg gattcatctt tttgttaatc catgtgttta ttatatgtga     1620 ctattttgt aaacgaagtt tctgttgaga ataggctaa ggacctctat aacaggtatg     1680
ccacctgggg ggtatggcaa ccacatggcc ctcccagcta cacaaagtcg tggtttgcat     1740
gagggcatgc tgcacttaga gatcatgcat gagaaaaagt cacaagaaaa acaaattctt     1800
aaatttcacc atatttctgg gaggggtaat tgggtgataa gtggaggtgc tttgttgatc     1860 ttgtttttgcg aaatccagcc cctagaccaa gtagattatt tgtgggtagg ccagtaaatc     1920
ttagcaggtg caaacttcat tcaaatgttt ggagtcataa atgttatgtt tcttttgtt     1980 gtattaaaaa aaaaacctga atagtgaata ttgcccctca ccctccaccg ccagaagact     2040
gaattgacca aaattactct ttataaattt ctgcttttc ctgcactttg tttagccatc     2100
ttcggctctc agcaaggttg acactgtata tgttaatgaa atgctatta ttatgtaaat     2160 agtcatttta ccctgtggtg cacgtttgag caaacaaata atgacctaag cacagtattt     2220
attgcatcaa atatgtacca caagaaatgt agagtgcaag ctttacacag gtaataaaat     2280
gtattctgta ccatttatag atagtttgga tgctatcaat gcatgtttat attaccatgc     2340
tgctgtatct ggtttctctc actgctcaga atctcattta tgagaaacca tatgtcagtg     2400
gtaaagtcaa ggaaattgtt caacagatct catttattta agtcattaag caatagtttg     2460
cagcacttta acagcttttt ggttatttt acatttaag tggataacat atggtatata     2520
gccagactgt acagacatgt ttaaaaaaac acactgctta acctattaaa tatgtgttta     2580
```

```
                                                    -continued gaattttata agcaaatata aatactgtaa aaagtcactt tattttattt ttcagcatta     2640
tgtacataaa tatgaagagg aaattatctt caggttgata tcacaatcac ttttcttact     2700
ttctgtccat agtacttttt catgaaagaa atttgctaaa taagacatga aaacaagact     2760
gggtagttgt agatttctgc tttttaaatt acatttgcta attttagatt atttcacaat     2820
tttaaggagc aaaataggtt cacgattcat atccaaatta tgctttgcaa ttggaaaagg     2880
gtttaaaatt ttatttatat ttctggtagt acctgcacta actgaattga aggtagtgct     2940
tatgttattt ttgttctttt tttctgactt cggtttatgt tttcatttct ttggagtaat     3000
gctgctctag attgttctaa atagaatgtg ggcttcataa ttttttttc cacaaaaaca     3060 gagtagtcaa cttatatagt caattacatc aggacatttt gtgtttctta cagaagcaaa     3120
ccataggctc ctcttttcct taaaactact tagataaact gtattcgtga actgcatgct     3180
ggaaaatgct actattatgc taaataatgc taaccaacat ttaaaatgtg caaaactaat     3240
aaagattaca tttttattt ta                                              3262
```

NUCLEIC ACIDS ENCODING SODIUM CHANNEL SCN1A ALPHA SUBUNIT PROTEINS AND MUTATIONS ASSOCIATED WITH EPILEPSY

CROSS REFERENCE TO RELATED APPLICATIONS

This application is a Continuation Application of, and claims priority to, U.S. application Ser. No. 10/664,423, now U.S. Pat. No. 7,655,460, filed Sep. 17, 2003, which is a Divisional Application and claims priority to, U.S. application Ser. No. 09/718,355, now abandoned, filed Nov. 24, 2000, which claims priority to U.S. Provisional Application Ser. No. 60/167,623 filed on Nov. 26, 1999. All documents above are incorporated herein in their entirety by reference.

SEQUENCE LISTING

This application contains a Sequence Listing in computer readable form entitled Sequence Listing.txt, created Nov. 25, 2009 and amended on Dec. 2, 2010, having a size of 395 Kb. The computer readable form is incorporated herein by reference.

FIELD OF THE INVENTION

The present invention relates to epilepsy. More particularly, the present invention relates to idiopathic generalized epilepsy (IGE) and to the identification of three loci mapping to chromosome 2, which show a linkage with epilepsy in patients. The invention further relates to nucleic acid sequences, and protein sequences of these loci (SCNA), to variations and mutations in these sequences and to the use thereof to assess, diagnose, prognose or treat epilepsy.

BACKGROUND OF THE INVENTION

Epilepsy is one of the most common neurological conditions, occurring in about 1.0% of the general population. The disease is characterised by paroxysmal abnormal electrical discharges in the brain, which lead to transient cerebral dysfunction in the form of a seizure. A seizure is considered partial when the epileptic discharge is limited to part of one brain hemisphere, or generalised when it involves both cerebral hemispheres at the onset. The current classification of the epileptic syndromes rests on two criteria: 1) seizure type which may be generalised or partial at the onset, according to clinical and EEG features; and 2) etiology, which may be idiopathic, cryptogenic and symptomatic. Symptomatic epilepsies have multiple and heterogeneous causes including brain injury, CNS infection, migrational and metabolic disorders. In the majority (65%) of the patients with either generalised or partial epilepsy, there is no underlying cause (idiopathic) or the cause is though to be hidden or occult (cryptogenic). Also, in the idiopathic epileptic syndromes, there is no evidence of cerebral dysfunction other than the seizure, and the neurological examination is normal. There is now increasing evidence that in this latter group, genetic factors are important, especially for the idiopathic generalised epilepsy (IGE). In a recent study, Berkovic et al (1998) showed a 62% concordance rate in monozygotic twins overall for epilepsy. In this study, a higher concordance rate has been found in the generalised compared to the partial epilepsies, with 76% concordance rate for IGE. Recent studies using molecular genetic approaches have shown that many susceptibility genes for the epilepsies in human involve membrane ion channel and related proteins. These studies include the syndrome of benign familial neonatal convulsions where two loci have been identified [EBN1 on chromosome 20, the KCNQ2 gene (a potassium channel); and EBN2 on chromosome 8, the KCNQ3 gene (also a potassium channel)] (Bievert et al, 1998; Charlier et al, 1998; Singh et al, 1998), as well as autosomal dominant nocturnal frontal lobe epilepsy [ADNFLE chromosome 20, and the CHRNA4 gene (the neuronal nicotinic acetylcholine receptor alpha 4 subunit)] (Steinlein et al, 1995). More recently, there was a clinical description of a new syndrome (GEFS), which consisted of generalised epilepsy with febrile seizures. According to the current classification of epileptic syndrome, this syndrome would fall in the category of IGE, based on the seizure and electroencephalographic features. However, febrile seizures were present in all probants with GEFS, and the pattern of inheritance was clearly autosomal dominant, which are not part of the usual IGE phenotype. This unique GEFS syndrome has been shown to be associated with a mutation on the beta 1 subunit of brain voltage gated sodium channel (SCN1B) gene (Wallace et al, 1998). In addition, three different groups, including the group of the present inventors, have identified another locus on chromosome 2 in large kindred with this specific syndrome (GEFS). This region contains many candidate genes, including a cluster of alpha subunits of sodium channels (SCNA). Voltage gated sodium channels play an important role in the generation of action potential in nerve cells and muscle. The alpha subunit (SCNA) is the main component of the channel, and would be sufficient to generate an efficient channel when expressed in cells in vitro. In turn, the beta 1 and 2 subunits need an alpha subunit to give an effective channel. The role of these subunits would be to modify the kinetic properties of the channel, mainly by fast inactivation of the sodium currents. The mutation found in the GEFS syndrome on the SCN1B gene was shown to reduce the fast inactivation of the sodium channels as compared to a normal SCNB1, when co expressed with an alpha subunit. It is probable that this could be the mechanism by which the mutation induces an hyperexcitability state in the brain, leading to seizure in humans. Interestingly, the mechanism of action of most of the anticonvulsant drugs is through a reduction of the repetitive firing of neurons, which is also known to be dependent on fast inactivation. These finding make it likely that additional epilepsy genes will be identified by mutations in ion channels.

There thus remains a need to identify whether IGE is caused by a mutation in a sodium channel (SCNA). There also remains a need to assess whether a mutation(s) in SCNA is associated with GEFs. There also remains a need to determine whether a mutation that affects the fast inactivation of a sodium channel, given the particular phenotype of GEFS or IGE, could be linked to a region which includes SCNA genes.

The present invention seeks to meet these and other needs.

The present description refers to a number of documents, the content of which is herein incorporated by reference in their entirety.

SUMMARY OF THE INVENTION

In one embodiment, the present invention relates to a genetic assay for determining predisposition to epilepsy.

In another embodiment, the present invention relates to a use of at least one of the loci of the present invention or an equivalent thereof (e.g. a loci in linkage disequilibrium therewith) as a marker for epilepsy and to determine the optimal treatment thereof (e.g. to guide the treatment modalities, thereby optimizing treatment to a particular clinical situation).

Yet in another embodiment, the present invention relates to an assay to screen for drugs for the treatment and/or prevention of epilepsy. In a particular embodiment, such assays can be designed using cells from patients having a known genotype at one of the loci of the present invention. These cells harboring recombinant vectors can enable an assessment of the functionality of the SCN1A, and/or SCN2A and/or SCN3A and a combination thereof. Non-limiting examples of assays that could be used in accordance with the present invention include cis-trans assays similar to those described in U.S. Pat. No. 4,981,784.

It shall be understood that the determination of allelic variations in at least one of the loci of the present invention can be combined to the determination of allelic variation in other gene/markers linked to a predisposition to epilepsy. This combination of genotype analyses could lead to better diagnosis programs and/or treatment of epilepsy. Non-limiting examples of such markers include SCN1B, EBN1, KCNQ2, EBN2, KCNQ3, ADNFLE and CHRNA4.

In accordance with the present invention, there is therefore provided a method of determining an individual's predisposition to epilepsy, which comprises determining the genotype of at least one locus selected from the group consisting of SCN1A, SCN2A and SCN3A. In one particular embodiment, the present invention provides a method of determining an individual's predisposition to epilepsy, which comprises determining a polymorphism (directly or indirectly by linkage disequilibrium) in a biological sample of an individual and analyzing the allelic variation in at least one of the loci selected from SCN1A, SCN2A and SCN3A, thereby determining an individual's predisposition to epilepsy.

In accordance with the present invention, there is also provided a method for identifying, from a library of compounds, a compound with therapeutic effect on epilepsy or other neurological disorders comprising providing a screening assay comprising a measurable biological activity of SCN1A, SCN2A or SCN3A protein or gene; contacting the screening assay with a test compound; and detecting if the test compound modulates the biological activity of SCN1A, SCN2A or SCN3A protein or gene; wherein a test compound which modulates the biological activity is a compound with this therapeutic effect.

Also provided within the present invention is a compound having therapeutic effect on epilepsy or other neurological disorders, identified by a method comprising: providing a screening assay comprising a measurable biological activity of SCN1A, SCN2A or SCN3A protein or gene; contacting the screening assay with a test compound; and detecting if the test compound modulates the biological activity of SCN1A, SCN2A or SCN3A protein or gene, wherein a test compound which modulates the biological activity is a compound with this therapeutic effect.

SCN1A, SCN2A and SCN3A refers to genes and proteins for Sodium Channel, Neuronal Type I, Alpha Subunit isoforms, and are described at OMIM # 182389 (Online Mendelian Inheritance in Man). These genes are structurally distinct sodium channel alpha-subunit isoforms in brain, also known as brain types I, II and III, respectively. Gene, cDNA and protein sequences for the various isoforms are shown in SEQ ID NOS:1-98.

Numerous methods for determining a genotype are known and available to the skilled artisan. All these genotype determination methods are within the scope of the present invention. In a particular embodiment of a method of the present invention, the determination of the genotype comprises an amplification of a segment of one of the loci selected from the group consisting of SCN1A, SCN2A and SCN3A and in a particularly preferred embodiment, the amplification is carried out using polymerase chain reaction.

In a particular embodiment, a pair of primers is designed to specifically amplify a segment of one of the markers of the present invention. This pair of primers is preferably derived from a nucleic acid sequence of SCN1A, SCN2A or SCN3A or from sequences flanking these genes, to amplify a segment of SCN1A, SCN2A or SCN3A (or to amplify a segment of a loci in linkage disequilibrium with at least one of the loci of the present invention). While a number of primers are exemplified herein, other primer pairs can be designed, using the sequences of the SCN1A, SCN2A and SCN3A nucleic acids molecules described hereinbelow. The same would apply to primer pairs from loci in linkage disequilibrium with the markers of the present invention.

Restriction fragment length polymorphisms can be used to determine polymorphisms at the SCN1A, SCN2A and SCN3A loci (and equivalent loci).

While human SCN1A, SCN2A and SCN3A are preferred sequences (nucleic acid and proteins) in accordance with the present invention, the invention should not be so limited. Indeed, in view of the significant conservation of these genes throughout evolution, sequences from different species, and preferably mammalian species, could be used in the assays of the present invention. One non-limiting example is the rat SCN1A ortholog gene which shows 95% identity with the human SCN1A gene. The significant conservation of the mouse SCN1A gene can also be observed in OMIM (see above).

In order to provide a clear and consistent understanding of terms used in the present description, a number of definitions are provided hereinbelow.

As used herein the term "RFLP" refers to restriction fragment length polymorphism.

The terms "polymorphism", "DNA polymorphism" and the like, refer to any sequence in the human genome which exists in more than one version or variant in the population.

The term "linkage disequilibrium" refers to any degree of non-random genetic association between one or more allele(s) of two different polymorphic DNA sequences, that is due to the physical proximity of the two loci. Linkage disequilibrium is present when two DNA segments that are very close to each other on a given chromosome will tend to remain unseparated for several generations with the consequence that alleles of a DNA polymorphism (or marker) in one segment will show a non-random association with the alleles of a different DNA polymorphism (or marker) located in the other DNA segment nearby. Hence, testing of a marker in linkage disequilibrium with the polymorphisms of the present invention at the SCN1A, SCN2A and/or SCN3A genes (indirect testing), will give almost the same information as testing for the SCN1A, SCN2A and SCN3A polymorphisms directly. This situation is encountered throughout the human genome when two DNA polymorphisms that are very close to each other are studied. Linkage disequilibriums are well known in the art and various degrees of linkage disequilibrium can be encountered between two genetic markers so that some are more closely associated than others.

It shall be recognized by the person skilled in the art to which the present invention pertains, that since some of the polymorphisms or mutations herein identified in the SCN1A, SCN2A and/or SCN3A genes can be within the coding region of the genes and therefore expressed, that the present invention should not be limited to the identification of the polymorphisms/mutations at the DNA level (whether on genomic DNA, amplified DNA, cDNA, or the like). Indeed, the herein-identified polymorphisms and/or mutations could be detected at the mRNA or protein level. Such detections of polymorphism identification on mRNA or protein are known in the art. Non-limiting examples include detection based on oligos designed to hybridize to mRNA or ligands such as antibodies which are specific to the encoded polymorphism (i.e. specific to the protein fragment encoded by the distinct polymorphisms).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning A Laboratory Manual, Cold Spring Harbor Laboratories) and Ausubel et al. (1994, Current Protocols in Molecular Biology, Wiley, New York).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non limiting examples thereof include DNA (i.e. genomic DNA, cDNA, RNA molecules (i.e. mRNA) and chimeras of DNA and RNA. The nucleic acid molecule can be obtained by cloning techniques or synthesized. DNA can be double stranded or single stranded (coding strand or non coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (i.e. DNA, RNA or chimeras thereof) for practicing the present invention may be obtained according to well known methods.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hybridization thereof with its targeted sequence (see below and in Sambrook et al., 1989, Molecular Cloning A Laboratory Manual, 2nd Edition, CSH Laboratories; Ausubel et al., 1989, in Current Protocols in Molecular Biology, John Wiley & Sons Inc., N.Y.).

The term "DNA" molecule or sequence (as well as sometimes the term "oligonucleotide") refers to a molecule comprised of the deoxyribonucleotides adenine (A), guanine (G), thymine (T) and/or cytosine (C). Sometimes, in a double-stranded form, it can comprise or include a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. Of course, as very well-known, DNA molecules or sequences are often in single stranded form.

"Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred to above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 µg/ml denatured carrier DNA (i.e. salmon sperm DNA). The non specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA DNA hybrids can also be formed and detected. In such cases, the conditions of hybridization and washing can be adapted according to well known methods by the person of ordinary skill. Stringent conditions will be preferably used (Sambrook et al., 1989, supra).

Probes of the invention can be utilized with naturally occurring sugar-phosphate backbones as well as modified backbones including phosphorothioates, dithionates, alkyl phosphonates and "-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. More recently, PNAs have been described (Nielsen et al. 1999, Current Opin. Biotechnol. 10:71-75). PNAs could also be used to detect the polymorphisms of the present invention. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non limiting examples of labels include $^3$H, $^{14}$C, $^{32}$P, and $^{35}$S. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non limiting examples thereof include kinasing the 5' ends of the probes using gamma $^{32}$P ATP and polynucleotide kinase, using the Klenow fragment of Pol I of E. coli in the presence of radioactive dNTP (i.e. uniformly labeled DNA probe using random oligonucleotide primers in low melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well known methods.

As used herein, a "primer" defines an oligonucleotide which is capable of annealing to a target sequence, thereby creating a double stranded region which can serve as an initiation point for nucleic acid synthesis under suitable conditions.

Amplification of a selected, or target, nucleic acid sequence may be carried out by a number of suitable methods. See generally Kwoh et al., 1990, Am. Biotechnol. Lab. 8:14-25. Numerous amplification techniques have been described and can be readily adapted to suit particular needs of a person of ordinary skill. Non limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra). Preferably, amplification will be carried out using PCR.

Polymerase chain reaction (PCR) is carried out in accordance with known techniques. See, e.g., U.S. Pat. Nos. 4,683, 195; 4,683,202; 4,800,159; and 4,965,188 (the disclosures of all three U.S. patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise to a specific polypeptide or protein. It will be readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment of DNA within a larger segment that is not found in association therewith in nature. The term "heterologous" can be similarly used to define two polypeptidic segments not joined together in nature. Non limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "COAT" boxes. Prokaryotic promoters contain Shine Dalgamo sequences in addition to the 10 and 35 consensus sequences.

In accordance with one embodiment of the present invention, an expression vector can be constructed to assess the functionality of specific alleles of the SCN1A, SCN2A and SCN3A sodium channels. Non-limiting examples of such expression vectors include a vector comprising the nucleic acid sequence encoding one of the sodium channels (or part thereof) according to the present invention. These vectors can be transfected in cells. The sequences of the alpha subunit of the sodium channels in accordance with the present invention and their structure-function relationship could be assessed by a number of methods known to the skilled artisan. One non-limiting example includes the use of cells expressing the β-1 and β-2 subunits and the sequence of an alpha subunit in accordance with the present invention. For example, an alpha subunit having a mutation, which is linked to epilepsy, could be compared to a sequence devoid of that mutation, as a control. In such cells, the functionality of the sodium channel could be tested as known to the skilled artisan and these cells could be used to screen for agents which could modulate the activity of the sodium channel. For example, agents could be tested and selected, which would reduce the hyperexcitability state of the sodium channel (e.g. their reduction in fast inactivation). Agents known to the person of ordinary skill as affecting other sodium channels could be tested, for example, separately or in batches. Of course, it will be understood that the SCN1A, SCN2A and/or SCN3A genes expressed by these cells can be modified at will (e.g. by in vitro mutagenesis or the like).

As used herein, the designation "functional derivative" denotes, in the context of a functional derivative of a sequence whether a nucleic acid or amino acid sequence, a molecule that retains a biological activity (either function or structural; e.g. sodium channel function or structure) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid generally has chemico physical properties which are similar to that of the substituted amino acid. The similar chemico-physical properties include, similarities in charge, bulkiness, hydrophobicity, hydrophylicity and the like. The term "functional derivatives" is intended to include "fragments", "segments", "variants", "analogs" or "chemical derivatives" of the subject matter of the present invention. The genetic code, the chemico-physical characteristics of amino acids and teachings relating to conservative vs. non-conservative mutations are well-known in the art. Non-limiting examples of textbooks teaching such information are Stryer, Biochemistry, 3rd ed.; and Lehninger, Biochemistry, 3rd ed. The functional derivatives of the present invention can be synthesized chemically or produced through recombinant DNA technology. All these methods are well known in the art.

The term "variant" refers herein to a protein or nucleic acid molecule which is substantially similar in structure and biological activity to the protein or nucleic acid of the present invention.

As used herein, "chemical derivatives" is meant to cover additional chemical moieties not normally part of the subject matter of the invention. Such moieties could affect the physico-chemical characteristic of the derivative (i.e. solubility, absorption, half life, decrease of toxicity and the like). Such moieties are exemplified in Remington's Pharmaceutical Sciences (1980). Methods of coupling these chemical physical moieties to a polypeptide or nucleic acid sequence are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutation of nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

As used herein, "SCNA biological activity" refers to any detectable biological activity of SCN1A, SCN2A or SCN3A gene or protein (herein sometimes collectively called SCNA genes or SCNA proteins). This includes any physiological function attributable to an SCNA gene or protein. It can include the specific biological activity of SCNA proteins which is efflux of sodium or related ions. This includes measurement of channel properties such as, but not limited to: 1) the voltage-dependence of activation, a measure of the strength of membrane depolarization necessary to open the channels, 2) the voltage-dependence of steady state inactivation, a measure of the fraction of channels available to open at the resting membrane potential; and 3) the time course of inactivation. At a larger scale, SCNA biological activity includes transmission of impulses through cells, wherein changes in transmission characteristics caused by modulators of SCNA proteins can be identified. Non-limiting examples of such measurements of these biological activities may be made directly or indirectly, such as through the transient accumulation of ions in a cell, dynamics of membrane depolarization, etc. SCNA biological activity is not limited, however, to these most important biological activities herein identified. Biological activities may also include simple binding or pKa analysis of SCNA with compounds, substrates, interacting proteins, and the like. For example, by measuring the effect of a test compound on its ability to increase or inhibit such SCNA binding or interaction is measuring a biological activity of SCNA according to this invention. SCNA biological activity includes any standard biochemical measurement of SCNA such as conformational changes, phosphorylation status or any other feature of the protein that can be measured with techniques known in the art. Finally, SCNA biological activity also includes activities related to SCNA gene transcription or translation, or any biological activities of such transcripts or translation products.

As used herein, the terms "molecule", "compound", "agent" or "ligand" are used interchangeably and broadly to refer to natural, synthetic or semi synthetic molecules or compounds. The term "molecule" therefore denotes for example chemicals, macromolecules, cell or tissue extracts (from plants or animals) and the like. Non limiting examples of molecules include nucleic acid molecules, peptides, ligands (including, for example, antibodies and carbohydrates) and pharmaceutical agents. The agents can be selected and screened by a variety of means including random screening, rational selection and by rational design using for example protein or ligand modelling methods such as computer modelling. The terms "rationally selected" or "rationally designed" are meant to define compounds which have been chosen based on the configuration of the interacting domains of the present invention. As will be understood by the person of ordinary skill, macromolecules having non naturally occurring modifications are also within the scope of the term "molecule". For example, peptidomimetics, well known in the pharmaceutical industry and generally referred to as peptide analogs can be generated by modelling as mentioned above. Similarly, in a preferred embodiment, the polypeptides of the present invention are modified to enhance their stability. It should be understood that in most cases this modification should not alter the biological activity of the protein. The molecules identified in accordance with the teachings of the present invention have a therapeutic value in diseases or conditions in which sodium transport through the sodium channels is compromised by a mutation (or combination thereof) in one of the genes identified in accordance with the present invention. Alternatively, the molecules identified in accordance with the teachings of the present invention find utility in the development of compounds which can modulate the activity of the alpha subunit sodium channels and/or the action potential in nerve cells and muscles cells (e.g. restore the fast inactivation of the sodium channel to normal levels).

As used herein, agonists and antagonists also include potentiators of known compounds with such agonist or antagonist properties. In one embodiment, modulators of the fast inactivation of the sodium channel in accordance with the present invention can be identified and selected by contacting the indicator cell with a compound or mixture or library of molecules for a fixed period of time.

As used herein the recitation "indicator cells" refers to cells that express at least one sodium channel α subunit (SCNA) according to the present invention. As alluded to above, such indicator cells can be used in the screening assays of the present invention. In certain embodiments, the indicator cells have been engineered so as to express a chosen derivative, fragment, homolog, or mutant of the combination of genotypes of the present invention. The cells can be yeast cells or higher eukaryotic cells such as mammalian cells. In one particular embodiment, the indicator cell would be a yeast cell harboring vectors enabling the use of the two hybrid system technology, as well known in the art (Ausubel et al., 1994, supra) and can be used to test a compound or a library thereof. In another embodiment, the cis-trans assay as described in U.S. Pat. No. 4,981,784, can be adapted and used in accordance with the present invention. Such an indicator cell could be used to rapidly screen at high throughput a vast array of test molecules. In a particular embodiment, the reporter gene is luciferase or β-Gal.

It shall be understood that the "in vivo" experimental model can also be used to carry out an "in vitro" assay. For example, cellular extracts from the indicator cells can be prepared and used in an "in vitro" test. Non-limiting examples thereof include binding assays.

In some embodiments, it might be beneficial to express a fusion protein. The design of constructs therefor and the expression and production of fusion proteins and are well known in the art (Sambrook et al., 1989, supra; and Ausubel et al., 1994, supra).

Non-limiting examples of such fusion proteins include hemaglutinin fusions and Gluthione S transferase (GST) fusions and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the protein of the present invention to signal peptide sequences enabling a secretion of the fusion protein from the host cell. Signal peptides from diverse organisms are well known in the art. Bacterial OmpA and yeast Suc2 are two non-limiting examples of proteins containing signal sequences. In certain embodiments, it might also be beneficial to introduce a linker (commonly known) between the interaction domain and the heterologous polypeptide portion. Such fusion proteins find utility in the assays of the present invention as well as for purification purposes, detection purposes and the like.

For certainty, the sequences and polypeptides useful to practice the invention include without being limited thereto mutants, homologs, subtypes, alleles and the like. It shall be understood that generally, the sequences of the present invention should encode a functional (albeit defective) alpha subunit of sodium channels (SCNA). It will be clear to the person of ordinary skill that whether the SCNA sequence of the present invention, variant, derivative, or fragment thereof retains its function, can be determined by using the teachings and assays of the present invention and the general teachings of the art.

It should be understood that the SCNA protein of the present invention can be modified, for example by in vitro mutagenesis, to dissect the structure function relationship thereof and permit a better design and identification of modulating compounds. However, some derivative or analogs having lost their biological function may still find utility, for example for raising antibodies. These antibodies could be used for detection or purification purposes. In addition, these antibodies could also act as competitive or non competitive inhibitor and be found to be modulators of the activity of the SCNA proteins of the present invention.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra). The use of a mammalian cell as indicator can provide the advantage of furnishing an intermediate factor, which permits for example the interaction of two polypeptides which are tested, that might not be present in lower eukaryotes or prokaryotes. It will be understood that extracts from mammalian cells for example could be used in certain embodiments, to compensate for the lack of certain factors.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The present invention also provides polyclonal, monoclonal antibodies, or humanized versions thereof, chimeric antibodies and the like which inhibit or neutralize their respective interaction domains and/or are specific thereto.

From the specification and appended claims, the term therapeutic agent should be taken in a broad sense so as to also include a combination of at least two such therapeutic agents. Further, the DNA segments or proteins according to the present invention could be introduced into individuals in a number of ways. For example, cells can be isolated from the afflicted individual, transformed with a DNA construct according to the invention and reintroduced to the afflicted individual in a number of ways. Alternatively, the DNA construct can be administered directly to the afflicted individual. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e. DNA construct, protein, cells), the response and condition of the patient as well as the severity of the disease.

Composition within the scope of the present invention should contain the active agent (i.e. molecule, hormone) in an amount effective to achieve the desired therapeutic effect while avoiding adverse side effects. Typically, the nucleic acids in accordance with the present invention can be administered to mammals (i.e. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

The present invention also relates to a kit for diagnosing and/or prognosing epilepsy, and/or predicting response to a medication comprising an assessment of a genotype at SCNA loci of the present invention (or loci in linkage disequilibrium therewith) using a nucleic acid fragment, a protein or a ligand, a restriction enzyme or the like, in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross contaminated and the agents or solutions of each container can be added in a quantitative fashion from one compartment to another. Such containers will include in one particular embodiment a container which will accept the test sample (DNA protein or cells), a container which contains the primers used in the assay, containers which contain enzymes, containers which contain wash reagents, and containers which contain the reagents used to detect the extension products.

BRIEF DESCRIPTION OF THE DRAWINGS

Having thus generally described the invention, reference will now be made to the accompanying drawings, showing by way of illustration a preferred embodiment thereof, and in which:

FIG. 1 shows the IGE candidate region on ch 2q23-q31. Order and distance between markers are according to Gyapay et al., 1994.

FIG. 2 shows the PCR primers used for genomic PCR-SSCP of SCN1A (SEQ ID NOs: 99-188);

FIG. 3 shows the sequence of the SCN1A mutations found in epilepsy patients (SEQ ID NOs: 189-192 and 309);

FIG. 4 shows the PCR primers used for genomic PCR-SSCP of SCN2A (SEQ ID NOs: 193-306);

FIG. 5 shows the mutation found in epilepsy patients in SCN2A (SEQ ID NOs: 307 and 308);

FIG. 6 shows the PCR primers used for genomic PCR-SSCP of SCN3A (SEQ ID NOs: 310-399); and FIG. 7 shows the mutation found in epilepsy patients in SCN3A (SEQ ID NOs: 400-408).

Sequences are also shown in the Sequence Listing. For example, SEQ ID NO:1 shows the nucleic acid sequence of the adult form of SCN1A ; SEQ ID NO:2 shows the nucleic acid sequence of the neonatal form of SCN1A; SEQ ID NO:3 shows the protein sequence of the adult form of SCN1A; SEQ ID NO:4 shows the protein sequence of the neonatal form of SCN1A; SEQ ID NOS:5-32 show the genomic sequence of SCN1A; SEQ ID NO:33 shows the cDNA sequence of the adult form of SCN2A; SEQ ID NO:34 shows the cDNA sequence of the neonatal form of SCN2A; SEQ ID NO:35 shows the protein sequence of the adult form of SCN2A; SEQ ID NO:36 shows the protein sequence of the neonatal form of SCN2A; SEQ ID NOS.:37-64 show the genomic sequence of SCN2A; SEQ ID NO:65 shows the cDNA sequence of the adult form of SCN3A; SEQ ID NO:66 shows the cDNA sequence of the neonatal form of SCN3A; SEQ ID NO:67 shows the protein sequence of the adult form of SCN3A; SEQ ID NO:68 shows the protein sequence of the neonatal form of SCN3A; and SEQ ID NOS:69-98 show the genomic sequence of SCN3A. Rat SCNA1 sequences can be found in GenBank under accession numbers M22253 and X03638.

SEQ ID NOs:409-411 show the protein sequences of the D188V, E1238D and S1773Y variants of human SCN1A, respectively. SEQ ID NO:412 shows the nucleic acid coding sequence for human SCN1A. SEQ ID NOs:413- 440 show the nucleic acid sequences of exons 1 to 27 of the human SCN1A gene.

Other objects, advantages and features of the present invention will become more apparent upon reading of the following non restrictive description of preferred embodiments with reference to the accompanying drawing which is exemplary and should not be interpreted as limiting the scope of the present invention.

DESCRIPTION OF THE PREFERRED EMBODIMENT

Epilepsy is one of the most common neurological conditions, affecting 1-2% of the general population. Familial aggregation studies have shown an increased risk for epilepsy in relatives of probands with different types of epilepsy, and especially for the idiopathic generalized epilepsies (IGEs). The epilepsy genes identified to date account for a very small proportion of all the epilepsies. In addition, they have been identified in rare syndromes where the pattern of inheritance was clearly Mendelian. This is not the case for the vast majority of epileptic patients, however, where the pattern of inheritance is not compatible with a simple Mendelian model. In fact, most authors consider epilepsy to be the result of a combination of many different genetic and environmental factors, features of a complex trait. While the pattern of inheritance is not mendelian, sporadic IGE cases may be caused by specific mutations in the same genes. Based on this assumption, a large cohort of IGE patients was tested for mutation in the SCNA genes.

In order to localize the gene causing epilepsy in a large family segregating an autosomal dominant form of IGE, 41 family members, including 21 affected individuals, were genotyped. A detailed clinical description of this family has been reported elsewhere (Scheffer and Berkovic 1997). The majority of patients in this family present a benign epilepsy syndrome occurring in childhood and characterized by frequent generalized tonic-clonic seizures not always associated with fever: a syndrome called febrile seizures plus (FS+). However, several patients presented other types of generalized seizures (GTCS) as well, such as myoclonic seizures and absences (Scheffer and Berkovic 1997). Mean age at onset was 2.2 years and offset was 11.7 years. Neurological examination and intellect were normal in all individuals except one, who had moderate intellectual disability. EEG recordings were normal in most patients. However, in three individuals generalized epileptiform activity was found and four patients had mild or moderate diffuse background slowing. Table 1 shows the different types of seizures found in the 21 patients included in this study.

TABLE 1

Different types of generalized seizures found in the 21 patients included in the linkage analysis.

| Type of seizures | n |
|---|---|
| Febrile convulsions alone | 9 |
| GTCSs[a] + absence seizures | 4 |
| GTCSs + myoclonic seizures | 1 |
| GTCSs + atonic seizures | 1 |
| Solitary afebril GTCS | 1 |

TABLE 1-continued

Different types of generalized seizures found in the 21 patients included in the linkage analysis.

| Type of seizures | n |
|---|---|
| Secondary epilepsy + mental retardation | 1 |
| Unwitnessed events | 4 |

[a]GTCS: generalized tonic clonic seizure

A genome wide search examining 190 markers identified linkage of IGE to chromosome (ch) 2 based on an initial positive lod score for marker D2S294 (Z=4.4, (=0). A total of 24 markers were tested on ch 2q in order to define the smallest IGE candidate region. Table 2 shows the two-point lod scores for 17 markers spanning the IGE candidate region. The highest lod score (Zmax=5.29; (=0) was obtained with marker D2S324. Critical recombination events mapped the IGE gene to a 29 cM region flanked by markers D2S156 and D2S311, assigning the IGE locus to ch 2q23-q31 (FIG. 1). Although the relationship of FS+ with other IGE phenotypes remains unclear, the observation that in this family, several affected individuals have different types of generalized seizures, suggests that seizure predisposition determined by the ch 2q-IGE gene could be modified by other genes and/or environmental factors, to produce different seizure types.

TABLE 2

Two-point lod-scores for 17 markers localized on ch 2q23-q31.

| | Recombination fractions | | | | | | | | |
|---|---|---|---|---|---|---|---|---|---|
| Locus | 0 | 0.05 | 0.1 | 0.15 | 0.2 | 0.3 | 0.4 | Zmax | max |
| D2S142 | 0.99 | 1.94 | 1.97 | 1.85 | 1.68 | 1.22 | 0.66 | 1.98 | 0.078 |
| D2S284 | 1.3 | 1.18 | 1.06 | 0.94 | 0.82 | 0.57 | 0.3 | 1.3 | 0 |
| D2S306 | 1.9 | 2.82 | 2.74 | 2.52 | 2.25 | 1.6 | 0.85 | 2.82 | 0.057 |
| D2S156 | 2.15 | 3.05 | 2.96 | 2.73 | 2.43 | 1.73 | 0.93 | 3.05 | 0.056 |
| D2S354 | 4.72 | 4.26 | 3.82 | 3.4 | 2.97 | 2.1 | 1.13 | 4.72 | 0 |
| D2S111 | 5.15 | 4.71 | 4.26 | 3.78 | 3.29 | 2.26 | 1.17 | 5.15 | 0 |
| D2S124 | 3.5 | 3.2 | 2.89 | 2.58 | 2.26 | 1.58 | 0.84 | 3.5 | 0 |
| D2S382 | 4.31 | 3.93 | 3.54 | 3.14 | 2.74 | 1.91 | 1.02 | 4.31 | 0 |
| D2S399 | 0.48 | 0.4 | 0.33 | 0.27 | 0.22 | 0.14 | 0.08 | 0.48 | 0 |
| D2S294 | 4.4 | 4.04 | 3.65 | 3.25 | 2.84 | 2 | 1.07 | 4.4 | 0 |
| D2S335 | 4.76 | 4.32 | 3.91 | 3.51 | 3.1 | 2.22 | 1.21 | 4.76 | 0 |
| D2S333 | 1.42 | 1.23 | 1.04 | 0.87 | 0.72 | 0.45 | 0.22 | 1.4 | 0 |
| D2S324 | 5.29 | 4.72 | 4.16 | 3.63 | 3.13 | 2.15 | 1.14 | 5.29 | 0 |
| D2S384 | 3.85 | 3.52 | 3.17 | 2.82 | 2.45 | 1.69 | 0.89 | 3.85 | 0 |
| D2S152 | 1.9 | 1.7 | 1.52 | 1.36 | 1.2 | 0.87 | 0.48 | 1.9 | 0 |
| D2S311 | −0.81 | 1.62 | 1.66 | 1.58 | 1.46 | 1.11 | 0.63 | 1.66 | 0.085 |
| D2S155 | −5.21 | 0.57 | 1.12 | 1.29 | 1.29 | 1.04 | 0.59 | 1.3 | 0.17 |

Haplotypes using 17 markers spanning the IGE candidate region were constructed (data not shown). The centromeric boundary was defined by a recombination event between the markers D2S156 and D2S354; whereas a recombination between the markers D2S152 and D2S311 set the telomeric boundary. These critical recombination events localized the IGE gene to a 29 cM region flanked by markers D2S156 and D2S311 (FIG. 1).

Over the last four decades, family studies provided two important pieces of evidence supporting the role of genetic factors in determining susceptibility to seizures: 1) familial aggregation studies have shown evidence for an increased risk for epilepsy in relatives of probands with different types of epilepsy. In two studies standardized morbidity ratios for unprovoked seizures in relatives of individuals with idiopathic childhood-onset epilepsy varied from 2.5 to 3.4 in siblings and 6.7 in offspring (Anneger et al. 1982; Ottman et al. 1989); and 2) the presence of higher concordance rates for epilepsy in monozygotic than in dizygotic twins. Different studies showed concordance rates varying from 54 to 11% in monozygotic twins and 10 to 5% in dizygotic pairs (Inouye 1960; Lennox, 1960; Harvald and Hauge 1965; Corey et al. 1991; Silanpaa et al 1991).

It is now generally accepted that seizure susceptibility probably reflects complex interactions of multiple factors affecting neuronal excitability and that most common genetic epilepsies display familial aggregation patterns that are not explained by segregation of a single autosomal gene (Andermann 1982; Ottman et al. 1995). This of course significantly makes more complex one's ability to isolate genes which predispose or induce epilepsy. However, some specific epileptic syndromes, which aggregate in families, may result from definable monogenic abnormalities. These families present a unique opportunity to rapidly map genes that play a role in determining predisposition to seizures.

To date, there are a total of six loci (Greenberg et al. 1988; Leppert et al 1989; Lewis et al. 1993; Elmslie et al. 1997; Guipponi et al. 1997; Wallace et al. 1998), for which three genes have been identified in specific IGE syndromes (Bievert et al. 1998; Singh et al. 1998; Wallace et al. 1998). Interestingly, all three genes are ion channels, including a mutation found in the Na+-channel (1 in a Tasmania family with febrile seizures and generalized epilepsy (Wallace et al. 1998). While the candidate interval identified in our kindred remains large, a number of interesting genes map to the region. These include a cluster of Na+ channel genes and K+ channel genes (electronic data base search), as well as the GAD1 gene, which encodes for glutamate decarboxylase, an enzyme involved in the syntheses of -aminobutyric acid (GABA) (Bu and Tobin 1994). GABA is one of the major neurotransmitters involved in synaptic inhibition in the central nervous system (Barnard et al. 1987). However, the large size of the candidate interval will require further refinement of the locus prior to the identification of the gene responsible for IGE in the kindred studied herein.

Fifty-three % (9/17) of affected individuals in the large IGE family described herein, who had their seizures classified, had only febrile convulsions. However, 41% of patients (7/17) presented with different types of generalized seizures. These findings may indicate that, although the predisposition to IGE in this family is determined by a single gene localized on ch2q23-q31, the different types of generalized seizures occurring in the same family may have resulted from interactions among genetic and/or environmental modifiers.

In conclusion, a locus for IGE was mapped on ch 2q23-q31. This locus seems to be associated with a specific IGE syndrome, FS+. However, the relationship of FS+ with other IGE phenotypes, and the role of the ch 2q locus in other FS+ families and in other forms of IGE are still undetermined.

Having identified a locus for IGE on chromosome 2q23-q31, it was next verified whether mutations and/or polymorphisms could be linked to epilepsy. Public data bases were screened to identify potential genes in that chromosome region. The blasts of the data bases were also oriented to identify more specifically, membrane channels since seizures in mice and human are known to be associated with membrane channels. Having identified membrane channel coding sequences or parts thereof by the computer searches, the candidate genes, potentially involved in epilepsy, had to be validated as susceptibility genes for the disease. Two approaches were used. The first one was to test the candidate genes for mutations in a family comprising members having the disease (data not shown). The second approach was as follows. Since it is known that epilepsy results from a lower seizure threshold, and that generalized epilepsy results, in many instances, from a generalized lowering of the seizure threshold, the following hypothesis was formulated. The gene which results in epilepsy in the large family (that enabled the focusing chromosome 2q23-q31) should have other, less severe, mutations that would cause epilepsy in people who have only a weak family history of epilepsy. The sodium channel genes were chosen because they are involved in key electrical functions and could thus be good candidates. To formally test the hypothesis, many (60 to 70) unrelated cases of epilepsy were tested for mutations in these candidate genes. Surprisingly, mutations were found in all three candidate genes.

In order to assess whether mutations/polymorphisms could be identified and correlated to epilepsy, a panel of 70 to 80 epileptic patients (IGE) were tested for mutations in SCN1A, SCN2A and SCN3A, using Single-strand conformation polymorphism (SSCP). SSCP analysis enables the detection of mutations as small as single-base substitutions. Indeed, such substitutions, by altering the conformations of single-strand DNA molecules, affect the electrophoretic mobilities thereof in non-denaturing gels. Thus, one can distinguish among sequences by comparing the mobilities of wild type (wt), mutant DNA, or different alleles of a given locus. The identification of single base substitutions of genes using SSCP is well known in the art, and numerous protocols are available therefor. A non-limiting example thereof includes fluorescence-based SSCP analysis, following PCR carried out using fluorescent-labeled primers specific for the DNA regions one wishes to amplify.

Upon the identification of differences between normal and epileptic mobilities for one of the SCNA loci of the present invention, the amplified fragments were sequenced and the nucleic acid sequences between a normal patient and an epileptic patient (IGE) compared. This comparison enabled the identification of mutations in SCN1A, SCN2A, and SCN3A. To assess, whether this difference in sequence or mutation was significantly associated with the disease, SSCP analysis was performed once again using a large cohort of normal patients. This analysis enabled to show that the mutations identified by SSCP and confirmed by sequence analysis were not present in the large cohort of normal patients tested, thereby showing that the mutations identified correlated with IGE, for the population tested.

Taken together, these results show that SCN1A, SCN2A and SCN3A are validated genes associated with epilepsy and more specifically with IGE.

This invention now establishes, for the first time, that SCN1A, SCN2A, and SCN3A, is directly responsible for idiopathic generalized epilepsy (IGE) in certain human populations. Further, this discovery suggests that compounds which modulate the activity of SCN1A, SCN2A and SCN3A may have application far beyond the small groups of families with IGE, and may have applicability for treating many or all forms of epilepsy and related neurological disorders. It is therefore an object of this invention to provide screening assays using SCN1A, SCN2A and/or SCN3A which can identify compounds which have therapeutic benefit for epilepsy and related neurological disorders. This invention also claims those compounds, the use of these compounds in treating epilepsy and related neurological disorders, and any use of any compounds identified using such a screening assay in treating epilepsy and related neurological disorders.

Generally, high throughput screens for one or more SCN1A, SCN2A or SCN3A (herein collectively called SCNA) sodium channels modulators i.e. candidate or test compounds or agents (e.g., peptides, peptidomimetics, small molecules or other drugs) may be based on assays which measure biological activity of SCNA. The invention therefore provides a method (also referred to herein as a "screening assay") for identifying modulators, which have a stimulatory or inhibitory effect on, for example, SCNA biological activity or expression, or which bind to or interact with SCNA proteins, or which have a stimulatory or inhibitory effect on, for example, the expression or activity of SCNA interacting proteins (targets) or substrates.

Examples of methods available for cell-based assays and instrumentation for screening ion-channel targets are described in the review by Gonzalez et al. (Drug Discov. Today 4:431-439, 1999), and high-throughput screens for ion-channel drugs are described in review by Denyer et al. (Drug Discov. Today 3:323-332, 1998). Such assays include efflux of sodium or related ions that can be measured in a cell line (recombinant or non-recombinant) using fluorescence-based assays using both sodium indicator dyes and voltage sensing dyes. Preferred assays employ 140 guanidine flux and/or sodium indicator dyes such as SBFI and voltage sensing dyes such as DiBAC. Oxonal dyes such as DiBAC4 are responsive to membrane depolarization. Hyper-polarization results in removal of the dye from the cell by passive diffusion, while depolarization results in concentration of the dye within the cell.

In one embodiment, the invention provides assays for screening candidate or test compounds which interact with substrates of a SCNA protein or biologically active portion thereof.

In another embodiment, the invention provides assays for screening candidate or test compounds which bind to or modulate the activity of a SCNA protein or polypeptide or biologically active portion thereof.

In one embodiment, an assay is a cell-based assay in which a cell which expresses a SCNA protein or biologically active portion thereof, either natural or recombinant in origin, is contacted with a test compound and the ability of the test compound to modulate SCNA biological activity, e.g., modulation of sodium efflux activity, or binding to a sodium channel or a portion thereof, or any other measurable biological activity of SCNA is determined. Determining the ability of the test compound to modulate SCNA activity can be accomplished by monitoring, for example, the release of a neurotransmitter or other compound, from a cell which expresses SCNA such as a neuronal cell, e.g. a substantia nigra neuronal cell, or a cardiac cell upon exposure of the test compound to the cell. Furthermore, determining the ability of the test compound to modulate SCNA activity can be accomplished by monitoring, for example, the change in current or the change in release of a neurotransmitter from a cell which expresses SCNA upon exposure to a test compound. Currents in cells can be measured using the patch-clamp technique as described in the Examples below using the techniques described in, for example, Hamill et al. 1981 Pfluegers Arch. 391:85-100. Alternatively, changes in current can be measured by dye based fluorescence assays described below.

Determining the ability of the test compound to modulate binding of SCNA to a substrate can be accomplished, for example, by coupling the SCNA agent or substrate with a radioisotope or enzymatic label such that binding of the SCNA substrate to SCNA can be determined by detecting the labeled SCNA substrate in a complex. For example, compounds (e.g., SCNA agents or substrates) can be labeled with $^{125}I$, $^{35}S$, $^{14}O$, or $^{3}H$, either directly or indirectly, and the radioisotope detected by direct counting radio-emission or by scintillation counting. Alternatively, compounds can be enzymatically labeled with, for example, horseradish peroxidase or alkaline phosphatase. In these assays, compounds which inhibit or increase substrate binding to SCNA are useful for the therapeutic objectives of the invention.

It is also within the scope of this invention to determine the ability of a compound (e.g. SCNA substrate) to interact with SCNA without the labeling of any of the interactants. For example. a microphysiometer can be used to detect the interaction of a compound with SCNA without the labeling of either the compound or the SCNA (McConnell H. M. et al. (1992), Science 257:1906-1912). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between a compound and SCNA.

Modulators of SCNA can also be identified through the changes they induce in membrane potential. A suitable instrument for measuring such changes is the VIPR™ (voltage ion probe reader) from Aurora Biosciences. This instrument works together with a series of voltage-sensing ion probe assays. The probes sense changes in transmembrane electrical potential through a voltage-sensitive FRET mechanism for which the ratio donor fluorescence emission to acceptor fluorescence emission reveals the extent of cell depolarization for both sodium and potassium channels. Depolarization results from transport of a quencher across the membrane and far enough away from a membrane-bound fluorescence emitter to relieve the initial quenching and produce light at the emission wavelength of the emitter. The system follows fluorescence at two wavelengths, both the intensities and ratios change during cell depolarization. The reader permits detection of sub-second, real-time optical signals from living cells in a microplate format. The system is amenable to manual operation for assay development or automation via robots for high-throughput screening.

In another embodiment, the assay is a cell-based assay comprising a contacting of a cell containing a target molecule (e.g. another molecule, substrate or protein that interacts with or binds to SCNA) with a test compound and determining the ability of the test compound to indirectly modulate (e.g. stimulate or inhibit) the biological activity of SCNA by binding or interacting with the target molecule. Determining the ability of the test compound to indirectly modulate the activity of SCNA can be accomplished, for example, by determining the ability of the test compound to bind to or interact with the target molecule and thereby to indirectly modulate SCNA, to modulate sodium efflux, or to modulate other biological activities of SCNA. Determining the ability of the SCNA protein or a biologically active fragment thereof, to bind to or interact with the target molecule can be accomplished by one of the methods described above or known in the art for determining direct binding. In a preferred embodiment, determining the ability of the test compound's ability to bind to or interact with the target molecule and thereby to modulate the SCNA protein can be accomplished by determining a secondary activity of the target molecule. For example, the activity of the target molecule can be determined by detecting induction of a cellular second messenger of the target (e.g. intracellular $Ca^{2+}$, diacylglycerol, IP3, and the like), detecting catalytic/enzymatic activity of the target on an appropriate substrate, detecting the induction of a reporter gene (comprising a target-responsive regulatory element operatively linked to a nucleic acid encoding a detectable marker, such as luciferase), or detecting a target-regulated cellular response such as the release of a neurotransmitter. Alternatively, recombinant cell lines may employ recombinant reporter proteins which respond, either directly or indirectly to sodium efflux or secondary messengers all as known in the art.

In yet another embodiment, an assay of the present invention is a cell-free assay in which a SCNA protein or biologically active portion thereof, either naturally occurring or recombinant in origin, is contacted with a test compound and the ability of the test compound to bind to, or otherwise modulate the biological activity of, the SCNA protein or biologically active portion thereof is determined. Preferred biologically active portions of the SCNA proteins to be used in assays of the present invention include fragments which participate in interactions with non-SCNA molecules, (e.g. other channels for sodium, potassium or Ca+ or fragments thereof, or fragments with high surface probability scores for protein-protein or protein-substrate interactions). Binding of the test compound to the SCNA protein can be determined either directly or indirectly as described above. In a preferred embodiment, the assay includes contacting the SCNA protein or biologically active portion thereof with a known compound which binds SCNA to form an assay mixture, contacting the assay mixture with a test compound, and determining the ability of the test compound to interact with a SCNA protein, wherein determining the ability of the test compound to interact with a SCNA protein comprises determining the ability of the test compound to preferentially bind to SCNA or biologically active portion thereof as compared to the known compound.

In another embodiment, the assay is a cell-free assay in which a SCNA protein or biologically active portion thereof is contacted with a test compound and the ability of the test compound to modulate (e.g., stimulate or inhibit) the activity of the SCNA protein or biologically active portion thereof is determined. Determining the ability of the test compound to modulate the activity of a SCNA protein can be accomplished, for example, by determining the ability of the SCNA protein to bind to a SCNA target molecule by one of the methods described above for determining direct binding. Determining the ability of the SCNA protein to bind to a SCNA target molecule can also be accomplished using a technology such as real-time Biomolecular Interaction Analysis (BIA, Sjolander, S, and Urbaniczky, C. (1991) Anal. Chem. 63:2338-2345 and Szabo et al. (1995) Curr. Opin. Struct. Biol. 5:699-705). As used herein, "BIA" refers to a technology for studying biospecific interactions in real time, without labeling any of the interactants (e.g. BIA core). Changes in the optical phenomenon of surface plasmon resonance (SPR) can be used as an indication of real-time reactions between biological molecules.

In an alternative embodiment, determining the ability of the test compound to modulate the activity of a SCNA protein can be accomplished by determining the ability of the test compound to modulate the activity of an upstream or downstream effector of a SCNA target molecule. For example, the activity of the test compound on the effector molecule can be determined or the binding of the effector to SCNA can be determined as previously described.

The cell-free assays of the present invention are amenable to use of both soluble and/or membrane-bound forms of isolated proteins. In the case of cell-free assays in which a membrane-bound form of an isolated protein is used (e.g. a sodium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-IOO, Triton®X-114, Thesit®, Isotridecypoly(ethylene glycol ether)n. 3-[(3-cholamidopropyl)dimethyl-amino]-I-propane sulfonate (CHAPS), 3-[(3-cholamidopropyl)dim-ethylamino]-2-hydroxy-I-propane sulfonate (CHAPSO), or N-dodecyl-N,N-dimethyl-3-ammonio-1-propane sulfonate.

In more than one embodiment of the above assay methods of the present invention, it may be desirable to immobilize either SCNA or its target molecule to facilitate separation of complexed from uncomplexed forms of one or both of the proteins, as well as to accommodate automation of the assay. Binding of a. test compound to a SCNA protein or interaction of a SCNA protein with a target molecule in the presence and absence of a candidate compound, can be accomplished in any vessel suitable for containing the reactants. Examples of such vessels include microtitre plates, test tubes and microcentrifuge tubes. In one embodiment a fusion protein can be provided which adds a domain that allows one or both of the proteins to be bound to a matrix. For example. glutathione-S-transferase/SCNA fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or SCNA protein and the mixture incubated under conditions conducive to complex formation (e.g. at physiological conditions for salt and pH). Following incubation the beads or microtitre plate wells are washed to remove any unbound components, the matrix immobilized in the case of beads, complex determined either directly or indirectly, for example, as described above. Alternatively, the complexes can be dissociated from the matrix, and the level of SCNA binding or activity determined using standard techniques.

Other techniques for immobilizing proteins on matrices (and well-known in the art) can also be used in the screening assays of the invention. For example, either a SCNA protein or a SCNA target molecule can be immobilized utilizing conjugation of biotin and streptavidin. Biotinylated SCNA protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with SCNA protein or target molecules but which do not interfere with binding of the SCNA protein to its target molecule can be derivatized to the wells of the plate, and unbound target or SCNA protein trapped in the wells by antibody conjugation. Methods for detecting such complexes, in addition to those described above for the GST-immobilized complexes, include immunodetection of complexes using antibodies reactive with the SCNA protein or target molecule, as well as enzyme-linked assays which rely on detecting an enzymatic activity associated with the SCNA protein or target molecule.

In a preferred embodiment, candidate or test compounds or agents are tested for their ability to inhibit or stimulate a SCNA molecule's ability to modulate vesicular traffic and protein transport in a cell, e.g. a neuronal or cardiac cell using the assays described in for example Komada M. et al. (1999) Genes Dev. 13(11):1475-85, and Roth M. G. et al. (1999) Chem. Phys. Lipids. 98(12):141-52.

In another preferred embodiment candidate, or test compounds or agents are tested for their ability to inhibit or stimulate or regulate the phosphorylation state of a SCNA channel protein or portion thereof, or an upstream or downstream target protein, using for example an in vitro kinase assay. Briefly, a SCNA target molecule (e.g. an immunoprecipitated sodium channel from a cell line expressing such a molecule), can be incubated with radioactive ATP, e.g., [gamma-$^{32}$P]-ATP, in a buffer containing $M_gCl_2$ and $M_gCl_2$, e.g., 10 mM $M_gCl_2$ and 5 mM $M_gCl_2$. Following the incubation, the immunoprecipitated SCNA target molecule (e.g. the sodium channel), can be separated by SDS-polyacrylamide gel electrophoresis under reducing conditions, transferred to a membrane, e.g., a PVDF membrane, and autoradiographed. The appearance of detectable bands on the auto radiograph indicates that the SCNA substrate, e.g., the sodium channel, has been phosphorylated. Phosphoaminoacid analysis of the phosphorylated substrate can also be performed in order to determine which residues on the SCNA substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards. Assays such as those described in, for example, Tamaskovic R. et al. (1999) Biol. Chem. 380(5): 569-78.

In another preferred embodiment, candidate or test compounds or agents are tested for their ability to inhibit or stimulate a SCNA molecule's ability to associate with (e.g. bind) calcium, using for example, the assays described in Liu L. (1999) Cell Signal. 11(5):317-24 and Kawai T. et al. (1999) Oncogene 18(23):3471-80.

In another preferred embodiment, candidate or test compounds or agents are tested for their ability to inhibit or stimulate a SCNA molecule's ability to modulate chromatin formation in a cell using for example the assays described in Okuwaki M. et al. (1998) J. Biol. Chem. 273(51):34511-8 and Miyaji-Yamaguchi M. (1999) J. Mol. Biol. 290(2): 547-557.

In yet another preferred embodiment candidate or test compounds or agents are tested for their ability to inhibit or stimulate a SCNA molecule's ability to modulate cellular proliferation, using for example, the assays described in Baker F. L. et al. (1995) Cell Prolif. 28(1):1-15, Cheviron N. et al. (1996) Cell Prolif. 29(8):437-46. Hu Z. W. et al. (1999) J. Pharmacol. Exp. Ther. 290(1):28-37 and Elliott K. et al. (1999) Oncogene 18(24):3564-73.

In a preferred embodiment, candidate or test compounds or agents are tested for their ability to inhibit or stimulate a SCNA molecule's ability to regulate its association with the cellular cytoskeleton. Using for example, the assays similar to those described in Gonzalez C. et al. (1998) Cell Mol. Biol. 44(7):1117-27 and Chia C. P. et al. (1998) Exp. Cell Res. 244(1):340-8.

In another preferred embodiment, candidate or test compounds or agents are tested for their ability to inhibit or stimulate a SCNA molecule's ability to modulate membrane excitability, using for example, the assays described in Bar-Sagi D. et al. (1985) J. Biol. Chem. 260(8):4740-4 and Barker J. L. et al. (1984) Neurosci. Lett. 47(3):313-8.

In another preferred embodiment, candidate or test compounds or agents are tested for their ability to inhibit or stimulate a SCNA molecule's ability to modulate cytokine signaling in a cell, (e.g., a neuronal or cardiac cell), the assays described in Nakashima Y. et al. (1999) J. Bone Joint Surg. Am. 81 (5):603-15.

In another embodiment, modulators of SCNA expression are identified in a method wherein a cell is contacted with a candidate compound and the expression of SCNA mRNA or protein in the cell is determined. The level of expression of SCNA mRNA or protein in the presence of the candidate compound is compared to the level of expression of SCNA mRNA or protein in the absence of the candidate compound. The candidate compound can then be identified as a modulator of SCNA expression based on this comparison. For example, when expression of SCNA mRNA or protein is greater (statistically significantly greater) in the presence of the candidate compound than in its absence, the candidate compound is identified as a stimulator of SCNA mRNA or protein expression. Alternatively, when expression of SCNA mRNA or protein is less (statistically significantly less) in the presence of the candidate compound than in its absence, the candidate compound is identified as an inhibitor of SCNA mRNA or protein expression. The level of SCNA mRNA or protein expression in the cells can be determined by methods described herein or other methods known in the art for detecting SCNA mRNA or protein.

The assays described above may be used as initial or primary screens to detect promising lead compounds for further development. Often, lead compounds will be further assessed in additional, different screens. Therefore, this invention also includes secondary SCNA screens which may involve electrophysiological assays utilizing mammalian cell lines expressing the SCNA channels such as patch clamp technology or two electrode voltage clamp and FRET-based voltage sensor. Standard patch clamp assays express wild type and mutant channels in *Xenopus* oocytes, and examine their properties using voltage-clamp electrophysiological recording. Wild type sodium channels are closed at hyperpolarized membrane potentials. In response to membrane depolarization the channels open within a few hundred microseconds, resulting in an inward sodium flux, which is terminated within a few milliseconds by channel inactivation. In whole cell recordings, rapid activation and inactivation of thousands of sodium channels distributed throughout the cell membrane results in a transient inward sodium current that rises rapidly to peak amplitude and then decays to baseline within a few milliseconds.

Tertiary screens may involve the study of the identified modulators in rat and mouse models for epilepsy. Accordingly, it is within the scope of this invention to further use an agent identified as described herein in an appropriate animal model. For example, an test compound identified as described herein (e.g., a SCNA modulating agent, an antisense SCNA nucleic acid molecule, a SCNA-specific antibody, or a SCNA-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment (e.g. treatments of different types of epilepsy or CNS disorders), as described herein.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des. 12: 145, 1997). Examples of methods for the synthesis of molecular libraries can be found in the art, for example in: DeWitt et al. (1993) Proc. Natl. Acad. Sci. USA. 90:6909; Erb et al. (1994) Proc. Natl. Acad. Sci. USA 91:11422; Zuckermann et al. (1994), J. Med. Chem. 37:2678; Cho et al. (1993) Science 261:1303; Carell et al. (1994) Angew. Chem, Int. Ed Engl. 33:2059; Carell et al. (1994) Angew. Chem. Jnl. Ed. Engl. 33:2061; and in Gallop et al. (1994). Med. Chem. 37:1233. Libraries of compounds may be presented in solution (e.g. Houghten (1992) Biotechniques 13:412-421) or on beads (Lam (1991) Nature 354:82-84), chips (Fodor (1993) Nature 364:555-556). bacteria (Ladner U.S. Pat. No. 5,223,409), spores (Ladner USP '409), plasmids (Cull et al. (1992) Proc Natl Acad Sci USA 89:1865-1869) or on phage (Scott and Smith (1990); Science 249:386-390). Examples of methods for the synthesis of molecular libraries can be found in the art, for example in: DeWitt et al. (1993) Proc. Natl. Acad. Sci. USA. 90:6909; Erb et al. (1994) Proc. Natl. Acad. Sci. USA 91: 11422; Zuckermann et al. (1994), J. Med. Chem. 37:2678; Cho et al. (1993), Science 261:1303; Carell et al. (1994) Angew. Chem. Int. Ed. Engl. 33:2059, or luciferase, and the enzymatic label detected by determination of conversion of an appropriate substrate to product.

In summary, based on the disclosure herein, those skilled in the art can develop SCNA screening assays which are useful for identifying compounds which are useful for treating epilepsy and other disorders which relate to potentiation of SCNA expressing cells. The assays of this invention may be developed for low-throughput, high-throughput, or ultra-high throughput screening formats.

The assays of this invention employ either natural or recombinant SCNA protein. Cell fraction or cell free screening assays for modulators of SCNA biological activity can use in situ, purified, or purified recombinant SCNA proteins. Cell based assays can employ cells which express SCNA protein naturally, or which contain recombinant SCNA gene constructs, which constructs may optionally include inducible promoter sequences. In all cases, the biological activity of SCNA can be directly or indirectly measured; thus modulators of SCNA biological activity can be identified. The modulators themselves may be further modified by standard combinatorial chemistry techniques to provide improved analogs of the originally identified compounds.

Finally, portions or fragments of the SCNA cDNA sequences identified herein (and the corresponding complete gene sequences) can be used in numerous ways as polynucleotide reagents. For example, these sequences can be used to: (i) map their respective genes on a chromosome and thus, locate gene regions associated with genetic disease (mutations/polymorphisms) related to epilepsy or CNS disorders that involve SCNA directly or indirectly; (ii) identify an individual from a minute biological sample (tissue typing); and (iii) aid in forensic identification of a biological sample.

The present invention is illustrated in further detail by the following non-limiting examples.

EXAMPLE 1

Molecular Analysis

Genomic DNA was extracted from blood samples (Sambrook et al. 1989) or lymphoblastoid cell lines (Anderson and Gusella 1984) from each individual. A panel of 210 dinucleotide (CA)n repeat polymorphic markers with high heterozygosity (75%) was chosen from the 1993-94 Généthon map (Gyapay et al. 1994). Dinucleotide markers were spaced an average of 20 cM from each other throughout the 22 autosomes.

Genotyping of microsatellite markers was accomplished by polymerase chain reaction (PCR). The reaction mixture was prepared in a total volume of 13 μl, using 80 ng genomic DNA; 1.25 μl 10× buffer with 1.5 mM MgCl$_2$; 0.65 μl BSA (2.0 mg/ml); 100 ng of each oligonucleotide primer; 200 mM dCTP, dGTP and dTTP; 25 mM dATP; 1.5 mCi [$^{35}$S] dATP; and 0.5 units Taq DNA polymerase (Perkin-Elmer). Reaction samples were transferred to 96 well plates and were subjected to: 35 cycles of denaturation for 30 seconds at 94° C., annealing for 30 seconds at temperatures varying from 55° C. to 57° C. depending on the specificity of the oligonucleotide primers, and elongation for 30 seconds at 72° C. PCR reaction products were electrophoresed on 6% denaturing polyacrylamide sequencing gels.

EXAMPLE 2

Genetic Analysis

Two-point linkage analysis was carried out using the MLINK program version 5.1 from the LINKAGE computer package (Lathrop et al. 1984). Precise values for Zmax were calculated with the ILINK program from the same computer package. Lod scores were generated based on an autosomal dominant mode of inheritance, 80% penetrance, disease gene frequency of 1:500 and allele frequencies for all allele markers calculated from the pedigree using the computer program ILINK (Lathrop et al. 1984).

EXAMPLE 3

Mutations in SCN1A in IGE Patients

Genomic DNA from IGE and normal patients was obtained by conventional methods. Primers used to amplify the genomic DNA are shown in FIG. 2. Following PCR, SSCP analysis was performed and mutations in SCN1A were identified as follows (FIG. 3):

(1) Glu1238Asp; normal: GCA TTT GM GAT ATA; (SEQ ID NO: 189) patient R10191 who has an idiopathic generalized epilepsy (IGE): GCA TTT GAC GAT ATA (SEQ ID NO: 190) (found in 1 of 70 IGE patients). The mutation is thus a conservative aa change, in the extracellular domain between III-S1 and III-S2. Furthermore, this residue is located at the junction between the TM domain and the extracellular domain. It may thus influence gating activity. The aa change between adult and neonatal isoforms is at a similar juxta-TM domain position (between I-S3 and I-S4).

(2) Ser1773Tyr; normal: ATC ATA TcC TTC CTG (SEQ ID NO: 191), patient R9049 (affected with IGE): ATC ATA TmC TTC CTG:(TCC>TAC, (SEQ ID NO: 192)). This mutation is in the middle of IV-S6 TM domain; found in 1/70 IGE patients, and 0/150 control subjects tested. This mutation is interesting from a biological point of view for a number of reasons. First, this region of SCN gene (IV-S6) has been found to play a critical role in fast inactivation of the SCN, by mutagenesis experiments in rat SCN (McPhee et al., 1998). This is highly relevant for pathophysiology of epilepsy, since this may increase neuronal hyperexcitability. Moreover, in patients with GEFs, a mutation has been found in the SCNB1 subunit, causing impairment of the fast inactivation of the SCN (Wallace et al, 1999). Finally, many of the antiepileptic drugs (e.g. phenyloin, carbamazepine) primarily act by reducing the repetitive firing of neuron, which also involves fast inactivation of the SCN.

EXAMPLE 4

Mutations in SCN2A in IGE Patients

Genomic DNA from IGE and normal patients was obtained by conventional methods. Primers used to amplify the genomic DNA are shown in FIG. 4. Following PCR, SSCP analysis was performed and mutations in SCN2A were identified as follows (FIG. 5):

(1) Lys908Arg: normal: TAC AAA GM (SEQ ID NO: 307) for patient numbers always preceded by R; R9782 (Patient with IGE): TAC AGA GM (SEQ ID NO: 308). The mutation is thus a conservative aa change, located in an extracellular domain between TM domains IIS5 and IIS6; in 1/70 IGE patients; 0/96 normal controls. The mutation involves an important component of the SCN gene, since the S5 and S6 segments are thought to form the wall of the transmembrane pore which allows the sodium to enter the cell. This may have an influence on the gating control of the pore.

(2) Leu768Val, in individuals R8197, R9062 and R9822 (all IGE patients) (found in 3/70 IGE patients and 0/65 control subjects). The mutation is in the IV-S6 component of the sodium channel, which is important in the inactivation of the channel (see above for more detail).

EXAMPLE 5

Mutations in SCN3A in IGE Patients

Genomic DNA from IGE and normal patients was obtained by conventional methods. Primers used to amplify the genomic DNA are shown in FIG. 6. Following PCR, SSCP analysis was performed and mutations in SCN3A were identified as follows (FIG. 7):

(1) Asn43DEL: allele 1: CM GAT AAT GAT GAT GAG (SEQ ID NO: 400); allele 2: CM GAT-GAT GAT GAG (SEQ ID NO: 401); in open reading frame deletes 1 aa: DNDDEN->QDDDEN, in the cytoplasmic N-terminal segment; in IGE patients, the frequency of allele 1=131/146 (0.90); allele 2=15/146 (0.10); for IGE patients: homozygotes (22): R3958, R9632; heterozygotes (12): R9049, R9152, R9649, R9710, R9896, R10069, R10191, R10213, R9993, R10009, R10256. Of note, 2 patients are homozygous for the rare allele and all patients have IGE. In controls: allele 1=145/154 (0.94); allele 2=9/154 (0.06) and no 22 homozygotes were found.

(2) normal: tggtgtaaggtag (SEQ ID NO: 402), R10670 (IGE patient): tggtataaggtag (SEQ ID NO: 403), in conserved intron between 5N & 5A exons, significance uncertain.

(3) normal: cccttatatctccaac (SEQ ID NO: 404), R10250 (IGE patient): cccttatayctccaac (SEQ ID NO: 405); in conserved intron between 5N & 5A exons, significance uncertain.

(4) Val1035Ile: normal: AAA TAC GTA ATC GAT, R9269 (IGE patient): AAA TAC RTA ATC GAT (SEQ ID NO: 406); (GTA>ATA=Val>Ile) (SEQ ID NOs: 407 and 408). The mutation is thus a conservative aa change which destroys a SnaBI site (this could thus be used as a polymorphism identifiable by restriction enzyme digestion). In SCN1A, this Val is an Ile, therefore probably not a causative mutation. In cytoplasmic domain bw II-S6 & III-S1 TMs; found in 1/70 IGE alleles; and 0/70 controls.

EXAMPLE 6

SCN1A is Involved in Idiopathic Generalized Epilepsy

The assumption that SCN1A gene is involved in idiopathic generalised epilepsy in humans is based on many sets of evidence. First, a mutation has been found in a large Australian family with autosomal dominant epilepsy. The phenotype is idiopathic generalised epilepsy that is associated with febrile seizures (GEFS syndrome). The gene for this family has been previously mapped to the long arm of chromosome 2. The maximum lod score is 6.83 for marker D2S111. The candidate region is very large, spanning 21 cM between markers D2S156 and D2S311. However, within this interval, there is a cluster of sodium channel genes, including SCN1A which was hypothesized to be a candidate gene for the disease.

Screening by SSCP of a small panel of three (3) affected patients form the family, and 3 normal controls was carried-out at first. All the exons of the SCN1A gene have been amplified by PCR, and a SSCP variant in exon 4 was found for all of the affected individuals, and none of the controls. By sequencing an affected patient and a control, an A-T substitution at nucleotide 565 was found. This variation destroys a BamHI restriction site, this enzyme was thus used as a diagnostic test to screen all the affected patients from the family, as well as more control cases. All affected patients from the family have A565T substitution, and none of the unaffected patients in the same kindred. An A565T substitution was not found in more than 400 control chromosomes.

The A565T substitution corresponds to a non-conservative amino acid change (D188V). This amino acid is conserved in all sodium channels thus far identified, in all species. The only exception is SCN2A identified in rat by Numa et al, where the aspartic acid is replaced by asparagine. However, it is likely that this represents an error during replication of cDNA, since other investigators have cloned the same gene in rat and found that the aspartic acid is conserved at position 188. Moreover, the same group has shown that D188N has a functional effect on channel activation in oocytes (Escayg et al., Nature Genetics. 24(4):343-5, 2000). Of note, this A565T substitution has not been found in 150 epileptic patients and in 200 control patients. Thus, this substitution has yet to be identified after 700 chromosomes assessments.

In view of proving that D188V in SCN1A, identified in the large Australian family studied, is a pathogenic mutation, the oligonucleotide mismatch mutagenesis technique was used to introduce the mutation in rat SCN1A clone. RNA was isolated from mutant and wild-type clones, and injected into oocytes in view of recording sodium currents by the patch-clamp technique. The amplitude of the currents was dramatically reduced for the mutant. Also, a small shift in the inactivation curve was observed for the mutant, as compared to the wild-type. Taken together, these preliminary results confirm a functional effect of D188V mutation on SCN1A gene. (more detail below).

The results presented herein are corroborated by studies from other investigators. For example, several other groups have also found linkage to the same locus on chromosome 2 for families with GEFS or very similar syndromes. Mutations in SCN1A (Thr875Met mutation; Arg1648His) have been found to be the cause of the epileptic syndrome in at least two (2) of these families (Escayg et al., Nature Genetics. 24(4): 343-5, 2000). Also, GEFS syndrome has been shown to be caused by mutation in SCN1B gene. It is demonstrated that the beta subunits interact with alpha subunits of voltage-gated sodium channels to alter kinetics of sodium currents in cells. These data suggest a common mechanism for generating abnormal neuronal discharges in the brain of patients with idiopathic generalised epilepsy.

Finally, in the process of screening patients from the large kindred with GEFS described above, a large cohort of patients with idiopathic generalised epilepsy was also screened by SSCP. Two (2) SSCP variants, that were subsequently sequenced were thereby identified. The variation observed are shown in Table 3:

TABLE 3

| exon | DNA variation | IGE alleles | Control alleles |
|---|---|---|---|
| 1Ax17 | Glu1238Asp; conservative AA change in extracellular domain between III-S1 and III-S2 | 3/254 | 0/284 |
| 1Ax24.2 | Ser1773Tyr; middle of IV-S6 TM domain | 1/252 | 0/334 |

Previous functional studies have shown that amino acid substitution in the IV-S6 transmembrane domain of SCN2A significantly affects the rate of inactivation of the channel. It is thus likely that Ser1773Tyr will have an effect on the SCN1A gene function. Such functional studies are currently underway.

EXAMPLE 7

Further Validation of the Role of SCN1A, SCN2A, SCN3A, and Specific Mutations Thereof in IGE and Epilepsy in General A number of methods could be used to further validate the role of SCN1A, SCN2A, SCN3A, and specific mutations thereof in IGE. For example, additional patients could be screened for mutations in SCN1A, SCN2A, or SCN3A. Furthermore, additional normal patients could be screened in order to validate that the mutations identified significantly correlate with disease, as opposed to reflecting a polymorphism which is not linked to IGE. Polymorphisms which are not directly linked to IGE, if in linkage disequilibrium with a functional mutation linked to IGE, could still be useful in diagnosis and/or prognosis assays. In addition, functional studies can be carried. Numerous methods are amenable to the skilled artisan. One particularly preferred functional assay involves the use of Xenopus oocytes and recombinant constructs harboring normal or mutant sequence of SCN1A, SCN2A, or SCN3A. Xenopus oocytes have been used in functional assays to dissect the structure-function relationship of the cyclic AMP-modulated potassium channel using recombinant KCNQ2 and KCNQ3 (Schroeder et al., 1998). As well, it has been used to dissect the structure-function relationship of the beta subunit of the sodium channel (SCN1B gene; Wallace et al. 1998).

One such example of functional studies was investigated by assessing the effects of mutation D188V in the SCN1A gene on sodium channel function by introducing the mutation into a cDNA encoding the rat ortholog SCN1A gene. This rat gene shares >95% identity with the human SCN1A gene. The expression of wild type and mutant channels in Xenopus oocytes, and the examination of their properties using voltage-clamp electrophysiological recording is amenable to this Xenopus system. Wild type sodium channels are closed at hyperpolarized membrane potentials. In response to membrane depolarization the channels open within a few hundred microseconds, resulting in an inward sodium flux, which is terminated within a few milliseconds by channel inactivation. In whole cell recordings, rapid activation and inactivation of thousands of sodium channels distributed throughout the cell membrane results in a transient inward sodium current that rises rapidly to peak amplitude and then decays to baseline within a few milliseconds. Among the channel properties that are likely to be altered by mutations linked to epilepsy are: 1) the voltage-dependence of activation, a measure of the strength of membrane depolarization necessary to open the channels; 2) the voltage-dependence of steady state inactivation, a measure of the fraction of channels available to open at the resting membrane potential; and 3) the time course of inactivation. Preliminary results indicate that D188V mutant channels are identical to wild type channels with respect to the voltage-dependence of activation and to inactivation time course. However, steady state inactivation for the mutant channels is shifted to membrane potentials that are slightly more positive than observed in wild type channels. This positive shift should increase the fraction of channels available to open at rest. This could increase neuronal excitability and contribute to epileptogenesis. Thus, a functional consequence of a naturally occurring mutation in a sodium channel gene has been tentatively identified. Thus, the functional consequence of the D188M mutant could at least in part explain its role in epilepsy. Such a functional consequence is expected to be observed with other mutations identified above in SCNA1, SCNA2 and SCNA3.

It is recognized by the inventors that certain therapeutic agents have been identified for cardiac, muscular, chronic pain, acute pain and other disorders, and analgesics and anesthetics that are modulators of sodium channels. Use of these sodium channel modulators for treating epilepsy and related neurological disorders also falls within the scope of this invention. In one embodiment of this invention, sodium channel blockers are modified to achieve improved transport across the blood brain barrier in order to have direct effect on neuronal SCNA proteins and genes. Descriptions of such compounds are found at Hunter, J C et al. Current Opinion in CPNS Invest. Drugs. 1999 1(1):72-81; Muir K W et al. 2000. Cerebrovasc. Disc. 10(6):431-436; Winterer, G. 2000. Pharmacopsychiatry 33(5):182-8; Clare et al. 2000. Drug. Discov. Today 5(11):506-520; Taylor C P et al. 2000. Adv. Pharmacol. 39:47-98, and Pugsley M K et al. 1998. Eur. J. Pharmacol. 342(1)93-104.

It is also recognized by the inventors that compounds which modulate (i.e. either upregulate or downregulate) transcription and translation of SCNA genes are useful for treating epilepsy or related neurological disorders. According to this invention, test compounds which modulate the activity of promoter elements and regulatory elements of sodium channel genes are useful for treating these disorders.

Although the present invention has been described hereinabove by way of preferred embodiments thereof, it can be modified, without departing from the spirit and nature of the subject invention as defined in the appended claims.

REFERENCES

1) Andermann E (1982) Multifactorial inheritance of generalized and focal epilepsy. In: Anderson V E, Hauser W A, Penry J K, Sing C F (eds) GeneticBasis of the Epilepsies. New York, Raven Press, pp:355-374.
2) Anderson M A and Gusella J F (1984) Use of cyclosporin A in establishing Epstein Barr virus-transformed human lymphoblastoid cell lines. In vitro 20:856-858.
3) Annegor J F, Hauser W A, Anderson V E (1982) Risk of seizures among relatives of patients with epilepsy: families in a defined population. In: Anderson V E, Hauser W A, Sing L, Porter R (eds) The Genetic Basis of the Epilepsies, Raven Press, New York, pp 151-159.

4) Barnard E A, Darlison M G, Seeburg P (1987) Molecular biology of the GABAA receptor: the receptor/channel superfamily. Trends Neurosci 10:502-509.
5) Berkovic S F, et al. Epilepsies in twins: genetics of the major epileptic syndromes. Ann Neurol. 43:435 445 (1998). Bievert C, Schoeder B C, Kubisch C, Berkovic S F, Propping P, Jentsch T J, Steinlein O K (1998) A potassium channel mutation in neonatal human epilepsy. Science 279:403-406.
6) Bu D F, Tobin A J (1994) The exon-intron organization of the genes (GAD1 and GAD2) encoding two human glutamate decarboxylases (GAD67 and GAD65) suggests that they derive from a common ancestral GAD. Genomics 1:222-228.
7) Charlier C, et al. A pore mutation in a novel KGT like potassium channel gene in an idiopathic epilepsy family. Nat. Genet. 18:53 55 (1998).
8) Commission on Classification and Terminology of the International League against Epilepsy (1989) Proposal for revised clinical and eletroencephalographic classification of epileptic seizures. Epilepsia 22:489-501.
9) Corey L A, Berg K, Pellock J M, Solaas M H, Nance W E, DeLorenzo R J (1991) The occurrence of epilepsy and febrile seizures in Virginian and Norwegian twins. Neurology 41:433-436.
10) Elmslie F V, Rees M, Williamson M P, Kerr M, Kjeldsen M J, Pang K A, Sundqvist A, et al (1997) Genetic mapping of a major susceptibility locus for juvenile myoclonic epilepsy on chromosome 15q. Hum Mol Genet. 6:1329-1334.
11) Engel J J, Pedley T A (1998) What is epilepsy? In: Engel J J, Pedley T A (eds) Epilepsy a Comprehensive Textbook, Lippincott-Raven Publishers, Philadelphia, pp:1-10.
12) Escayg et al., Nature Genetics. 24(4):343-5, 2000.
13) Greenberg D A, Delgado-Escueta A V, Widelitz H, Sparkes R S, Treiman L, Maldonado H M, et al (1988) Juvenile myoclonic epilepsy (JME) may be linked to the BF and HLA loci on human chromosome 6. Am J Hum Genet 31:185-192.
14) Guipponi M, Rivier F, Vigevano F, Beck C, Crespel A, Echenne B, Lucchini P, et al (1997) Linkage mapping of benign familial infantile seizures (BFIS) to chromosome 19q. Hum Mol Genet 6:473-477.
15) Gyapay G, Morissette J, Vignal A, et al. (1994) The 1993-94 Genethon human genetic linkage map. Nat Genet 7:246-339.
16) Harvald B and Hauge M (1965) Hereditary factors elucidated by twin studies. In: Neel J V, Shaw M W, Schull W J (eds) Genetics and the Epidemiology of Chronic Diseases, Washington Public Health Service Publications 1163:61-76.
17) Inouye E (1960) Observations on forty twin index cases with chronic epilepsy and their co-twins. J Nery Ment Dis 130: 401-416.
18) Lathrop G M, Lalouel J M, (1984) Easy calculations of lod scores and genetic risks on small computers. Am J Hum Genet. 36:460-465.
19) Lennox W G, Lennox M A (1960) Epilepsy and related disorders. Boston, Little Brown.
20) Leppert M, Anderson V E, Quattlebaum T, Staufe D, O'Connell P, Nakamura Y, Lalouel J M, et al (1989) Benign familial neonatal convulsions linked to genetic markers on chromosome 20. Nature 337:647-648.
21) Lewis T B, Leach R J, Ward K, O'Connell P, Ryan S G (1993) Genetic Heterogeneity in benign familial neonatal convulsions: identification of a new locus on chromosome 8q. Am J Hum Genet 53:670-675.
22) McPhee et al., 1998, J. Biol. Chem. 273:1121-1129.
23) Ottman R, Annegers J F, Hauser W A, Kurland L T (1989) Seizure risk in offspring of parents with generalized versus partial epilepsy. Epilepsia 30:157-161.
24) Ottman R, Hauser W A, Barker-Cummings C, Lee J H, Risch N (1997) Segregation analysis of cryptogenic epilepsy and an empirical test of the validity of the results. Am J Hum Genet 60:667-675.
25) Sambrook J, Fritsch E F, Maniatis T (eds) (1989) Molecular cloning: a laboratory manual, 2nd ed. Cold Spring Harbor Laboratory, Cold Spring Harbor, N.Y., pp E.3-E.4.
26) Scheffer I E and Berkovic S F (1997) Generalised epilepsy with febrile seizures plus: a genetic disorder with heterogeneous clinical phenotypes. Brain 120: 479-490.
27) Schroeder et al., 1998, Nature 396:687-690.
28) Silanpaa M, Koskenvuo M, Romanov K, Kaprio J (1991) Genetic factors in epileptic seizures: evidence from a large twin population. Acta Neurol Scand 84:523-526.
29) Singh N A, Charlier C, Stauffer D, DuPont B R, Leach R J, Melis R, Ronen G M, et al (1998) A novel potassium channel gene, KCNQ2, is mutated in an inherited epilepsy of newborns. Nat Genet 18:25-29.
30) Steinlein O K, et al. A missense mutation in the neuronal nicotinic acetylcholine receptor alpha 4 subunit is associated with autosomal dominant nocturnal frontal lobe epilepsy. Nat. Genet. 11:201 203 (1995).
31) Wallace R H, Wang D W, Sing R, Scheffer I E, George-Jr A L, Phillips H A, Saar K, et al (1998) Febrile seizures and generalized epilepsy associated with a mutation in the Nat-channel betel subunit gene SCN1B. Nat Genet 19:366-370.

---

The invention claimed is:

1. A purified human SCN1A sodium channel nucleic acid molecule, wherein said nucleic acid molecule comprises a nucleic acid sequence selected from the group consisting of:
   (a) the nucleic acid sequence of SEQ ID NO: 1;
   (b) the nucleic acid sequence of SEQ ID NO: 412 which encodes an alpha subunit of the human SCN1A;
   (c) a nucleic acid sequence at least 95% identical to (a) or (b); and
   (d) a full complement of (a), (b) or (c).

2. The nucleic acid molecule of claim 1, wherein said nucleic acid encodes a polypeptide at least 99% identical to the SCN1A alpha subunit set forth in SEQ ID NO: 3.

3. The nucleic acid molecule of claim 1(a), 1(b) or 1(c), wherein said nucleic acid encodes a polypeptide having sodium channel activity.

4. A purified nucleic acid molecule of the human SCN1A sodium channel, wherein said nucleic acid molecule comprises:
   (a) a nucleic acid sequence encoding an SCN1A alpha subunit having sodium channel activity;
   (b) a nucleic acid sequence encoding an SCN1A alpha subunit having the amino acid sequence of SEQ ID NO: 3, or an amino acid sequence at least 99% identical to SEQ ID NO:3; and
   (c) a nucleic acid sequence comprising at least one exonic sequence of the human SCN1A gene, wherein said exonic sequence is selected from the group consisting of SEQ ID NOs:413 to 440.

5. A purified human SCN1A sodium channel nucleic acid molecule, wherein said nucleic acid comprises the nucleic acid sequence of SEQ ID NO:1, or SEQ ID NO:412, or a full-length complement of either of SEQ ID NO:1 or 412.

6. A purified human SCN1A sodium channel nucleic acid molecule selected from the group consisting of:
   (a) a nucleic acid comprising a sequence encoding an SCN1A alpha subunit having a sequence:
       (i) differing from SEQ ID NO: 3 only by a D188V amino acid substitution;
       (ii) differing from SEQ ID NO: 3 only by an E1238D amino acid substitution;
       (iii) differing from SEQ ID NO: 3 only by an S1773Y amino acid substitution; or
       (iv) being at least 95% identical to (i), (ii) or (iii), and comprising one of the mutations at amino acid position 188, 1238 or 1773;
   (b) an SCN1A nucleic acid fragment selected from the group consisting of an amplified segment:
       (v) consisting of the nucleic acid sequence of SEQ ID NO:417;
       (vi) comprising a nucleic acid sequence differing from SEQ ID NO:417 only by a mutation at nucleotide 90;
       (vii) consisting of the nucleic acid sequence of SEQ ID NO:433;
       (viii) comprising a nucleic acid sequence differing from SEQ ID NO:433 only by a mutation at nucleotide 9;
       (ix) consisting of the nucleic acid sequence of SEQ ID NO:440; or
       (x) comprising the nucleic acid sequence differing from SEQ ID NO:440 only by a mutation at nucleotide 466; and
   (c) a full-length complement of (a) or (b).

7. A vector comprising the purified nucleic acid molecule of claim 1.

8. A vector comprising the nucleic acid molecule of claim 2.

9. A vector comprising the purified nucleic acid molecule of claim 4.

10. A vector comprising the nucleic acid of claim 6.

11. An isolated cell harbouring the vector of claim 7.

12. An isolated cell harbouring the vector of claim 8.

13. An isolated cell harbouring the vector of claim 9.

14. An isolated cell harboring the vector of claim 10.

15. A method for determining whether a subject has a predisposition to idiopathic generalized epilepsy, said method comprising determining whether the sequence of the alpha subunit SCN1A nucleic acid molecule of claim 1 in a sample obtained from a subject:
   (i) encodes a mutation at one or more of residues 188, 1238, or 1773 of SEQ ID NO: 3;
   (ii) comprises a mutation at the second nucleotide in the codon encoding residue 188 of SEQ ID NO: 3;
   (iii) comprises a mutation at the third nucleotide in the codon encoding residue 1238 of SEQ ID NO: 3; or (iv) comprises a mutation at the second nucleotide in the codon encoding residue 1773 of SEQ ID NO: 3, wherein the presence of at least one of said mutations in the alpha subunit SCN1A nucleic acid molecule indicates that the subject is predisposed to idiopathic generalized epilepsy.

16. The method of claim 15, wherein said mutation is a mutation at position 188 of SEQ ID NO:3 replacing an aspartic acid residue by a valine residue.

17. The method of claim 15, wherein said mutation is a mutation at position 1238 of SEQ ID NO:3 replacing a glutamic acid residue by an aspartic acid residue.

18. The method of claim 15, wherein said mutation is a mutation at position 1773 of SEQ ID NO:3 replacing a serine residue by a tyrosine residue.

19. The method of claim 15, wherein said method comprises amplifying a nucleic acid molecule comprising a sequence selected from the group consisting of:
  (i) SEQ ID NO:417;
  (ii) SEQ ID NO:433;
  (iii) SEQ ID NO:440; and
  (iv) a full complement of SEQ ID NO:417, 433 or 440.

* * * * *